US010925885B2

(12) United States Patent
Cable et al.

(10) Patent No.: US 10,925,885 B2
(45) Date of Patent: Feb. 23, 2021

(54) THYROMIMETICS FOR THE TREATMENT OF FATTY LIVER DISEASES

(71) Applicant: Metabasis Therapeutics, Inc., San Diego, CA (US)

(72) Inventors: Edward E. Cable, San Diego, CA (US); Mark D. Erion, Del Mar, CA (US)

(73) Assignee: Metabasis Therapeutics, Inc., San Diego, CA (US)

(*) Notice: Subject to any disclaimer, the term of this patent is extended or adjusted under 35 U.S.C. 154(b) by 46 days.

(21) Appl. No.: 16/195,782

(22) Filed: Nov. 19, 2018

(65) Prior Publication Data

US 2019/0083515 A1 Mar. 21, 2019

Related U.S. Application Data

(60) Division of application No. 12/955,292, filed on Nov. 29, 2010, now Pat. No. 10,130,643, which is a continuation of application No. 11/814,824, filed as application No. PCT/US2006/128058 on May 26, 2006, now abandoned.

(60) Provisional application No. 60/684,572, filed on May 26, 2005.

(51) Int. Cl.
| | |
|---|---|
| *A61K 31/683* | (2006.01) |
| *A61K 31/661* | (2006.01) |
| *A61K 31/662* | (2006.01) |
| *A61K 31/665* | (2006.01) |
| *A61K 31/192* | (2006.01) |

(52) U.S. Cl.
CPC .......... *A61K 31/683* (2013.01); *A61K 31/192* (2013.01); *A61K 31/661* (2013.01); *A61K 31/662* (2013.01); *A61K 31/665* (2013.01)

(58) Field of Classification Search
CPC ... A61K 31/683; A61K 31/662; A61K 31/192
See application file for complete search history.

(56) References Cited

U.S. PATENT DOCUMENTS

| | | |
|---|---|---|
| 3,120,551 A | 2/1964 | Goldschmidt et al. |
| 3,357,887 A | 12/1967 | Kagan et al. |
| 4,069,343 A | 1/1978 | Sellstedt et al. |
| 4,069,347 A | 1/1978 | McCarthy et al. |
| 4,423,227 A | 12/1983 | Batz et al. |
| 4,426,453 A | 1/1984 | Cree et al. |
| 4,554,290 A | 11/1985 | Boger et al. |
| 4,673,691 A | 6/1987 | Bachynsky |
| 4,766,121 A | 8/1988 | Ellis et al. |
| 4,826,876 A | 5/1989 | Ellis et al. |
| 4,910,305 A | 3/1990 | Ellis et al. |
| 5,061,798 A | 10/1991 | Emmett et al. |
| 5,116,828 A | 5/1992 | Miura et al. |
| 5,158,978 A | 10/1992 | Rubin |
| 5,232,946 A | 8/1993 | Hurnaus et al. |
| 5,284,971 A | 2/1994 | Walker et al. |
| 5,324,522 A | 6/1994 | Krenning et al. |
| 5,401,772 A | 3/1995 | Yokoyama et al. |
| 5,519,163 A | 5/1996 | Gibbs et al. |
| 5,569,674 A | 10/1996 | Yokoyama et al. |
| 5,571,840 A | 11/1996 | Mayor et al. |
| 5,627,173 A | 5/1997 | Graeve et al. |
| 5,654,468 A | 8/1997 | Yokoyama et al. |
| 5,663,159 A | 9/1997 | Starrett, Jr. et al. |
| 5,741,803 A | 4/1998 | Pool et al. |
| 5,753,254 A | 5/1998 | Khan et al. |
| 5,854,282 A | 12/1998 | Mellin |
| 5,883,294 A | 3/1999 | Scanlan et al. |
| 5,922,775 A | 7/1999 | Kun et al. |
| 5,951,989 A | 9/1999 | Heymann |
| 6,107,517 A | 8/2000 | Scanlan et al. |
| 6,117,873 A | 9/2000 | Acklin et al. |
| 6,147,061 A | 11/2000 | Reiter |
| 6,194,454 B1 | 2/2001 | Dow |
| 6,221,911 B1 | 4/2001 | Lavin et al. |
| 6,236,946 B1 | 5/2001 | Scanlan et al. |
| 6,266,622 B1 | 7/2001 | Scanlan et al. |
| 6,326,398 B1 | 12/2001 | Chiang et al. |
| 6,344,481 B1 | 2/2002 | Cornelius et al. |
| 6,361,992 B1 | 3/2002 | Szkudlinski et al. |
| 6,380,255 B1 | 4/2002 | Lavin et al. |
| 6,414,002 B1 | 7/2002 | Cheng et al. |
| 6,414,026 B1 | 7/2002 | Billingham |
| 6,441,015 B2 | 8/2002 | Aspnes et al. |
| 6,465,687 B1 | 10/2002 | Li et al. |
| 6,468,755 B1 | 10/2002 | Shoelson |
| 6,492,424 B1 | 12/2002 | Apelqvist et al. |
| 6,495,533 B1 | 12/2002 | Matsui et al. |

(Continued)

FOREIGN PATENT DOCUMENTS

| | | | |
|---|---|---|---|
| CN | 107469086 A | 12/2017 | |
| EP | 0 580 550 | 1/1994 | |
| EP | 1297833 A1 * | 4/2003 | ........... C07D 209/42 |
| EP | 1471049 A1 * | 10/2004 | ......... C07D 295/192 |
| EP | 1 666 035 | 6/2006 | |
| WO | WO 89/08458 | 9/1989 | |
| WO | WO 90/08155 | 7/1990 | |
| WO | WO 90/10636 | 9/1990 | |

(Continued)

OTHER PUBLICATIONS

Alex et al.,Drugs and Their Structural Motifs, Chapter 1, pp. 28-29, Metabolism, Pharmacokinetics and Toxicity of Functional Groups—Impact of Chemical Building Blocsk on ADMET, 2010.
Amma, L.L., et al., "Distinct Tissue-Specific Roles for Thyroid Hormone Receptors p. And al in Regulation of Type 1 Deiodinase Expression," Mot. Endocrinol. 15:467-475, The Endocrine Society (2001).

(Continued)

*Primary Examiner* — Sudhakar Katakam
(74) *Attorney, Agent, or Firm* — Knobbe, Martens, Olson & Bear LLP

(57) ABSTRACT

The present invention is directed toward the use of thyromimetic compounds that are thyroid receptor ligands, pharmaceutically acceptable salts thereof, and to prodrugs of these compounds for preventing, treating, or ameliorating fatty liver diseases such as steatosis, non-alcoholic fatty liver disease, and non-alcoholic steatohepatitis.

25 Claims, 4 Drawing Sheets

(56) References Cited

U.S. PATENT DOCUMENTS

| | | |
|---|---|---|
| 6,534,676 B2 | 3/2003 | Markin et al. |
| 6,545,015 B2 | 4/2003 | Cheng et al. |
| 6,545,018 B2 | 4/2003 | Chiang et al. |
| 6,555,582 B1 | 4/2003 | Schwartz et al. |
| 6,566,372 B1 | 5/2003 | Zhi et al. |
| 6,576,636 B2 | 6/2003 | Webb et al. |
| 6,608,049 B2 | 8/2003 | Waltering et al. |
| 6,620,830 B2 | 9/2003 | Chiang |
| 6,625,201 B1 | 9/2003 | Wang et al. |
| 6,664,291 B2 | 12/2003 | Chiang et al. |
| 6,673,815 B2 | 1/2004 | Devasthale et al. |
| 6,680,340 B2 | 1/2004 | Cheng et al. |
| 6,689,896 B2 | 2/2004 | Kukkola |
| 6,716,877 B2 | 4/2004 | Markin |
| 6,723,744 B2 | 4/2004 | Aspnes et al. |
| 6,727,271 B2 | 4/2004 | Cheng et al. |
| 6,747,048 B2 | 6/2004 | Zhang et al. |
| 6,787,652 B1 | 9/2004 | Dow et al. |
| 6,794,406 B2 | 9/2004 | Haning et al. |
| 6,806,381 B2 | 10/2004 | Chidambaram et al. |
| 6,825,201 B2 | 11/2004 | Wang et al. |
| 6,831,102 B2 | 12/2004 | Rangeland |
| 6,852,706 B1 | 2/2005 | Heber-Katz |
| 6,875,782 B2 | 4/2005 | Cheng et al. |
| 6,982,348 B2 | 1/2006 | Kori et al. |
| 7,015,246 B2 | 3/2006 | Schmeck et al. |
| 7,402,602 B2 | 7/2008 | Bigg et al. |
| 7,514,419 B2 | 4/2009 | Erion et al. |
| 7,799,782 B2 | 9/2010 | Munson et al. |
| 7,829,552 B2 | 11/2010 | Erion et al. |
| 10,130,643 B2 * | 11/2018 | Cable .............. A61K 31/665 |
| 2001/0051645 A1 | 12/2001 | Chiang |
| 2001/0051657 A1 | 12/2001 | Chiang et al. |
| 2002/0006946 A1 | 1/2002 | Aspnes et al. |
| 2002/0045751 A1 | 4/2002 | Kukkola |
| 2002/0049226 A1 | 4/2002 | Chiang et al. |
| 2002/0107390 A1 | 8/2002 | Kukkola |
| 2002/0123521 A1 | 9/2002 | Lavin |
| 2003/0027862 A1 | 2/2003 | Haning et al. |
| 2003/0040535 A1 | 2/2003 | Aspnes et al. |
| 2003/0078288 A1 | 4/2003 | Haning et al. |
| 2003/0078289 A1 | 4/2003 | Aspnes et al. |
| 2003/0114521 A1 | 6/2003 | Chiang et al. |
| 2003/0153513 A1 | 8/2003 | Shiomi et al. |
| 2003/0166724 A1 | 9/2003 | Rangeland |
| 2004/0029187 A1 | 2/2004 | Palmer |
| 2004/0039028 A1 | 2/2004 | Zhang et al. |
| 2004/0077694 A1 | 4/2004 | Chiang et al. |
| 2004/0097589 A1 | 5/2004 | Yi-Lin et al. |
| 2004/0110951 A1 | 6/2004 | Chiang |
| 2004/0116387 A1 | 6/2004 | Malm et al. |
| 2004/0116391 A1 | 6/2004 | Piccariello et al. |
| 2004/0142868 A1 | 7/2004 | Sleeman |
| 2004/0152783 A1 | 8/2004 | Olon et al. |
| 2004/0157844 A1 | 8/2004 | Dow et al. |
| 2004/0219218 A1 | 11/2004 | Martino et al. |
| 2004/0220147 A1 | 11/2004 | Malm et al. |
| 2005/0004184 A1 | 1/2005 | Ryono et al. |
| 2005/0038122 A1 | 2/2005 | Rangeland |
| 2005/0054727 A1 | 3/2005 | Rangeland |
| 2005/0085541 A1 | 4/2005 | Shiohara et al. |
| 2006/0046980 A1 | 3/2006 | Erion et al. |
| 2009/0118236 A1 | 5/2009 | Erion et al. |
| 2010/0081634 A1 | 4/2010 | Erion et al. |
| 2015/0045389 A1 | 2/2015 | Madden et al. |
| 2016/0319548 A1 | 11/2016 | Shevlin |
| 2017/0105956 A1 | 4/2017 | Kaminski et al. |
| 2018/0243263 A1 | 8/2018 | Jain et al. |
| 2018/0360846 A1 | 12/2018 | Lefebvre |
| 2019/0255080 A1 | 8/2019 | Lian et al. |
| 2019/0343850 A1 | 11/2019 | Lian et al. |
| 2020/0179412 A1 | 6/2020 | Lian et al. |

FOREIGN PATENT DOCUMENTS

| | | | |
|---|---|---|---|
| WO | WO 91/06569 | 5/1991 | |
| WO | WO 91/11181 | 8/1991 | |
| WO | WO 95/00135 | 1/1995 | |
| WO | WO 95/24919 | 9/1995 | |
| WO | WO 96/05190 | 2/1996 | |
| WO | WO 96/40048 | 12/1996 | |
| WO | WO 97/21993 | 6/1997 | |
| WO | WO 98/07435 | 2/1998 | |
| WO | WO 98/41216 | 9/1998 | |
| WO | WO 98/57919 | 12/1998 | |
| WO | WO-9900353 A1 * | 1/1999 | ............ C07C 59/68 |
| WO | WO 99/26966 | 6/1999 | |
| WO | WO 99/29321 | 6/1999 | |
| WO | WO 99/38376 | 8/1999 | |
| WO | WO 99/45016 | 9/1999 | |
| WO | WO 99/62507 | 12/1999 | |
| WO | WO 00/00468 | 1/2000 | |
| WO | WO 00/07972 | 2/2000 | |
| WO | WO 00/39077 | 7/2000 | |
| WO | WO 00/51971 | 9/2000 | |
| WO | WO 00/52015 | 9/2000 | |
| WO | WO 00/58279 | 10/2000 | |
| WO | WO 01/13936 | 3/2001 | |
| WO | WO 01/18013 | 3/2001 | |
| WO | WO 01/36365 | 5/2001 | |
| WO | WO 01/60784 | 8/2001 | |
| WO | WO 01/72692 | 10/2001 | |
| WO | WO 01/79287 | 10/2001 | |
| WO | WO 01/94293 | 12/2001 | |
| WO | WO 01/98256 | 12/2001 | |
| WO | WO 02/03914 | 1/2002 | |
| WO | WO 02/04515 | 1/2002 | |
| WO | WO 02/05834 | 1/2002 | |
| WO | WO 02/11666 | 2/2002 | |
| WO | WO 02/26752 | 4/2002 | |
| WO | WO 02/32408 | 4/2002 | |
| WO | WO 02/060374 | 8/2002 | |
| WO | WO 02/062780 | 8/2002 | |
| WO | WO 02/066017 | 8/2002 | |
| WO | WO 02/072528 | 9/2002 | |
| WO | WO 02/079181 | 10/2002 | |
| WO | WO 02/092550 | 11/2002 | |
| WO | WO 03/003013 | 1/2003 | |
| WO | WO 03/015771 | 2/2003 | |
| WO | WO 03/018515 | 3/2003 | |
| WO | WO 03/039456 | 5/2003 | |
| WO | WO 03/061557 | 7/2003 | |
| WO | WO 03/061567 | 7/2003 | |
| WO | WO 03/070169 | 8/2003 | |
| WO | WO 03/075835 | 9/2003 | |
| WO | WO 03/084915 | 10/2003 | |
| WO | WO 03/094845 | 11/2003 | |
| WO | WO 03/099864 | 12/2003 | |
| WO | WO 03/105760 | 12/2003 | |
| WO | WO 04/007430 | 1/2004 | |
| WO | WO 2004/005342 | 1/2004 | |
| WO | WO 04/014318 | 2/2004 | |
| WO | WO 04/018421 | 3/2004 | |
| WO | WO 04/026097 | 4/2004 | |
| WO | WO 04/041208 | 5/2004 | |
| WO | WO 04/065620 | 8/2004 | |
| WO | WO 04/066929 | 8/2004 | |
| WO | WO 04/067482 | 8/2004 | |
| WO | WO 04/078947 | 9/2004 | |
| WO | WO 04/091636 | 10/2004 | |
| WO | WO 04/093799 | 11/2004 | |
| WO | WO 04/103289 | 12/2004 | |
| WO | WO 05/009433 | 2/2005 | |
| WO | WO 05/016862 | 2/2005 | |
| WO | WO 05/021895 | 3/2005 | |
| WO | WO 05/028488 | 3/2005 | |
| WO | WO 05/042556 | 5/2005 | |
| WO | WO 05/051298 | 6/2005 | |
| WO | WO 05/123729 | 12/2005 | |
| WO | WO 06/128055 | 11/2006 | |
| WO | WO 06/128056 | 11/2006 | |
| WO | WO 2006/128058 | 11/2006 | |

(56) References Cited

FOREIGN PATENT DOCUMENTS

| WO | WO 07/009913 | 1/2007 |
|---|---|---|
| WO | WO 2009/089093 | 7/2009 |
| WO | WO 2011/038207 | 3/2011 |
| WO | WO 2017/184811 | 10/2017 |
| WO | WO 2018/053036 | 3/2018 |
| WO | WO 2018/094265 | 5/2018 |
| WO | WO 2018/193006 | 10/2018 |
| WO | WO 2018/226604 | 12/2018 |
| WO | WO 2019/005816 | 1/2019 |
| WO | WO 2020/117962 | 6/2020 |
| WO | WO 2020/117987 | 6/2020 |

OTHER PUBLICATIONS

Anderson, S.N., et al., "Activation of Electrophilic Aromatic Substitution by the Substituent—CH2Co(dmgH)2py. Products of Reaction of Benzylcobaloximes with Halogens in Acetic Acid," J. Chem. Soc. Perkin Trans. II 311-318, Royal Society of Chemistry (1972).
Annett, R.G., et al., "Enzymatically catalysed decarboxylation of P-carboxyaspartic acid (Asa)," Can. J. Chem. 68:886-887, NRC Research Press (1990).
Antons, K.A., et al., "Clinical Perspectives of Starin-Induced Rhabdomyolysis," Am. J. Med. 119:400-409, Excerpta Medica (May 2006).
Apriletti, J.W., et al., "Molecular and Structural Biology of Thyroid Hormone Receptors," Clin. Exp. Pharmacol. Physiol. 25:S2-SI 1, Blackwell Science Asia (1998).
Archer, S.J., et al., "Hepatitis C Virus NS3 Protease Requires Its NS4A Cofactor Peptide for Optimal Binding of a Boronic Acid Inhibitor as Shown by NMR,"Chem. Biol. 9:79-92, Elsevier Science Ltd (Jan. 2002).
Arnold, S., et al., "3,5-Diiodothyronine binds to subunit Va of cytochrome-c oxidase and abolishes the allosteric inhibition of respiration by ATP," Eur. J. Biochem. 252:325-330, Blackwell Science Ltd (1998).
Arnold, L.A., et al., "Discovery of Small Molecule Inhibitors of the Interaction of the Thyroid Hormone Receptor with Transciptional Coregulators," J. Biol. Chem. 280:43048-43055, American Society for Biochemistry and Molecular Biology (Dec. 2005).
Auerbach, B.J., et al., "Comparative Effects of HMG-CoA reductase inhibitors on apo B production in the casein-fed rabbit: Atorvastatin versus Lovastatin," Atherosclerosis 115:173-180, Elsevier Science Ltd (1995).
Auberson, Y.P., et al., "N-Phosphonoalky1-5-Aminomethylquinoxaline-2,3- Diones: In Vivo Active AMPA and NMDA (Glycine) Antagonists," Bioorg. Med. Chem. Lett. 9:249-254, Elsevier Science Ltd (1999).
Ayajiki, K., et al., "Endothelial and Neuronal Functions in Cerebral and Temporal Arteries from Monkeys Fed a High Cholesterol Diet," J. Cardiovascular Pharmacol. 40:456-466, Lippincott Williams & Wilkins (Sep. 2002).
Ball, S.G. et al. "3,5-Diiodo-L-thyronine (T2) has selective thyromimetic effects in vivo and in vitro," J. Mal. Endocrinol. 19:137-147, Society for Endocrinology (1997).
Baxter, J.D., et al., "Structure-Based Design and Synthesis of a Thyroid Homone Receptor (TR) Antagonist," Endocrinology 143:517-524, Endocrine Society (Feb. 2002).
Baxter, J.D., et al., "Selective activation of thyroid hormone signaling pathways by GC-1: a new approach to controlling cholesterol and body weight," Trends Endocrinol. Metab. 15:154-157, Elsevier Science Ltd (May/Jun. 2004).
Beg, M.A.A. and Clark, H.C., "Chemistry of the Trifluoromethyl Group, Part III. Phenyltrifluoromethylphospine and Related Compounds," Can. J. Chem. 39:564- 570, NRC Research Press (1962).
Beg, M.A.A. and Clark, H.C., "Chemistry of the Trifluoromethyl Group, Part IV. Diphenyltrifluoromethylphophine and Complex Formation by Phenyltrifluoromethylphospines," Can. J. Chem. 40:283-288, NRC Research Press (1962).

Benayoud, F. and Hammond, G.B., "An expedient synthesis of (a,a-difluoroprop- 2-ynyl) phosphonate esters," Chem. Commun. 1447-1448, Royal Society of Chemistry (1996).
Bianco, Ac., et al., "Biochemistry, Cellular and Molecular Biology, and Physiolgical Roles of the lodothyronine Selenodeiodinases," Endocrine Rev. 23:38-89, the Endocrine Society (Feb. 2002).
Bilger, C., et al., "A Convenient One-Pot Synthesis of Aralkyl Bromides and Iodides by Reductive Halogenation of Aromatic Carbonyl Compounds," Synthesis 902-904, Georg Thieme Verlag (1988).
Blennemann, B., et al., "Tissue-Specific Regulation of Fatty Acid Synthesis by Thyroid Hormone," Endocrinology 130:637-643, the Endocrine Society (1992).
Bobyleva, V., et al., "Decrease in mitochondrial energy coupling by thyroid hormones: a physiological effect rather than a pathological hyperthyroidism consequence," FEBS Lett. 430:409-413, Elsevier Science Ltd (1998).
Bocan, T.M.A., et al., "HMG-CoA reductase and ACAT inhibitors act synergistically to lower plasma cholesterol and limit atherosclerotic lesion development in the cholesterol-fed rabbit," Atherosclerosis 139:21-30, Elsevier Science Ltd. (1998).
Bogardus, J.B. and Higuchi, T., "Kinetics and Mechanism of Hydorolysis of Labile Quaternary Ammonium Derivatives of Tertiary Amines," J. Pharm. Sci. 71:729-735, Wiley (1982).
Bohmer, V. and Vogt, W., "7.(o-Hydroxyphenyl)methylphosphonic acids: Synthesis and Potentiometric Determination of their pKa Values," Helvetica Chimica Acta 76:139-149, Verlag Helvetica Chimica Acta (1993).
Boyd, E.A., et al., "Facile Synthesis of Functionalised Phenylphosphinic Acid Derivatives," Tetrahedron Lett. 37:1651-1654, Elsevier Science Ltd (1996).
Boyd, E.A. and Regan, AC., "Synthesis of y-Keto-substituted Phosphinic Acids from Bis(trimethylsilyl)phosponite and a,P-Unsaturated Ketones," Tetrahedron Lett. 332:813-816, Elsevier Science Ltd (1992).
Boyer et al., "Synthesis and Biological Evaluation of a Series of Liver-Selective Phosphonic Acid Thyroid Hormone Receptor Agonists and Their Prodrugs", J. Med. Chem., 51:7075-7093 (2008).
Briel, D., et al., "3-Amino-5-phenoxythiophenes: Syntheses and Structure- Function Studies of a Novel Class of Inhibitors of Cellular L-Triiodothyronine Uptake," J. Med. Chem. 42:1849-1854, American Chemical Society (1999).
Brown, K., et al., "Accelerator Mass Spectrometry for Biomedical Research," Meth. Enzymol. 402:423-443, Academic Press (Nov. 2005).
Christian, M.S. and Trenton, N.A., "Evaluation of thyroid function in neonatal and adult rats: the neglected endocrine mode of action," Pure Appl. Chem. 75:2055-2068, International Union of Pure and Applied Chemistry (Nov. 2003).
Cimmino, M., et al., "Demonstration of in vivo metabolic effects of 3,5-di- iodothyronine," J. Endocrinol. 149:319-325, Society for Endocrinology (1996).
Clutterbuck, P.W. And Cohen, J.B., "The Aryl and Alkyl Sulphonamides," J. Chem. Soc. 123:2507-2515, Royal Society of Chemistry (1923).
Collazo, A-M.G., et al., "Thyroid receptor ligands. Part 5: Novel bicyclic agonist ligands selective for the thyroid hormone recepter B," Bioorg. Med. Chem. Lett. 16:1240-1244, Elsevier Science Ltd. (Mar. 2006).
Columbano, A., et al., "The Thyroid Hormone Receptor- Agonist GC-1 Induces Cell Proliferation in Rat Liver and Pancreas," Endocrinology 147:3211-3218, Endocrine Society (Mar. 2006).
Corrie, J.E.T. And Trentham, D.R., "Synthetic, Mechanistic and Photochemical Studies of Phosphate Esters of Substituted Benzoins," J. Chem. Soc. Perkin Trans. 1: 2409-2417, Chemical Society (1992).
Crimmins, M.T., et al., "Asymmetric Aldol Additions: Use of Titanium Tetrachloride and (-)-Sparteine for the Soft Enolization of N-Acyl Oxazolidinones, Oxazolidinethiones, and Thiazolidinethiones," J. Org. Chem. 66:894-902, American Chemical Society (2001).

(56) References Cited

OTHER PUBLICATIONS

Croxall, W.J., et al., "Organic Reactions with Boron Fluoride. Xl. The Condensation of Propylene with m-andp-Hydroxybenzoic acids," J. Am. Chem. Soc. 57:1549-1551, American Chemical Society (1935).
Danzi, S., et al., "Triiodothyronine-mediated myosin heavy chain gene transcription in the heart," Am. J. Physiol. Heart Circ. Physiol. 284:H2255-H2262, the American Physiological Society (2003).
Database CAplus, Chemical Abstract Service, Columbus Ohio, Enrion, M.D., et al., "Preparation of phosphonic acid-containing liver-selective thyromimetics effective against metabolic diseases," WO 2005-0512986, 16 pages (created Jun. 2005).
Davis, R. And Untch, K.G., "Direct one-step Conversion of Alcohols into Nitriles," J. Org. Chem. 46:2985-2987, American Chemical Society (1981).
Davis, P.J., et al., "Comparison of the mechanisms of nongenomic actions of thyroid hormone and steroid hormones," J. Endocrinol. Invest. 25: 377-388, Italian Society of Endocrinology (Apr. 2002).
De Brabandere, V.I., et al., "Isotope Dilution-Liquid Chromatography/ Electrospray Ionization-Tandem Mass Spectrometry for the Determination of Serum Thyroxine as a Potential Reference Method," Rapid Commun. Mass Spectrometry 12:1099-1103, Wiley (1998).
De Sandro, V., et al., "Comparison of the Effects of Propylthiouracil, Amiodarone, Diphenylhydantoin, Phenobarbital, and 3-Methylcholanthrene on Hepatic and Renal T4 Metabolisn and Thyroid Gland Function in Rats," Toxicol. Appl. Pharmacol. 111:263-278, Academic Press (1991).
Demori, I., et al., "3,-5-diiodothyronine Mimics the Effect of Triiodothyronine on Insulin-like growth Factor Binding Protein-4 Expression in Cultured Rat Hepatocytes," Harm. Metab. Res. 36:679-685, Georg Thieme Verlag (Oct. 2004).
Deprele, S. And Montchamp, J.-L., "A novel and convenient preparation of hypophosphite esters," J. Organometallic Chem. 643-644:154-163, Elsevier Science Ltd (Aug. 2002).
Dhawan, B. And Redmore, D., "1,2-Alkanediol Bis(Dihydrogen Phosphates),".
Dingwall, J.G., et al., "Diethoxymethylphosphonites and Phospinates. Intermediates for the Synthesis of a,P-and y-Aminoalkylphosphonous Acids," Tetrahedron 45:3787-3808, Pergamon Press (1989).
DiStefano III, J.J. And Feng, D., "Comparative Aspects of the Distrubution, Metabolism, and Excretion of Six Iodothyronines in the Rat," Endocrinology 123:2514-2525, Endocrine Society (1988).
Docter, R., et al., "Inhibition of Uptake of Thyroid Hormone into Rat Hepatocytes by Preincubation with N-Bromoacety1-3,3 ',5-Triiodothyronine," Endocrinology 123:1520-1525, the Endocrine Society (1988).
Dow, R.L., et al., "Discovery of a Novel Series of 6-Azauracil-Based Thyroid Hormone Receptor Ligands: Potent, Trp Subtype-Selective Thyromimetics," Bioorg. Med. Chem. Lett. 13:379-382, Elsevier Science Ltd (Nov. 2003).
Drechsler, U. And Hanack, M., "An Easy Route from Catechols to Phthalonitriles," Synlett 1207-1208, Georg Thieme Verlag (1998).
Earle, M.J., et al., "The first high yield green route to a pharmaceutical in a room temperature ionic liquid," Green Chem. 2:261-262, Royal Society of Chemistry (2000).
Ebdrup, S., et al., "Structure-activity relationship for aryl and heteroarly boronic acid inhibitors of homone-sensitive lipase," Bioorg. Med. Chem. 13:2305-2312, Elsevier Science Ltd (Jan. 2005).
Edmundson, R.S., et al., "Cyclic Organophosphorus Compounds. Part 23. Configurational Assignments in the 4-Phenyl-I ,3,2A.5-dioxaphosphorinane Series. X-Ray Molecular Structure of cis-2-Benzylamino-4-phenyl-1,3,2-dioxaphosphorinane 2- Oxide," J. Chem. Res. Synop. 5:122-123, Science Reviews, Ltd. (1989).
Edwards, M.L., et al., "Difluoromethyldiphenylphosphine oxide. A new reagent for conversion of carbonyl compounds to 1,1-difluoroolefins," Tetrahedron Lett. 31:5571-5574, Elsevier Science Ltd (1990).

Eisch, J.J., et al., "Rearrangement and Cleavage of [(Aryloxy)methyl]silanes by Organolithium Reagents: Conversion of Phenols into Benzylic alcohols," J. Org. Chem. 47:5051-5056, American Chemical Society (1982).
Ekins, R., "Validity of Analog Free Thyroxin Immunoassays" Clin. Chem.
Erion, M.D., et al., "Design, Synthesis, and Characterization of a Series of Cytochrome P450 3A-Activated Prodrugs (HepDirect Prodrugs) Useful for Targeting Phosph(on)ate-Based Drugs to the Liver," J. Am. Chem. Soc. 126:5154-5163, American Chemical Society (Apr. 2004).
Erion, M.D., et al., "Liver-Targeted Drug Delivery Using HepDirect Prodrugs," J. Pharmacol. Exper. Ther. 312:554-560, American Society for Pharmacology and Experimental Therapeutics (Feb. 2005).
Fabiano, E., et al., "A Simple Conversion of Alcohols into Amines," Synthesis.
Faergemann, J., et al., "Dose-Response Effects of Tri-iodothyroacetic Acid (Triac) and other Thyroid Hormone Analogues on Glucocorticoid-Induced Skin Atrophy in the Haired Mouse," Acta Derm. Venereal. 82:179-183, Society for the Publication of Acta Dermato-Venereologica (Mar. 2002).
Farquhar, D., et al., "Biologically-Cleavable Phosphate Protective Groups: 4- Acyloxy-1,3,2-Dioxaphosphorinanes as Neutral Latent Precursors of Dianionic Phosphates," Tetrahedron Lett. 36:655-658, Elsevier Science Ltd. (1995).
Feinstein, S., et al., "Submitral Atheromatous Lesions in Monkey and Man", Clin. Cardiol. 6:109-115, John Wiley & Sons, Inc. (1983).
Feng, W., et al., "Hormone-Dependent Coactivator Binding to a Hydrophobic Cleft on Nuclear Receptors," Science 280:1747-1749, American Association for the Advancement of Science (1998).
Field, L.D. And Wilkinson, M.P., "A new Synthesis of 1,2-Bis(Bis(Trifluoromethyl)Phosphino)ethane," Tetrahedron Lett. 33:7601-7604, Elsevier Science Ltd (1992).
Fieser, L.F. andArdao, M.I., "Investigation of the Chemical Nature of Gonyleptidine," J. Am. Chem. Soc. 78:774-781, American Chemical Society (1956).
Fleischmann, K., et al., "Synthesis of HR 916 B: the First Technically Feasible Route to the 1- (Pivaloyloxy)ethyl Esters of Cephalosporins," Liebigs Ann. 1735- 1741, Verlag Chemie (1996).
Fong, T.-L., et al., "Hyperthyroidism and Hepatic Dysfunction," J. Clin. Gastroenterol. 14:240-244, Raven Press (1992).
Freitas, F.R.S., et al., "Spared bone mass in rats treated with thyroid hormone receptor TRf3-selective compound GC-1," Am. J. Physiol. Endocrinol. Metab. 285:E1 135-El 141, American Physiological Society (Sep. 2003).
Freitas, F.R.S., et al.,"The Thyroid Hormone Receptor f3-Specific Agonist GC-1 Selectivity Affects the Bone Development of Hypothyroid Rats," J. Bone Mineral Res. 20:294-304, American Society for Bone and Mineral Research (Nov. 2004).
Froestl, W., et al., "Phosphinic Acid Analogues of Gaba. I. New Potent and Selective GABAB Agonists," J. Med. Chem. 38:3297-3312, American Chemical Society (1995).
Froestl, W., et al., "Phosphinic Acid Analogues of Gaba. 2. Selective, Orally Active Gabab Antagonists," J. Med. Chem. 38:3313-3331, American Chemical Society (1995).
Fujitaki, et al., "Preclinical Pharmacokinetics of a HepDirect Prodrug of a Novel Phosphonate-Containing Thyroid Hormone Receptor Agonist," the American Society for Pharmacology and Experimental Therapeutics, vol. 36, No. 11, 2008.
Gallagher, M. J. And Honegger, H., "Organophosphorus Intermediates. Vi. The Acid-Catalysed Reaction of Trialkyl Orthoformates with Phosphinic Acid," Aust. J. Chem. 33:287-294, Commonwealth Scientific and Industrial Research Organization (1980).
Gilman, H. And Calloway, N_O_, "Super-Aromatic Properties ofFuran. II. The Friedel-Crafts Reaction," J. Am. Chem. Soc. 55:4197-4205, American Chemical Society (1933).
Goglia, F., et al., "In Vitro binding of 3,5-di-iodo-L-thyronine to rat liver mitochondria," J. Mo!. Endocrinol. 13: 275-282, Society for Endocrinology (1994).
Goglia, F. "Biological Effects of 3,5-Diiodothyronine (T2) ," Biochemistry (Moscow) 70:164-172, Pleiades Publishing, Inc. (Feb. 2005).

(56) References Cited

OTHER PUBLICATIONS

Goglia, F. et al.,"Interaction of diiodothyronines with isolated cytochrome c oxidase," FEBS Lett. 346:295-298, Elsevier Science Ltd. (1994).
Goodrich,P. et al.,"Kinetic Study of the Metal Triflate Catalyzed Benzoylation of Anisole in an Ionic Liquid," Ind. Eng. Chem. Res. 45:6640-6647, American Chemical Society (Sep. 2006).
Goswami, A., et al., "Inhibition by coumadin anticoagulants of enzymatic outer ring monodeiodination of iodothyronines," Biochem. Biophys. Res. Commun. 104:1231-1238, Academic Press (1982).
Goya, R.G., et al., "Effects of Growth Hormone and Thyroxine on Thymulin Secretion in Aging Rats," Neuroendocrinology 58:338-343, S. Karger AG, Basel (1993).
Greco, M.N., et al., "Discovery of Potent, Selective, Orally Active, Nonpeptide Inhibitors of Human Mast Cell Chymase," J. Med. Chem. 50:1727-1730, American Chemical Society (Mar. 2007).
Gregory, R.B. And Berry, M.N., "On the thyroid hormone-induced increase in respiratory capacity of isolated rat hepatocytes," Biochim. Biophys. Acta I 098:61- 67, Elsevier Science Ltd. (1991).
Gronemeyer, H., et al., "Principles for Modulation of the Nuclear Receptor Superfamily" Nature Reviews, Drug Discovery 3:950-964, Nature Publishing Group (Nov. 2004).
Grover, G.J., et al., "Development of the Thyroid Homone Receptor P-Subtype Agonist KB-141: A Strategy for Body Weight Reduction and Lipid Lowering with Minimal Cardiac Side Effects," Cardiovascular Drug Rev. 23:133-148, Blackwell Publishing (Nov. 2005).
Grover, G.J., et al., "Selective thyroid hormone receptor-p. activation:a strategy for reduction of weight, cholesterol, and lipoprotein (a) with reduced cardiovascular liability," PNAS J00:10067-10072, National Academy of Sciences (Aug. 2003).
Guernik, S., et al., "A novel system consisting of Rh-DuPHOS and ionic liquid for asymmetric hydrogenations," Chem. Commun. 2314-2315, Royal Society of Chemistry (2001).
Hadvary, P. And Weller, T., "202. Conformationally Restricted Analogs of Platelet-Activating Factor (PAF)," Helvetica Chimica Acta 69:1862-1871, Verlag Helvetica Chimica Acta (1986).
Hashimoto, A., et al., "Design and synthesis of complementing ligands for mutant thyroid hormone receptor TRP(R320H): a tailor-made approach toward the treatment of resistance to thyroid hormone," Bioorg. Med. Chem. 13:3627- 3639, Elsevier Science Ltd (Jun. 2005).
Hayakawa, Y., et al., "A General Approach to Nucleoside 3'- and 5'-Monophosphates," Tetrahedron Lett. 28:2259-2262, Elsevier Science Ltd. (1987).
Hedfors, A., et al., "Thyroid Receptor Ligands. 3. Design and Synthesis of 3,5- Dihalo-4-alkoxyphenylalkanoic Acids as Indirect Antagonistis of the Thyroid Hormone Receptor," J. Med. Chem. 48:3114-3117, American Chemical Society (May 2005).
Heimberg, M., et al., "Plasma Lipoproteins and Regulation of Heptic Metabolism of Fatty Acids in Altered Thyroid States," Endocrine Rev. 6:590-607, Endocrine Society (1985).
Hennemann, G., et al., "Carrier-Mediated Transport of Thyroid Hormone into Rat Hepatocytes is Rate-Limiting in Total Cellular Uptake and Metabolism," Endocrinology 119:1870-1872, Endocrine Society (1986).
Hennemann, G., "Notes on the History of Cellular Uptake and Deiodination of Thyroid Hormone," Thyroid 15:753-756, Mary Ann Liebert Publishers (Aug. 2005).
Holy, a, "Phosphonomethoxyalkyl Analogs of Nucleotides," Curr. Pharm. Des. 9:2567-2595, Bentham Science Publishers (Dec. 2003).
Horst, C., et al., "3,5-Di-iodo-L-thyronine suppresses TSH in rats in vivo and in rat pituitary fragments in vitro," J. Endocrinol. 145:291-297, Society for Endocrinology (1995).
Horst, C. et al.,"Rapid Stimulation of hepatic oxygen consumption by 3,5-di- iodo-L-thyronine," . Biochem. J. 261:945-950, Portland Press (1989).
Howarth, J., et al., "Sodium Borohydride Reduction of Aldehydes and Ketones in the Recyclable Ionic Liquid [BMIM]PF 6," Synth. Commun. 31:2935-2938, Taylor & Francis (2001).

Huddleston, J.G., et al., "Characterization and comparison of hydrophilic and hydrophobic room temperature ionic liquids incorporating the imidazolium cation," Green Chem. 3:156-164, Royal Society of Chemistry (2001).
Hum, G., et al., "Synthesis of [Difluoro-(3-alkenylphenyl)-methyl]-phosphonic Acids on Non-crosslinked Polystyrene and Their Evaluation as Inhibitors of Ptpib," Bioorg. Med. Chem. Lett. 12:3471-3474, Elsevier Science Ltd (Aug. 2002).
Hume, J R. et al. "Anion Transport in Heart," Physiol. Rev. 80:31-81, the American Physiological ' Society (2000).
Hunter, D.H., et al., "Crown ether catalysis of decarboxylation and decarbalkoxylation of j3-keto acids and malonates: a synthetic application," Can. J. Chem. 58:2271-2277, Nrc Research Press (1980).
Ichikawa, K., et al., "Mechanism ofliver-selective thyromimetic activity of Sk&F L-94901: evidence for the presence of a cell-type-specific nuclear iodothyronine transport process," J Endocrinol. 165:391397, Society for Endocrinology (2000).
Ing, H.R., "The Pharmacology of Homologous Series," Fortschritte der Arzneimittelforschung. Progress in drug research. Progres des recherches pharmaceutiques 20:306-309, Birkhauser Verlag (1964).
Iyer, S. And Liebeskind, L.S., "Regiospecific Synthesis of 2-Methoxy-3-methyl- 1,4-benzoquinones fromMaleoylcobalt Complexes andAlkynes via Lewis Acid Catalysis. A Highly Convergent Route to Isoquinoline Quinones," J Am. Chem. Soc. 109:2759-2770, American Chemical Society (1987).
Jepson, E.M., "Thyroxine analogues as hypocholesterolemic agents," Am. Heart J 67:422-424, Mosby (1964).
Johnson, E.O., et al., "Experimentally-induced hyperthyroidism is associated with activation of the rat hypothalamic-pituitay-adrenal axis," Eur. J Endocrinol. 153:177-185, BioScientifica Ltd (Jul. 2005).
Jones, P.B. And Porter, N.A., "2-Aroylbenzoyl Serine Proteases: Photoreversible Inhibtion or Photoaffinity Labeling'?," J Am. Chem. Soc. 121:2753-2761, American Chemical Society (1999).
Jorgensen, E.C., "Thyroid Hormones and Analogs. II. Structure-Activity Relationships," in: Hormonal Proteins and Peptides, Li, C.H., eds., Academic Press, New York, NY, pp. 107-204 (1978).
Jorgensen, E.C., "Thyroid Hormones and Analogs. I. Synthesis, Physical Properties and Theoretical Calculations," in: Hormonal Proteins and Peptides, Li, C.H., eds., Academic Press, New York, NY, pp. 56-105 (1978).
Jorgensen, E.C. And Murray, W.J., "Thyroxine Analogs. 22. Thyromimetic Activity of Halogen-Free Derivatives of 3,5-Dimethyl-L-Thyronine,"J Med. Chem. 17:434-439 (1974).
Kadenbach, B., et al., "Mitochondrial Energy Metabolsim is Regulated via Nuclear-Coded Subunits of Cytochrome C Oxidase," Free Radical Biol. Med. 29:211-221, Elsevier Science Ltd (2000).
Kazemifard, A.G., et al., "Identification and quantitation of sodium-thyroxine and its degradation products by LC using electrochemical and MS detection," J Pharm. Biomed. Anal. 25:697-71 I, Elsevier Science Ltd. (2001).
Kennedy, J.A., et al., "Influence oflmiprarnine on the Hypothalamic/Pituitary/Thyroid Axis of the Rat," Metabolism 46:1429-1434, W.B. Saunders (1997).
Kennedy, J.F, et al., "Isolation of thyroxine-binding globulin (TBG) by immunoadsorption chromatography: some physical and immunochemical characteristics of TBG," Clinica Chimica Acta 129:251-261, Elsevier Science Ltd (1983).
Knolker, H.-J. and Filali, S., "Transition Metal Complexes in Organic Synthesis, Part 69. Total Synthesis of theAmaryllidaceae Alkaloids Anhydrolycorinone and Hippadine Using Iron-and Palladium-Mediated Coupling Reactions," Synlett 1752-1754, Georg Thieme Verlag (Jun. 2003).
Kobayashi, H., et al., "Organization ofNucleosides Supported by Boronic-Acid- Appended Poly(L-lysine): Creation of a Novel RNA Mimic," Bull. Chem. Soc. Jpn. 74:1311-1317, The Chemical Society of Japan (2001).
Koehler, K., et al., "Thyroid Receptor Ligands. 6. A High Affinity "Direct Antagonist" Selective for the Thyroid Hormone Receptor," J. Med. Chem. 49:6635-6637, American Chemical Society (Oct. 2006).

(56) References Cited

OTHER PUBLICATIONS

Koerner, D., et al., "Binding of Selected Iodothyronine Analogues to Receptor Sites of Isolated Rat Hepatic Nuclei," J. Biol.Chem. 250:6417-6423, American Society for Biochemistry and Molecular Biology (1975).

Krause, B.R., et al., "Opposite effects of beza:fibrate and gemfibrozil in both normal and hypertriglyceridemic rats," Atherosclerosis 127:91-101, Elsevier Science Ltd (1996).

Kvetny, J., "3,5-T2 Stimulates Oxygen Consumption, But Not Glucose Uptake in Human Mononuclear Blood Cells," Horm. Metab. Res. 24:322-325, Georg Thieme Verlag (1992).

Lacoste, Am., et al., "Research Regarding Aminoalkylphosphonic Acids. II. - Iodine Derivatives of the Phosphonic Analog of Tyrosine," Bull. Soc. Chim. Biol. 49:1827-1835, Masson Et Cie (1967).

Lacoste, A.-M., et al., "Biochemistry- Synthesis and biological properties of the phosphonic analog of thyroxine," C.R. Acad. Sci. Paris 267:1890-1892, Gauthier Villars Editeur (1968).

Lacoste, A.-M., et al., "Endrocrinology. Action of the phosphonic analog of thyroxine on post-embryonic development of the tadpole of Rana dalmatina Bon," Biol. Soc. Bordeaux 1684-1689 (1967).

Lanni, A., et al., "Specific Binding sites for 3,3'-diiodo-L-thyronine (3,3'-T2) in rat liver mitochondria," Fees Lett. 351:237-240, Elsevier Science Ltd (1994).

Lanni, A., et al., "Effect of 3,3'-di-iodothyronine and 3,5-diiodothyronine on rat liver mitochondria," J. Endocrinol. 136:59-64, Society for Endocrinology (1993).

Lanni, A., et al., "Effect of 3,3'-diiodothyronine and 3,5-diiodothyronine on rat liver oxidative capacity," Mol. Cell. Endocrinol. 86:143-148, Elsevier Scientific Publishers Ireland (1992).

Lanni, A., et al., "Rapid stimulation in vitro of rat liver cytochrome oxidase activity by 3,5-diiodo-I- thyronine and by 3,3'-diiodo-L-thyronine," Mol. Cell. Endocrinol. 99:89-94, Elsevier Science Ltd (1994).

Lanni, A., et al., "Expression of uncoupling protein-3 and mitochondrial activity in the transition from hypothyroid to hyperthyroid state in rat skeletal muscle," Febs Lett. 444:250-254, Elsevier Science Ltd. (1999).

Lanni, A., et al., "Calorigenic effect of diiodothyronines in the rat," J. Physiol 494:831-837, Blackwell Publishing (1996).

Laskorin, B.N., et al., "Preparation and Investigation of the Steric Structure of Sterically Hindered a-oxo Phosphoryl Compounds," Zhurnal Obshchei Khimii 44:1716-1720, RossiiskayaAkademiya Nauk (1974).

Lee, S-G. et al., "Microwave-assisted Kabachnik-Fields Reaction in Ionic Lee, ' Liquid," Bull. Korean Chem. Soc. 23:667-668, The Korean Chemical Society (Mar. 2002).

Lee,Y.-P.,et al. "Effects of Thyroid Hormones on the Guinea Pig," Endocrinology 86:241-250, The Endocrine Society (1970).

Leonard, J.L. And Rosenberg, I.N., "Iodothyronine 5'-Deiodinase from Rat Kidney: Substrate Specificity and the 5'-Deiodination of Reverse Triiodothrvonine," Endocrinolof!V 107:1376-1383, The Endocrine Society (1980).

Leonard, J.L. And Rosenberg, I.N., "Thyroxine 5'-Deiodinase Activity of Rat Kidney: Observations on Activation by Thiols and Inhibition by Propylthiouracil," Endocrinology 103:2137-2144, The Endocrine Society (1978).

Lewis, D.S. "Effects of dietary cholestrol on adipose tissue lipoprotein lipase in the baboon," Biochim. Biophys. Acta 879:44-50, Elsevier Science Ltd (1986).

Li, Y.-L., et al., "Thyroid receptor ligands. Part 4: 4'-amido bioisosteric ligands selective for the thyroid hormone receptor beta," Bioorg. Med. Chem. Lett. 16:884-886, Elsevier Science Ltd (Feb. 2006).

Liddle, C., et al., "Separate and Interactive Regulation of Cytochrome P450 3A4 by Triiodothyronine, Dexamethasone, and Growth Hormone in Cultured Hepatocytes," J. Clin. Endocrinol. Metab. 83:24112416, the Endocrine Society (1998).

Lin, C.-C., et al., Pharmacokinetics of Pradefovir and PMEA in Healthy Volunteers After Oral Dosing of Pradefovir,11 J Clin. Pharmacol. 45:1250-1258, Sage Science Press (Nov. 2005).

Linsel-Nitschke, P. And Tall, AR., "HDL as a Target in the Treatment of Atherosclerotic Cardiovascular Disease," Nature Reviews, Drug Discovery 4:193-205, Nature Publishing Group (Mar. 2005).

Liotta, D., et al., "A Simple, Inexpensive Procedure for the Large-Scale Production of Alkyl Quinones," J Org. Chem. 48:2932-2933, American Chemical Society (1983).

Lombardi, A., et al., "Characterization of the binding of 3, 3'-di-iodo-L-thyronine to rate liver mitochondria," J Endocrinol. 154:119-124, Society for Endocrinology (1997).

Lombardi, A., et al., "Effect of 3,5-di-iodo-L-thyronine on the mitochondrial energy-transduction apparatus," Biochem. J 330:521-526, Portland Press (1998).

Lukashev, N.V., et al., "Palladium-Catalyzed Cross-Coupling Reactions of Organocopper Derivatives of Methylphosphonic Esters and Amides with Aryl and Hetaryl Iodides," Russian J. Gen. Chem. 71:172- 178, Kluwer Academic Publishers (2001).

Mackenzie, P.I., et al., "Regulation of UDP Glucuronosyltransferase Genes," Curr. Drug Metab. 4:249-257, Bentham Science Publishers (Jun. 2003).

Mains, R.E. and Eipper, B.A., "Tissue Culture of Primary Rat Anterior Pituitary Cells" in Regulatory Peptides: From Molecular Biology to Function, Costa, E., Trabucchi, M., eds., Raven Press, New York City, NY, pp. 1-8 (1982).

Makinen, M.W. and Lee, C.-P., "Biochemical Studies of Skeletal Muscle Mitochondria: I. Microanalysis of Cytochrome Content, Oxidative and Phosphorylative Activities of Mammalian Skeletal Muscle Mitochondria," Arch. Biochem. Biophys. 126:75-82, Academic Press (1968).

Malevannaya, R.A., et al., "(Dialkoxyphosphinyl) Acetic Acids and Some of Their Analogs," Zhurnal Obshchei Khimii 41:1426-1434, Rossiiskaya Akademiya Nauk (1971).

Marcune, B.F., et al., "Selective displacement of aryl fluorides with hydroquinone: synthesis of 4- phenoxyphenols" Tetrahedron Lett. 46:7823-7826, Elsevier Science Ltd (Nov. 2005).

Marimuthu, A., et al., "TR Surfaces and Conformations Required to Bind Nuclear Receptor Corepressor" Mal. Endocrinol. 16:271-286, The Endocrine Society (Feb. 2002).

Matsui, T., et al., "Discovery of Novel Phosphonic Acid Derivatives as New Chemical Leads for Inhibitors of TNF-a Production," Bioorg. Med. Chem. 10:3807-3815, Elsevier Science Ltd (Aug. 2002).

McClain, R.M., "Mechanistic considerations for the relevance of animal data on thyroid neoplasia to human risk assessment," Mutation Res. 333:131-142, Elsevier Science Ltd. (1995).

Mertins, K., et al., "Transition-Metal-Catalyzed Benzylation of Arenes and Heteroarenes," Angew. Chem. Int. Ed. 44:238-242, Wiley-VCR Verlag GmbH & Co. (Dec. 2004).

Middleton, W.J., "New Fluorinating Reagents. Dialkylaminosulfur Fluorides," J. Org. Chem. 40:574-578, American Chemical Society (1975).

Miyahara, E.H., et al., "Thyroid hormone receptor-P-selective agonist GC-24 spares skeletal muscle type Ito II fiber shift," Cell Tissue Res. 321:233-241, Springer-Verlag (Aug. 2005).

Mocchegiani, E., et al., "Neuroendocrine-thymus interactions. I. In vitro modulation of thymic factor secretion by thyroid hormones," J. Endocrinol. Invest. 13:139-147, Italian Society of Endocrinology (1990).

Moreno, M., et al., "How the thyroid controls metabolism in the rat: different roles for triiodothyronine and diiodothyronines," J. Physiol. 505:529-538, Cambridge Univ. Press (1997).

Morkin, E., et al., "Pilot Studies on the Use of 3, 5-Diiodothyropropionic Acid, a Thyroid Hormone Analog, in the Treatment of Congestive Heart Failure," Cardiology 97:218-225, S. Karger AG, Basel (Jul. 2002).

Moscioni, Ad. And Gartner, L.M., "Thyroid Hormone and Hepatic UDP- Glucuronosyl Transferase Activity: Contrary Effects in Rat and Mouse," Res. Commun. Chem. Pathol. Pharmacol. 39:445-462, Pjd Publications Ltd (1983).

Murphy-Jolly, M.B., et al., "The synthesis of tris(perfluoroalkyl)phosphines," Chem. Commun. 4479-4480, Royal Society of Chemistry (Aug. 2005).

(56) References Cited

OTHER PUBLICATIONS

Nabeshima, T., et al., "Rate-accelerating Metal Ion Effects on Decarboxylation of a-Keto Acids by a Thiazolium Ion bearing a Metal Binding Site," J. Chem. Soc. Chem. Commun. 373-374, Royal Society of Chemistry (1991).
Ness, G.C., et al., "Effects of L-Triiodothyronine and the Thyromimetic L-94901 on Serum Lipoprotein Levels and Hepatic Low-Density Lipoprotein Receptor, 3- Hydroxy-3-methylglutaryl Coenzyme a Reductase, and Apo A-I Gene Expression," Biochem. Pharmacol. 56:121-129, Elsevier Science Ltd (1998).
Nguyen, N.-H., et al., "Hammett Analysis of Selective Thyroid Hormone Receptor Modulators Reveals Structural and Electronic Requirements for Homone Antagonists," J. Am. Chem. Soc. 127:4599-4608, American Chemical Society (Mar. 2005).
Nishinaga, et al., "Model Reactions for the Biosynthesis of Thyroxine. XII. The Nature of a Thyroxine Precursor Formed in the Synthesis of Thyroxine from Diiodotyrosine and Its Keto Acid Analog," Biochemistry 7:388-397, American Chemical Society (1968).
Nurtdinov, S.Kh., et al., "Reactions of Alkylphosphonous Dichlorides with Carboxylic Acid Chlorides," Zhurnal Obshchei Khimii 41:2486-2490, Rossiiskaya Akademiya Nauk (1971).
Ocasio, Cory A, and Scanlan, T.S., "Clinical prospects for new thyroid hormone analogues" Curr. Opin. Endocrinol. Diabetes 12:363-370, Lippincott Williams & Wilkins (Oct. 2005).
Ocasio, Cory A, and Scanlan, T.S., "Design and characterization of a thyroid hermone receptor a (TRa)-Specific Agonist," ACS Chem. Biol. 1:585-593, American Chemical Society (Oct. 2006).
O'Reilly, Ian, and Murphy, M.P., "Studies on the rapid stimulation of mitochondrial respiration by thyroid hormones." Acta Endocrinol. 127:542-546, Romanian Society for Endocrinology (1992).
O'Reilly, Ian, and Murphy, M.P., "Treatment of hypothyroid rats with T2 (3,5-di- iodo-L-thyronine) rapidly stimulates respiration in subsequently isolated mitochondria," Biochem. Soc. Trans. 20:59S, Portland Press (1991).
Osuka, A, et al., "Synthesis of Arenephosphonates by Copper(!) Iodide- Promoted Arylation of Phosphite Anions," Synthesis 69-71, George Thieme Verlag- Stuttart (1983).
Pan, S.-Y., et al., "Bifendate treatment attenuates hepatic steatosis in cholesterol/bile salt- and high-fat diet-induced hypercholesterolemia in mice," Eur. J. Pharmacol. 552:170-175 Elsevier Science Ltd (Dec. 2006).
Panne, P., et al., "Cyanide initiated perfluoroorganylations with perfluoroorgano silicon comoounds" J. Fluorine Chem. 112:283-286 Elsevier Science Ltd (2001).
Petervari, E., et al., "Hyperphagia of hyperthyroidism: Is neuropeptide Y involved?" Regulatory Peptides 131:103-110, Elsevier Science Ltd (Nov. 2005).
Prashad, M., "Phosphonate vs. Phosphinate Elimination during Olefination of Aldehydes," Tetrahedron Lett. 34:1585-1588, Elsevier Science Ltd (1993).
Psarra, A.-M.G., et al., "The mitochondrion as a primary site of action of steroid and thyroid hormones: Presence and action of steroid and thyroid hormone receptors in mitochondria of animal cells." Mo!. Cell. Endocrinol. 246:21-33, Elsevier Science Ltd (Feb. 2006).
Pue, M.A., et al., "The disposition of SK&F L-94901, a selective thyromimetic in rat, dog and cynomolgus monkey," Eur. J. Drug Metab. Pharmacokinetics 14:209-219, Edition Medecine Et Hygiene (1989).
Radominska-Pandya, A., et al., "A Historical Overview of the Heterologous Expression of Mammalian Udp-Glucuronosyltransferase Isoforms Over the Past Twenty Years," Curr. Drug Metab. 6:141-160, Bentham Science Publishers Ltd. (Apr. 2005).
Rai, R., and Katzenellenbogen, J.A., "Effect of Conformational Mobility and Hydrogen-Bonding Interactions on the Selectivity of Some Guanidinoaryl- Substituted Mechanism-Based Inhibitors of Trypsin-like Serine Proteases," J. Med. Chem. 35:42974305, American Chemical Society (1992).

Rashid, S., et al., "Effect of Atorvastatin on High-Density Lipoprotein Apolipoprotein A-I Production and Clearance in the New Zealand White Rabbit," Circulation 106:2955-2960, Lippincott Williams & Wilkins (Dec. 2002).
Razumov, A.I. And Gazizov, M.B., "Reactivity of Organophosphorus Carbonyl- Containing Compounds Iv. Synthesis, Properties, and Structure of Acylphosphinic Esters," Zhurnal Obshchei Khimii 37:2738- 27'42, Rossiiskaya Akademiya Nauk (1967).
Reiter et al.{Phosphinic acid-based MMP-13 inhibitors that spare MMP-1 and MMP-3, Bioorganic & Medicinal398Chemistry Letters (2003), 13(14), 2331-2336.
Ren, S.G., et al., "Dose-Response Relationship Between Thyroid Hormone and Growth Velocity in Cynomolgus Monkeys," J. Clin. Endocrinol. Metab. 66:1010-1013, the Endocrine Society (1988).
Ribeiro, R.C.J., et al., "X-ray Crystallographic and Functional Studies of Thyroid Hormone Receptor," J. Steroid Biochem. Molec. Biol. 65:133-141, Pergamon Press (1998).
Rooda, S.J.E., et al., "Metabolism of Triiodothyronine in Rat Hepatocytes,".
Ross J. And Xiao, J. "Friedel-Crafts acylation reactions using metal triflates in ionic liquid," Green Chem. 4:129-133, Royal Society of Chemistry (Feb. 2002).
Ruhlandt-Senge, K. And Englich, U., "Synthesis and characterization of the first discrete potassium thiolates displaying three different coordination spheres at potassium in one molecule," Chem. Commun. 147-148, Royal Society of Chemistry (1996).
Saitoh, H. And Aungst, B.J., "Improvement of the Intestinal Absorption of a Peptidomimetic, Boronic Acid Thrombin Inhibitor Possibly Utilizing the Oligopeptide Transporter," Pharm. Res. 16:1786-1789, Plenum Publishing Corporation (1999).
Sakamoto, T., et al., "Cross-Coupling of N-Heteroaryl Halides with Active Methylene Compounds in the Presence of Tetrakis(triphenylphosphine)palladium," Chem. Pharm. Bull. 36:1664-1668, Pharmaceutical Society of Japan (1988).
Sakamoto, T., et al., "Palladium-Catalyzed Condensation of Aryl Halides with Phenylsulfonylacetonitrile and Diethyl Cyanomethylphosphonate," Chem. Pharm. Bull. 38:1513-1517, Pharmaceutical Society of Japan (1990).
Samuels, H.H., et al., "Depletion ofL-3,5,3'-Triiodothyronine and L-Thyroxine in Euthyroid Calf Serum for Use in Cell Culture Studies of the Action of Thyroid Hormone," Endocrinolof!V 105:80-85, The Endocrine Society (1979).
Sano, M. And Yamatera, H., "Potential Energy Surface of [Cu(H2o)6]2+ and [Zn(H20)6] 2+ Derived From Ab lnitio MO Calculations," Chem. Lett. 1495-1496, The Chemical Society of Japan (1980).
Sass, D.A. et al. "Nonalcoholic Fatty Liver Disease: A Clinical Review," Dig. Dis. Sci. 50:171-180, Springer Science Business Media, Inc. (Jan. 2005).
Saulnier, M.G., et al., "Microwave-assisted synthesis of primary amine HX salts from halides and 7M ammonia in methanol," Tetrahedron Lett. 45:397-399, Elsevier Science Ltd. (Jan. 2004).
Schlosser, M. And Geneste, H., "The Organometallic Route to Benzylamine Type Monoamine Oxidase Inhibitors," Tetrahedron 54:10119-10124, Pergamon Press (1998).
Schmitt, L. et al., "Synthesis of Arylalkylmonofluorophosphonates as Myo- Inositol monophosphatase Ligands," Tetrahedron Lett. 39:4009-4012, Elsevier Science Ltd. (1998).
Schroder-van der Elst, J.P., et al., "Effects of 5,5'-diphenylhydantoin on the thyroid status in rats," Eur. J. Endocrinol. 134:221-224, BioScientifica Ltd (1996).
Selenkow, H.A. And Asper, Jr., S.P., "Biological Activity of Compounds Structurally Related to Thyroxine," Physiol. Rev. 35:426-474, American Physiological Society (1955).
Shi, Y., et al., "Mutant-Selective Thyromimetics for the Chemical Rescue of Thyroid Hormone Receptor Mutants Associated with Resistance to Thyroid Hormone," Biochemistry 44:4612-4626, American Chemical Society (Mar. 2005).
Smith, C.L. And O'Malley, B.W., "Coregulator Function: A Key to Understanding Tissue Specificity of Selective Receptor Modulators," Endocrine Rev. 25:45-71, The Endocrine Society (Feb. 2004).
Soldin, SJ., et al., "The measurement of free thyroxine by isotope dilution tandem mass spectrometry," Clinica Chimica Acta 358:113-118, Elsevier Science Ltd (Aug. 2005).

(56) References Cited

OTHER PUBLICATIONS

Song, K., et al., "Induction of angiotensin converting enzyme and angiotensin II receptors in the atherosclerotic aorta of high-cholesterol fed Cynomolgus monkeys," Atherosclerosis 138:171-182, Elsevier Science Ltd (1998).
Stanton, J.L., et al., "Synthesis and Biological Activity of Phenoxyphenyl Oxamic Acid Derivatives Related to L-Thyronine," Bioorg. Med. Chem. Lett. 10:1661-1663, Elsevier Science Ltd (2000).
Sterling, K. And Brenner, M.A., "Thyroid Hormone Action: Effect of Triiodothyronine on Mitochondrial Adenine Nucleotide Translocase in Vivo and in Vitro," Metabolism 44:193-199, W.B. Saunders (1995).
Tai, S.S.-C., et al., "Candidate Reference Method for Total Thyroxine in Human Serum: Use of Isotope-Dilution Liquid Chromatography-Mass Spectrometry with Electrospray Ionizaton," Clin. Chem. 48:637- 642, American Association for Clinical Chemistry (Jan. 2002).
Takayama, S., et al., "Antithyroid Effects of Propylthiouracil and Sulfamonomethoxine in Rats and Monkeys," Toxicol. Applied Pharmacol. 82:191-199, Academic Press (1986).
Tal, D.M. And Karlish, S.J.D., "Synthesis of a Novel Series of ArylmethylisothiouroniumDerivatives," Tetrahedron 51:3823-3830, Pergamon Press (1995).
Taylor, a.H., et al., "Beneficial Effects of a Novel Thyromimetic on Lipoprotein Metabolism," Mo!. Pharmacol. 52:542-547, American Society for Pharmacology and Experimental Therapeutics (1997).
Taylor, S.D., et al., "Synthesis of Aryl(DifluoromethylenePhosphonates) via Electrophilic Fluorination of a-Carbanions of Benzylic Phosphonates with N-Fluorobenzenesulfonimide," Tetrahedron 54:1691-1714, Pergamon Press (1998).
Thienpont, L.M., et al., "Isotope Dilution-Gas Chromatography/Mass Spectrometry and Liquid Chromatography/Electrospray Ionization-Tandem Mass Spectrometry for the Determination of Triiodo-L-Thyronine in Serum," Rapid Commun. Mass Spectrometry 13:1924-1931, John Wiley & Sons, Ltd (1999).
Thornber, C.W., "Isosterismand Molecular Modification in Drug Design," Chem. Soc. Rev. 8:563-580, Chemical Society (1979).
Togashi, M., et al., "Conformational adaptation of nuclear receptor ligand binding domains to agonists: Potential for novel approaches to ligand design," J. Steroid Biochem. Mo!. Biol. 93:127-137, Elsevier Science Ltd (Feb. 2005).
Tomilov, AP., et al., "Electrochemical synthesis of diethyl fluoromethanephosphonate," J. Fluorine Chem. 82:39-41, Elsevier Science Ltd. (1997).
Toussaint, 0., et al., "The Copper(I)-Catalyzed Decarboxylation of Malonic Acids: AN ew Mild and Quantitative Method," Synthesis 1029-1031, Georg Thieme Verlag (1986).
Trost, S.U., et al., "The Thyroid Hormone Receptor-13-Selective Agonist GC-1 Differentially Afftects Plasma Lipids and Cardiac Activity," Endocrinology 141:3057-3064, The Endocrine Society (2000).
Tsuchimoto, T., et al., "Scandium(III) Triflate Catalyzed Friedel-Crafts Alkylation Reactions," J. Org. Chem. 62:6997-7005, American Chemical Society (1997).
Underwood, A.H., et al., "A thyromimetic that decreases plasma cholesterol levels without increasing cardiac activity," Nature 324:425-429, Nature Publishing Group (1986).
Van Rompaey, K., et al., "A versatile synthesis of 2-substituted 4-amino-1,2,4,5- tetrahydro-2-benzazepine-3-ones," Tetrahedron 59:4421-4432, Pergamon Press (Apr. 2003).
Vaughan, M.K., et al., "Chronic Exposure to Short Photoperiod Inhibits Free Thyroxine Index and Plasma Levels of TSH, T4, Triiodothyronine (T3) and Cholesterol in Female Syrian Hamsters," Comp. Biochem. Physiol. 7JA:615-618, Pergamon Press Ltd (1982).
Veer, G.V.D.S., et al., "Temperature Effects on Free-Thyroxine Measurements: Analytical and Clinical Consequences," Clin. Chem. 38:1327-1331, American Association for Clinical Chemistry (1992).

Verd, J.C., et al., "Different effect of simvastatin and atorvastatin on key enzymes :involved in VLDL synthesis and catabolism in high fat/cholestrol fed rabbits," Br. J. Pharmacol. 127:1479-1485, Nature Publishing Group (1999).
Villicev, C.M., et al., "Thyroid hormone receptor -specific agonist GC-1 increases energy expenditure and prevents fat-mass accumulation in rats," J. Endocrinol. 193:21-29, Society for Endocrinology (Jan. 2007).
Visser, T.J., et al., "Deiodination of Thyroid Hormone by Human Liver," J. Clin. Endocrinol. Metab. 67:17-24, The Endocrine Society (1988).
Walker, D.M., et al., "Design and Synthesis of y-Oxygenated Phosphinothricins as Inhibitors of Gluamine Synthetase," J. Chem. Soc. Perkin Trans. 1 659-666, Royal Society of Chemistry (1990).
Wang, B., et al., "Effects of triiodo-thyronine on angiotensin-induced cardiomyocyte hypertrophy: reversal of increased -myosin heavy chain gene expression," Can. J. Physiol. Pharmacol. 84:935-941, NRC Research Press (Aug. 2006).
Wang, R., et al., "Salsalate Administration—A Potential Pharmacological Model of the Sick Euthyroid Syndrome," J. Clin. Endocrinol. Metab. 83:3095-3099, Endocrine Society (1998).
Waschbiisch, R., et al., "A high yield:ing synthesis of diethyl-l-fluoromethylphosphonate in pure form," C. R Acad. Sci. Paris, t. I, Serie II c 1:49-52, Elsevier Science Ltd (1998).
Wasserscheid, P. And Keim, W., "Ionic Liquids-New "Solutions" for Transition Metal Catalysis," Angew Chem. Int. Ed. 39:3772-3789, Wiley-VCR Verlag GmbH (2000).
Webb,P. et al. "Design of thyroid hormone receptor antagonists from first principles," J. Steroid .' Biochem. Mo!. Biol. 83:59-73, Elsevier Science Ltd (Dec. 2002).
Wechter, W.J., et al., "Hypocholesterolemic Agents. Thyroalkanols," J. Med. Chem. 8:474-478, American Chemical Society (1965).
Wells, P.G. et al.,"Effect of thyrotoxicosis on liver blood flow and propranolol disposition after long-term dosing," Clin. Pharmacol. Ther. 33:603-608, Nature Publishing Group (1983).
Welton, T., "Room-Temperature Ionic Liquids. Solvents for Synthesis and Catalysis," Chem. Rev. 99:2071-2083, American Chemical Society (1999).
Wibom, R., et al., "A sensitive method for measuring ATP-formation in rat muscle mitochondria," Scand. J Clin. Lab. Invest. 50:143-152, Taylor & Francis Health Sciences (1990).
Wienand, a, et al., "Design, Synthesis and Biological Evaluation of Selective Boron-containing Thrombin Inhibitors," Bioorg. Med. Chem. 7:1295-1307, Elsevier Science Ltd. (1999).
Willnow, T.E. And Herz, J., "Animal models for disorders of hepatic lipoprotein metabolism," J Mal. Med. 73:213-220, Springer-Verlag (1995).
Winder, W.W., et al., "Effects of thyroid hormone administration on skeletal muscle mitochondria," Am. J Physiol. 228:1341-1345, American Physiological Society (1975).
Wondisford, F.E., "Unlikely partners in weight loss'?," Cell Metab. 3:81-82, Cell Press (Feb. 2006).
Wu, K.-M. And Farrelly, J.G., "Preclinical Development of New Drugs that Enhance Thyroid Hormone Metabolism and Clearance: Inadequacy of Using Rats as an Animal Model for Predicting Human Risks in an IND and NDA," Am. J Therap. 13:141-144, Lippincott Williams & Wilkins (Mar./Apr. 2006).
Wu, Y., et al., "Removal of Thiazolidinethione Auxiliaries with Benzyl Alcohol Mediated by Dmap," J Org. Chem. 69:6141-6144, American Chemical Society (May 2004).
Xu, L., et al., "Heck Reaction in Ionic Liquids and the in Situ Identification of N- Heterocyclic Carbene Complexes of Palladium," Organometallics 19:1123-1127, American Chemical Society (2000).
Yang, W., et al., "Boronic Acid Compounds as Potential Pharmaceutical Agents," Med. Res. Rev. 23:346-368, Wiley Periodicals, Inc. (May 2003).
Yang, C. And Pittman, Jr., C.U., "Reductions of Organic Functional Groups Using NaBHi or NaBH,JLiCI in Diglyme at 125 to 162 °C," Synth. Commun. 28:2027- 2041, Georg Thieme Verlag (1998).
Ye, L.' et al.' "Thyroid Receptor Ligands. I. Agonist Ligands Selective for the Thyroid Receptor pl," J Med. Chem. 46:1580-1588, American Chemical Society (Mar. 2003).

(56) References Cited

OTHER PUBLICATIONS

Yen, P.M. "Physiological and Molecular Basis of Thyroid Hormone Action," Physiol.460 ' Rev. 81:1097-1142, American Physiological Society (2001).
Yoshihara, H.A.1., et al., "Structural Determinants of Selective Thyromimetics" J. Med. Chem. 46:3152-3161, American Chemical Society (Jul. 2003).
Yoshioka, R., et al., "The Optical Resolution and Asymmetric Transformation of DL-p- Hydroxypheny!glycine with (+)-1-Phenylethanesulfonic Acid," Bull. Chem. Soc. Jpn. 60:649-652, the Chemical Society of Japan (1987).
Yu K.-L., et al. "Concerning the Phosphorylation of Vicinal Dials," Synth. Commun. 18:465-468, Taylor & Francis, Inc. (1988).
Zalkow, L.H., et al., "Studies in the Synthesis of Camptothecin. An Efficient Synthesis of2,3-Dihydro-1H-pyrrolo[3,4-b]quinoline," J. Chem. Soc. 3551-3554, Royal Society of Chemistry (1971).
Zenker, N. and Jorgensen, E.C., "Thyroxine Analogs. I. Synthesis of 3,5-Diiodo- 4-(2'-alkylphenoxy)- DL-phenylalanines," J. Am. Chem. Soc. 81:4643-4647, American Chemical Society (1959).
Zhang, N. and Casida, J.E., "Novel Irreversible Butyrylcholinesterase Inhibitors: 2-Chloro-1- (substituted-phenyl)ethylphosphonic Acids," Bioorg. Med. Chem. 10:1281-1290, Elsevier Science Ltd (Nov. 2002).
Zhang, J. and Lazar, M.A., "The Mechanism of Action of Thyroid Hormones," Annu. Rev. Physiol. 62:439-466, Annual Reviews (2000).
Alonso-Merino, et al., "Thyroid hormones inhibit TGF-β signaling and attenuate fibrotic responses," PNAS, 2016, vol. 113(24), pp. E3451-E3460.
Austin, Glycogen Storage Disease, the Paitient-Parent Handbook. May 1, 2016.
Ayers, et al., "Thyroid hormone analogues: their role in treatment of hyperlipidemia," J. Endocrinol. . Diabetes Obes 2(3): 1042. 2014.
Bhattacharya, "Investigation and management of the hepatic glycogen storage diseases," Transl Pediatrics, vol. 4, No. 3, Jan. 1, 2015.
Eisch, J.J., et al., "Rearrangement and Cleavage of [(Aryloxy)methyl]silanes by OrganolithiumReagents: Conversion of Phenols into Benzylic Alcohols," J. Orf[. Chem. 47:5051-5056, American Chemical Society (1982).
Brooks, et al., "Large Animal Models and New Therapies for Glycogen Storage Disease," J Inherit Metab Dis. May 2015; 38(3): 505-509.
Cabalska, et al., "Treatment with D-thyroxine of patients with glycogen storage diseases type VI and Via," Materia Medica Polona, Wydawnietwa Handlu Zagranicznego, Warsaw, PL, vol. 19, No. 4, Sep. 30, 1987.
Cable, et al., "Reduction of Hepatic Steatosis in Rats and Mice After Treatment with a Liver-Targeted Thyroid Hormone Receptor Agonist," Hepatology, 2009, vol. 49, pp. 407-417.
Carvalho, et al., "Glycogen Storage Disease type 1a—a secondary cause for hyperlipidemia: report of five cases," Journal of Diabetes & Metabolic Disorders 2013, 12:25.
Chou, et al., "Glycogen storage disease type 1 and G6Pase-6 deficiency: etiology and therapy," Nat Rev Endocrinol. Dec. 2010; 6(12): 676-688.
Connolly, et al., "Future Pharmacotherapy for Non-alcoholic Steatohepatitis (NASH): Review of Phase 2 and 3 Trials," Journal of Clinical and Translational Hepatology (2018) vol. 6, pp. 264-275. Epub Jun. 28, 2018.
Duntas, "Thyroid Disease and Lipids," Thyroid, vol. 12, Number4, 2002.
Endres, et al., "D-Thyroxine Treatment in Glycogen Storage Disease Type Via," Pediatric Research, vol. 18, No. 8, Aug. 1, 1984.
Erion, et al., "Targeting thyroid hormone receptor-β agonists to the liver reduces cholesterol and triglycerides andimproves the therapeutic index," PNAS, Sep. 25, 2007, vol. 104, No. 39.
Garibaldi, et al. "Destrothyroxine treatment of phosphorylase-kinase deficiency glycogenosis in four boys," Helvetica Paediatrica Acta, Schwabe, Basel, CH, vol. 33, No. 4-5, Oct. 31, 1978.
Grundy, et al., "Implications of Recent Clinical Trials for the National cholesterol Education Program Adult Treatment Panel III Guidelines," Circulation. 2004;110:227-239; downloaded from http://circ.ahajournals.org/.
Hansen, et al., "Mouse models of nonalcoholic steaohepatitis in preclinical drug development," Drug Discovery Today, vol. 22, No. 11, Nov. 2017.
Haugen, et al., "Drugs That Suppress TSH or Cause Central Hypothyroidism," Best Pract Res Clin endocrinol. Metab. Dec. 2009; 23(6): 793-800.
Holt, "Thyroxine Therapy in Glycogen-Storage Disease," Nutrition Reviews, vol. 14, No. 7, Jul. 27, 1956.
Hopper et al., 1999, CAS: 130:332269.
Ibrahini et al., 2000, CAS: 133:14000.
Jain, M.R., et al., "Dual PPARα/γ agonist saroglitazar improves liver histopathology and biochemistry in experimental Nash models", Liver International, (2018) vol. 38, pp. 1084-1094. Epub Dec. 14, 2017.
Jakobsson, T., et al., " Potential Role of Thyroid Receptor β Agonists in the Treatment of Hyperlipidemia", Drugs (2017) vol. 77, pp. 1613-1621.
Kido et al., "Current status of hepatic glycogen storage disease in Japan: clinical manifestations, treatments and long-term outcomes," Joural of Human Genetics (2013) 58, 285-292.
Kishnani, et al., "Diagnosis and management of glycogen storage disease type I: A practice guideline of the American College of Medical Genetics and Genomics," Genetics in Medicine, submitted Aug. 12, 2014.
Koulischer, "Glycogen-Storage Disease : A Study on the Effect of Sodium/-Thyroxine and Glucagon," AMA Journal of Diseases of Children, vol. 91, No. 2, Feb. 1, 1956.
Lian, B., "Evaluation of the Thyroid Receptor Agonist VK2809 on Liver Disease in Dio-Nash Mice,", Hepatology, Oct. 2017, vol. 66, No. Suppl. 1, Sp. Iss. SI, p. 1038A.
Lonsdale, et al., "Normalization of Hepatic Phosphorylase Kinase Activity and Glycogen Concentration in Glycogen Storage Diseas Type IX During Treatment with Sodium D Thyroxine," American Journal of Human Genetics; Annual Meeting of the American Society of Human Genetics, vol. 29, No. 6, Nov. 1, 1977.
Madrigal-Matute, et al., "Regulation of Liver Metabolism by Autophagy," Reviews in Basic and Clinical Gastroenterology and Hepatology, Gastroenterology 2016 150:328-339.
Raparti et al., "Selective thyroid hormone receptor modulators," Indian J. Endocrinol. Metab. Mar.-Apr. 2013; 17(2): 211-218.
Reuters Market News, "Brief-Viking Therapeutics says statistically significant reductions in fibrosis, liver collage, after 8 weeks of VK2809 treatment," [retrieved from Internet on Jul. 28, 2018] <URL: https://www.reuters.com/article/brief-viking-therapeutics-says-statistic/brief-viking-therapeutics-says-statistically-significant-reductions-in-fibrosis-liver-collagen-after-8-weeks-of-vk2809-treatment-idUSFWN1J308Y> Published online Jun. 6, 2017.
Ryono et al., 2004, CAS: 927006.
Tacke, et al., "An update on the recent advances in antifibrotic therapy," Expert Review of Gastroenterology & Hepatology (2018) vol. 12(11), pp. 1143-1152. Epub Oct. 3, 2018.
Tyree, E.B., et al., "Effect of L-Triiodothyronine on Radiation-Induced Pulmonary Fibrosis in Dogs", Radiation Research (1966) vol. 28, pp. 30-36.
Yao, et al., "Regulation of fatty acid composition and lipid storage by thyroid hormone in mouse liver," Cell & Bioscience, Biomed Central Ltd. vol. 4, No. 1 Jul. 30, 2014.
Yu, G., et al., "Thyroid hormone inhibits lung fibrosis in mice by improving epithelial mitochondrial function", Nature Medicine (2018) vol. 24(1), pp. 39-49. Epub Dec. 4, 2017.
Viking Therapeutics, Press releases, "Viking Therapeutics Announces Presentation of Data from in Vivo Proof-of-Concept Study of VK2809 in Glycogen Storage Disease la (GSD la) at the 13th International Congress of Inborn Errors of Metabolism (ICIEM)", [retrieved from internet on Jun. 8, 2018] <URL: http://ir.vikingtherapeutics.com/2017-09-07-Viking-Therapeutics-Announces-Presentation-of-Data-from-In-Vivo-Proof-of-Concept-Study-of-VK2809-in-Glycogen-Storage-Disease-la-GSD-la-at-the-13th-International-Congress-of-Inborn-Errors-of-Metabolism-ICIEM> published on Sep. 7, 2017.

(56) References Cited

OTHER PUBLICATIONS

Viking Therapeutics—News & Events, "Viking Therapeutics Presents Results from in Vivo Study of VK2809 in Biopsy-Confirmed Non-Alcoholic Steatohepatitis (NASH) at the Annual Meeting of the American Association for the Study of Liver Diseases (AASLD)", Oct. 24, 2017, San Diego <URL: http://ir.vikingtherapeutics.com/2017-10-24-Viking-Therapeutics-Presents-Results-from-In-Vivo-Study-of-VK2809-in-Biopsy-Confirmed-Non-Alcoholic-Steatohepatitis-NASH-at-the-Annual-Meeting-of-the-American-Association-for-the-Study-of-Liver-Diseases-Aasld> [retrieved from Internet on Feb. 9, 2020].

Viking Therapeutics—News & Events, "Viking Therapeutics Announces Results of Gene Expression Analysis from in Vivo Study of VK2809 in Non-Alcoholic Steatohepatitis (NASH)", Sep. 11, 2017, San Diego <URL: http://ir.vikingtherapeutics.com/2017-09-11-Viking-Therapeutics-Announces-Results-of-Gene-Expression-Analysis-from-In-Vivo-Study-of-VK2809-in-Non-Alcoholic-Steatohepatitis-Nash> [retrieved from Internet on Feb. 9, 2020].

\* cited by examiner

THYROMIMETICS FOR THE TREATMENT OF FATTY LIVER DISEASES

CROSS-REFERENCE TO RELATED APPLICATIONS

This application is a divisional of U.S. application Ser. No. 12/955,292, filed Nov. 29, 2010, which is a continuation of U.S. application Ser. No. 11/814,824, filed Feb. 12, 2008, which is a 371 of international PCT Application No. PCT/US2006/128058, filed May 26, 2006 which claims the benefit, under 35 U.S.C. § 119(e), of the earlier filing date of U.S. Provisional Application No. 60/684,572, filed May 26, 2005, the contents of which is incorporated by reference herein in its entirety, including figures.

FIELD OF THE INVENTION

The present invention is directed toward the use of thyromimetic compounds that are thyroid receptor ligands, pharmaceutically acceptable salts thereof, and to prodrugs of these compounds for preventing, treating, or ameliorating fatty liver diseases such as steatosis, non-alcoholic fatty liver disease, and non-alcoholic steatohepatitis.

BACKGROUND OF THE INVENTION

The following description of the background is provided to aid in understanding, but is not admitted to be, or to describe, prior art. All publications and their cited references are incorporated by reference in their entirety.

Thyroid hormones (TH) are synthesized in the thyroid in response to thyroid stimulating hormone (TSH), which is secreted by the pituitary gland in response to various stimulants (e.g., thyrotropin-releasing hormone (TRH) from the hypothalamus). Thyroid hormones are iodinated O-aryl tyrosine analogues excreted into the circulation primarily as 3,3',5,5'-tetraiodothyronine (T4). T4 is rapidly deiodinated in local tissues by thyroxine 5'-deiodinase to 3,3',5'-triiodothyronine (T3), which is the most potent TH. T3 is metabolized to inactive metabolites via a variety of pathways, including pathways involving deiodination, glucuronidation, sulfation, deamination, and decarboxylation. Most of the circulating T4 and T3 is eliminated through the liver.

THs have profound physiological effects in animals and humans. Hyperthyroidism is associated with increased body temperature, general nervousness, weight loss despite increased appetite, muscle weakness and fatigue, increased bone resorption and enhanced calcification, and a variety of cardiovascular changes, including increased heart rate, increased stroke volume, increased cardiac index, cardiac hypertrophy, decreased peripheral vascular resistance, and increased pulse pressure. Hypothyroidism is generally associated with the opposite effects.

The biological activity of THs is mediated largely through thyroid hormone receptors (TRs). TRs belong to the nuclear receptor superfamily, which, along with its common partner, the retinoid X receptor, form heterodimers that act as ligand-inducible transcription factors. Like other nuclear receptors, TRs have a ligand binding domain and a DNA binding domain and regulate gene expression through ligand-dependent interactions with DNA response elements (thyroid response elements, TREs). Currently, the literature shows that TRs are encoded by two distinct genes (TRα and TRβ), which produce several isoforms through alternative splicing (Williams, *Mol. Cell Biol.* 20(22):8329-42 (2000); Nagaya et al., *Biochem. Biophys. Res. Commun.* 226(2):426-30 (1996)). The major isoforms that have so far been identified are TRα-1, TRα-2, TRβ-1 and TRβ-2. TRα-1 is ubiquitously expressed in the rat with highest expression in skeletal muscle and brown fat. TRβ-1 is also ubiquitously expressed with highest expression in the liver, brain and kidney. TRβ-2 is expressed in the anterior pituitary gland and specific regions of the hypothalamus as well as the developing brain and inner ear. In the rat and mouse liver, TRβ-1 is the predominant isoform (80%). The TR isoforms found in human and rat are highly homologous with respect to their amino acid sequences which suggest that each serves a specialized function.

TSH is an anterior pituitary hormone that regulates thyroid hormone production. TSH formation and secretion is in turn regulated by the hypothalamic TRH. TSH controls the uptake of iodide by the thyroid, the subsequent release of iodinated thyronines from thyroglobulin (e.g., T3, T4) as well as possibly the intrapituitary conversion of circulating T4 to T3. Compounds that mimic T3 and T4 can negatively regulate both TSH and TRH secretion resulting in suppression of TSH levels and decreased levels of T3 and other iodinated thyronines. Negative regulation of TSH is postulated based on co-transfection and knockout studies (Abel et al., *J. Clin. Invest.* 104:291-300 (1999)) to arise through activation of the thyroid receptor TRβ, possibly the isoform TRβ-2, which is highly expressed in the pituitary.

The most widely recognized effects of THs are an increase in metabolic rate, oxygen consumption and heat production. T3 treatment increases oxygen consumption in isolated perfused liver and isolated hepatocytes. (Oh et al., *J. Nutr.* 125(1):112-24 (1995); Oh et al., *Proc. Soc. Exp. Biol. Med.* 207(3):260-7 (1994)). Liver mitochondria from hyperthyroid rats exhibit increased oxygen consumption (Carreras et al., *Am. J. Physiol. Heart Circ. Physiol.* 281(6):H2282-8 (2001)) and higher activities of enzymes in the oxidative pathways (Dummler et al., *Biochem. J.* 317(3):913-8 (1996), Schmehl et al., *FEBS Lett.* 375(3):206-10 (1995), Harper et al., *Can. J. Physiol. Pharmacol.* 72(8):899-908 (1994)). Conversely, mitochondria from hypothyroid rats show decreased oxygen consumption. Increased metabolic rates are associated with increased mitochondrial biogenesis and the associated 2- to 8-fold increase in mitochondrial mRNA levels. Some of the energy produced from the increased metabolic rate is captured as ATP (adenosine 5'-triphosphate), which is stored or used to drive biosynthetic pathways (e.g., gluconeogenesis, lipogenesis, lipoprotein synthesis). Much of the energy, however, is lost in the form of heat (thermogenesis), which is associated with an increase in mitochondrial proton leak possibly arising from TH-mediated effects on mitochondrial membrane, uncoupling proteins, enzymes involved in the inefficient sn-glycerol 3-phosphate shuttle such as mitochondrial sn-glycerol 3-phosphate dehydrogenase (mGPDH), and/or enzymes associated with proton leakage such as the adenine nucleotide transporter (ANT), $Na^+/K^+$-ATPase, $Ca^{2+}$-ATPase and ATP synthase.

THs also stimulate metabolism of cholesterol to bile acids. Hyperthyroidism leads to decreased plasma cholesterol levels, which is likely due to increased hepatic LDL receptor expression. Hypothyroidism is a well-established cause of hypercholesterolemia and elevated serum LDL. L-T3 is known to lower plasma cholesterol levels. The effects of T3 are attributed to TRβ since TRβ-deficient mice are resistant to T3-induced reduction in cholesterol levels. The effects on cholesterol levels have been postulated to result from direct effects on LDL receptor expression, enzymes involved in conversion of cholesterol to bile acids such as the rate-limiting enzyme cholesterol 7α-hydroxylase (CYP7A) and/or possibly enzymes involved in cholesterol synthesis such as HMG CoA reductase. In addition, THs are known to affect levels of other lipoproteins linked to atherosclerosis. THs stimulate apo AI and the secretion of apo AI in HDL while reducing apo B100. Accordingly, one would expect T3 and T3 mimetics to inhibit the atherosclerotic process in the cholesterol fed animal.

THs simultaneously increase de novo fatty acid synthesis and oxidation through effects on enzymes such as ACC, FAS, and spot-14. THs increase circulating free fatty acids (FFA) levels in part by increasing production of FFAs from adipose tissue via TH-induced lipolysis. In addition, THs increase mitochondrial enzyme levels involved in FFA oxidation, e.g., carnitine palmitoyltransferase 1 (CPT-1) and enzymes involved in energy storage and consumption.

The liver represents a major target organ of THs. Microarray analysis of hepatic gene expression from livers of hypothyroid mice and mice treated with T3 showed changes in mRNA levels for 55 genes (14 positively regulated and 41 negatively regulated) (Feng et al., *Mol. Endocrinol.* 14(7): 947-55 (2000)). Others have estimated that approximately 8% of the hepatic genes are regulated by T3. Many of these genes are important to both fatty acid and cholesterol synthesis and metabolism. T3 is also known to have other effects in liver, including effects on carbohydrates through increased glycogenolysis and gluconeogenesis and decreased insulin action.

The heart is also a major target organ of THs. THs lower systemic vascular resistance, increase blood volume and produce inotropic and chronotropic effects. Overall TH results in increased cardiac output, which may suggest that T3 or T3 mimetics might be of use to treat patients with compromised cardiac function (e.g., patients undergoing coronary artery bypass grafting (CABG) or cardiac arrest) (U.S. Pat. No. 5,158,978). The changes in cardiac function are a result of changes in cardiac gene expression. Increased protein synthesis and increased cardiac organ weight are readily observed in T3-treated animals and represent the side effect of T3 that limits therapeutic use. TRβ knockout mice exhibit high TSH and T4 levels and increased heart rate suggesting that they retain cardiac sensitivity and therefore that the cardiac effects are via TRα. TRα knockouts exhibit reduced heart rates.

THs also play a role in the development and function of brown and white adipose tissue. Both TRα and TRβ are expressed in brown adipose tissue (BAT). THs induce differentiation of white adipose tissue (WAT) as well as a variety of lipogenic genes, including ACC, FAS, glucose-6-phosphate dehydrogenase and spot-14. Overall, THs play an important role in regulating basal oxygen consumption, fat stores, lipogenesis and lipolysis (Oppenheimer et al., *J. Clin. Invest.* 87(1):125-32 (1991)).

TH has been used as an antiobesity drug for over 50 years. In the 1940s TH was used alone, whereas in the 1950s it was used in combination with diuretics and in the 1960s in combination with amphetamines. Hyperthyroidism is associated with increased food intake but is also associated with an overall increase in the basal metabolic rate (BMR). Hyperthyroidism is also associated with decreased body weight (ca. 15%) whereas hypothyroidism is associated with a 25-30% increase in body weight. Treating hypothyroidism patients with T3 leads to a decrease in body weight for most patients but not all (17% of the patients maintain weight).

The effectiveness of TH treatment is complicated by the need for supraphysiological doses of T3 and the associated side effects, which include cardiac problems, muscle weakness and erosion of body mass. Long-term therapy has also been associated with bone loss. With these side effects, the medical community has tended to use thyroxine at low doses as an adjunct to dietary treatments. At these doses, TH has little effect on body weight or BMR The effectiveness of T3 to induce weight loss may be attenuated by defects in TH action. In comparison to normal animals, higher T3 doses were required in ob/ob mice to affect oxygen consumption, which was only observed in muscle, with no changes in liver and BAT. (Oh et al., *J. Nutr.* 125(1):112-24 (1995); Oh et al., *Proc. Soc. Exp. Biol. Med.* 207(3):260-7 (1994)). These effects were at least partially attributed to decreased uptake of T3 by the liver.

T3 analogues have been reported. Many were designed for use as cholesterol-lowering agents. Analogues that lower cholesterol and various lipoproteins (e.g., LDL cholesterol and Lp(a)) without generating adverse cardiac effects have been reported (e.g., Underwood et al., *Nature* 324:425-9 (1986)). In some cases the improved therapeutic profile is attributed to increased specificity for the TR-β wherein other cases it may be due to enhanced liver distribution. (Stanton et al., *Bioorg. Med. Chem. Lett.* 10(15):1661-3 (2000); Dow et al., *Bioorg. Med. Chem. Lett.* 13(3):379-82 (2003)).

T3 and T3 mimetics are thought to inhibit atherosclerosis by modulating the levels of certain lipoproteins known to be independent risk factors or potential risk factors of atherosclerosis, including, low density lipoprotein (LDL)-cholesterol, high density lipoprotein (HDL)-cholesterol, apoAI, which is a major apoprotein constituent of high density lipoprotein (HDL) particles and lipoprotein (a) or Lp(a).

Lp(a) is an important risk factor, elevated in many patients with premature atherosclerosis. Lp(a) is considered highly atherogenic (de Bruin et al., *J. Clin. Endocrinol. Metab.* 76:121-126 (1993)). In man, Lp(a) is a hepatic acute phase protein that promotes the binding of LDL to cell surfaces independent of LDL receptors. Accordingly, Lp(a) is thought to provide supplementary cholesterol to certain cells, e.g., cells involved in inflammation or repair. Lp(a) is an independent risk factor for premature atherosclerosis. Lp(a) is synthesized in the liver.

Apolipoprotein AI or apoAI is the major component of HDL, which is an independent risk factor of atherosclerosis. apoAI is thought to promote the efflux of cholesterol from peripheral tissues and higher levels of HDL (or apoAI) result in decreased risk of atherosclerosis.

Hyperthyroidism worsens glycemic control in type 2 diabetics. TH therapy is reported to stimulate hepatic gluconeogenesis. Enzymes specific to gluconeogenesis and important for controlling the pathway and its physiological role of producing glucose are known to be influenced by TH therapy. Phosphoenolpyruvate carboxykinase (PEPCK) is upregulated by TH (Park et al, *J. Biol. Chem.* 274:211 (1999)) whereas others have found that glucose 6-phosphatase is upregulated (Feng et al., *Mol. Endocrinol.* 14:947 (2000)). TH therapy is also associated with reduced glycogen levels.

TH therapy results in improved non insulin stimulated and insulin stimulated glucose utilization and decreased insulin resistance in the muscle of ob/ob mice. (Oh et al., *J. Nutr.* 125:125 (1995)).

There is still a need for novel thyromimetics that can be used to modulate cholesterol levels, to treat obesity, and other metabolic disorders especially with reduced undesirable effects.

SUMMARY OF THE INVENTION

Fatty acids consist of an alkyl chain with a terminal carboxyl group. Unsaturated fatty acids occur commonly in humans and contain up to six double bonds per chain. Most fatty acids in humans have a length of C16, C18 or C20. Fatty acids are stored primarily as esters of glycerol. Triglycerides (TGs) are triacylglycerols, i.e., where all three hydroxyls are esterified with a fatty acid. In addition to TGs, glycerol esterified with only one fatty acid (monoacylglycerol) or two fatty acids (diacylglycerols, DAGs) are found. The distribution of esterification sites on glycerol is influenced by many factors and may have important biological function. Fatty acids are also used in the synthesis of other molecules, e.g., esters of cholesterol which can be degraded back to the parent molecule by esterases, and various phospholipids, including lysophosphatidic acid and phosphatidic acid, which consist of phosphorylated acylated glycerols. Many of these products have biological activity suggesting that modulation of their levels may result in beneficial or detrimental effects.

Fatty acids are taken up by the liver from the circulation. Fatty acids derived from the diet enter the circulation after ingestion and passage through the lymphatic system. Once in the circulation the fatty acids are taken up by tissues and used as a source of energy either immediately or in the future. If not used immediately, the fatty acids are usually converted to TGs. Subsequently, TGs are hydrolyzed to generate the free fatty acids and glycerol. Both are often transported from cells such as adipocytes, which store large quantities of TGs, to the liver. Lipolysis of TGs occurs through the action of lipases. For example, lipoprotein lipase hydrolyzes triacylglycerols in plasma lipoproteins. Another example is hormone sensitive lipase (HSL), which hydrolyzes TGs stored in the adipocyte. HSL is very sensitive to certain hormones, such as insulin which inactivates the enzyme, glucagon, epinephrine, and ACTH.

Fatty acids in the liver are also supplied by de novo synthesis from small molecule intermediates derived from metabolic breakdown of sugars, amino acids and other fatty acids. Accordingly, excess dietary protein and carbohydrate are readily converted to fatty acids and stored as TGs. A key enzyme in fatty acid synthesis is acetyl-CoA carboxylase, which controls the overall synthesis of fatty acid by controlling the synthesis of malonyl CoA from acetyl CoA. Fatty acid synthase then catalyzes the addition of two carbon units to the activated carboxyl end of a growing chain. The result is the fatty acid palmitate. Palmitate is the precursor fatty acid for nearly all other fatty acids. Enzymes are available that lead to unsaturated fatty acids or elongated fatty acids.

Fatty acids are used for energy production primarily through oxidation in mitochondria. The first step entails conversion of the fatty acid to a fatty acyl CoA by acyl-CoA synthetase. Since the oxidizing enzymes are located inside the inner mitochondrial membrane and the membrane is impermeable to CoA and its derivative; carnitine is used along with carnitine palmitoyltransferase (CPT) to transfer acyl-CoAs into the mitochondria. This step is rate-limiting in fatty acid oxidation. Two carbon units are removed from the carboxy terminus using four enzyme-catalyzed reactions. The product is acyl-CoA which can then be used in the synthesis of fatty acids (futile cycling), ketone bodies, or enters the TCA cycle where it is converted to $CO_2$ and ATP. Some of the energy generated by fatty acid oxidation is stored as ATP, some used in the biosynthesis of other molecules, while some is lost in the form of heat. Agents that increase heat production can enable net energy expenditure.

Fat accumulation occurs when there is net energy intake relative to energy expenditure. Energy is often stored as fat, more specifically TGs. Ideally, fat is stored in the adipocyte which is its natural storage site. When in excess, however, fat is stored in other tissues, some of which can be negatively effected. Fat accumulation in the liver will depend on a multitude of factors, including fatty acid delivery from the circulation, lipogenesis (i.e., de novo lipid synthesis) in the liver, and free fatty acid oxidation.

TH is well known to augment catecholamine stimulation of lipolysis in adipocytes. Adrenergic responsiveness is influenced by the thyroid status with clear differences observed in the hypothyroid relative to hyperthyroid states (Bilezikian et al., *Endocr. Rev.* 4:378-388 (1983); Fisher et al., *Biochemistry* 6:637-647 (1967); Debons et al., *J. Lipid Res.* 2:86 (1961); Malbon et al., *TIPS* 9:33-36 (1988)). In the postabsorptive state, plasma fatty acids are derived mostly from lipolysis of TGs in adipose tissue. Hyperthyroidism is known to enhance this process. T4 is reported to cause a diminution of lipoprotein lipase activity in the mammary gland and adipose tissue (Del Prado et al., *Biochem. J.* 301:495-501 (1994)). A decrease in lipoprotein lipase activity in the peripheral tissues was postulated to contribute to the higher TGs found in the serum of chronic hyperthyroid rats.

Total splanchnic uptake of fatty acids is increased in hyperthyroid patients. This is thought to arise from fatty acid blood concentration as well as augmented splanchnic blood flow. The latter would be expected as a means to compensate for the increased metabolic demand of the liver in the hyperthyroid state (Heimberg et al., *Endocrine Rev.* 6:590 (1985)).

TH is known to increase the expression of genes encoding for lipogenic enzymes and proteins closely related to lipogenesis such as hepatic S14. S14 protein is known to regulate the transcription of lipogenic genes. Hepatic fatty acid synthase (FAS) is another gene important for lipogenesis. TREs are associated with the FAS gene and TH is known to positively regulate transcription of FAS. Acetyl CoA carboxylase (ACC) is also increased with TH. Fatty acid production is increased in rodents with elevated TH levels (Roncari et al., *J. Biol. Chem.* 250:4134-4138 (1975)).

TH increases fatty acid oxidation. Hyperthyroidism is associated with an increase in basal metabolic rate and correspondingly higher energy demand. Hypothyroidism is associated with decreased metabolic rate. In the hyperthyroid state, the major fuel is fatty acids since the hyperthyroid mammal is thought to have limited capacity for conservation of carbohydrate as glycogen. Increased oxidation of fatty acids leads to increased production of the products of fatty acid oxidation, i.e., $CO_2$ and ketone bodies in the hyperthyroid state. The rate-limiting enzyme in fatty acid oxidation is CPT-1. CPT-1 expression appears to be controlled by TH based on the discovery of a TRE in the CPT-1 promoter region (Barrero et al., *Biochem. Biophys. Res. Comm.*, 279:81-88 (2000)). Moreover, hypothyroidism decreases CPT-1 expression and hyperthyroidism results in an increase.

TH is thought to increase mitochondrial enzyme activity. This could occur by increased expression in certain genes in the mitochondria or by increased mitochondria. Increases in mitochondria and/or mitochondrial enzymes associated with thermogenesis such as glycerol-3-phosphate dehydrogenase, cytochrome C oxidase, ATPases and possibly uncoupling proteins (e.g., UCP2) could result in increased fatty acid oxidation and net energy expenditure. While the liver is not the organ most commonly cited in the literature for the effect of TH on energy expenditure and thermogenesis (usually fat and muscle), it is a highly metabolic organ with a capacity for oxidizing free fatty acids. Furthermore, the liver is relatively inefficient in its ability to capture the energy produced from FFA oxidation in the form of ATP. Consequently, the liver is a relatively thermogenic organ. THs are known to increase hepatic CPT-1 and mitochondrial GPDH activities.

TH results in increased hepatic lipogenesis and increased fatty acid delivery to the liver from the periphery as a result of enhanced lipolysis. Simultaneously, TH increases fatty acid oxidation. Fat accumulation in the liver would likely depend on the contribution of each component. It is known that thyrotoxic patients are characterized by some degree of fatty infiltration into liver and by cytoplasmic vacuolization, nuclear irregularity, and hyperchromatism in hepatocytes (Donner et al., Arch. Intern. Med., 120:25-32 (1967); Klion et al., Am. J. Med. 50:317-324 (1971)). Liver fat accumulation can be associated with liver toxicity which could arise from direct or indirect effects of TH, e.g., accumulation of fat is associated with liver toxicity.

Severe hyperthyroidism, thyrotoxicosis, is associated with a variety of abnormalities of liver function which are thought to be related to mitochondrial dysfunction. Extensive DNA fragmentation and increased caspase-3 activity and caspase-9 activity were observed along with a decrease in the number or cristae (Upadhyay et al., Hepatology, 39:1120-1130 (2004)). In some cases liver function is reported to be compromised 45% to 90%. Ultrastructural and functional changes in the mitochondria, such as enlargement, mass increase, and formation of megamitochondria have been reported in the liver of hyperthyroid patients.

TH is known to induce hyperphagia which results in an increased consumption of calories. The increased consumption of both fats as well as carbohydrates and proteins results in conversion to fatty acids and in increased fat stores if not compensated by an equal or greater increase in energy expenditure.

TH is associated with a reduction in total fat pool and weight loss. Reduction in the pool is thought to be due to an enhanced activity of the hormone sensitive lipase in adipose tissue. While the pool may decrease and fat content in the periphery may decrease, FFAs produced from enhanced lipolysis could result in the accumulation of fat in the liver. In one study, thyroxine treatment is reported to decrease liver TG 5-fold after one week but rebound 4-fold by the end of five weeks of treatment (Vans et al., Horm. Metab. Res. 31:514-518 (1999)).

Nonalcoholic fatty liver disease (NAFLD) is a clinico-pathological term that encompasses a disease spectrum ranging from simple TG accumulation in hepatocytes to hepatic steatosis with inflammation (nonalcoholic steatohepatitis, NASH) to fibrosis and cirrhosis. NAFLD is the most frequent cause of liver enzyme elevations. The prevalence of NAFLD in the population is estimated to be 14-28%. Hepatic insulin resistance is associated with hepatic steatosis.

Products from TG metabolism, e.g., DAGs and long chain AcylCoAs (LCACoA) are thought to negatively effect insulin response through effects on the insulin receptor phosphorylation. Long chain CoAs and DAG increase Ser/Thr phosphorylation of insulin receptor substrates (IRS1-3) and thereby disrupt Tyr phosphorylation of these substrates by the insulin receptor. The resulting hepatic insulin resistance contributes to the development of compensatory hyperinsulinemia which further drives fat accumulation via SREBP1. Reduction in TGs may reduce the levels of DAGs and LCACoAs and therefore improve the response to insulin. Improved response to insulin may also diminish further fat accumulation.

Oxidative stress results from an imbalance between pro-oxidant and antioxidant chemical species that leads to oxidative damage. Oxidation of fatty acids is an important source of reactive oxygen species (ROS). Some of the consequences of increased ROS is depleted ATP, destruction of membranes via lipid peroxidation, and release of proinflammatory cytokines. An increase in liver triglycerides may lead to increased oxidative, stress in the hepatocytes, and the progression of hepatic steatosis to NASH. Human livers with NASH have increased lipid peroxidation and impaired mitochondrial function. This can result in cell death, hepatic stellate cell activation and fibrosis and inflammation. All of these activities may cause patients with NAFLD to be at risk for NASH, a more serious disease with higher risk of liver cirrhosis and hepatocellular carcinoma. TH is known to increase fatty acid oxidation and mitochondrial enzyme activity which could result in increased ROS and liver damage. Prodrugs that are activated by P450s may also cause an increase in ROS.

Thus, it was unknown whether delivery of a thyroid mimetic would result in liver damage and an increase in fat content. It was also unknown whether a non-liver toxic thyromimetic could reduce liver fat or whether it could reduce liver fat in a sustained manner or whether it could reduce liver fat without adverse effects on the cardiovascular system, adverse effects on the thyroid axis, mitochondrial function, reductions in whole body fat, reductions in serum free fatty acids or without either muscle wasting or bone loss. Prior to the discoveries of the present invention, the effects of thyroid hormone agonists on fat homeostasis have been focused on modulation of whole body weight. There have been no studies reporting the effects of thyroid hormone on liver fat content, but many studies have reported decreases in body weight following treatment with either a natural or synthetic thyroid hormone agonist. Lastly, it was unclear whether reduction in fat would occur and ultimately be beneficial toward preventing or treating liver diseases associated with NAFLD, including liver cirrhosis, liver cancer, and diseases associated with hepatic insulin resistance, such as diabetes.

Prior to the discoveries of the present invention it was unexpected that a synthetic thyroid hormone would produce effects in the liver, e.g., decreases in hepatic fat content measured either chemically or histologically, that are not produced by the naturally occurring ligand, T3.

1. T3 has not been reported to decrease liver fat in a sustained manner (as measured by chemical or histologic means) and without negative effects on the heart or thyroid axis; although T3 is known to increase metabolic rate and decrease body weight.
2. synthetic thyroid agonists have not been reported to decrease hepatic steatosis, although some thyromimetics have been shown to increase metabolic rate and decrease body weight.

Thus, it was unexpected when the present Inventors discovered that the synthetic thyroid hormone agonists TRIAC, Compound 17, Compound 7, and Compound 6 all demonstrated a significant decrease in hepatic triglyceride content following systemic administration of the compounds, while T3 did not demonstrate a decrease in hepatic triglyceride content. TRIAC, Compound 17 and T3, however, decreased body weight, while Compound 7 and Compound 6 did not decrease body weight.

Further, surprisingly the present Inventors discovered that oral administration of Compound cis-13-1 decreased hepatic steatosis measured both chemically and histologically in ob/ob mice while n had no significant effect on hepatic steatosis in ob/ob mice. Compound cis-13-1 had no effect on epididymal fat pad weight, while T3 significantly decreased epididymal fat pad weight, consistent with induction of lipolysis following T3 administration.

Further, surprisingly the present Inventors discovered that oral administration of Compounds cis-13-1 and 18 decreased hepatic steatosis measured histologically in ZDF rats.

Further, surprisingly the present Inventors discovered that oral administration of Compound cis-13-1 decreased hepatic steatosis measured histologically DIO mice.

Further, surprisingly liver triglyceride levels were reduced after treatment with thyromimetics of the present invention for 10 weeks in the DIO mouse, for 9 weeks in the ob/ob mouse, and after one week in the normal Sprague-Dawley rat. Administration of thyromimetics led to improved liver histology in the ob/ob mouse, the DIO mouse and the ZDF rat and led to improved mitochondrial morphology after 10 weeks of treatment in the DIO mouse. In some models, reduced liver fat led to reduced liver enzymes (e.g., ob/ob mice treated for 9 weeks).

Therefore, surprisingly the present Inventors discovered that synthetic thyroid agonists, such as TRIAC and Compounds 7, 18, 6, 17, and cis-13-1 decreased hepatic steatosis, measured either histologically or chemically, while T3 did not decrease hepatic steatosis, measured either histologically or chemically. However, in the models tested, T3 and the reported synthetic thyroid agonists Compound 18, Compound 17 and TRIAC did decrease body weight and/or peripheral fat content as previously reported. Since the natural ligand, T3, did not produce a decrease in hepatic steatosis, measured either histologically or chemically, but retained the extrahepatic effects of weight loss or loss of peripheral fat mass, it is completely unexpected that synthetic thyroid agonists would decrease hepatic fat content. The loss of hepatic fat was observed with either previously investigated synthetic thyroid agonists, or novel phosphorous containing thyroid agonists.

The present invention relates to the use of thyromimetic compounds in methods of decreasing fat content in the liver of an animal comprising administering to said animal a therapeutically effective amount of a thyromimetic compound, a pharmaceutically acceptable salt thereof, or prodrugs thereof or pharmaceutically acceptable salts of said prodrugs. The invention further relates to methods of preventing, treating, or ameliorating fatty liver disease in an animal comprising administering to said animal a therapeutically effective amount of a thyromimetic compound, a pharmaceutically acceptable salt thereof, or prodrugs thereof or pharmaceutically acceptable salts of said prodrugs. The thyromimetic compounds bind to thyroid receptors in the liver. Activation of these receptors results in modulation of gene expression of genes regulated by thyroid hormones. In one aspect, the thyromimetic compounds used in the method of the invention are useful for improving efficacy, improving the therapeutic index, e.g., decreasing non-liver related toxicities and side effects, or for improving liver selectivity, i.e., increasing distribution of an active drug to the liver relative to extrahepatic tissues and more specifically increasing distribution of an active drug to the nucleus of liver cells relative to the nucleus of extrahepatic tissue cells (including heart, kidney and pituitary). Prodrugs of the compounds are useful for increasing oral bioavailability and sustained delivery of the thyromimetics.

In another aspect, the present invention relates to the use of compounds of Formula I-IX. The compounds of Formula I-IX may be an active form or a prodrug thereof. Further included in the present invention is the use of pharmaceutically acceptable salts, including but not limited to acid addition salts and physiological salts, and co-crystals of said compounds of Formula I-IX. Further included in the present invention is the use of prodrugs of compounds of Formula I-IX that are active forms, and pharmaceutically acceptable salts, including but not limited to acid addition salts and physiological salts, and co-crystals thereof.

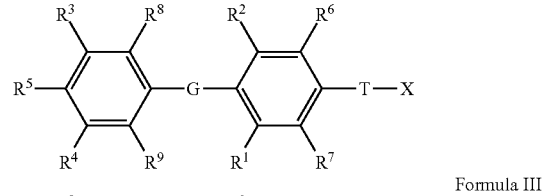

Formula I

Formula II

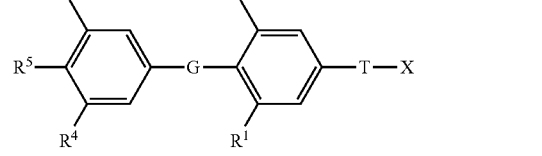

Formula III

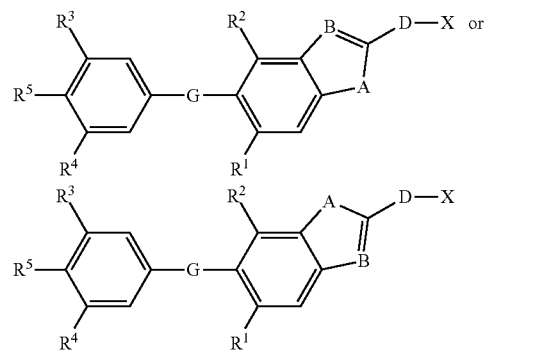

Formula IV

Formula V

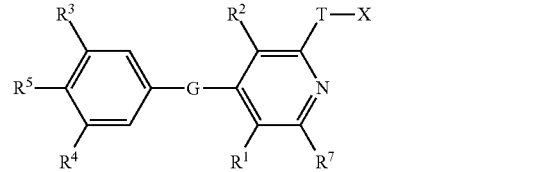

Formula VI

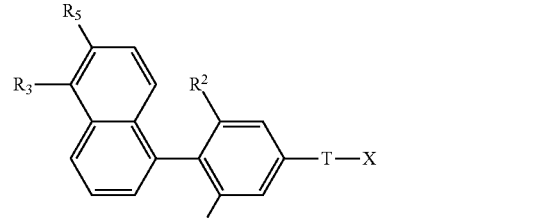

Formula VII

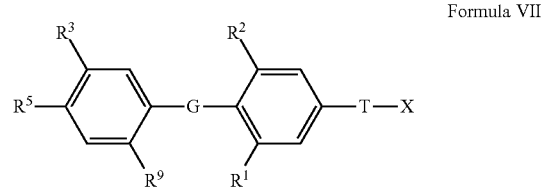

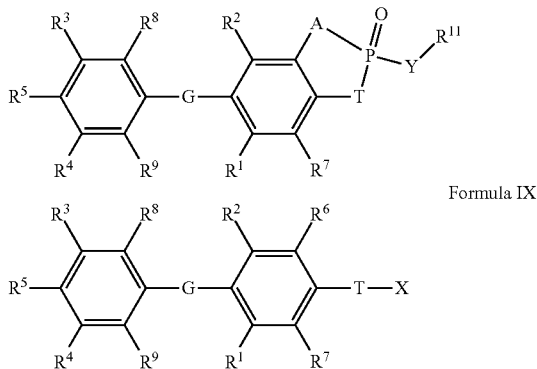

Some of the compounds of Formula I-IX have asymmetric centers. Thus, included in the present invention is the use of racemic mixtures, enantiomerically enriched mixtures, diastereomeric mixtures, including diastereomeric enriched mixtures, and individual stereoisomers of the compounds of Formula I-IX and prodrugs thereof.

DEFINITIONS

Figure 1:
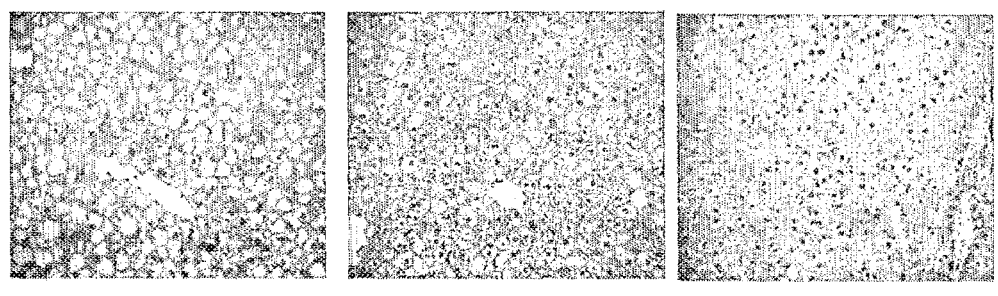
FIG. 1 shows hematoxylin and eosin (H & E) stained sections of liver from an ob/ob mouse rat treated with vehicle, T3 (100 nmole/kg/d), or Compound cis-13-1 (30 mg/kg/d).
Figure 2A:
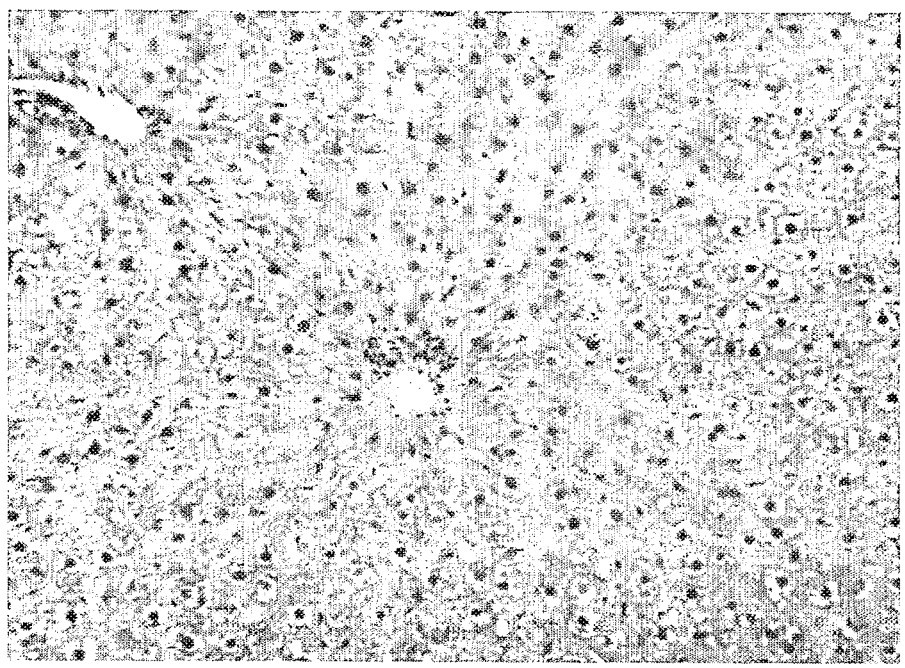
FIG. 2A shows an H & E stained section of liver from a ZDF rat treated with vehicle.
Figure 2B:
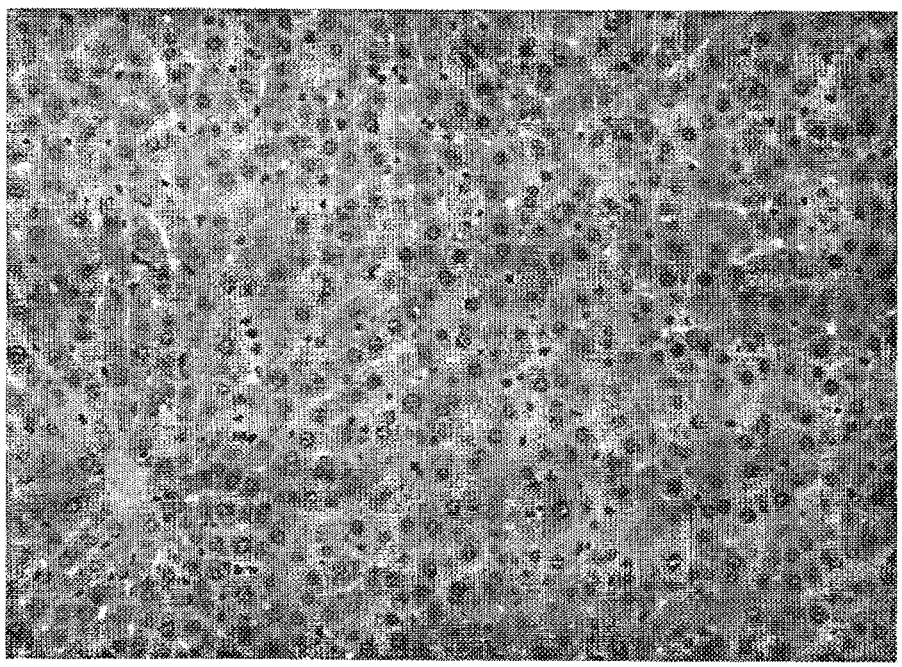
FIG. 2B shows an H & E stained section of liver from a ZDF rat treated with Compound cis-13-1 (0.2 mg/kg/d).
Figure 2C:
FIG. 2C shows an H & E stained section of liver from a ZDF rat treated with Compound cis-13-1 (1 mg/kg/d).
Figure 2D:
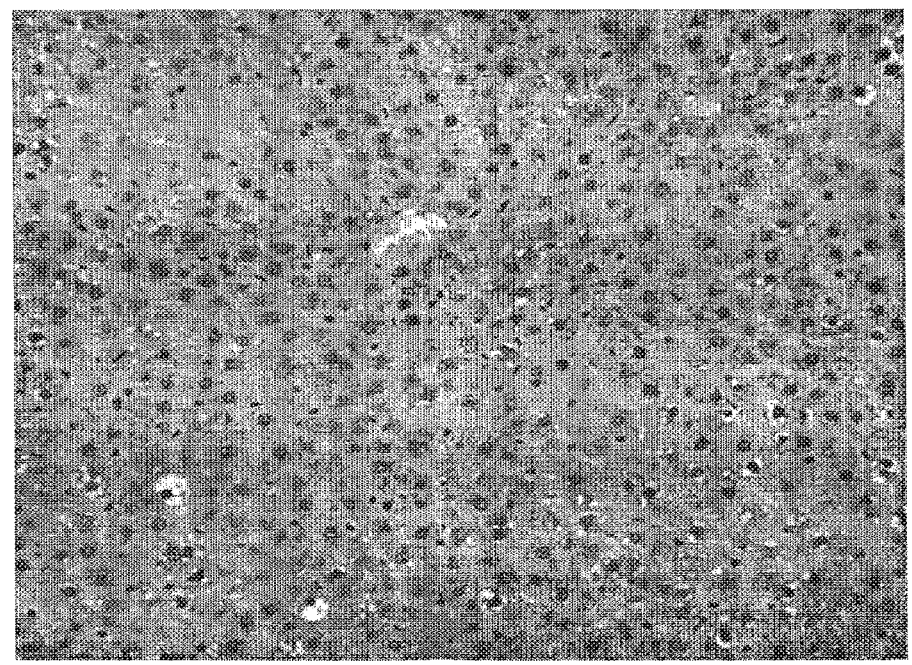
FIG. 2D shows an H & E stained section of liver from a ZDF rat treated with Compound cis-13-1 (2.5 mg/kg/d).

As used herein, the following terms are defined with the following meanings, unless explicitly stated otherwise.

T groups that have more than one atom are read from left to right wherein the left atom of the T group is connected to the phenyl group bearing the $R^1$ and $R^2$ groups, and the right atom of the T group is linked to the carbon, phosphorus, or other atom in X or E. For example, when T is —O—CH$_2$— or —N(H)C(O)— it means -phenyl-O—CH$_2$—X and -phenyl-N(H)C(O)—X.

The term "alkyl" refers to a straight or branched or cyclic chain hydrocarbon radical with only single carbon-carbon bonds. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. Alkyl groups are $C_1$-$C_{12}$.

The term "aryl" refers to aromatic groups which have 5-14 ring atoms and at least one ring having a conjugated pi electron system and includes carbocyclic aryl, heterocyclic aryl and biaryl groups, all of which may be optionally substituted.

Carbocyclic aryl groups are groups which have 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups which have 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl.

The term "optionally substituted" or "substituted" includes groups substituted by one to six substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower arylalkyloxyalkyl.

"Substituted aryl" and "substituted heteroaryl" refers to aryl and heteroaryl groups substituted with 1-3 substituents. These substituents are selected from the group consisting of lower alkyl, lower alkoxy, lower perhaloalkyl, halo, hydroxy, and amino.

The term "-aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "alkylaryl-" refers to an aryl group substituted with an alkyl group. "Lower alkylaryl-" refers to such groups where alkyl is lower alkyl.

The term "lower" referred to herein in connection with organic radicals or compounds respectively refers to 6 carbon atoms or less. Such groups may be straight chain, branched, or cyclic.

The term "higher" referred to herein in connection with organic radicals or compounds respectively refers to 7 or more carbon atoms. Such groups may be straight chain, branched, or cyclic.

The term "cyclic alkyl" or "cycloalkyl" refers to alkyl groups that are cyclic of 3 to 10 carbon atoms, and in one aspect are 3 to 6 carbon atoms Suitable cyclic groups include norbornyl and cyclopropyl. Such groups may be substituted.

The term "heterocyclic," "heterocyclic alkyl" or "heterocycloalkyl" refer to cyclic groups of 3 to 10 atoms, and in one aspect are 3 to 6 atoms, containing at least one heteroatom, in a further aspect are 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The terms "arylamino" (a), and "aralkylamino" (b), respectively, refer to the group —NRR' wherein respectively, (a) R is aryl and R' is hydrogen, alkyl, aralkyl, heterocycloalkyl, or aryl, and (b) R is aralkyl and R' is hydrogen, aralkyl, aryl, alkyl or heterocycloalkyl.

The term "acyl" refers to —C(O)R where R is alkyl, heterocycloalkyl, or aryl.

The term "carboxy esters" refers to —C(O)OR where R is alkyl, aryl, aralkyl, cyclic alkyl, or heterocycloalkyl, all optionally substituted.

The term "carboxyl" refers to —C(O)OH.

The term "oxo" refers to =O in an alkyl or heterocycloalkyl group.

The term "amino" refers to —NRR' where R and R' are independently selected from hydrogen, alkyl, aryl, aralkyl and heterocycloalkyl, all except H are optionally substituted; and R and R' can form a cyclic ring system.

The term "-carboxylamido" refers to —CONR$_2$ where each R is independently hydrogen or alkyl.

The term "-sulphonylamido" or "-sulfonylamido" refers to —S(=O)$_2$NR$_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "sulphonyl" or "sulfonyl" refers to —SO$_2$R, where R is H, alkyl, aryl, aralkyl, or heterocycloalkyl.

The term "sulphonate" or "sulfonate" refers to —SO$_2$OR, where R is —H, alkyl, aryl, aralkyl, or heterocycloalkyl.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl. "1-Alkenyl" refers to alkenyl groups where the double bond is between the first and second carbon atom. If the 1-alkenyl group is attached to another group, e.g., it is a W substituent attached to the cyclic phosphonate, it is attached at the first carbon.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-Alkynyl" refers to alkynyl groups where the triple bond is between the first and second carbon atom. If the 1-alkynyl group is attached to another group, e.g., it is a W substituent attached to the cyclic phosphonate, it is attached at the first carbon.

The term "alkylene" refers to a divalent straight chain, branched chain or cyclic saturated aliphatic group. In one aspect the alkylene group contains up to and including 10 atoms. In another aspect the alkylene group contains up to and including 6 atoms. In a further aspect the alkylene group contains up to and including 4 atoms. The alkylene group can be either straight, branched or cyclic.

The term "acyloxy" refers to the ester group —O—C(O)R, where R is H, alkyl, alkenyl, alkynyl, aryl, aralkyl, or heterocycloalkyl.

The term "aminoalkyl-" refers to the group NR$_2$-alk- wherein "alk" is an alkylene group and R is selected from —H, alkyl, aryl, aralkyl, and heterocycloalkyl.

The term "alkylaminoalkyl-" refers to the group alkyl-NR-alk- wherein each "alk" is an independently selected alkylene, and R is H or lower alkyl. "Lower alkylaminoalkyl-" refers to groups where the alkyl and the alkylene group is lower alkyl and alkylene, respectively.

The term "arylaminoalkyl-" refers to the group aryl-NR-alk- wherein "alk" is an alkylene group and R is —H, alkyl, aryl, aralkyl, or heterocycloalkyl. In "lower arylaminoalkyl-," the alkylene group is lower alkylene.

The term "alkylaminoaryl-" refers to the group alkyl-NR-aryl- wherein "aryl" is a divalent group and R is —H, alkyl, aralkyl, or heterocycloalkyl. In "lower alkylaminoaryl-," the alkyl group is lower alkyl.

The term "alkoxyaryl-" refers to an aryl group substituted with an alkyloxy group. In "lower alkyloxyaryl-," the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-," each alkyl and alkylene is lower alkyl and alkylene, respectively.

The term "alkylthio-" refers to the group alkyl-S—.

The term "alkylthioalkyl-" refers to the group alkyl-S-alk- wherein "alk" is an alkylene group. In "lower alkylthioalkyl-," each alkyl and alkylene is lower alkyl and alkylene, respectively.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "amido" refers to the NR$_2$ group next to an acyl or sulfonyl group as in NR$_2$—C(O)—, RC(O)—NR$^1$—, NR$_2$—S(=O)$_2$— and RS(=O)$_2$—NR$^1$—, where R and R$^1$ include —H, alkyl, aryl, aralkyl, and heterocycloalkyl.

The term "carboxamido" refer to NR$_2$—C(O)— and RC(O)—NR$^1$—, where R and R$^1$ include —H, alkyl, aryl, aralkyl, and heterocycloalkyl. The term does not include urea, —NR—C(O)—NR—.

The terms "sulphonamido" or "sulfonamido" refer to NR$_2$—S(=O)$_2$— and RS(=O)$_2$—NR$^1$—, where R and R$^1$ include —H, alkyl, aryl, aralkyl, and heterocycloalkyl. The term does not include sulfonylurea, —NR—S(=O)$_2$—NR—.

The term "carboxamidoalkylaryl" and "carboxamidoaryl" refers to an aryl-alk-NR$^1$—C(O), and ar-NR$^1$—C(O)-alk-, respectively where. "ar" is aryl, "alk" is alkylene, R$^1$ and R include H, alkyl, aryl, aralkyl, and heterocycloalkyl.

The term "sulfonamidoalkylaryl" and "sulfonamidoaryl" refers to an aryl-alk-NR$^1$—S(=O)$_2$—, and ar-NR$^1$—S(=O)$_2$—, respectively where "ar" is aryl, "alk" is alkylene, R$^1$ and R include —H, alkyl, aryl, aralkyl, and heterocycloalkyl.

The term "hydroxyalkyl" refers to an alkyl group substituted with one —OH.

The term "haloalkyl" refers to an alkyl group substituted with halo.

The term "cyano" refers to —C≡N.

The term "nitro" refers to —NO$_2$.

The term "acylalkyl" refers to an alkyl-C(O)-alk-, where "alk" is alkylene.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkylene group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "co-crystal" as used herein means a crystalline material comprised of two or more unique solids at room temperature, each containing distinctive physical characteristics, such as structure, melting point and heats of fusion. The co-crystals of the present invention comprise a co-crystal former H-bonded to a compound of the present invention. The co-crystal former may be H-bonded directly to the compound of the present invention or may be H-bonded to an additional molecule which is bound to the compound of the present invention. The additional molecule may be H-bonded to the compound of the present invention or bound ionically to the compound of the present invention. The additional molecule could also be a second API. Solvates of compounds of the present invention that do not further comprise a co-crystal former are not "co-crystals" according to the present invention. The co-crystals may however, include one or more solvate molecules in the crystalline lattice. That is, solvates of co-crystals, or a co-crystal further comprising a solvent or compound that is a liquid at room temperature, is included in the present invention as a co-crystal.

The co-crystals may also be a co-crystal between a co-crystal former and a salt of a compound of the present invention, but the compound of the present invention and the co-crystal former are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other.

Crystalline material comprised of solid compound of the present invention and one or more liquid solvents (at room temperature) are included in the present invention as "solvates." A "hydrate" is where the solvent is water. Other forms of the present invention include, but are not limited to, anhydrous forms and de-solvated solvates.

The ratio of the compound of the present invention to co-crystal former or solvent may be specified as stoichiometric or non-stoichiometric. 1:1, 1.5:1, 1:1.5, 2:1, 1:2, and 1:3 ratios of API:co-crystal former/solvent are examples of stoichiometric ratios.

The term "binding" means the specific association of the compound of interest to the thyroid hormone receptor. One method of measuring binding in this invention is the ability of the compound to inhibit the association of $^{125}$I-T3 with a mixture of thyroid hormone receptors using nuclear extracts or purified or partially purified thyroid hormone receptor (for example, alpha or beta) in a heterologous assay.

The term "energy expenditure" means basal or resting metabolic rate as defined by Schoeller et al., *J Appl Physiol.* 53(4):955-9 (1982). Increases in the resting metabolic rate can also be measured using increases in O$_2$ consumption and/or CO$_2$ efflux and/or increases in organ or body temperature.

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis [3-hydroxy-2-naphthalenecarboxylic acid], phosphoric acid, polygalacturonic acid, stearic acid, succinic acid, sulfuric acid, sulfosalicylic acid, tannic acid, tartaric acid, terephthalic acid, and p-toluenesulfonic acid.

The term "patient" means an animal.

The term "animal" includes birds and mammals. In one embodiment a mammal includes a dog, cat, cow, horse, goat, sheep, pig or human. In one embodiment the animal is a human. In another embodiment the animal is a male. In another embodiment the animal is a female.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, R$_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of the present invention fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

Prodrugs of carboxylic acid-containing thyromimetics are convertible by solvolysis or under physiological conditions to the free carboxylic acids. Examples of prodrugs include carboxylic acid esters, and are preferably lower alkyl esters, cycloalkyl esters, lower alkenyl esters, benzyl esters, aryl esters, mono- or di-substituted lower alkyl esters, e.g., the ω-(amino, mono- or di-lower alkylamino, carboxy, lower alkoxycarbonyl)-lower alkyl esters, and the α-(lower alkanoyloxy, lower alkoxycarbonyl or di-lower alkylaminocarbonyl)-lower alkyl esters, such as the pivaloyloxymethyl ester.

Prodrugs of phosphorus-containing thyromimetics breakdown chemically or enzymatically to a phosphonic acid or phosphinic acid group or a monoester thereof in vivo. As employed herein the term includes, but is not limited to, the following groups and combinations of these groups:

Acyloxyalkyl esters which are well described in the literature (Farquhar et al., *J. Pharm. Sci.* 72:324-325 (1983)).

Other acyloxyalkyl esters are possible in which a cyclic alkyl ring is formed. These esters have been shown to generate phosphorus-containing nucleotides inside cells through a postulated sequence of reactions beginning with deesterification and followed by a series of elimination reactions (e.g., Freed et al., *Biochem. Pharm,* 38:3193-3198 (1989)).

Another class of these double esters known as alkyloxycarbonyloxymethyl esters, as shown in formula A, where R is alkoxy, aryloxy, alkylthio, arylthio, alkylamino, and arylamino; R', and R" are independently —H, alkyl, aryl, alkylaryl, and heterocycloalkyl have been studied in the area of β-lactam antibiotics (Nishimura et al., *J. Antibiotics* 40(1):81-90 (1987); for a review see Ferres, H., *Drugs of Today,* 19:499 (1983)). More recently Cathy, M. S. et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

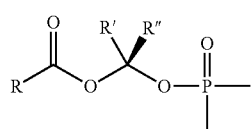

Formula A wherein R, R', and R" are independently H, alkyl, aryl, alkylaryl, and alicyclic (see WO 90/08155; WO 90/10636).

Other acyloxyalkyl esters are possible in which a cyclic alkyl ring is formed such as shown in formula B. These esters have been shown to generate phosphorus-containing nucleotides inside cells through a postulated sequence of reactions beginning with deesterification and followed by a series of elimination reactions (e.g., Freed et al., *Biochem. Pharm.* 38:3193-3198 (1989)).

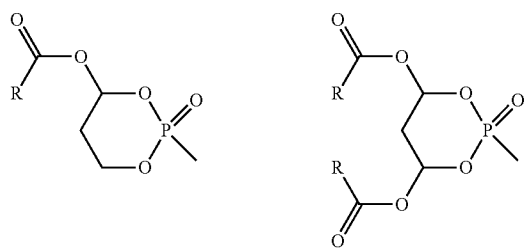

Formula B wherein R is —H, alkyl, aryl, alkylaryl, alkoxy, aryloxy, alkylthio, arylthio, alkylamino, arylamino, or cycloalkyl.

Aryl esters have also been used as phosphonate prodrugs (e.g., DeLambert et al., *J. Med. Chem.* 37(7):498-511 (1994); Serafinowska et al., *J. Med. Chem.* 38(8):1372-9 (1995). Phenyl as well as mono and poly-substituted phenyl proesters have generated the parent phosphonic acid in studies conducted in animals and in man (Formula C). Another approach has been described where Y is a carboxylic ester ortho to the phosphate (Khamnei et al., *J. Med. Chem.* 39:4109-15 (1996)).

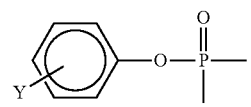

Formula C wherein Y is —H, alkyl, aryl, alkylaryl, alkoxy, acyloxy, halogen, amino, alkoxycarbonyl, hydroxy, cyano, and heterocycloalkyl.

Benzyl esters have also been reported to generate the parent phosphonic acid. In some cases, using substituents at the para-position can accelerate the hydrolysis. Benzyl analogs with 4-acyloxy or 4-alkyloxy group [Formula D, X=—H, OR or O(CO)R or O(CO)OR] can generate the 4-hydroxy compound more readily through the action of enzymes, e.g., oxidases, esterases, etc. Examples of this class of prodrugs are described in Mitchell et al., *J. Chem. Soc. Perkin Trans.* 12345(1992); WO 91/19721.

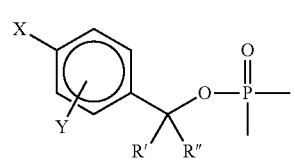

Formula D wherein X and Y are independently —H, alkyl, aryl, alkylaryl, alkoxy, acyloxy, hydroxy, cyano, nitro, perhaloalkyl, halo, or alkyloxycarbonyl; and R' and R" are independently —H, alkyl, aryl, alkylaryl, halogen, and cyclic alkyl.

Thio-containing phosphonate proesters may also be useful in the delivery of drugs to hepatocytes. These proesters contain a protected thioethyl moiety as shown in formula E. One or more of the oxygens of the phosphonate can be esterified. Since the mechanism that results in deesterification requires the generation of a free thiolate, a variety of thiol protecting groups are possible. For example, the disulfide is reduced by a reductase-mediated process (Puech et al., *Antiviral Res.* 22:155-174 (1993)). Thioesters will also generate free thiolates after esterase-mediated hydrolysis Benzaria, et al., *J. Med. Chem.* 39(25):4958-65 (1996)). Cyclic analogs are also possible and were shown to liberate phosphonate in isolated rat hepatocytes. The cyclic disulfide shown below has not been previously described and is novel.

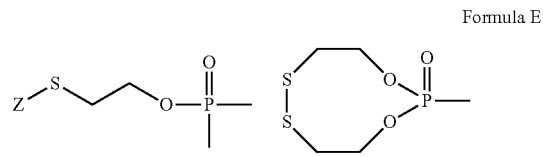

Formula E wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al., *J. Med. Chem.* 38(8):1372-9 (1995); Starrett et al., *J. Med. Chem.* 37:1857 (1994); Martin et al. *J. Pharm. Sci.* 76:180 (1987); Alexander et al., *Collect. Czech. Chem. Commun.* 59:1853 (1994); and EP 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

E-1

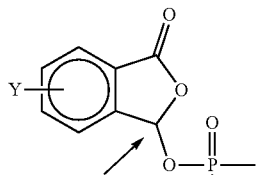

3-phthalidyl

E-2

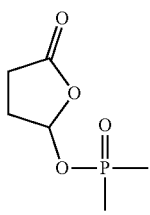

2-oxotetrahydrofuran-5-yl

E-3

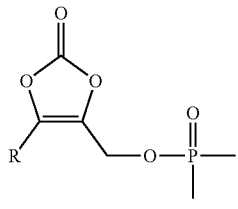

2-oxo-4,5-
didehydro-1,3-
dioxolanemethyl wherein R is —H, alkyl, cycloalkyl, or heterocycloalkyl; and
wherein Y is —H, alkyl, aryl, alkylaryl, cyano, alkoxy, acyloxy, halogen, amino, heterocycloalkyl, and alkoxycarbonyl.

The prodrugs of Formula E-3 are an example of "optionally substituted heterocycloalkyl where the cyclic moiety contains a carbonate or thiocarbonate."

Propyl phosphonate proesters can also be used to deliver drugs into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

Formula F

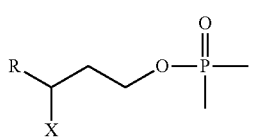

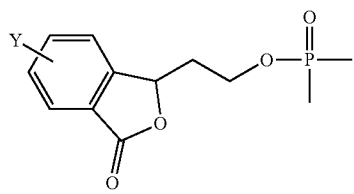

wherein R is alkyl, aryl, heteroaryl;

X is hydrogen, alkylcarbonyloxy, alkyloxycarbonyloxy; and

Y is alkyl, aryl, heteroaryl, alkoxy, alkylamino, alkylthio, halogen, hydrogen, hydroxy, acyloxy, amino.

Phosphoramidate derivatives have been explored as phosphate prodrugs (e.g., McGuigan et al., *J. Med. Chem.* 42:393 (1999) and references cited therein) as shown in Formula G and H.

Formula G

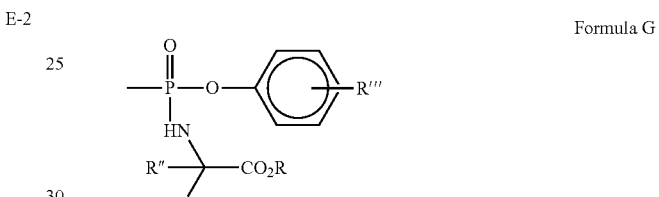

Formula H

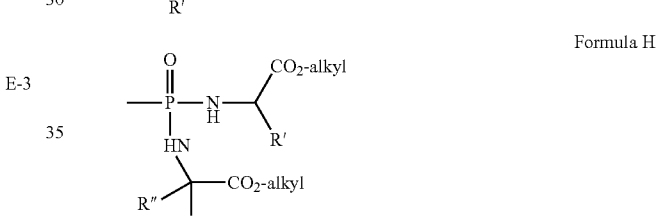

Cyclic phosphoramidates have also been studied as phosphonate prodrugs because of their speculated higher stability compared to non-cyclic phosphoramidates (e.g., Starrett et al., *J. Med. Chem.* 37:1857 (1994)).

Another type of phosphoramidate prodrug was reported as the combination of S-acyl-2-thioethyl ester and phosphoramidate (Egron et al., *Nucleosides Nucleotides* 18:981 (1999)) as shown in Formula J:

Formula J

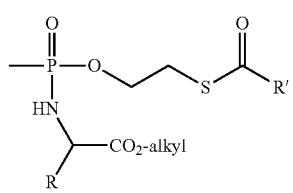

Other prodrugs are possible based on literature reports such as substituted ethyls, for example, bis(trichloroethyl) esters as disclosed by McGuigan, et al., *Bioorg Med. Chem. Lett.* 3:1207-1210 (1993), and the phenyl and benzyl combined nucleotide esters reported by Meier, C. et al., *Bioorg. Med. Chem. Lett.* 7:99-104 (1997).

The structure

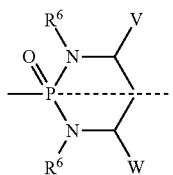

has a plane of symmetry running through the phosphorus-oxygen double bond when $R^6=R^6$, $V=W$, and V and W are either both pointing up or both pointing down. The same is true of structures where each —$NR^6$ is replaced with —O—.

The term "cyclic phosphonate ester of 1,3-propane diol", "cyclic phosphonate diester of 1,3-propane diol", "2 oxo $2\lambda^5$ [1,3,2] dioxaphosphonane", "2 oxo [1,3,2] dioxaphosphonane", "dioxaphosphonane" refers to the following:

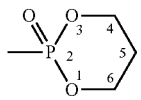

The phrase "together V and Z are connected via an additional 3-5 atoms to form a cyclic group containing 5-7 atoms, optionally containing 1 heteroatom, substituted with hydroxy, acyloxy, alkylthiocarbonyloxy, alkoxycarbonyloxy, or aryloxycarbonyloxy attached to a carbon atom that is three atoms from both Y groups attached to the phosphorus" includes the following:

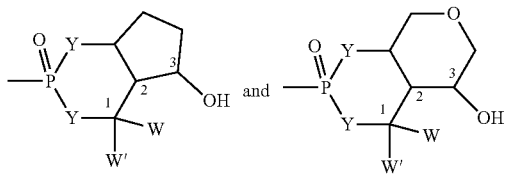

The structure shown above (left) has an additional 3 carbon atoms that forms a five member cyclic group. Such cyclic groups must possess the listed substitution to be oxidized.

The phrase "together V and Z are connected via an additional 3-5 atoms to form a cyclic group, optionally containing one heteroatom, that is fused to an aryl group attached at the beta and gamma position to the Y attached to the phosphorus" includes the following:

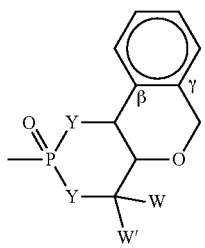

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

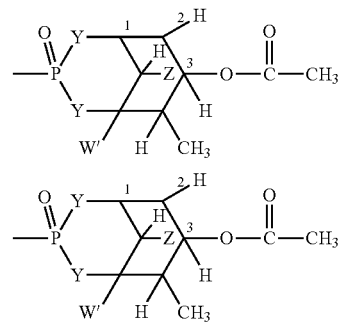

The structure above has an acyloxy substituent that is three carbon atoms from a Y, and an optional substituent, —$CH_3$, on the new 6-membered ring. There has to be at least one hydrogen at each of the following positions: the carbon attached to Z; both carbons alpha to the carbon labeled "3"; and the carbon attached to "OC(O)$CH_3$" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

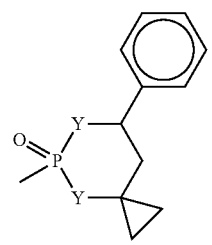

The structure above has V=aryl, and a spiro-fused cyclopropyl group for W and W'.

The term "cyclic phosphon(amid)ate" refers to

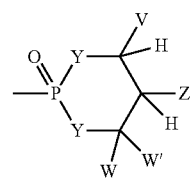

where Y is independently —O— or —$NR^V$—. The carbon attached to V must have a C—H bond. The carbon attached to Z must also have a C—H bond.

The naming of the compounds is done by having the ring bearing the groups $R^5$ and $R^3$ be a substituent on the ring bearing the $R^1$ and $R^2$ groups. The naming of the prodrugs is done by having the diaryl system with its linker T (Formula I, II, III, V, VI, and VIII) or D (Formula IV) be a substituent on the phosphorus atom contained in X. For example: [3-R¹-5-R²-4-(4'-R⁵-3'-R³-benzyl)phenoxy]methylphosphonic acid represents the formula:

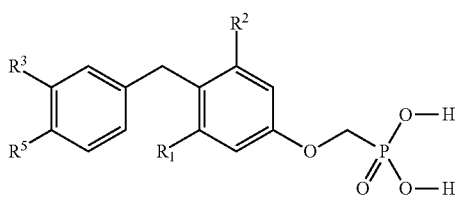

[3-R¹-5-R²-4-(4'-R⁵-3'-R³-phenoxy)phenoxy]methylphosphonic acid represents the formula:

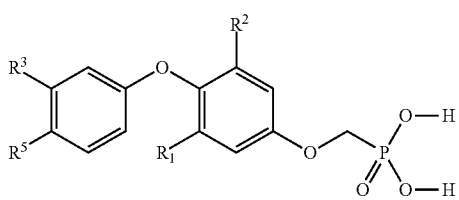

N-[3-R¹-5-R²-4-(4'-R⁵-3'-R³-phenoxy)phenyl]carbamoylphosphonic acid represents the formula:

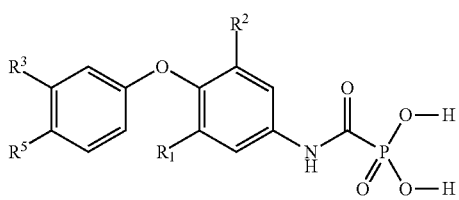

2-[(3-R¹-5-R²-4-(4'-R⁵-3'-R³-benzyl)phenoxy)methyl]-4-aryl-2-oxo-2λ⁵-[1,3,2]-dioxaphosphonane:

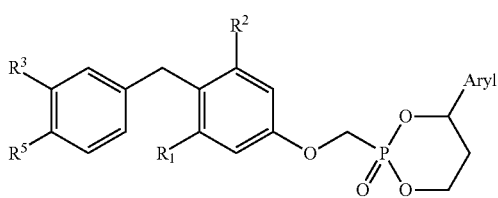

2-[(3-R¹-5-R²-4-(4'-R⁵-3'-R³-phenoxy)phenoxy)methyl]-4-aryl-2-oxo-2λ⁵-[1,3,2]-dioxaphosphonane:

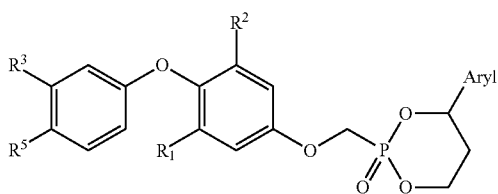

The term "cis" stereochemistry refers to the spatial relationship of the V group and the carbon attached to the phosphorus atom on the six-membered ring. The formula below shows a cis stereochemistry.

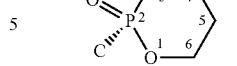

The term "trans" stereochemistry refers to the spatial relationship of the V group and the carbon, attached to the phosphorus atom, on the six-membered ring. The formula below shows a trans-stereochemistry.

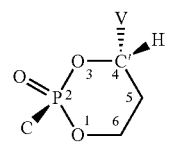

The formula below shows another trans-stereochemistry.

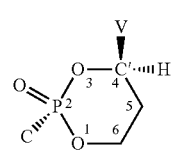

The terms "S-configuration," "S-isomer" and "S-prodrug" refers to the absolute configuration S of carbon C'. The formula below shows the S-stereochemistry.

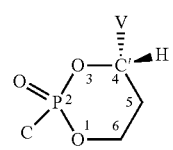

The terms "R-configuration," "R-isomer" and "R-prodrug" refers to the absolute configuration R of carbon C'. The formula below shows the R-stereochemistry.

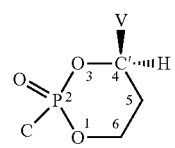

The term "percent enantiomeric excess (% ee)" refers to optical purity. It is obtained by using the following formula:

$$\frac{[R]-[S][R]-[S]}{[R]+[S]} \times 100 = \% R - \% S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

The term "liver" refers to liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or, a prodrug. The ratio can be determined by measuring tissue levels at a specific time or may represent an AUC based on values measured at three or more time points.

The term "phosphorus-containing compounds" refers to compounds that contain $PO_3H_2$, $PO_3^{2-}$, $PO_2HR$, $PO_2R^-$, and monoesters and phosphamic acid derivatives thereof.

The term "surrogates of carboxylic acid" refers to groups that possess near equal molecular shapes and volumes as carboxylic acid and which exhibit similar physical and biological properties. Examples of surrogates of carboxylic acid include, but are not limited to, tetrazole, 6-azauracil, acylsulphonamides, sulfonic acids, thiazolidinedione, hydroxamic acid, oxamic acid, malonamic acid, and carboxylic acid amides. Because phosphorus-containing thyromimetics (e.g., phosphonic acid-, phosphonic acid monoester-, and phosphinic acid-containing compounds) have a markedly different biological activity as compared to carboxylic acid-containing thyromimetics, phosphonic acid, phosphonic acid monoester, and phosphinic acid are not considered to be surrogates of carboxylic acid in these compounds.

The term "inhibitor of fructose-1,6-biphosphatase" or "FBPase inhibitor" refers to compounds that inhibit FBPase enzyme activity and thereby block the conversion of fructose 1,6-bisphosphate, the substrate of the enzyme, to fructose 6-phosphate. These compounds have an $IC_{50}$ of equal to or less than 50 µM on human liver FBPase measured according to the procedure found in U.S. Pat. No. 6,489,476.

The term "increased or enhanced liver specificity" refers to an increase in the liver specificity ratio in animals treated with a compound of the present invention and a control compound. In one embodiment the test compound is a phosphorus-containing compound and in another embodiment the test compound is a prodrug thereof. In one embodiment the control compound is a phosphorus-containing compound of the present invention. In another embodiment the control compound is the corresponding carboxylic acid derivative of the phosphorus-containing test compound.

The term "enhanced oral bioavailability" refers to an increase of at least 50% of the absorption of the dose of the parent drug, unless otherwise specified. In an additional aspect the increase in oral bioavailability of the prodrug (compared to the parent drug) is at least 100%, that is a doubling of the absorption. Measurement of oral bioavailability usually refers to measurements of the prodrug, drug, or drug metabolite in blood, plasma, tissues, or urine following oral administration compared to measurements following systemic administration of the compound administered orally.

The terms "treating" or "treatment" of a disease includes a slowing of the progress or development of a disease after onset or actually reversing some or all of the disease effects. Treatment also includes palliative treatment.

The term "preventing" includes a slowing of the progress or development of a disease before onset or precluding onset of a disease.

The term "thyroid hormone receptors" (TR) refers to intracellular proteins located in cell nuclei that, following the binding of thyroid hormone, stimulate transcription of specific genes by binding to DNA sequences called thyroid hormone response elements (TREs). In this manner TR regulates the expression of a wide variety of genes involved in metabolic processes (e.g., cholesterol homeostasis and fatty acid oxidation) and growth and development in many tissues, including liver, muscle and heart. There are at least two forms of TR; TR alpha (on chromosome 17) and TR beta (on chromosome 3). Each of these isoforms also has two main isoforms: TR alpha-1 and TR alpha-2; and TR beta-1 and TR beta-2, respectively. TRs are high affinity receptors for thyroid hormones, especially triiodothyronine.

The term "ACC" refers to acetyl CoA carboxylase.

The term "FAS" refers to fatty acid synthase.

The term "spot-14" refers to a 17 kilodalton protein expressed in lipogenic tissues and is postulated to play a role in thyroid hormone stimulation of lipogenesis. (Campbell, M C et al., *Endocrinology* 10:1210 (2003).

The term "CPT-1" refers to carnitine palmitoyltransferase-1.

The term "CYP7A" refers to cholesterol 7-alpha hydroxylase, which is a membrane-bound cytochrome P450 enzyme that catalyzes the 7-alpha-hydroxylation of cholesterol in the presence of molecular oxygen and NADPH-ferrihemoprotein reductase. CYP7A, encoded by CYP7, converts cholesterol to 7-alpha-hydroxycholesterol which is the first and rate-limiting step in the synthesis of bile adds.

The term "apoAI" refers to Apolipoprotein AI found in HDL and chylomicrons. It is an activator of LCAT and a ligand for the HDL receptor.

The term "mGPDH" refers to mitochondrial glycerol-3-phosphate dehydrogenase.

The term "hypercholesterolemia" refers to presence of an abnormally large amount of cholesterol in the cells and plasma of the circulating blood.

The term "hyperlipidemia" or "lipemia" refers to the presence of an abnormally large amount of lipids in the circulating blood.

The term "atherosclerosis" refers to a condition characterized by irregularly distributed lipid deposits in the intima of large and medium-sized arteries wherein such deposits provoke fibrosis and calcification. Atherosclerosis raises the risk of angina, stroke, heart attack, or other cardiac or cardiovascular conditions.

The term "obesity" refers to the condition of being obese. Being obese is defined as a body mass index (BMI) of 30.0 or greater; and extreme obesity is defined at a BMI of 40 or greater. "Overweight" is defined as a body mass index of 25.0 to 29.9 (This is generally about 10 percent over an ideal body weight)

The term "coronary heart disease" or "coronary disease" refers to an imbalance between myocardial functional requirements and the capacity of the coronary vessels to supply sufficient blood flow. It is a form of myocardial ischemia (insufficient blood supply to the heart muscle) caused by a decreased capacity of the coronary vessels.

The term "diabetes" refers to a heterogeneous group of disorders that share glucose intolerance in common. It refers to disorders in which carbohydrate utilization is reduced and that of lipid and protein enhanced; and may be characterized by hyperglycemia, glycosuria, ketoacidosis, neuropathy, or nephropathy.

The term "non-insulin-dependent diabetes mellitus" (NIDDM or type 2 diabetes) refers to a heterogeneous disorder characterized by impaired insulin secretion by the pancreas and insulin resistance in tissues such as the liver, muscle and adipose tissue. The manifestations of the disease include one or more of the following: impaired glucose tolerance, fasting hyperglycemia, glycosuria, increased hepatic glucose output, reduced hepatic glucose uptake and glycogen storage, reduced whole body glucose uptake and utilization, dyslipidemia, fatty liver, ketoacidosis, microvascular diseases such as retinopathy, nephropathy and neuropathy, and macrovascular diseases such as coronary heart disease.

The term "impaired glucose tolerance (IGT)" refers to a condition known to precede the development of overt type 2 diabetes. It is characterized by abnormal blood glucose excursions following a meal. The current criteria for the diagnosis of IGT are based on 2-h plasma glucose levels post, a 75 g oral glucose test (144-199 mg/dL). Although variable from population to population studied, IGT progresses to full blown NIDDM at a rate of 1.5 to 7.3% per year, with a mean of 3-4% per year. Individuals with IGT are believed to have a 6 to 10-fold increased risk in developing NIDDM. IGT is an independent risk factor for the development of cardiovascular disease.

The terms "fatty liver" and "liver steatosis" are interchangeable and refer to a disease or disorder characterized by significant lipid deposition in the liver hepatocytes (parenchyma cells). Simple fatty liver or liver steatosis is not associated with any other liver abnormalities such as scarring or inflammation. Fatty liver or liver steatosis is a common occurrence in patients who are very overweight or have diabetes mellitus.

The term "NonAlcoholic SteatoHepatitis (NASH) refers to a disease or disorder characterized by inflammation of the liver in combination with fatty liver. NASH is a possible diagnosis when other causes of liver inflammation such as hepatitis B and C viruses, autoimmune disorders, alcohol, drug toxicity, and the accumulation of copper (Wilson's Disease) or iron (hemochromatosis) are excluded.

The term "NonAlcoholic Fatty Liver Disease (NAFLD) refers to a wide spectrum of liver disease ranging from (and including) simple fatty liver (steatosis), to nonalcoholic steatohepatitis (NASH), to cirrhosis (advanced scarring of the liver). All of the stages of NAFLD have fatty liver in common. In NASH, fat accumulation is associated with varying degrees of inflammation (hepatitis) which may lead to scarring (fibrosis) of the liver.

Steatosis can be most readily diagnosed with noninvasive imaging modalities, such as ultrasound, magnetic resonance imaging, or computed tomography as examples, or following a percutaneous biopsy. Using ultrasound as an example of a noninvasive imaging diagnosis tool, the sonographic findings of diffuse fatty change include a diffuse hyperechoic echotexture (bright liver), increased liver echotexture compared with the kidneys, vascular blurring, and deep attenuation (Yajima et al., *Tohoku J Exp Med* 139(1):43-50 (1983)). Using percutaneous biopsy, the histological features of NAFLD are indistinguishable from those of alcohol-induced liver disease, of which, predominant macrovesicular steatosis alone in >33% of hepatocytes will be used as the definition. Other histologic features, such as varying amounts of cytologic ballooning and spotty necrosis, scattered mixed neutrophilic-lymphocytic inflammation, glycogen nuclei, Mallory's hyaline, and perisinusoidal fibrosis may be present, but are not required for a diagnosis of NAFLD.

The term "insulin resistance" is defined clinically as the impaired ability of a known quantity of exogenous or endogenous insulin to increase whole body glucose uptake and utilization. As insulin regulates a wide variety of metabolic processes in addition to glucose homeostasis (e.g., lipid and protein metabolism), the manifestations of insulin resistance are diverse and include one or more of the following: glucose intolerance, hyperinsulinemia, a characteristic dyslipidemia (high triglycerides; low high-density lipoprotein cholesterol, and small, dense low-density lipoprotein cholesterol), obesity, upper-body fat distribution, fat accumulation in the liver (non-alcoholic fatty liver disease), NASH (non-alcoholic steatohepatitis), increased hepatic glucose output, reduced hepatic glucose uptake and storage into glycogen, hypertension, and increased prothrombotic and antifibrinolytic factors. This cluster of cardiovascular-metabolic abnormalities is commonly referred to as "The Insulin Resistance Syndrome" or "The Metabolic Syndrome" and may lead to the development of type 2 diabetes, accelerated atherosclerosis, hypertension or polycystic ovarian syndrome.

The Metabolic Syndrome" or "Metabolic Syndrome X" is characterized by a group of metabolic risk factors in one person. They include:

Central obesity (excessive fat tissue in and around the abdomen)

Atherogenic dyslipidemia (blood fat disorders—mainly high triglycerides and low HDL cholesterol—that foster plaque buildups in artery walls)

Raised blood pressure (130/85 mmHg or higher)

Insulin resistance or glucose intolerance (the body can't properly use insulin or blood sugar)

Prothrombotic state (e.g., high fibrinogen or plasminogen activator inhibitor [−1] in the blood)

Proinflammatory state (e.g., elevated high-sensitivity C-reactive protein in the blood)

According to the present invention, "Metabolic Syndrome" or "Metabolic Syndrome X" is identified by the presence of three or more of these components:

Central obesity as measured by waist circumference:
  Men: Greater than 40 inches
  Women: Greater than 35 inches Fasting blood triglycerides greater than or equal to 150 mg/dL Blood HDL cholesterol:
  Men: Less than 40 mg/dL
  Women: Less than 50 mg/dL Blood pressure greater than or equal to 130/85 mmHg, Fasting glucose greater than or equal to 110 mg/dL The term "thyroid responsive element" or "TRE" refers to an element that usually consists of directly repeated half-sites with the consensus sequence AGGTCA. (Harbers et al., *Nucleic Acids Res.* 24(12):2252-2259 (1996)). TREs contain two half-sites of the AGGTCA motif which can be arranged as direct repeats, inverted repeats, or everted repeats.

The term "thyroid responsive genes" refers to genes whose expression is affected by triiodothyronine (Menjo et al., *Thyroid* 9(9):959-67 (1999); Helbing et al., *Mol. Endocrinol.* 17(7):1395-409 (2003)).

The term "TSH" or "thyrotropin" refers to thyroid stimulating hormone.

The term "atherogenic proteins" refers to proteins that induce, stimulate, enhance or prolong atherosclerosis and diseases related to atherosclerosis, including but not limited to coronary heart disease. Atherogenic proteins include apoAI and Lp (a).

The term "thyroid hormone, or TH" includes for example natural iodinated thyronines from thyroglobulin (e.g., T3, T4), as well as drugs such as Levothyroxine sodium which is the sodium salt of a levorotatory isomer of T4 and a commonly used drug as replacement therapy in hypothyroidism. Other uses include the treatment of simple nonendemic goiter, chronic lymphocytic thyroiditis and thyrotropin-dependent thyroid carcinoma. Liothyronine sodium is the sodium salt of a levorotatory isomer of T3. Liotrix is a 4:1 mixture of levothyroxine and liothronine. Thyroid is a preparation derived from dried and defatted thyroid glands of animals.

The term "thyromimetic" or "T3 mimetic" as used herein, is intended to cover any moiety which binds to a thyroid receptor and acts as an agonist, antagonist, partial agonist/antagonist, or inverse agonist of T3. The thyromimetic may be further specified as an agonist, an antagonist, a partial agonist, or a partial antagonist. The thyromimetics of the present invention presumably bind the T3 binding site and can inhibit T3 binding to a thyroid hormone receptor utilizing a heterologous displacement reaction. Thyromimetics of the present invention that can produce one of or more of the effects mediated by naturally occurring T3 in a target tissue or cell would be considered an agonist or partial agonist. Thyromimetics of the present invention that can inhibit one of more of the effects mediated by naturally occurring T3 in a target tissue or cell would be considered an antagonist, partial agonist, or inverse agonist. Thyromimetics do not include T3, T4, or other naturally occurring thyroid hormones.

The term "metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary heart disease, cardiovascular disease.

The term "mitochondrial biogenesis" or "mitochondrial-genesis" refers to the rate at which nascent mitochondria are synthesized. Mitochondrial biogenesis that occurs during cell replication provides enough new mitochondria for both the parent and daughter cells. Mitochondrial biogenesis that occurs in the absence of cell replication leads to an increase in the number of mitochondria within a cell.

As used herein, the term "significant" or "statistically significant" means a result (i.e. experimental assay result) where the p-value is ≤0.05 (i.e. the chance of a type I error is less than 5%) as determined by an art-accepted measure of statistical significance appropriate to the experimental design.

All references cited herein are incorporated by reference in their entirety.

DETAILED DESCRIPTION

The present invention relates to methods of decreasing the fat content of the liver in an animal comprising administering thyromimetic compounds, pharmaceutically acceptable salts and prodrugs thereof, and pharmaceutically acceptable salts of the prodrugs, where the compounds bind to a thyroid hormone receptor.

The present invention further relates to methods of preventing, treating, or ameliorating fatty liver diseases in an animal comprising administering thyromimetic compounds, pharmaceutically acceptable salts and prodrugs thereof, and pharmaceutically acceptable salts of the prodrugs, where the compounds bind to a thyroid hormone receptor.

Thyroid hormones and thyroid hormone mimetics bind to thyroid hormone receptors in the nucleus of cells and can change expression levels of genes encoding proteins that play an important role in metabolic diseases. By altering the expression of thyroid hormone-responsive genes in the liver, thyromimetic compounds can decrease the level of fat in the liver. Fatty liver diseases that can be prevented, treated, or ameliorated with thyroid hormone mimetics include steatosis, non-alcoholic fatty liver disease, and non-alcoholic steatohepatitis (NASH).

In one aspect, the thyromimetic compounds, pharmaceutically acceptable salts and prodrugs thereof, and pharmaceutically acceptable salts of the prodrugs used in these methods bind to at least one thyroid hormone receptor with an Ki of ≤100 nM relative to T3, or ≤90 nM, ≤80 nM, ≤70 nM, ≤60 nM, ≤50 nM, ≤40 nM, ≤30 nM, ≤20 nM, ≤10 nM, ≤50 nM, ≤1 nM, ≤0.5 nM. Thyroid hormone receptor binding is readily determined using assays described in the literature. For example, nuclear extracts from animal livers can be prepared according to the methods described by Yokoyama et al. (*J. Med. Chem.*, 38: 695-707 (1995)). Binding assays can also be performed using purified thyroid hormone receptors. For example, using the methods used by Chiellini et al. (*Bioorg. Med. Chem.*, 10: 333-346 (2002)) competition ligand binding affinities are determined using $^{125}$I-T3 and the human thyroid receptors TRα1 and TRβ1. The latter methods advantageously enable determination of thyroid receptor selectivity.

In another aspect, the thyromimetic compounds, pharmaceutically acceptable salts and prodrugs thereof, and pharmaceutically acceptable salts of the prodrugs used in these methods cause at least a 50%, 2 fold, 3 fold, 4 fold, 6 fold or 8 fold increase or decrease in the expression of one or more thyroid hormone-responsive genes. Changes in gene expression can be detected in cells or in vivo. Prodrugs of the thyromimetics can increase cellular uptake but in some cases are poorly converted to the active compound due to low levels of the enzymes required for the conversion. Changes in gene expression in vivo require either the compounds of the invention to be taken up by the tissue following administration or for the prodrug to remain intact after administration long enough to distribute to the target organ and cell. Following distribution to the cell, enzymes or other conditions responsible for cleaving the prodrug must act on the prodrug and convert it to the active compound. The compound must then be able to be transported to the nucleus. If a portion of the compound is excreted from the cell it must be retransported back across the cellular membrane and nuclear membrane. The prodrugs of the present invention that are activated in the liver and excreted by the liver as active compounds are retransported back across the cellular and nuclear membrane and into the nucleus.

The liver is a major target organ of thyroid hormone with an estimated 8% of the hepatic genes regulated by thyroid hormone. Quantitative fluorescent-labeled cDNA microarray hybridization was used to identify thyroid-responsive genes in the liver as shown in Table 1 below (Feng et al., *Mol. Endocrinol.*, 14: 947-955 (2000)). Hepatic RNA from T3-treated and hypothyroid mice were used in the study. Thyroid hormone treatment affected the expression of 55 genes from the 2225 different mouse genes sampled with 14 increasing >2-fold and 41 decreasing >60%.

TABLE 1

GENES REGULATED BY T3
List of Hepatic Genes Regulated by T3 Determined by cDNA Microarray Analyses

| Function Clone ID | Genes | Accession No. | Fold |
|---|---|---|---|
| \multicolumn{4}{c}{Carbohydrate and fatty acid metabolism, and insulin action} | | | |
| 580906 | Spot 14 gene | X95279 | 8.8 |
| 523120 | Glucose-6-phosphatase | U00445 | 3.8 |
| 615159 | Carbonyl reductase (Cbr1) | U31966 | 3.3 |
| 571409 | Insulin-like growth factor binding protein 1 precursor | X81579 | 3.0 |
| 481636 | Fatty acid transport protein (FATP) | U15976 | 1.8 |
| 550993 | Cyp4a-10 | X69296 | 0.3 |
| 583329 | PHAS-II | U75530 | 0.3 |
| 616283 | Serine/threonine kinase (Akt2) | U22445 | 0.3 |
| 583333 | Putative transcription factor of the insulin gene | X17500 | 0.3 |
| 533177 | Nuclear-encoded mitochondrial acyltransferase | L42996 | 0.2 |
| 608607 | Glycerophosphate dehydrogenase | J02655 | 0.3 |
| \multicolumn{4}{c}{Cell proliferation, Replication} | | | |
| 614275 | B61 | U26188 | 2.3 |
| 597868 | Bcl-3 | M90397 | 2.5 |
| 493127 | Kinesin-like protein (KipIp) | AF131865 | 2.0 |
| 582689 | Chromodomain-helicase-DNA binding protein CHD-1 | P40201 | 0.4 |
| 524471 | NfiB1-protein (exon 1-12) | Y07685 | 0.3 |
| 516208 | Putative ATP-dependent RNA helicase PL10 | J04847 | 0.3 |
| 558121 | Murine vik5variant in the kinase | S53216 | 0.1 |
| 573247 | C11 protein | X81624 | 0.3 |
| 522108 | Thymic stromal stimulating factor | D43804 | 0.3 |
| 613942 | Ubiquitin-activating enzyme E1 X | D10576 | 0.3 |
| \multicolumn{4}{c}{Signal transduction} | | | |
| 573046 | β-2 Adrenergic receptor | X15643 | 3.4 |
| 583258 | Protein kinase C inhibitor (mPKCl) | U60001 | 2.1 |
| 616040 | Inhibitory G protein of adenylate cyclase, α chain | M13963 | 0.3 |
| 583353 | Terminal deoxynucleotidyltransferase | 04123 | 0.3 |
| 550956 | Rho-associated, coiled-coil forming protein kinase p160 | U58513 | 0.2 |
| 582973 | Protein kinase C, Θ type | AB011812 | 0.3 |
| 442989 | Protein kinase ζ | M94632 | 0.5 |
| 607870 | Lamin A | D13181 | 0.3 |
| \multicolumn{4}{c}{Glycoprotein synthesis} | | | |
| 375144 | α-2,3-Sialyltransferase | D28941 | 0.3 |
| 481883 | β-Galactoside α 2,6-sialyltransferase | D16106 | 0.3 |
| \multicolumn{4}{c}{Cellular immunity} | | | |
| 615872 | T-complex protein 1, d subunit | P80315 | 0.3 |
| 618426 | H-2 class I histocompatibility antigen | Q61147 | 0.3 |
| 614012 | FK506-binding protein (FKBP65) | L07063 | 0.3 |
| 604923 | FK506-binding protein (FKBP23) | AF040252 | 0.2 |
| \multicolumn{4}{c}{Cytoskeletal protein} | | | |
| 374030 | Myosin binding protein H (MyBP-H) | U68267 | 2.2 |
| 613905 | AM2 receptor | X67469 | 0.3 |
| 616518 | Cytoskeletal β-actin | X03672 | 0.3 |
| 614948 | Actin, α cardiac | M15501 | 0.3 |
| 607364 | Skeletal muscle actin | M12866 | 0.3 |
| 597566 | Capping protein a-subunit | G565961 | 0.3 |
| 483226 | Actin, γ-enteric smooth muscle | M26689 | 0.3 |
| \multicolumn{4}{c}{Others} | | | |
| 552837 | Major urinary protein 2 precursor | M27608 | 3.9 |
| 521118 | β-Globin | AB020013 | 2.3 |
| 493218 | α-Globin | L75940 | 2.7 |
| 585883 | Putative SH3-containing protein SH3P12 | AF078667 | 0.3 |
| 615239 | Membrane-type matrix metalloproteinase | X83536 | 0.2 |
| 402408 | ece1 (endothelin-converting enzyme) | W78610 | 0.2 |
| 635768 | α-Adaptin | P17426 | 0.3 |
| 634827 | Glucose regulated protein 78 | D78645 | 0.3 |
| 616189 | Lupus la protein homolog | L00993 | 0.3 |
| 588337 | EST | AI646753 | 0.4 |
| 335579 | Virus-like (VL30) retrotransposon BVL-1 | X17124 | 0.3 |
| 557037 | TGN38B | D50032 | 0.3 |
| 597390 | Mitochondrial genome | L07096 | 0.4 |
| 616563 | Arylsulfatase A | X73230 | 0.3 |

Genes reported to be affected by thyroid hormone are identified using a variety of techniques include microarray analysis. Studies have identified genes that are affected by T3 and T3 mimetics that are important in metabolic diseases.

T3-responsive genes in the liver include genes affecting lipogenesis, including spot 14, fatty acid transport protein, malic enzyme, fatty acid synthase (Blennemann et al., *Mol. Cell. Endocrinol.* 110(1-2):1-8 (1995)) and CYP4A. HMG CoA reductase and LDL receptor genes have been identified as affecting cholesterol synthesis and as being responsive to T3. CPT-1 is a T3 responsive gene involved in fatty acid oxidation. Genes affecting energy expenditure, including mitochondrial genes such as mitochondrial sn-glycerol 3-phosphate dehydrogenase (mGPDH), and/or enzymes associated with proton leakage such as the adenine nucleotide transporter (ANT), $Na^+/K^+$-ATPase, $Ca^{2+}$-ATPase and ATP synthase are also T3 responsive genes. T3 responsive genes affecting glycogenolysis and gluconeogenesis, include glucose 6-phosphatase and PEPCK.

Compounds used in the methods bind to thyroid receptors and produce a change in some hepatic gene expression. Evidence for agonist activity is obtained using standard assays described in the literature. One assay commonly used entails a reporter cell assay wherein cells, e.g., HeLa cells, Hek293 cells, Chinese hamster ovary cells, are transfected with an expression vector for human $TR\alpha 1$ or $TR\beta 1$ and subsequently with a reporter vector encoding a secreted form of alkaline phosphatase containing whose expression is under the control of a thyroid hormone response element. Agonist activity is measured by exposing the cells to the compounds, especially prodrugs of the compounds that are cleaved to the active compound by cell homogenates, followed by determining alkaline phosphatase activity in the cell culture medium using a chemiluminescent assay (Grover et al., *Proc. Natl. Acad. Sci. U.S.A.*, 100(17):10067-72 (2003)).

Particularly useful T3 mimetics in these methods would minimize effects on thyroid function, thyroid production of circulating iodinated thyronines such as T3 and T4, and/or the ratio of T3 to T4. Some T3 mimetics distribute more readily to the liver and result in pharmacological effects at doses that do not adversely affect thyroid function, thyroid production of circulating iodinated thyronines such as T3 and T4, and/or the ratio of T3 to T4. In one embodiment the compounds used in the present invention have a therapeutic index, defined as the difference between the dose at which a significant effect is observed for a use disclosed herein, e.g., decreasing fat content in the liver, and the dose at which a significant decrease in T3 or significant decrease in T4, or significant change in the ratio of T3 to T4 is observed, is at least 50 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold or at least 10000 fold. In one embodiment, rather than a significant amount, the amount of change in T3 or T4 is a decrease selected from; at least 5%, 10%, 15%, 20%, 25% or at least 30% of circulating levels.

As discussed above, the previous use of T3 and T3 mimetics to treat metabolic diseases have been limited by the deleterious side-effects on the heart. Attempts to overcome this limitation have focused on selectively targeting the liver over the heart using T3 mimetics that selectively bind $TR\beta$ over $TR\alpha$. Because the heart expresses mainly $TR\alpha$, previous investigators have attempted to increase the therapeutic index of T3 mimetics by increasing the selectively of the compounds for $TR\beta$ which is expressed in the liver. Other work has led to the discovery of phosphorus-containing compounds, including prodrugs, that selectively distribute to the liver over the heart. These compounds are able to selectively target the liver and thereby increase the therapeutic index as compared to T3 and T3 mimetics containing a carboxylic acid. Compounds having increased liver selectivity, e.g., due to liver-selective distribution or TR selectivity, can therefore be dosed at levels that are effective in treating metabolic and other disorders where the liver is the drug target without significantly negatively affecting heart function.

Changes in the therapeutic index are readily determined using assays and methods well described in the literature. Genes in extrahepatic tissues are monitored using methods well understood by those skilled in the art. Assays include using cDNA microarray analysis of tissues isolated from treated animals. The sensitivity of the heart to T3 makes analysis of T3-responsive genes in the heart as well as the functional consequences of these changes on cardiac properties one further strategy for evaluating the therapeutic index of the compounds of the present invention. Cardiac genes measured include mGPDH, myosin heavy and light chain. One method of measuring the effects of T3 mimetics on the heart is by the use of assays that measure T3 mediated myosin heavy chain gene transcription in the heart.

A variety of methods are described that provide a means for evaluating the functional consequences of T3-cardiac action, including measurement of cardiac hypertrophy (heart weight to body weight ratio), heart rate, and various hemodynamic parameters, including systolic and diastolic arterial pressure, end-systolic left ventricular pressure and maximal speeds of contraction and relaxation using methods described by Trost et al., (*Endocrinology* 141:3057-64 (2000)).

Other methods are also available to assess the therapeutic index including effects on muscle wasting and bone density.

The therapeutic index is determined by administering to animals a wide range of doses and determining the minimal dose capable of inducing a response in the liver relative to the dose capable of inducing a response in the heart.

Some thyromimetic compounds are often poorly transported into cultured cells. Accordingly, cell reporter assays, while often useful for confirming agonist activity, may not provide a suitable indication of potency. Thus, evidence of agonist activity is often more readily obtained in vivo. In vivo assays include but are not limited to treating animals with a thyromimetic or a prodrug and monitoring the expression of T3-responsive genes in the liver or the functional consequences of changes of T3-responsive genes.

In one aspect, compounds useful in the methods of the invention bind to thyroid receptors and produce changes in the expression of two or more hepatic genes. Animals used for testing compounds useful in the methods include normal rats and mice, animals made hypothyroid using methods well described in the literature, including thyroid hormone receptor knockout mice (e.g., $TR\alpha^{-/-}$ such as those used in Grover et al., 2003), or animals exhibiting high cholesterol (e.g., high cholesterol fed rat or hamster), obesity and/or diabetes (e.g., fa/fa rat, Zucker diabetic fatty rat, ob/ob mice, db/db mice, high fat fed rodent). (Liureau et al., *Biochem Pharmacol.* 35(10):1691-6 (1986); Trost et al., *Endocrinology* 141(9):3057-64 (2000); and Grover, *PNAS* 2003). The drug or prodrug is administered by a variety of routes including by bolus injection, oral, and continuous infusion. Animals are treated for 1-28 days and the liver, heart and blood are isolated. Changes in gene transcription relative to vehicle treated animals and T3-treated animals are determined using northern blot analysis, RNase protection or reverse-transcription and subsequent PCR. While methods are available for monitoring changes in thousands of hepatic genes, only a small number need to be monitored to demonstrate the biological effect of compounds in this invention. Typically, genes such as spot-14, FAS, mGPDH, CPT-1, and LDL receptor are monitored. Changes of >1.5 fold in two or more genes is considered proof that the compound modulates T3-responsive genes in vivo. Alternative methods for measuring changes in gene transcription include monitoring the activity or expression level of the protein encoded by the gene. For instance, in cases where the genes encode enzyme activities (e.g., FAS, mGPDH), direct measurements of enzyme activity in appropriately extracted liver tissue can be made using standard enzymological techniques. In cases where the genes encode receptor functions (e.g., the LDL receptor) ligand binding studies or antibody-based assays (e.g., Western blots) can be performed to quantify the number of receptors expressed. Depending on the gene, TR agonists will either increase or decrease enzyme activity or increase or decrease receptor binding or number.

The functional consequences of changing the expression levels of hepatic genes responsive to T3 is many-fold and readily demonstrated using assays well described in the literature. Administering thyromimetic compounds that bind to a TR to animals can result in changes in lipids, including hepatic and/or plasma cholesterol levels; changes in lipoprotein levels including LDL-cholesterol, lipoprotein a (Lp (a)); changes in hepatic glycogen levels; and changes in energy expenditure as measured by changes in oxygen consumption and in some cases animal weight. For example, the effect on cholesterol is determined using cholesterol fed animals such as normal rats and hamsters, or $TR\alpha^{-/-}$ knockout mice. Cholesterol is measured using standard tests. Hepatic glycogen levels are determined from livers isolated from treated animals. Changes in energy expenditure are monitored by measuring changes in oxygen consumption ($MV_{o_2}$). A variety of methods are well described in the literature and include measurement in the whole animal using Oxymax chambers (U.S. Pat. No. 6,441,015). Livers from treated rats can also be evaluated (Fernandez et al., *Toxicol Lett.* 69(2):205-10 (1993)) as well as isolated mitochondria from liver (Carreras et al., *Am. J. Physiol. Heart Circ. Physiol.* 281(6):H2282-8 (2001)). Hepatocytes from treated rats can also be evaluated (Ismail-Beigi et al., *J. Gen. Physiol.* 73(3):369-83 (1979)).

Provided are methods of reducing fat content in the liver or of preventing, treating, or ameliorating fatty liver disease (e.g., steatosis, NASH or NAFLD) in an animal, the method comprising the step of administering to a patient an amount of a thyromimetic compound, a prodrug thereof, or a pharmaceutically acceptable salt or co-crystal thereof. In one embodiment said compound is an active form. In another embodiment said compound is a prodrug. In another embodiment said compound or a prodrug thereof comprises a stereocenter. In another embodiment said compound is administered as a racemic mixture. In another embodiment said compound is administered as an enantiomerically enriched mixture. In another embodiment said compound is administered as a diastereomeric mixture. In still another embodiment said compound is administered as an individual stereoisomer.

While T3 administration may have some effect on fat content in liver, such effect would only occur at high doses of T3, i.e., doses at which T3-related toxicities occur. Further, even if T3 administration lowers fat content in liver, the activity decreases over time, e.g., in the space of four to five weeks. Thus, in one embodiment of the invention, thyromimetic compounds are administered at doses that significantly reduce fat content in the liver but are below the doses at which an effect is observed with T3. In an additional embodiment, thyromimetic compounds are administered that maintain fat-reducing activity for long periods of time, e.g., 1, 2, 3, 4, 6, 8, 12 weeks or longer without any loss in efficacy. In a further embodiment, thyromimetic compounds are administered that maintain fat-reducing activity for long periods of time, e.g., 1, 2, 3, 4, 6, 8, 12 weeks or longer, wherein efficacy of the compounds decreases over time but at a slower rate than the decrease in efficacy observed with T3. For example, the decrease in efficacy may be about 10, 20, 30, 40, 50, 60, 70, 80, 90, 100, 200, or 400% or more slower than the decrease in efficacy observed with T3.

In another embodiment of the invention, the thyromimetic compounds reduce fat content in liver without significantly affecting peripheral fat, visceral fat, or epididymal fat. In another embodiment, the thyromimetic compounds cause an increase in oxidation of free fatty acids in the liver. In a further embodiment, the thyromimetic compounds increase oxidation of triglycerides, cholesterol esters, and/or long chain acetyl-CoA esters in the liver. In certain embodiments, oxidation is increased by about 10, 20, 30, 40, 50, 60, 70, 80, 90, 100, 200, or 400% or more.

In one aspect of the invention, the thyromimetic compounds reduce fat content in liver in the absence of any negative effects on the heart. Negative effects include one or more of significant increase in heart rate, significant raising of blood pressure, significant increase in heart rate, significant increase in left ventricular contractility, significant increase in systolic blood pressure, and significant increase in diastolic blood pressure.

In another aspect of the invention, the thyromimetic compounds reduce fat content in liver in the absence of any significant change in total body weight, significant change in TSH or TRH levels, significant change in liver enzymes, significant change in serum free fatty acid levels, or significant liver mitochondrial damage.

Provided are pharmaceutical compositions a compound useful in the present invention. Also provided are pharmaceutical compositions of the present invention having an oral bioavailability of least 20%, 25%, 30%, 35%, 40%, 45%, 50%, 55%, 60%, 65%, 70% 75% or at least 80%.

Also provided are pharmaceutical compositions comprising a first compound useful in the present invention and a second compound useful for decreasing the fat content of the liver, useful for the prevention, treatment, or amelioration of a fatty liver disease such as steatosis, NASH, or NAFLD, or useful for the prevention, treatment, or amelioration of a disease or disorder that is related to or results in fatty liver disease. In one embodiment, a composition comprising said first and second compound is a single unit dose. In another embodiment, said unit does is in the form of a tablet, hard capsule or soft gel capsule.

Also provided are kits for decreasing that fat content of liver or for the prevention, treatment, or amelioration of a fatty liver disease such as steatosis, NASH, or NAFLD, the kits comprising:

a) a first pharmaceutical composition comprising a thyromimetic compound or a prodrug thereof;

b) a second pharmaceutical composition comprising an additional compound useful for decreasing the fat content of the liver, useful for the prevention, treatment, or amelioration of a fatty liver disease such as steatosis, NASH, or NAFLD, or useful for the prevention, treatment, or amelioration of a disease or disorder that is related to or results in fatty liver disease; and c) at least one container for containing said first or second or both first and second pharmaceutical composition.

Also provided is the use of a compound of the present invention for the manufacture of a medicament for decreasing the fat content of liver or for the prevention, treatment or amelioration of a fatty liver disease such as steatosis, NASH, and NAFLD.

In one embodiment, compounds used in the present methods are compounds that selectively distribute to the liver. In one embodiment, the compounds have at least 10 fold, 25 fold, 50 fold, 75 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold 6000 fold, 7000 fold, 8000 fold, 9000 fold, 10,000 fold, 20,000 fold, 30,000 fold, 40,000 fold or 50,000 fold greater selectivity. In one embodiment the selectivity for the liver is compared to the heart. In another embodiment the selectivity for the liver is compared to the pituitary. In another embodiment the selectivity for the liver is compared to the kidney.

In a further embodiment, compounds used in the present methods are compounds of the present invention that bind at least one thyroid hormone receptor with an Ki of ≤100 nM, ≤90 nM, ≤80 nM, ≤70 nM, ≤60 nM, ≤50 nM, ≤40 nM, ≤30 nM, ≤20 nM, ≤10 nM, ≤50 nM, ≤1 nM, or ≤0.5 nM relative to T3. In one embodiment said thyroid hormone receptor is TRα. In one embodiment said thyroid hormone receptor is TRβ. Also provided are compounds that bind at least one thyroid hormone receptor with an Ki of ≥100 nM, ≥90 nM, ≥80 nM, ≥70 nM, ≥60 nM, ≥50 nM, ≥40 nM, ≥30 nM, ≥20 nM, ≥10 nM, ≥50 nM, ≥1 nM, or ≥0.5 nM relative T3, but in each case ≤150 nM. In one embodiment said thyroid hormone receptor is TRα. In one embodiment said thyroid hormone receptor is TRβ. In one embodiment said thyroid hormone receptor is TRα1. In one embodiment said thyroid hormone receptor is TRβ1. In one embodiment said thyroid hormone receptor is TRα2. In one embodiment said thyroid hormone receptor is TRβ2.

Novel methods described herein describe the use of thyromimetic compounds that bind to TRs. In one aspect, compounds described below include compounds of Formula I-IX. The compounds of the present invention can be used in the methods described herein.

Compounds Useful in the Invention

The compounds useful in the invention are thyromimetic compounds that bind to and activate thyroid receptors in the liver. The present invention relates to compounds of Formula I-IX, including stereoisomers and mixtures of stereoisomers thereof, pharmaceutically acceptable salts thereof, co-crystals thereof, and prodrugs (including stereoisomers and mixtures of stereoisomers thereof) thereof, and pharmaceutically acceptable salts and co-crystals of the prodrugs.

The compounds of the present invention may be either crystalline, amorphous or a mixture thereof. Compositions comprising a crystalline form a compound of the present invention may contain only one crystalline form of said compound or more than one crystalline form. For example, the composition may contain two or more different polymorphs. The polymorphs may be two different polymorphs of the free form, two or more polymorphs of different co-crystal forms, two or more polymorphs of different salt forms, a combination of one or more polymorphs of one or more co-crystal forms and one or more polymorphs of the free form, a combination of one or more polymorphs of one or more salt forms and one or more polymorphs of the free form, or a combination of one or more polymorphs of one or more co-crystal forms and one or more polymorphs of one or more salt forms.

Pharmaceutically acceptable base addition salts of the compounds herein are included in the present invention. Pharmaceutically acceptable base addition salts refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to: sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

Pharmaceutically acceptable acid addition salts of the compounds herein having a base functional group (e.g., a prodrug whereby the carboxylic acid or surrogate thereof is protected with a group comprising a base functional group) are also included in the present invention. Pharmaceutically acceptable acid addition salts refer to those salts which retain the biological effectiveness and properties of the free base, which are not biologically or otherwise undesirable. These salts are prepared from addition of an inorganic acid or an organic acid to the free base. Salts derived from inorganic acids include, but are not limited to: acistrate, hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, laurylsulphonate. bromide, fumarate, pamoate, glucuronate, hydroiodide, iodide, sulfate, xinofoate and chloride salts.

The compounds of the present invention may be pure or substantially pure or have a purity of at least 75%, 80%, 85%, 90%, 91%, 92%, 93%, 94%, 95%, 96%, 97%, 98%, 99% or a purity at least 99.5%. The compounds may also be part of a pharmaceutically acceptable composition. The compounds may also be part of a biological material or sample. Thus, included in the present invention are cells and tissues comprising a compound of the present invention. The cells or tissues can be in vivo, ex vivo or in vitro. Examples include liver or liver cells (e.g., hepatocytes), blood, gastric fluid (simulated or actual), intestinal fluid (simulated or actual) and urine.

In one aspect, the invention relates to the use of a compound of Formula I:

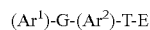

wherein:

Ar$^1$ and Ar$^2$ are substituted aryl groups;

G is an atom or group of atoms that links Ar$^1$ and Ar$^2$ through a single C, S, O, or N atom;

T is an atom or group of atoms linking Ar$^2$ to E through 1-4 contiguous atoms or is absent; and E is a functional group or moiety with a pKa≤7.4, carboxylic acid or esters thereof, sulfonic acid, tetrazole, hydroxamic acid, 6-azauracil, thiazolidinedione, acylsulfonamide, other carboxylic acid surrogates known in the art, phosphonic acid, phosphonic acid monoester, phosphinic acid, or a prodrug thereof, or an atom or group of atoms containing an O or N that binds the thyroid hormone binding pocket of a TRα or TRβ.

In another aspect, the invention relates to the use of a compound of Formula II:

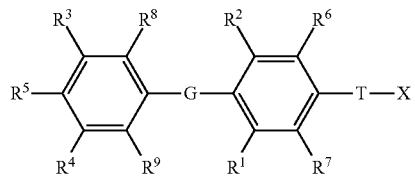

wherein:

G is selected from the group consisting of —O—, —S—, —Se—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-, or CH$_2$ linked to any of the preceding groups;

T is selected from the group consisting of —(C$^a{}_2$)$_k$—, —CR$^b$=CR$^b$—(CR$^a{}_2$)$_n$—, —(CR$^a{}_2$)$_n$—CR$^b$=CR$^b$—, —(CR$^a{}_2$)—CR$^b$=CR$^b$—(CR$^a{}_2$)—, —O(CR$^b{}_2$)(CR$^a{}_2$)$_n$—, —S(CR$^b{}_2$)(CR$^a{}_2$)$_n$—, —N(R$^c$)(CR$^b{}_2$)(CR$^a{}_2$)$_n$—, —N(R$^b$)C(O)(CR$^a{}_2$)$_n$—, —(CR$^a{}_2$)$_n$CH(NR$^b$R$^c$)—, —C(O)(CR$^a{}_2$)$_m$—, —(CR$^a{}_2$)$_m$C(O)—, —(CR$^a{}_2$)C(O)(CR$^a{}_2$)$_n$—, —(CR$^a{}_2$)$_n$C(O)(CR$^a{}_2$)—, —C(O)NH(CR$^b{}_2$)(CR$^a{}_2$)$_p$— and —(CH$_2$)$_n$C(O)N(R$^b$)C(R$^a{}_2$)—;

k is an integer from 0-4;
m is an integer from 0-3;
n is an integer from 0-2;
p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, R$^2$, R$^6$, and R$^7$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy and cyano; or R$^6$ and T are taken together along with the carbons they are attached to form a ring of 5 to 6 atoms with 0-2 unsaturations, not including the unsaturation on the ring to which R$^6$ and T are attached, including 0 to 2 heteroatoms independently selected from —NR$^1$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a{}_2$)— or —C(O)— bonded to a ring carbon or a ring nitrogen;

R$^1$ is selected from the group consisting of hydrogen, —C(O)C$_1$-C$_4$ alkyl and —C$_1$-C$_4$ alkyl; or R$^1$ and R$^7$ are taken together along with the carbons to which they are attached to form an optionally substituted ring of 5 to 6 atoms with 0-2 unsaturations, not including the unsaturation on the ring to which R$^1$ and R$^7$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^8$ and R$^9$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a{}_2$)aryl, C(O)aryl, C(O) alkyl and cyano;

R$^3$ and R$^4$ are each independently selected from the group consisting of hydrogen, halogen, —CF$_3$, —OCF$_3$, cyano, optionally, substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_m$aryl, optionally substituted —(CR$^a{}_2$)$_m$cycloalkyl, optionally substituted —(CR$^a{}_2$)$_n$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^h$, —C(O)OR$^h$, —C(O)R$^e$, —N(R$^b$)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, optionally substituted —(CR$^b{}_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which $R^3$ and $R^8$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom; or $R^8$ and G are taken together along with the carbon atoms to which they are attached to form an optionally substituted ring of formula —CH=CH—CH=, —N=CH—CH=, —CH=N—CH= or —CH=H—N=;

$R^5$ is selected from the group consisting of —OH, optionally substituted —$OC_1$-$C_6$ alkyl, —$OC(O)R^e$, —OC(O)O$R^h$, —F, —$NHC(O)R^e$, —NHS(=O)$R^e$, —NHS(=O)$_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another aspect, the invention relates to the use of a compound of Formula III:

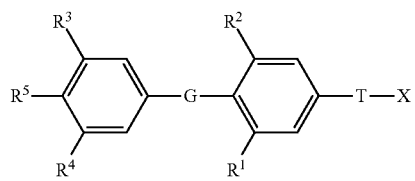

wherein:

G is selected from the group consisting of —O—, —S—, —Se—, —S(=O)—, —S(=O)$_2$—, —Se—, —$CH_2$—, —$CF_2$—, —CHF—, —C(O)—, —CH(OH)—, —CH($C_1$-$C_4$ alkyl)-, —CH($C_1$-$C_4$ alkoxy)-, —C(=$CH_2$)—, —NH—, and —N($C_1$-$C_4$ alkyl)-, or $CH_2$ linked to any of the preceding groups;

T is selected from the group consisting of —(C$R^a_2$)$_k$—, —$CR^b$=$CR^b$—(C$R^a_2$)$_n$—, —(C$R^a_2$)$_n$—$CR^b$=$CR^b$—, —(C$R^a_2$)—$CR^b$=$CR^b$—(C$R^a_2$)—, —O(C$R^b_2$)(C$R^a_2$)$_n$—, —S(C$R^b_2$)(C$R^a_2$)$_n$—, —N($R^e$)(C$R^b_2$)(C$R^a_2$)$_n$—, —N($R^b$)C(O)(C$R^a_2$)$_n$—, —(C$R^a_2$)$_n$CH(N$R^b R^c$)—, —C(O)(C$R^a_2$)$_m$—, —(C$R^a_2$)$_m$C(O)—, —(C$R^a_2$)C(O)(C$R^a_2$)$_n$—, —(C$R^a_2$)$_n$C(O)(C$R^a_2$)—, —C(O)NH(C$R^b_2$)(C$R^a_2$)$_p$—, and —(CH$_2$)$_n$C(O)N($R^b$)C($R^a$)$_2$—;

k is an integer from 0-4;
m is an integer from 0-3;
n is an integer from 0-2;
p is an integer from 0-1;

Each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —NR-$^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and optionally substituted —$C_1$-$C_4$ alkyl;

Each $R^c$ is independently selected from the group consisting of hydrogen and optionally substituted —$C_1$-$C_4$ alkyl, optionally substituted —C(O)—$C_1$-$C_4$ alkyl, and —C(O)H;

$R^1$ and $R^2$ are each independently selected from the group consisting of hydrogen, halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano; with the proviso that at least one of $R^1$ and $R^2$ is not hydrogen;

$R^3$ and $R^4$ are each independently selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, optionally substituted —(C$R^a_2$)$_m$aryl, optionally substituted —(C$R^a_2$)$_m$cycloalkyl, optionally substituted —(C$R^a_2$)$_m$heterocycloalkyl, —O$R^d$, —S$R^d$, —S(=O)$R^e$, —S(=O)$_2R^e$, —S(=O)$_2NR^f R^g$, —C(O)N$R^f R^g$, —C(O)O$R^h$, —C(O)$R^e$, —N($R^b$)C(O)$R^e$, —N($R^b$)C(O)N$R^f R^g$, —N($R^b$)S(=O)$_2R^e$, —N($R^b$)S(=O)$_2NR^f R^g$, and —N$R^f R^g$;

Each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —(C$R^b_2$)$_n$aryl, optionally substituted —(C$R^b_2$)$_n$cycloalkyl, optionally substituted —(C$R^b_2$)$_n$heterocycloalkyl, and —C(O)N$R^f R^g$;

Each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —(C$R^a_2$)$_n$aryl, optionally substituted —(C$R^a_2$)$_n$cycloalkyl, and optionally substituted —(C$R^a_2$)$_n$heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —(C$R^b_2$)$_n$aryl, optionally substituted —(C$R^b_2$)$_n$cycloalkyl, and optionally substituted —(C$R^b_2$)$_n$heterocycloalkyl, or $R^f$ and $R^g$ may together form an optionally substituted heterocyclic ring, said heterocyclic ring may contain a second heterogroup within the ring selected from the group consisting of O, N$R^c$, and S, wherein said optionally substituted heterocyclic ring may be substituted with 0-4 substituents selected from the group consisting of optionally substituted —$C_1$-$C_4$ alkyl, —O$R^b$, oxo, cyano, —$CF_3$, optionally substituted phenyl, and —C(O)O$R^h$;

Each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —(C$R^b_2$)$_n$aryl, optionally substituted —(C$R^b_2$)$_n$cycloalkyl, and optionally substituted —(C$R^b_2$)$_n$heterocycloalkyl;

$R^5$ is selected from the group consisting of —OH, optionally substituted —$OC_1$-$C_6$ alkyl, —$OC(O)R^e$, —OC(O)O$R^h$, —F, —$NHC(O)R^e$, —NHS(=O)$R^e$, —NHS(=O)$_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —NR$^h$, —O—, and —S—, with the proviso that when there are 2 heteroatoms in the ring and both heteroatoms are different than nitrogen then both heteroatoms have to be separated by at least one carbon atom; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In one embodiment of the compound of Formula III:

G is selected from the group consisting of —O—, —S, and —CH$_2$;

T is selected from the group consisting of —(CR$^a_2$)$_n$—, —O(CR$^b_2$)(CR$^a_2$)$_p$—, —S(CR$^b_2$)(CR$^a_2$)$_p$—, —N(R$^c$)(CR$^b_2$)(CR$^a_2$)$_p$—, —N(R$^b$)C(O)(CR$^a_2$)$_p$—, —(CR$^a_2$)CH(NR$^b$R$^c$)—, and —C(O)NH(CR$^b_2$)—;

n is an integer from 0-2;

p is an integer from 0-1;

Each R$^a$ is independently selected from the group consisting of hydrogen, —CH$_3$, halogen, —OH, —OCH$_3$, —OCF$_3$, and —NR$^b$R$^c$; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and —CH$_3$;

Each R$^c$ is independently selected from the group consisting of hydrogen and —CH$_3$, —C(O)—CH$_3$, and —C(O)H;

R$^1$ and R$^2$ are each independently selected from the group consisting of hydrogen, halogen, —CH$_3$, —CF$_3$, and cyano; with the proviso that at least one of R$^1$ and R$^2$ is not hydrogen;

R$^3$ is selected from the group consisting of hydrogen, halogen, optionally substituted —C$_1$-C$_6$ alkyl, optionally substituted —(CR$^a_2$)$_m$aryl, optionally substituted —(CR$^a_2$)$_m$cycloalkyl, optionally substituted —(CR$^a_2$)$_m$heterocycloalkyl, —S(=O)$_2$R$^e$, —S(=O)$_2$NR$^f$R$^g$, —C(O)NR$^f$R$^g$, and —C(O)R$^e$;

R$^4$ is selected from the group consisting of hydrogen, halogen, and optionally substituted —C$_1$-C$_6$ alkyl;

Each R$^e$ is selected from the group consisting of optionally substituted —C$_1$-C$_6$ alkyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_6$ alkyl, optionally substituted —(CR$^b_2$)$_n$aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, said heterocyclic ring may contain a second heterogroup within the ring selected from the group consisting of O, NR$^e$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_6$ alkyl, optionally substituted —(CR$^b_2$)$_n$aryl, optionally substituted —(CR$^b_2$)$_n$cycloalkyl, and optionally substituted —(CR$^b_2$)$_n$heterocycloalkyl;

R$^5$ is selected from the group consisting of —OH, —OCH$_3$, —OC(O)R$^e$, —OC(O)OR$^e$, and —NHC(O)R$^e$; or R$^3$ and R$^5$ are taken together along with the carbons they are attached to form an optionally substituted ring of 5 atoms with 1 unsaturation, not including the unsaturation on the ring to which R$^3$ and R$^5$ are attached, including 0 to 2 heteroatoms independently selected from —NR$^h$, —O—, and —S—, with the proviso that when there are 2 heteroatoms in the ring and both heteroatoms are different than nitrogen then both heteroatoms have to be separated by at least one carbon atom; and X is carboxylic acid or esters thereof, carboxylic acid amid; sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another embodiment of the compound of Formula III:

G is selected from the group consisting of —O—, —S, and —CH$_2$;

T is selected from the group consisting of a bond, —(CH$_2$)$_n$—, —OCH$_2$—, —SCH$_2$—, —NHCH$_2$—, —NHC(O)(CH$_2$)$_p$—, and —(CH$_2$)CH(NH$_2$)—, and —C(O)NH(CH$_2$)—;

n is an integer from 0-2;

p is an integer from 0-1;

R$^1$ and R$^2$ are each independently selected from the group consisting of hydrogen, Cl, Br, I, —CH$_3$, —CF$_3$, and cyano; with the proviso that at least one of R$^1$ and R$^2$ is not hydrogen;

R$^3$ is selected from the group consisting of hydrogen, halogen, optionally substituted —C$_1$-C$_6$ alkyl, optionally substituted —(CH$_2$)aryl, optionally substituted —CH(OH)aryl, optionally substituted —(CH$_2$)cycloalkyl, optionally substituted —CH(OH)cycloalkyl, optionally substituted —(CH$_2$)heterocycloalkyl, optionally substituted —CH(OH)heterocycloalkyl, —S(=O)$_2$R$^e$, —S(=O)$_2$NR$^f$R$^g$, —C(O)NR$^f$R$^g$, and —C(O)R$^e$;

R$^4$ is selected from the group consisting of hydrogen, F, Cl, Br, iodo, and CH$_3$;

Each R$^e$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

R$^f$ and R$^g$ are each independently selected from the group consisting of hydrogen, optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl, or R$^f$ and R$^g$ may together form an optionally substituted heterocyclic ring, said heterocyclic ring may contain a second heterogroup within the ring selected from the group consisting of O, NR$^e$, and S, wherein said optionally substituted heterocyclic ring may be substituted with 0-4 substituents selected from the group consisting of optionally substituted —C$_1$-C$_4$ alkyl, —OR$^e$, oxo, cyano, —CF$_3$, optionally substituted phenyl, and —C(O)OR$^h$;

Each R$^h$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

R$^5$ is selected from the group consisting of —OH, —OCH$_3$, —OC(O)R$^e$, —OC(O)OR$^e$, and —NHC(O)R$^e$; or R$^3$ and R$^5$ are taken together along with the carbons they are attached to form an optionally substituted ring of 5 atoms with 1 unsaturation, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; and X is carboxylic acid or esters thereof, carboxylic acid amide, sulfonic acid, tetrazole, hydroxamic acid, oxamic acid; malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another aspect, the invention relates to the use of a compound of Formula IV:

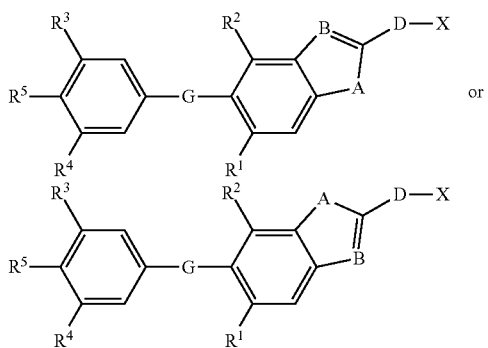

wherein:

A is selected from the group consisting of $-NR^i-$, $-O-$, and $-S-$;

B is selected from the group consisting of $-CR^b-$, and $-N-$;

$R^1$ is selected from the group consisting of hydrogen, $-C(O)C_1-C_4$ alkyl and $-C_1-C_4$ alkyl;

$R^b$ is selected from the group consisting of hydrogen and optionally substituted $-C_1-C_4$ alkyl;

G is selected from the group consisting of $-O-$, $-S-$, $-Se-$, $-S(=O)-$, $-S(=O)_2-$, $-CH_2-$, $-CF_2-$, $-CHF-$, $-C(O)-$, $-CH(OH)-$, $-NH-$, and $-N(C_1-C_4$ alkyl)-, or $CH_2$ linked to any of the preceding groups;

D is selected from the group consisting of a bond, $-(CR^a_2)-$, and $-C(O)-$;

n is an integer from 0-2;

Each $R^a$ is independently selected from the group consisting of hydrogen, optionally substituted $-C_1-C_4$ alkyl, halogen, $-OH$, optionally substituted $-O-C_1-C_4$ alkyl, $-OCF_3$, optionally substituted $-S-C_1-C_4$ alkyl, $-NR^bR^c$, optionally substituted $-C_2-C_4$ alkenyl, and optionally substituted $-C_2-C_4$ alkynyl; with the proviso that when one $R^a$ is attached to C through an O, S, or N atom, then the other $R^a$ attached to the same C is a hydrogen, or attached via a carbon atom;

$R^1$ and $R^2$ are each independently selected from the group consisting of halogen, optionally substituted $-C_1-C_4$ alkyl, optionally substituted $-S-C_1-C_3$ alkyl, optionally substituted $-C_2-C_4$ alkenyl, optionally substituted $-C_2-C_4$ alkynyl, $-CF_3$, $-OCF_3$, optionally substituted-$O-C_1-C_3$ alkyl, and cyano;

$R^3$ and $R^4$ are each independently selected from the group consisting of hydrogen, halogen, $-CF_3$, $-OCF_3$, cyano, optionally substituted $-C_1-C_{12}$ alkyl, optionally substituted $-C_2-C_{12}$ alkenyl, optionally substituted $-C_2-C_{12}$ alkynyl, optionally substituted $-(CR^a_2)_m$aryl, optionally substituted $-(CR^a_2)_m$cycloalkyl, optionally substituted $-(CR^a_2)_m$heterocycloalkyl, $-OR^d$, $-SR^d$, $-S(=O)R^e$, $-S(=O)_2R^e$, $-S(=O)_2NR^fR^g$, $-C(O)NR^fR^g$, $-C(O)OR^h$, $-C(O)R^e$, $-N(R^b)C(O)R^e$, $-N(R^b)C(O)NR^fR^g$, $-N(R^b)S(=O)_2R^e$, $-N(R^b)S(=O)_2NR^fR^g$, and $-NR^fR^g$;

Each $R^d$ is selected from the group consisting of optionally substituted $-C_1-C_{12}$ alkyl, optionally substituted $-C_2-C_{12}$ alkenyl, optionally substituted $-C_2-C_{12}$ alkynyl, optionally substituted $-(CR^b_2)_n$aryl, optionally substituted $-(CR^b_2)_n$cycloalkyl, optionally substituted $-(CR^b_2)_n$heterocycloalkyl, and $-C(O)NR^fR^g$;

Each $R^e$ is selected from the group consisting of optionally substituted $-C_1-C_{12}$ alkyl, optionally substituted $-C_2-C_{12}$ alkenyl, optionally substituted $-C_2-C_{12}$ alkynyl, optionally substituted $-(CR^a_2)_n$aryl, optionally substituted $-(CR^a_2)_n$cycloalkyl, and optionally substituted $-(CR^a_2)_n$heterocycloalkyl;

$R^f$ and $R^g$ are each independently selected from the group consisting of hydrogen, optionally substituted $-C_1-C_{12}$ alkyl, optionally substituted $-C_2-C_{12}$ alkenyl, optionally substituted $-C_2-C_{12}$ alkynyl, optionally substituted $-(CR^b_2)_n$aryl, optionally substituted $-(CR^b_2)_n$cycloalkyl, and optionally substituted $-(CR^b_2)_n$heterocycloalkyl, or $R^f$ and $R^g$ may together form an optionally substituted heterocyclic ring, which may contain a second heterogroup selected from the group consisting of O, $NR^c$, and S, wherein said optionally substituted heterocyclic ring may be substituted with 0-4 substituents selected from the group consisting of optionally substituted $-C_1-C_4$ alkyl, $-OR^b$, oxo, cyano, $-CF_3$, optionally substituted phenyl, and $-C(O)OR^h$;

Each $R^h$ is selected from the group consisting of optionally substituted $-C_1-C_{12}$ alkyl, optionally substituted $-C_2-C_{12}$ alkenyl, optionally substituted $-C_2-C_{12}$ alkynyl, optionally substituted $-(CR^b_2)_n$aryl, optionally substituted $-(CR^b_2)_n$cycloalkyl, and optionally substituted $-(CR^b_2)_n$heterocycloalkyl;

$R^5$ is selected from the group consisting of $-OH$, optionally substituted $-OC_1-C_6$ alkyl, $-OC(O)R^e$, $-OC(O)OR^h$, $-F$, $-NHC(O)R^e$, $-NHS(=O)R^e$, $-NHS(=O)_2R^e$, $-NHC(=S)NH(R^h)$, and $-NHC(O)NH(R^h)$; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In one embodiment of the compound of Formula IV:

A is selected from the group consisting of $-NR^i-$, $-O-$, and $-S-$;

B is selected from the group consisting of $-CR^b-$, and $-N-$;

$R^i$ is selected from the group consisting of hydrogen, $-C(O)C_1-C_4$ alkyl and $-C_1-C_4$ alkyl;

$R^b$ is selected from the group consisting of hydrogen and optionally substituted $-C_1-C_4$ alkyl;

G is selected from the group consisting of $-O-$, $-S-$, and $-CH_2-$;

D is selected from the group consisting of a bond, $-(CR^a_2)-$, and $-C(O)-$;

n is an integer from 0-2;

Each $R^a$ is independently selected from the group consisting of hydrogen, $-CH_3$, halogen, $-OH$, $-OCH_3$, $-OCF_3$, and $-NR^bR^c$; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and $-CH_3$;

Each $R^e$ is independently selected from the group consisting of hydrogen, —$CH_3$, —C(O)—$CH_3$, and —C(O)H;

$R^1$ and $R^2$ are each independently selected from the group consisting of hydrogen, halogen, —$CH_3$, —$CF_3$, and cyano; with the proviso that at least one of $R^1$ and $R^2$ is not hydrogen;

$R^3$ is selected from the group consisting of hydrogen, halogen, optionally substituted —$C_1$-$C_6$ alkyl, optionally substituted —$(CR^a{}_2)_m$aryl, optionally substituted —$(CR^a{}_2)_m$cycloalkyl, optionally substituted —$(CR^a{}_2)_m$heterocycloalkyl, —S(=O)$_2R^e$, —S(=O)$_2$NR$^f$R$^g$, —C(O)NR$^f$R$^g$, and —C(O)R$^e$, $R^4$ is selected from the group consisting of hydrogen, halogen, and optionally substituted —$C_1$-$C_6$ alkyl;

Each $R^e$ is selected from the group consisting of optionally substituted —$C_1$-$C_6$ alkyl, optionally substituted —$(CR^a{}_2)_n$aryl, optionally substituted —$(CR^a{}_2)_n$cycloalkyl, and optionally substituted —$(CR^a{}_2)_n$heterocycloalkyl;

$R^f$ and $R^g$ are each independently selected from the group consisting of hydrogen, optionally substituted —$C_1$-$C_6$ alkyl, optionally substituted —$(CR^b{}_2)_n$aryl, optionally substituted —$(CR^b{}_2)_n$cycloalkyl, and optionally substituted —$(CR^b{}_2)_n$heterocycloalkyl, or $R^f$ and $R^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —$C_1$-$C_4$ alkyl, —OR$^b$, oxo, cyano, —$CF_3$, optionally substituted phenyl, and —C(O)OR$^h$;

Each $R^h$ is selected from the group consisting of optionally substituted —$C_1$-$C_6$ alkyl, optionally substituted —$(CR^b{}_2)_n$aryl, optionally substituted —$(CR^b{}_2)_n$cycloalkyl, and optionally substituted —$(CR^b{}_2)_n$heterocycloalkyl;

$R^5$ is selected from the group consisting of —OH, —OCH$_3$, —OC(O)R$^e$, —OC(O)OR$^e$, and —NHC(O)R$^e$; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another embodiment of the compound of Formula IV:

A is selected from the group consisting of —NR$^i$—, —O—, and —S—;

B is selected from the group consisting of —CR$^b$—, and —N—;

$R^1$ is selected from the group consisting of hydrogen, —C(O)C$_1$-C$_4$ alkyl and —C$_1$-C$_4$ alkyl;

$R^b$ is selected from the group consisting of hydrogen and optionally substituted —$C_1$-$C_4$ alkyl;

G is selected from the group consisting of —O—, —S—, and —CH$_2$—;

D is selected from the group consisting of a bond, —(CH$_2$)—, and —C(O)—;

n is an integer from 0-2;

$R^1$ and $R^2$ are each independently selected from the group consisting of hydrogen, Cl, Br, I, —CH$_3$, —CF$_3$, and cyano; with the proviso that at least one of $R^1$ and $R^2$ is not hydrogen;

$R^3$ is selected from the group consisting of hydrogen, halogen, optionally substituted —$C_1$-$C_6$ alkyl, optionally substituted —(CH$_2$)aryl, optionally substituted —CH(OH)aryl, optionally substituted —(CH$_2$)cycloalkyl, optionally substituted —CH(OH)cycloalkyl, optionally substituted —(CH$_2$)heterocycloalkyl, optionally substituted —CH(OH)heterocycloalkyl, —S(=O)$_2$R$^e$, —S(=O)$_2$NR$^f$R$^g$, —C(O)NR$^f$R$^g$, and —C(O)R$^e$;

$R^4$ is selected from the group consisting of hydrogen, F, Cl, Br, iodo, and CH$_3$;

Each $R^e$ is selected from the group consisting of optionally substituted —$C_1$-$C_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

$R^f$ and $R^g$ are each independently selected from the group consisting of hydrogen, optionally substituted —$C_1$-$C_6$ alkyl, optionally substituted —(CH$_2$)$_n$aryl, optionally substituted —(CH$_2$)$_n$cycloalkyl, and optionally substituted —(CH$_2$)$_n$heterocycloalkyl, or $R^f$ and $R^g$ may together form an optionally substituted heterocyclic ring, said heterocyclic ring may contain a second heterogroup within the ring selected from the group consisting of O, NR$^e$, and S, wherein said optionally substituted heterocyclic ring may be substituted with 0-4 substituents selected from the group consisting of optionally substituted —$C_1$-$C_4$ alkyl, —OR$^e$, oxo, cyano, —CF$_3$, optionally substituted phenyl, and —C(O)OR$^h$;

Each $R^h$ is selected from the group consisting of optionally substituted —$C_1$-$C_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

$R^5$ is selected from the group consisting of —OH, —OCH$_3$, —OC(O)R$^e$, —OC(O)OR$^e$, and —NHC(O)R$^e$; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In a further aspect, the invention relates to the use of a compound of Formula V:

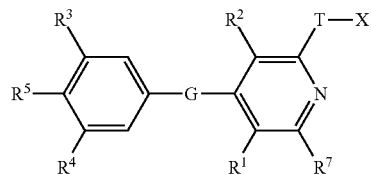

wherein:

G is selected from the group consisting of —O—, —S—, —Se—, —S(=O)—, —S(=O)$_2$—, —CH$_2$—, —CF$_2$—, —C(O)—, —CH(OH)—, —NH—, and —N(C$_1$-C$_4$ alkyl)-, or CH$_2$ linked to any of the preceding groups;

T is selected from the group consisting of —(CR$^a{}_2$)$_k$—, —CR$^b$=CR$^b$—(CR$^a{}_2$)$_n$—, —(CR$^a{}_2$)$_n$—CR$^b$=CR$^b$—, —(CR$^a{}_2$)—CR$^b$=CR$^b$—(CR$^a{}_2$)—, —O(CR$^b{}_2$)(CR$^a{}_2$)$_n$—, —S(CR$^b{}_2$)(CR$^a{}_2$)$_n$, —N(R$^c$)(CR$^b{}_2$)(CR$^a{}_2$)$_n$—, —N(R$^b$)C(O)(CR$^a{}_2$)$_n$—, —(CR$^a{}_2$)$_n$CH(NR$^b$R$^c$)—, —C(O)(CR$^a{}_2$)$_m$—, —(CR$^a{}_2$)$_m$C(O)—, and —(CH$_2$)$_n$C(O)N(R$^b$)C(R$^a$)$_2$—;

k is an integer from 0-4;

m is an integer from 0-3;

n is an integer from 0-2;

p is an integer from 0-1;

Each $R^a$ is independently selected from the group consisting of hydrogen, optionally substituted —$C_1$-$C_4$ alkyl, halogen, —OH, optionally substituted —O—$C_1$-$C_4$ alkyl, —OCF$_3$, optionally substituted —S—$C_1$-$C_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$alkyl, and —C(O)H;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^8$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a{}_2$)aryl, C(O)aryl, C(O)alkyl and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_m$aryl, optionally substituted —(CR$^a{}_2$)$_m$cycloalkyl, optionally substituted —(CR$^a{}_2$)$_m$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, optionally substituted —(CR$^b{}_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, which may contain a second heterogroup selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH=CH—CH=, —N=CH—CH=, —CH=N—CH= or —CH=CH—N=;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form a ring of 5 to 6 atoms with 0-2 unsaturations, not including the unsaturation on the ring to which R$^3$ and R$^5$ are attached, including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom;

R$^7$ is selected from the group consisting of hydrogen, halogen, amino, hydroxyl, —O—C$_1$-C$_4$ alkyl, —SH and —S—C$_1$-C$_4$ alkyl; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphor& acid monoester, phosphinic acid, or a prodrug thereof.

In one embodiment of the compound of Formula V:

G is selected from the group consisting of —O—, —S—, and —CH$_2$—;

T is selected from the group consisting of —(CR$^a{}_2$)$_n$—, —O(CR$^b{}_2$)(CR$^a{}_2$)$_p$—, —S(CR$^b{}_2$)(CR$^a{}_2$)$_p$—, —N(R$^e$)(CR$^a{}_2$)(CR$^a{}_2$)$_p$—, —N(R$^b$)C(O)(CR$^a{}_2$)$_p$—, —(CR$^a{}_2$)CH(NR$^b$R$^c$)—, and —C(O)NH(CR$^a{}_2$)—;

n is an integer from 0-2;

p is an integer from 0-1;

Each R$^a$ is independently selected from the group consisting of hydrogen, —CH$_3$, halogen, —OH, —OCH$_3$, —OCF$_3$, and —NR$^b$R$^c$; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and —CH$_3$;

Each R$^c$ is independently selected from the group consisting of hydrogen, —CH$_3$, —C(O)—CH$_3$, and —C(O)H;

R$^1$ and R$^2$ are each independently selected from the group consisting of hydrogen, halogen, —CH$_3$, —CF$_3$, and cyano; with the proviso that at least one of R$^1$ and R$^2$ is not hydrogen;

R$^8$ is selected from the group consisting of hydrogen, halogen, —CH$_3$, —CF$_3$, and cyano;

R$^3$ is selected from the group consisting of hydrogen, halogen, optionally substituted —C$_1$-C$_6$ alkyl, optionally substituted —(CR$^a{}_2$)$_m$aryl, optionally substituted —(CR$^a{}_2$)$_m$cycloalkyl, optionally substituted —(CR$^a{}_2$)$_m$heterocycloalkyl, —S(=O)$_2$R$^e$, —S(=O)$_2$NR$^f$R$^g$, —C(O)NR$^f$R$^g$, and —C(O)R$^e$, R$^4$ is selected from the group consisting of hydrogen, halogen, and optionally substituted —C$_1$-C$_6$ alkyl;

Each R$^e$ is selected from the group consisting of optionally substituted —C$_1$-C$_6$ alkyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl;

R$^f$ and R$^g$ are each independently selected from the group consisting of hydrogen, optionally substituted —C$_1$-C$_6$ alkyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_6$ alkyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl;

R$^5$ is selected from the group consisting of —OH, —OCH$_3$, —OC(O)R$^e$, —OC(O)OR$^e$, and —NHC(O)R$^e$; or R$^3$ and R$^5$ are taken together along with the carbons they are attached to form an optionally substituted ring of 5 atoms with 1 unsaturation, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^7$ is selected from the group consisting of hydrogen, halogen, amino, hydroxyl, —O—CH$_3$, —SH and —S—CH$_3$; and X is carboxylic acid or esters thereof, carboxylic acid amid; sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another embodiment of the compound of Formula V:

G is selected from the group consisting of —O—, —S, and —CH$_2$;

T is selected from the group consisting of a bond, —(CH$_2$)$_n$, —OCH$_2$—, —SCH$_2$—, —NHCH$_2$—, —NHC(O)(CH$_2$)$_p$—, —(CH$_2$)CH(NH$_2$)—, and —C(O)NH(CH$_2$)—;

n is an integer from 0-2;

p is an integer from 0-1;

R$^1$ and R$^2$ are each independently selected from the group consisting of hydrogen, Cl, Br, I, —CH$_3$, —CF$_3$, and cyano; with the proviso that at least one of R$^1$ and R$^2$ is not hydrogen;

R$^8$ is selected from the group consisting of hydrogen, halogen, —CH$_3$, —CF$_3$, and cyano;

R$^3$ selected from the group consisting of hydrogen, halogen, optionally substituted —C$_1$-C$_6$ alkyl, optionally substituted —(CH$_2$)aryl, optionally substituted —CH(OH)aryl, optionally substituted —(CH$_2$)cycloalkyl, optionally substituted —CH(OH)cycloalkyl, optionally substituted —(CH$_2$)heterocycloalkyl, optionally substituted —CH(OH)heterocycloalkyl, —S(=O)$_2$R$^e$, —S(=O)$_2$NR$^f$R$^g$, —C(O)NR$^f$R$^g$, and —C(O)R$^e$;

R$^4$ is selected from the group consisting of hydrogen, F, Cl, Br, iodo, and CH$_3$;

Each R$^e$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

R$^f$ and R$^g$ are each independently selected from the group consisting of hydrogen, optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^e$, oxo, cyano, —CF$_3$, optionally substituted phenyl, and —C(O)OR$^h$;

Each R$^h$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

R$^5$ is selected from the group consisting of —OH, —OCH$_3$, —OC(O)R$^e$, —OC(O)OR$^e$, and —NHC(O)R$^e$; or R$^3$ and R$^5$ are taken together along with the carbons they are attached to form an optionally substituted ring of 5 atoms with 1 unsaturation, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^7$ is selected from the group consisting of hydrogen, F, Cl, amino, hydroxyl, and —O—CH$_3$; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another aspect, the invention relates to the use of a compound of Formula VI:

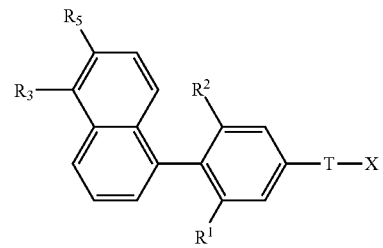

wherein:

T is selected from the group consisting of —(CR$^a{}_2$)$_k$—, —CR$^b$=CR$^b$—(CR$^a{}_2$)$_n$—, —(CR$^a{}_2$)$_n$—CR$^b$=CR$^b$—, —(CR$^a{}_2$)—CR$^b$=CR$^b$—(CR$^a{}_2$)—, —O(CR$^b{}_2$)(CR$^a{}_2$)$_n$, —S(CR$^b{}_2$)(CR$^a{}_2$)$_n$—, —N(R$^c$)(CR$^b{}_2$)(CR$^a{}_2$)$_n$—, —N(R$^b$)C(O)(CR$^a{}_2$)$_n$—, —(CR$^a{}_2$)$_n$CH(NR$^b$R$^c$)—, —C(O)(CR$^a{}_2$)$_m$—, —(CR$^a{}_1$)$_m$C(O)—, —(CR$^a{}_2$)C(O)(CR$^a{}_2$)$_n$—, —(CR$^a{}_2$)$_n$C(O)(CR$^a{}_2$)—, —C(O)NH(CR$^b{}_2$)(CR$^a{}_2$)$_p$—, and —(CH$_2$)$_n$C(O)N(R$^b$)C(R$^a$)$_2$—;

k is an integer from 0-4;
m is an integer from 0-3;
n is an integer from 0-2;
p is an integer from 0-1;

Each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and optionally substituted —$C_1$-$C_4$ alkyl;

Each $R^c$ is independently selected from the group consisting of hydrogen and optionally substituted —$C_1$-$C_4$ alkyl, optionally substituted —C(O)—$C_1$-$C_4$ alkyl, and —C(O)H;

$R^1$ and $R^2$ are each independently selected from the group consisting of hydrogen, halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano; with the proviso that at least one of $R^1$ and $R^2$ is not hydrogen;

$R^3$ is selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_m$aryl, optionally substituted —$(CR^a_2)_m$cycloalkyl, optionally substituted —$(CR^a_2)_m$heterocycloalkyl, —$OR^d$, —$SR^d$, —S(=O)$R^e$, —S(=O)$_2R^e$, —S(=O)$_2$$NR^fR^g$, —C(O)$NR^fR^g$, —C(O)$OR^h$, —C(O)$R^e$, —N($R^b$)C(O)$R^e$, —N($R^b$)C(O)$NR^fR^g$, —N($R^b$)S(=O)$_2R^e$, —N($R^b$)S(=O)$_2NR^fR^g$, and —$NR^fR^g$;

Each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, optionally substituted —$(CR^b_2)_n$heterocycloalkyl, and —C(O)$NR^fR^g$;

Each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_n$aryl, optionally substituted —$(CR^a_2)_n$cycloalkyl, and optionally substituted —$(CR^a_2)_n$heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, and optionally substituted —$(CR^b_2)_n$heterocycloalkyl, or $R^f$ and $R^g$ may together form an optionally substituted heterocyclic ring, said heterocyclic ring may contain a second heterogroup within the ring selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —C(O)$OR^h$;

Each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, and optionally substituted —$(CR^b_2)_n$heterocycloalkyl;

$R^5$ is selected from the group consisting of —OH, optionally substituted —$OC_1$-$C_6$ alkyl, —OC(O)$R^e$, —OC(O)$OR^h$, —F, —NHC(O)$R^e$, —NHS(=O)$R^e$, —NHS(=O)$_2R^e$, —NHC(=S)NH($R^h$), and —NHC(O)NH($R^h$); and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In one embodiment of the compound of Formula VI

T is selected from the group consisting of —$(CR^a_2)_n$—, —O($CR^b_2$)($CR^a_2$)$_p$—, —S($CR^b_2$)($CR^a_2$)$_p$—, —N($R^c$)($CR^b_2$)($CR^a_2$)$_p$—, —N($R^b$)C(O)($CR^a_2$)$_p$—, —($CR^a_2$)CH($NR^bR^c$)—, and —C(O)NH($CR^b_2$)—;

n is an integer from 0-2;
p is an integer from 0-1;

Each $R^a$ is independently selected from the group consisting of hydrogen, —$CH_3$, halogen, —OH, —$OCH_3$, —$OCF_3$, and —$NR^bR^c$; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and —$CH_3$;

Each $R^c$ is independently selected from the group consisting of hydrogen and —$CH_3$, —C(O)—$CH_3$, and —C(O)H;

$R^1$ and $R^2$ are each independently selected from the group consisting of hydrogen, halogen, —$CH_3$, —$CF_3$, and cyano; with the proviso that at least one of $R^1$ and $R^2$ is not hydrogen;

$R^3$ is selected from the group consisting of hydrogen, halogen, optionally substituted —$C_1$-$C_6$ alkyl, optionally substituted —$(CR^a_2)_m$aryl, optionally substituted —$(CR^a_2)_m$cycloalkyl, optionally substituted —$(CR^a_2)_m$heterocycloalkyl, —S(=O)$_2R^e$, —S(=O)$_2NR^fR^g$, —C(O)$NR^fR^g$, and —C(O)$R^e$;

Each $R^e$ is selected from the group consisting of optionally substituted —$C_1$-$C_6$ alkyl, optionally substituted —$(CR^a_2)_n$aryl, optionally substituted —$(CR^a_2)_n$cycloalkyl, and optionally substituted —$(CR^a_2)_n$heterocycloalkyl;

$R^f$ and $R^g$ are each independently selected from the group consisting of hydrogen, optionally substituted —$C_1$-$C_6$ alkyl, optionally substituted —$(CR^b_2)_n$aryl, optionally substituted —$(CR^b_2)_n$cycloalkyl, and optionally substituted —$(CR^b_2)_n$heterocycloalkyl, or $R^f$ and $R^g$ may together form an optionally substituted heterocyclic ring, said heterocyclic ring may contain a second heterogroup within the ring selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —C(O)$OR^h$;

Each $R^h$ is selected from the group consisting of optionally substituted —$C_1$-$C_6$ alkyl, optionally substituted —$(CR^b_2)_n$aryl, optionally substituted —$(CR^b_2)_n$cycloalkyl, and optionally substituted —$(CR^b_2)$heterocycloalkyl;

$R^5$ is selected from the group consisting of —OH, —$OCH_3$, —OC(O)$R^e$, —OC(O)$OR^e$, and —NHC(O)$R^e$; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another embodiment of the compound of Formula VI:

T is selected from the group consisting, of a bond, —$(CH_2)_n$—, —$OCH_2$—, —$SCH_2$—, —$NHCH_2$—, —$NHC(O)(CH_2)_p$—, —$(CH_2)CH(NH_2)$—, and —$C(O)NH(CH_2)$—;

n is an integer from 0-2;

p is an integer from 0-1;

$R^1$ and $R^2$ are each independently selected from the group consisting of hydrogen, Cl, Br, I, —$CH_3$, —$CF_3$, and cyano; with the proviso that at least one of $R^1$ and $R^2$ is not hydrogen;

$R^3$ is selected from the group consisting of hydrogen, halogen, optionally substituted —$C_1$-$C_6$ alkyl, optionally substituted —$(CH_2)$aryl, optionally substituted —$CH(OH)$aryl, optionally substituted —$(CH_2)$cycloalkyl, optionally substituted —$CH(OH)$cycloalkyl, optionally substituted —$(CH_2)$heterocycloalkyl, optionally substituted —$CH(OH)$heterocycloalkyl, —$S(=O)_2R^e$, —$S(=O)_2NR^fR^g$, —$C(O)NR^fR^g$, and —$C(O)R^e$;

Each $R^e$ is selected from the group consisting of optionally substituted —$C_1$-$C_6$ alkyl, optionally substituted —$(CH_2)_n$aryl, optionally substituted —$(CH_2)_n$cycloalkyl, and optionally substituted —$(CH_2)_n$heterocycloalkyl;

$R^f$ and $R^g$ are each independently selected from the group consisting of hydrogen, optionally substituted —$C_1$-$C_6$ alkyl, optionally substituted —$(CH_2)_n$aryl, optionally substituted —$(CH_2)_n$cycloalkyl, and optionally substituted —$(CH_2)_n$heterocycloalkyl, or $R^f$ and $R^g$ may together form an optionally substituted heterocyclic ring, said heterocyclic ring may contain a second heterogroup within the ring selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^e$, oxo, cyano, —$CF_3$, optionally substituted phenyl, and —$C(O)OR^h$;

Each $R^h$ is selected from the group consisting of optionally substituted —$C_1$-$C_6$ alkyl, optionally substituted —$(CH_2)_n$aryl, optionally substituted —$(CH_2)_n$cycloalkyl, and optionally substituted —$(CH_2)_n$heterocycloalkyl;

$R^5$ is selected from the group consisting of —OH, —$OCH_3$, —$OC(O)R^e$, —$OC(O)OR^e$, and —$NHC(O)R^e$; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphoric acid, phosphoric acid monoester, phosphinic acid, or a prodrug thereof.

In a further aspect, the invention relates to the use of a compound of Formula VII:

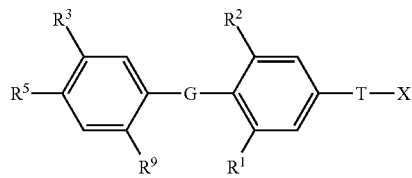

wherein:

G is selected from the group consisting of —O—, —S—, —Se—, —S(=O)—, —$S(=O)_2$—, —$CH_2$—, —$CF_2$—, —CHF—, —C(O)—, —CH(OH)—, —NH—, and —$N(C_1$-$C_4$ alkyl)-, or $CH_2$ linked to any of the preceding groups;

T is selected from the group consisting of —$(CR^a_2)_k$—, —$CR^b=CR^b$—$(CR^a_2)_n$—, —$(CR^a_2)_n$—$CR^b=CR^b$—, —$(CR^a_2)$—$CR^b=CR^b$—$(CR^a_2)$—, —$O(CR^b_2)(CR^a_2)_n$—, —$S(CR^b_2)(CR^a_2)_n$—, —$N(R^c)(CR^b_2)(CR^a_2)_n$—, —$N(R^b)C(O)(CR^a_2)_n$—, —$(CR^a_2)_nCH(NR^bR^c)$—, —$C(O)(CR^a_2)_m$—, —$(CR^a_2)_mC(O)$—, —$(CR^a_2)C(O)(CR^a_2)_n$—, —$(CR^a_2)_nC(O)(CR^a_2)$—, —$C(O)NH(CR^b_2)(CR^a_2)_p$—, and —$(CH_2)_nC(O)N(R^b)C(R^a)_2$—;

k is an integer from 0-4;

m is an integer from 0-3;

n is an integer from 0-2;

p is an integer from 0-1;

Each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and optionally substituted —$C_1$-$C_4$ alkyl;

Each $R^c$ is independently selected from the group consisting of hydrogen and optionally substituted —$C_1$-$C_4$ alkyl, optionally substituted —C(O)—$C_1$-$C_4$ alkyl, and —C(O)H;

$R^1$ and $R^2$ are each independently selected from the group consisting of hydrogen, halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano; with the proviso that at least one of $R^1$ and $R^2$ is not hydrogen;

$R^3$ is selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_m$aryl, optionally substituted —$(CR^a_2)_n$cycloalkyl, optionally substituted —$(CR^a_2)_n$heterocycloalkyl, —$OR^d$, —$SR^d$, —$S(=O)R^e$, —$S(=O)_2R^e$, —$S(=O)_2NR^fR^g$, —$C(O)NR^fR^g$, —$C(O)OR^h$, —$C(O)R^e$, —$N(R^b)C(O)R^e$, —$N(R^b)C(O)NR^fR^g$, —$N(R^b)S(=O)_2R^e$, —$N(R^b)S(=O)_2NR^fR^g$, and —$NR^fR^g$;

Each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, optionally substituted —$(CR^b_2)_n$heterocycloalkyl, and —$C(O)NR^fR^g$;

Each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_n$aryl, optionally substituted —$(CR^a_2)_n$cycloalkyl, and optionally substituted —$(CR^a_2)_n$heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, and optionally substituted —$(CR^b_2)_n$heterocycloalkyl, or $R^f$ and $R^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form an optionally substituted ring of 5 to 6 atoms with 0-2 unsaturations, not including, the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^9$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a{}_2$)aryl, C(O)aryl, C(O)alkyl and cyano; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In one embodiment of the compound of Formula VII:

G is selected from the group consisting of —O—, —S—, and —CH$_2$—;

T is selected from the group consisting of —(CR$^a{}_2$)$_n$—, —O(CR$^b{}_2$)(CR$^a{}_2$)$_p$—, —S(CR$^b{}_2$)(CR$^a{}_2$)$_p$—, —N(R$^c$)(CR$^b{}_2$)(CR$^a{}_2$)$_p$—, —N(R$^b$)C(O)(CR$^a{}_2$)$_p$—, —(CR$^a{}_2$)CH(NR$^b$R$^c$)—, and —C(O)NH(CR$^b{}_2$)—;

n is an integer from 0-2;

p is an integer from 0-1;

Each R$^a$ is independently selected from the group consisting of hydrogen, —CH$_3$, halogen, —OH, —OCH$_3$, —OCF$_3$, and —NR$^b$R$^c$; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and —CH$_3$;

Each R$^c$ is independently selected from the group consisting of hydrogen, —CH$_3$, —C(O)—CH$_3$, and —C(O)H;

R$^1$ and R$^2$ are each independently selected from the group consisting of hydrogen, halogen, —CH$_3$, —CF$_3$, and cyano; with the proviso that at least one of R$^1$ and R$^2$ is not hydrogen;

R$^3$ is selected from the group consisting of hydrogen, halogen, optionally substituted —C$_1$-C$_6$ alkyl, optionally substituted —(CR$^a{}_2$)$_m$aryl, optionally substituted —(CR$^a{}_2$)$_m$cycloalkyl, optionally substituted —(CR$^a{}_2$)$_m$heterocycloalkyl, —S(=O)$_2$R$^e$, —S(=O)$_2$NR$^f$R$^g$, —C(O)NR$^f$R$^g$, and —C(O)R$^e$;

Each R$^e$ is selected from the group consisting of optionally substituted —C$_1$-C$_6$ alkyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl;

R$^f$ and R$^g$ are each independently selected from the group consisting of hydrogen, optionally substituted —C$_1$-C$_6$ alkyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_6$ alkyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl;

R$^5$ is selected from the group consisting of —OH, —OCH$_3$, —OC(O)R$^e$, —OC(O)OR$^e$, and —NHC(O)R$^e$; or R$^3$ and R$^5$ are taken together along with the carbons they are attached to form an optionally substituted ring of 5 atoms with 1 unsaturation, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^9$ is selected from the group consisting of optionally substituted —C$_1$-C$_4$ alkyl, —(CR$^a{}_2$)aryl, C(O)aryl and C(O)alkyl; and X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In another embodiment of the compound of Formula VII:

G is selected from the group consisting of —O—, —S—, and —CH$_2$—;

T is selected from the group consisting of a bond, —(CH$_2$)$_n$—, —OCH$_2$—, —SCH$_2$—, —NHCH$_2$—, —NHC(O)(CH$_2$)$_p$—, —(CH$_2$)CH(NH$_2$)—, and —C(O)NH(CH$_2$)—;

n is an integer from 0-2;

p is an integer from 0-1;

R$^1$ and R$^2$ are each independently selected from the group consisting of hydrogen, Cl, Br, I, —CH$_3$, —CF$_3$, and cyano; with the proviso that at least one of R$^1$ and R$^2$ is not hydrogen;

R$^3$ is selected from the group consisting of hydrogen, halogen, optionally substituted —C$_1$-C$_6$ alkyl, optionally substituted —(CH$_2$)aryl, optionally substituted —CH(OH)aryl, optionally substituted —(CH$_2$)cycloalkyl, optionally substituted —CH(OH)cycloalkyl, optionally substituted —(CH$_2$)heterocycloalkyl, optionally substituted —CH(OH)heterocycloalkyl, —S(=O)$_2$R$^e$, —S(=O)$_2$NR$^f$R$^g$, —C(O)NR$^f$R$^g$, and —C(O)R$^e$;

Each R$^e$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

$R^f$ and $R_g$ are each independently selected from the group consisting of hydrogen, optionally substituted —$C_1$-$C_6$ alkyl, optionally substituted —$(CH_2)_n$aryl, optionally substituted —$(CH_2)_n$cycloalkyl, and optionally substituted —$(CH_2)_n$heterocycloalkyl, or $R^f$ and $R^g$ may together form an optionally substituted heterocyclic ring, said heterocyclic ring may contain a second heterogroup within the ring selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^e$, oxo, cyano, —$CF_3$, optionally substituted phenyl, and —$C(O)OR^h$;

Each $R^h$ is selected from the group consisting of optionally substituted —$C_1$-$C_6$ alkyl, optionally substituted —$(CH_2)_n$aryl, optionally substituted —$(CH_2)_n$cycloalkyl, and optionally substituted —$(CH_2)_n$heterocycloalkyl;

$R^5$ is selected from the group consisting of —OH, —$OCH_3$, —$OC(O)R^e$, —$OC(O)OR^e$, and —$NHC(O)R^e$; or $R^3$ and $R^5$ are taken together along with the carbons they are attached to form an optionally substituted ring of 5 atoms with 1 unsaturation, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

$R^9$ is selected from the group consisting of optionally substituted —$C_1$-$C_4$ alkyl, —$CH_2$-aryl, C(O)aryl and C(O)alkyl;

X is carboxylic acid or esters thereof, carboxylic acid amide, sulfonic acid, tetrazole, hydroxamic acid, oxamic acid, malonamic acid, 6-azauracil, thiazolidinedione, acylsulfonamide, other carboxylic acid surrogates known in the art, phosphonic acid, phosphonic acid monoester, phosphinic acid, or a prodrug thereof.

In a further aspect, the invention relates to the use of a compound of Formula VIII:

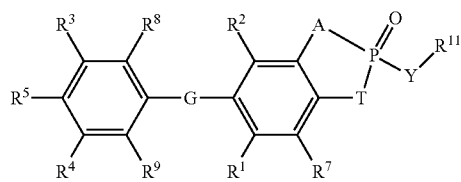

wherein:

G is selected from the group consisting of —O—, —S—, —Se—, —S(=O)—, —S(=O)$_2$—, —Se—, —$CH_2$—, —$CF_2$—, —CHF—, —C(O)—, —CH(OH)—, —CH($C_1$-$C_4$ alkyl)-, —CH($C_1$-$C_4$ alkoxy)-, —C(=$CH_2$)—, —NH—, and —N($C_1$-$C_4$ alkyl)-, or $CH_2$ linked to any of the preceding groups;

A and T are each independently selected from the group consisting of —$(CR^a_2)$—, —$(CR^a_2)_2$—, —O$(CR^b_2)$—, —S$(CR^b_2)$—, —$N(R^c)(CR^b_2)$—, —$N(R^b)C(O)$—, —C(O)$(CR^a_2)$—, —$(CR^a_2)C(O)$—, —$(CR^b_2)O$—, —$(CR^b_2)S$—, and —$(CR^b_2)N(R^c)$—;

Each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and optionally substituted —$C_1$-$C_4$ alkyl;

Each $R^c$ is independently selected from the group consisting of hydrogen and optionally substituted —$C_1$-$C_4$ alkyl, optionally substituted —C(O)—$C_1$-$C_4$ alkyl, and —C(O)H;

$R^1$, $R^2$, and $R^7$ are each independently selected from the group consisting of hydrogen, halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano; with the proviso that at least one of $R^1$ and $R^2$ is not hydrogen;

$R^8$ and $R^9$ are each independently selected from the group consisting of hydrogen, halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, hydroxy, $(CR^a_2)$aryl, C(O)aryl, C(O)alkyl and cyano;

$R^3$ and $R^4$ are each independently selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_m$aryl, optionally substituted —$(CR^a_2)_m$cycloalkyl, optionally substituted —$(CR^a_2)_m$heterocycloalkyl, —$OR^d$, —$SR^d$, —S(=O)$R^e$, —S(=O)$_2R^e$, —S(=O)$_2NR^fR^g$, —C(O)$OR^h$, —C(O)$R^e$, —$N(R^b)C(O)R^e$, —$N(R^b)C(O)NR^fR^g$, —$N(R^b)S(=O)_2R^e$, —$N(R^b)S(=O)_2NR^fR^g$, and —$NR^fR^g$;

Each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, optionally substituted —$(CR^b_2)_n$heterocycloalkyl, and —C(O)$NR^fR^g$;

Each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_n$aryl, optionally substituted —$(CR^a_2)_n$cycloalkyl, and optionally substituted —$(CR^a_2)_n$heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, and optionally substituted —$(CR^b_2)_n$heterocycloalkyl, or $R^f$ and $R^g$ may together form an optionally substituted heterocyclic ring, said heterocyclic ring may contain a second heterogroup within the ring selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —$C(O)OR^h$;

Each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$aryl, optionally substituted —$(CR^b_2)_n$cycloalkyl, and optionally substituted —$(CR^b_2)_n$heterocycloalkyl; or $R^3$ and $R^8$ are taken together along with the carbon atoms to which they are attached to form an optionally substituted ring of 5 to 6 atoms with 0-2 unsaturations, not including the unsaturation on the ring to which $R^3$ and $R^8$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom; or $R^8$ and G are taken together along with the carbon atoms to which they are attached to form an optionally substituted ring of formula —CH=CH—CH=, —NH=CH—CH=, —CH=N—CH= or —CH=CH—N=;

$R^5$ is selected from the group consisting of —OH, optionally substituted —$OC_1$-$C_6$ alkyl, —$OC(O)R^e$, —OC(O)$OR^h$, —F, —$NHC(O)R^e$, —$NHS(=O)R^e$, —$NHS(=O)_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

Y is selected from the group consisting of —O—, and —$NR^v$—;

when Y is —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z_2$, —$NR^z$—C(O)—$R^y$, —$C(R^z)_2$—OC(O)$R^y$, —$C(R^z)_2$—O—C(O)$OR^y$, —$C(R^z)_2OC(O)SR^y$, -alkyl-S—C(O)$R^y$, -alkyl-S—S-alkylhydroxy, and -alkyl-S—S—S-alkylhydroxy;

when Y is —$NR^v$—, then $R^{11}$ attached to —$NR^v$— is independently selected from the group consisting of —H, —$[C(R^z)_2]_q$—$COOR^y$, —$C(R^x)_2COOR^y$, —$[C(R^z)_2]_q$—C(O)$SR^y$, and -cycloalkylene-$COOR^y$;

m is an integer from 0-3;

n is an integer from 0-2;

q is an integer 2 or 3;

Each $R^z$ is selected from the group consisting of $R^y$ and —H;

Each $R^y$ is selected from the group consisting of alkyl, aryl, heterocycloalkyl, and aralkyl;

Each $R^x$ is independently selected from the group consisting of —H, and alkyl, or together $R^x$ and $R^x$ form a cycloalkyl group;

Each $R^v$ is selected from the group consisting of —H, lower alkyl, acyloxyalkyl, alkoxycarbonyloxyalkyl, and lower acyl;

and pharmaceutically acceptable salts and prodrugs thereof and pharmaceutically acceptable salts of said prodrugs.

In one embodiment of the compound of Formula VIII:

G is selected from the group consisting of —O—, —S—, and —$CH_2$—;

A and T are each independently selected from the group consisting of —($CR^a_2$)—, —($CR^a_2$)$_2$—, —O($CR^b_2$)—, —S($CR^b_2$)—, —N($R^c$)($CR^b_2$)—, —N($R^b$)C(O)—, —C(O)($CR^a_2$)—, —($CR^a_2$)C(O)—, —($CR^b_2$)O—, —($CR^b_2$)S—, and —($CR^b_2$)N($R^c$)—;

Each $R^a$ is independently selected from the group consisting of hydrogen, —$CH_3$, halogen, —OH, —$OCH_3$, —$OCF_3$, and —$NR^bR^c$; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and —$CH_3$;

Each $R^c$ is independently selected from the group consisting of hydrogen and —$CH_3$, —C(O)—$CH_3$, and —C(O)H;

$R^1$, $R^2$, and $R^7$ are each independently selected from the group consisting hydrogen, halogen, —$CH_3$, —$CF_3$, and cyano; with the proviso that at least one of $R^1$ and $R^2$ is not hydrogen;

$R^8$ and $R^9$ are each independently selected from the group consisting of hydrogen, halogen, —$CH_3$, —$CF_3$, ($CR^a_2$)aryl, C(O)aryl, C(O)alkyl and cyano;

$R^3$ is selected from the group consisting of hydrogen, halogen, optionally substituted —$C_1$-$C_6$ alkyl, optionally substituted —($CR^a_2$)$_m$aryl, optionally substituted —($CR^a_2$)$_m$cycloalkyl, optionally substituted —($CR^a_2$)$_m$heterocycloalkyl, —$S(=O)_2R^e$, —$S(=O)_2NR^fR^g$, —C(O)$NR^fR^g$, and —C(O)$R^e$;

$R^4$ is selected from the group consisting of hydrogen, halogen, and optionally substituted —$C_1$-$C_6$ alkyl;

Each $R^e$ is selected from the group consisting of optionally substituted —$C_1$-$C_6$ alkyl, optionally substituted —($CR^a_2$)$_n$aryl, optionally substituted —($CR^a_2$)$_n$cycloalkyl, and optionally substituted —($CR^b_2$)$_n$heterocycloalkyl;

$R^f$ and $R^g$ are each independently selected from the group consisting of hydrogen, optionally substituted —$C_1$-$C_6$ alkyl, optionally substituted —($CR^b_2$)$_n$aryl, optionally substituted —($CR^b_2$)$_n$cycloalkyl, and optionally substituted —($CR^b_2$)$_n$heterocycloalkyl, or $R^f$ and $R^g$ may together form an optionally substituted heterocyclic ring, said heterocyclic ring may contain a second heterogroup within the ring selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —C(O)$OR^h$;

Each $R^h$ is selected from the group consisting of optionally substituted —$C_1$-$C_6$ alkyl, optionally substituted —($CR^b_2$)$_n$aryl, optionally substituted —($CR^b_2$)$_n$cycloalkyl, and optionally substituted —($CR^b_2$)$_n$heterocycloalkyl; or $R^3$ and $R^8$ are taken together along with the carbon atoms to which they are attached to form an optionally substituted ring of 6 atoms with 0-2 unsaturations, not including the unsaturation on the ring to which $R^3$ and $R^8$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom; or $R^8$ and G are taken together along with the carbon atoms to which they are attached to form an optionally substituted ring of formula —CH=CH—CH=; $R^5$ is selected from the group consisting of —OH, —$OCH_3$, —$OC(O)R^e$, —OC(O)$OR^e$, and —$NHC(O)R^e$; or $R^3$ and $R^5$ are taken together along with the carbons they are attached to form an optionally substituted ring of 5 atoms with 1 unsaturation, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

Y is selected from the group consisting of —O—, and —NR$^v$—;

when Y is —O—, R$^{11}$ attached to —O— is independently selected from the group consisting of —H, alkyl, —C(R$^z$)$_2$—OC(O)R$^y$, —C(R$^z$)$_2$—O—C(O)OR$^y$, and -alkyl-S—C(O)R$^y$;

when Y is —NR$^v$—, then R$^{11}$ attached to —NR$^v$— is independently selected from the group consisting of —H, —C(R$^z$)$_2$—COOR$^y$, and —C(R$^x$)$_2$COOR$^y$;

Each R$^z$ is selected from the group consisting of R$^y$ and —H;

Each R$^y$ is selected from the group consisting of alkyl and aryl;

Each R$^x$ is independently selected from the group consisting of —H and alkyl;

Each R$^v$ is selected from the group consisting of —H and lower alkyl;

and pharmaceutically acceptable salts of said prodrugs and pharmaceutically acceptable salts and prodrugs thereof and pharmaceutically acceptable salts of said prodrugs.

In one embodiment of the compound of Formula VIII:

G is selected from the group consisting of —O—, —S—, and —CH$_2$—;

A and T are each independently selected from the group consisting of —CH$_2$—, —(CH$_2$)$_2$—, —OCH$_2$—, —SCH$_2$—, —NH(CH$_2$)—, —NHC(O)—, —C(O)CH$_2$—, —CH$_2$C(O)—, —CH$_2$O—, —CH$_2$S—, and —CH$_2$)NH—;

R$^1$, R$^2$, and R$^7$ are each independently selected from the group consisting hydrogen, Cl, Br, I, —CH$_3$, —CF$_3$, and cyano; with the proviso that at least one of R$^1$ and R$^2$ is not hydrogen;

R$^8$ and R$^9$ are, each independently selected from the group consisting of hydrogen, Cl, Br, I, —CH$_3$, —CF$_3$, (CH$_2$)aryl, C(O)aryl, C(O)alkyl;

R$^3$ is selected from the group consisting of hydrogen, halogen, optionally substituted —C$_1$-C$_6$ alkyl, optionally substituted —(CH$_2$)aryl, optionally substituted —CH(OH)aryl, optionally substituted —(CH$_2$)cycloalkyl, optionally substituted —CH(OH)cycloalkyl, optionally substituted —(CH$_2$)heterocycloalkyl, optionally substituted —CH(OH)heterocycloalkyl, —S(=O)$_2$R$^e$, —S(=O)$_2$NR$^f$R$^g$, —C(O)NR$^f$R$^g$, and —C(O)R$^e$;

R$^4$ is selected from the group consisting of hydrogen, F, Cl, Br, iodo, and CH$_3$;

Each R$^e$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl;

R$^f$ and R$^g$ are each independently selected from the group consisting of hydrogen, optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^e$, oxo, cyano, —CF$_3$, optionally substituted phenyl, and —C(O)OR$^b$;

Each R$^h$ is selected from the group consisting of optionally substituted —C$_1$-C$_6$ alkyl, optionally substituted —(CH$_2$)$_n$aryl, optionally substituted —(CH$_2$)$_n$cycloalkyl, and optionally substituted —(CH$_2$)$_n$heterocycloalkyl; or R$^3$ and R$^8$ are taken together along with the carbon atoms to which they are attached to form an optionally substituted ring of 6 atoms with 2 unsaturations, not including the unsaturation on the ring to which R$^3$ and R$^8$ are attached, including 0 to 1 —N—; or R$^8$ and G are taken together along with the carbon atoms to which they are attached to form an optionally substituted ring of formula —CH=CH—CH=; R$^5$ is selected from the group consisting of —OH, —OCH$_3$, —OC(O)R$^e$, —OC(O)OR$^e$, and —NHC(O)R$^e$; or R$^3$ and R$^5$ are taken together along with the carbons they are attached to form an optionally substituted ring of 5 atoms with 1 unsaturation, not including the unsaturation on the ring to which R$^3$ and R$^5$ are attached, including 0 to 2 heteroatoms independently selected, from —NR$^h$—, —O—, and —S—, with the proviso that when there are 2 heteroatoms in the ring and both heteroatoms are different than nitrogen then both heteroatoms have to be separated by at least one carbon atom;

Y is selected from the group consisting of —O—, and —NR$^v$—;

when Y is —O—, R$^{11}$ attached to —O— is independently selected from the group consisting of —H, alkyl, —CH$_2$—OC(O)R$^y$, —CH(CH$_3$)—OC(O)R$^y$, —CH$_2$—O—C(O)OR$^y$, —CH(CH$_3$)—O—C(O)OR$^y$, and —(CH$_2$)$_2$—S—C(O)R$^y$;

when Y is —NR$^v$—, R$^{11}$ attached to —NR$^v$— is independently selected from the group consisting of —H and —C(R$^x$)$_2$COOR$^y$;

Each R$^y$ is selected from the group consisting of alkyl, aryl, heterocycloalkyl, and aralkyl;

and pharmaceutically acceptable salts and prodrugs thereof and pharmaceutically acceptable salts of said prodrugs.

In a further aspect, the invention relates to the use of a compound of Formula IX:

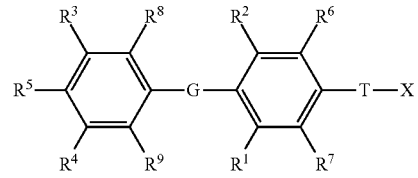

wherein:

G is selected from the group consisting of —O—, —S—, —Se—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-, or CH$_2$ linked to any of the preceding groups;

T is selected from the group consisting of —(CR$^a_2$)$_n$CHO—, —(CR$^a_2$)$_n$CH(NR$^b$R$^c$)—, —(CR$^a_2$)$_n$CHS—, —C(O)(CR$^a_2$)$_p$CHO—, —C(O)(CR$^a_2$)$_p$CH(NR$^b$R$^c$)—, —C(O)(CR$^a_2$)$_p$CHS—, —(CR$^a_2$)$_p$C(O)CHO—, —(CR$^a_2$)$_p$C(O)CH(NR$^b$R$^c$)—, and —(CR$^a_2$)pC(O)CHS—, k is an integer from 0-4;

m is an integer from 0-3;

n is an integer from 0-2;

p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, R$^2$, R$^6$, and R$^7$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; with the proviso that at least one of R$^1$ and R$^2$ is not hydrogen;

R$^8$ and R$^9$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a{}_2$)aryl, C(O)aryl, C(O)alkyl and cyano; or R$^1$ and R$^7$ are taken together along with the carbon atoms to which they are attached to form an optionally substituted ring of 5 to 6 atoms with 0-2 unsaturations, not including the maturation on the ring to which R$^1$ and R$^7$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_m$aryl, optionally substituted —(CR$^a{}_2$)$_m$cycloalkyl, optionally substituted —(CR$^a{}_2$)$_m$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, optionally substituted —(CR$^b{}_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$_b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring of formula —CH=CH—CH=, N=CH—CH=, —CH=N—CH= or —CH=CH—N=;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form an optionally substituted ring of 5 to 6 atoms with 0-2 unsaturations not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y";

Y" is selected from the group consisting of hydrogen, —C$_1$-C$_6$-alkyl, —CF$_3$, optionally substituted —C$_2$-C$_6$ alkenyl, optionally substituted —C$_2$-C$_6$ alkynyl, optionally substituted —(CR$^a{}_2$)$_n$aryl, optionally substituted —(CR$^a{}_2$)$_n$cycloalkyl, optionally substituted (CR$^a{}_2$)$_n$heterocycloalkyl, —(CR$^a{}_2$)$_k$ S(=O)R$^e$, —(CR$^a{}_2$)$_k$S(=O)$_2$R$^e$, —(CR$^a{}_2$)$_k$S(=O)$_2$NR$^f$R$^g$, —(CR$^a{}_2$)$_k$C(O)NR$^f$R$^g$, —(CR$^a{}_2$)$_k$C(O)OR$^h$, and —(CR$^a{}_2$)$_k$C(O)R$^e$;

Y is selected from the group consisting of —O—, and —NR$^v$—;

when Y is —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z{}_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy;

when Y is —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

q is an integer 2 or 3;

Each R$^x$ is selected from the group consisting of R$^y$ and —H;

Each R$^y$ is selected from the group consisting of alkyl, aryl, heterocycloalkyl, and aralkyl;

Each $R^x$ is independently selected from the group consisting of —H, and alkyl, or together $R^x$ and $R^x$ form a cycloalkyl group;

Each $R^v$ is selected from the group consisting of —H, lower alkyl, acyloxyalkyl, alkoxycarbonyloxyalkyl, and lower acyl;

and pharmaceutically acceptable salts and prodrugs thereof and pharmaceutically acceptable salts of said prodrugs.

In one embodiment of the compound of Formula IX:

G is selected from the group consisting of —O—, —S—, and —CH$_2$—;

T is selected from the group consisting of —(CR$^a{}_2$)$_n$CHO—, —(CR$^a{}_2$)$_n$CH(NR$^b$R$^c$)—, and —(CR$^a{}_2$)$_n$CHS—;

k is an integer from 0-4;

m is an integer from 0-3;

n is an integer from 0-2;

p is an integer from 0-1;

Each $R^a$ is independently selected from the group consisting of hydrogen, —CH$_3$, halogen, —OH, —OCH$_3$, —OCF$_3$, and —NR$^b$R$^c$; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and —CH$_3$;

Each $R^c$ is independently selected from the group consisting of hydrogen and —CH$_3$, —C(O)—CH$_3$, and —C(O)H;

$R^1$, $R^2$, $R^6$, and $R^7$ are each independently selected from the group consisting of hydrogen, halogen, —CH$_3$, —CF$_3$, and cyano; with the proviso that at least one of $R^1$ and $R^2$ is not hydrogen;

$R^8$ and $R^9$ are each independently selected from the group consisting of hydrogen, halogen, —CH$_3$, —CF$_3$, (CR$^a{}_2$)aryl, C(O)aryl, C(O)alkyl and cyano; or $R^1$ and $R^7$ are taken together along with the carbon atoms to which they are attached to form an optionally substituted ring of 5 atoms with 0-1 unsaturations, not including the unsaturation on the ring to which $R^1$ and $R^7$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

$R^3$ is selected from the group consisting of hydrogen, halogen, optionally substituted —C$_1$-C$_6$ alkyl, optionally substituted —(CR$^a{}_2$)$_m$aryl, optionally substituted —(CR$^a{}_2$)$_m$cycloalkyl, optionally substituted —(CR$^a{}_2$)$_m$heterocycloalkyl, —S(=O)$_2$R$^e$, —S(=O)$_2$NR$^f$R$^g$, —C(O)NR$^f$R$^g$, and —C(O)R$^e$;

$R^4$ is selected from the group consisting of hydrogen, halogen, and optionally substituted —C$_1$-C$_6$ alkyl;

Each $R^e$ is selected from the group consisting of optionally substituted —C$_1$-C$_6$ alkyl, optionally substituted —(CR$^a{}_2$)$_n$aryl, optionally substituted —(CR$^a{}_2$)$_n$cycloalkyl, and optionally substituted —(CR$^a{}_2$)heterocycloalkyl;

$R^f$ and $R^g$ are each independently selected from the group consisting of hydrogen, optionally substituted —C$_1$-C$_6$ alkyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl, or $R^f$ and $R^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each $R^h$ is selected from the group consisting of optionally substituted —C$_1$-C$_6$ alkyl, optionally substituted —(CR$^a{}_2$)$_n$aryl, optionally substituted —(CR$^b{}_2$)$_n$cycloalkyl, and optionally substituted —(CR$^b{}_2$)heterocycloalkyl; or $R^3$ and $R^8$ are taken together along with the carbon atoms to which they are attached to form an optionally substituted ring of 6 atoms with 0-2 unsaturations, not including the unsaturation on the ring to which $R^3$ and $R^8$ are attached, including 0 to 2 heteroatoms independently selected from —O—, and —S—, with the proviso that when there are 2 heteroatoms in the ring and both heteroatoms are different than nitrogen then both heteroatoms have to be separated by at least one carbon atom; or $R^8$ and G are taken together along with the carbon atoms to which they are attached to form an optionally substituted ring of formula —CH=CH—CH=;

$R^5$ is selected from the group consisting of —OH, —OCH$_3$, —OC(O)R$^e$, —OC(O)OR$^e$, and —NHC(O)R$^e$; or $R^3$ and $R^5$ are taken together along with the carbons they are attached to form an optionally substituted ring of 5 atoms with 1 unsaturation, not including the unsaturation on the ring to which $R^3$ and $R^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y''';

Y'' is hydrogen, —C$_1$-C$_6$-alkyl, —CF$_3$, optionally substituted —(CR$^a{}_2$)$_n$aryl, —(CR$^a{}_2$)$_k$S(=O)$_2$NR$^f$R$^g$, —(CR$^a{}_2$)$_k$C(O)NR$^f$R$^g$, —(CR$^a{}_2$)$_k$C(O)OR$^h$;

Y is selected from the group consisting of —O—, and —NR$^v$—;

when Y is —O—, R$^{11}$ attached to —O— is independently selected from the group consisting of —H, alkyl, —C(R$^z$)$_2$—OC(O)R$^y$, —C(R$^z$)$_2$—O—C(O)OR$^y$, and -alkyl-S—C(O)R$^y$;

when Y is —NR$^v$—, then R$^{11}$ attached to —NR$^v$— is independently selected from the group consisting of —H, —C(R$^z$)$_2$—COOR$^y$, and —C(R$^x$)$_2$COOR$^y$;

Each $R^z$ is selected from the group consisting of R$^y$ and —H;

Each $R^y$ is selected front the group consisting of alkyl and aryl;

Each $R^x$ is independently selected from the group consisting of —H and alkyl;

Each $R^v$ is selected from the group consisting of —H and lower alkyl;

and pharmaceutically acceptable salts of said prodrugs and pharmaceutically acceptable salts and prodrugs thereof and pharmaceutically acceptable salts of said prodrugs.

In one embodiment of the compound of Formula IX:

G is selected from the group consisting of —O—, —S—, and —CH$_2$—;

T is selected from the group consisting of —CH$_2$CHO—, —CH$_2$CHNH—, and —CH$_2$CHS—;

$R^1$, $R^2$, $R^6$, and $R^7$ are each independently selected from the group consisting of hydrogen, Cl, Br, I, —CH$_3$, —CF$_3$, and cyano; with the proviso that at least one of $R^1$ and $R^2$ is not hydrogen;

$R^8$ and $R^9$ are each independently selected from the group consisting of hydrogen, Cl, Br, I, —CH$_3$, —CF$_3$, (CH$_2$)aryl, C(O)aryl, C(O)alkyl; or $R^1$ and $R^7$ are taken together along with the carbon atoms to which they are attached to form an optionally substituted ring of 5 atoms with 0 unsaturations, not including the unsaturation on the ring to which $R^1$ and $R^7$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

$R^3$ is selected from the group consisting of hydrogen, halogen, optionally substituted —$C_1$-$C_6$ alkyl, optionally substituted —($CH_2$)aryl, optionally substituted —CH(OH)aryl, optionally substituted —($CH_2$)cycloalkyl, optionally substituted —CH(OH)cycloalkyl, optionally substituted —($CH_2$)heterocycloalkyl, optionally substituted —CH(OH)heterocycloalkyl, —S(=O)$_2R^e$, —S(=O)$_2NR^fR^g$, —C(O)NR$^f$R$^g$, and —C(O)R$^e$;

$R^4$ is selected from the group consisting of hydrogen, F, Cl, Br, iodo, and $CH_3$;

Each $R^e$ is selected from the group consisting of optionally substituted —$C_1$-$C_6$ alkyl, optionally substituted —($CH_2$)$_n$aryl, optionally substituted —($CH_2$)$_n$cycloalkyl, and optionally substituted —($CH_2$)$_n$heterocycloalkyl;

$R^f$ and $R^g$ are each independently selected from the group consisting of hydrogen, optionally substituted —$C_1$-$C_6$ alkyl, optionally substituted —($CH_2$)$_n$aryl, optionally substituted —($CH_2$)$_n$cycloalkyl, and optionally substituted —($CH_2$)$_n$heterocycloalkyl, or $R^f$ and $R^g$ may together form an optionally substituted heterocyclic ring, said heterocyclic ring may contain a second heterogroup within the ring selected from the group consisting of O, $NR^e$, and S, wherein said optionally substituted heterocyclic ring may be substituted with 0-4 substituents selected from the group consisting of optionally substituted —$C_1$-$C_4$ alkyl, —$OR^e$, oxo, cyano, —$CF_3$, optionally substituted phenyl, and —C(O)$OR^h$;

Each $R^h$ is selected from the group consisting of optionally substituted —$C_1$-$C_6$ alkyl, optionally substituted —($CH_2$)$_n$aryl, optionally substituted —($CH_2$)$_n$cycloalkyl, and optionally substituted —($CH_2$)$_n$heterocycloalkyl; or $R^3$ and $R^8$ are taken together along with the carbon atoms to which they are attached to form an optionally substituted ring of 6 atoms with 2 unsaturations, not including the unsaturation on the ring to which $R^3$ and $R^8$ are attached, including 0 to 1 —N—; or $R^8$ and G are taken together along with the carbon atoms to which they are attached to form an optionally substituted ring of formula —CH=CH—CH=;

$R^5$ is selected from the group consisting of —OH, —$OCH_3$, —OC(O)$R^e$, —OC(O)$OR^e$, and —NHC(O)$R^e$; or $R^3$ and $R^5$ are taken together along with the carbons they are attached to form an optionally substituted ring of 5 atoms with 1 unsaturation, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y";

Y" is selected from the group consisting of hydrogen, —$C_1$-$C_3$-alkyl, —$CF_3$, optionally substituted —($CH_2$)$_p$aryl, —($CH_2$)$_p$S(=O)$_2NH_2$, —($CH_2$)$_p$C(O)$NH_2$, —($CH_2$)$_k$C(O)OH, and —($CH_2$)$_k$C(O)$OCH_3$;

Y is selected from the group consisting of —O—, and —$NR^v$—;

when Y is —O—, $R^{11}$ attached to —O— is independently selected from the group consisting of —H, alkyl, —$CH_2$—OC(O)$R^y$, —CH($CH_3$)—OC(O)$R^y$, —$CH_2$—O—C(O)$OR^y$, —CH($CH_3$)—O—C(O)$OR^y$, and —($CH_2$)$_2$—S—C(O)$R^y$;

when Y is —$NR^v$—, $R^{11}$ attached to —$NR^v$— is independently selected from the group consisting of —H and —C($R^x$)$_2$COOR$^y$;

Each $R^y$ is selected from the group consisting of alkyl, aryl, heterocycloalkyl, and aralkyl;

and pharmaceutically acceptable salts and prodrugs thereof and pharmaceutically acceptable salts of said prodrugs.

In one embodiment of the compound of Formula II, III, IV, V, VI, VII, or IX:

X is P(O)YR$^{11}$Y'R$^{11}$ or P(O)YR$^{11}$Y";

Y" is selected from the group consisting of hydrogen, —$C_1$-$C_6$-alkyl, —$CF_3$, optionally substituted —$C_2$-$C_6$ alkenyl, optionally substituted —$C_2$-$C_6$ alkynyl, optionally substituted —($CR^a_2$)$_n$aryl, optionally substituted —($CR^a_2$)$_n$cycloalkyl, optionally substituted —($CR^a_2$)$_n$heterocycloalkyl, —($CR^a_2$)$_k$ S(=O)$R^e$, —($CR^a_2$)$_k$(=O)$_2R^e$, —($CR^a_2$)$_k$S(=O)$_2NR^fR^g$, —($CR^a_2$)$_k$C(O)NR$^f$R$^g$, —($CR^a_2$)$_k$C(O)$OR^h$, and —($CR^a_2$)$_k$C(O)$R^e$;

Y and Y' are each independently selected from the group consisting of —O—, and —$NR^v$—;

when Y is —O— and Y" is hydrogen, —$C_1$-$C_6$-alkyl, —$CF_3$, optionally substituted —$C_2$-$C_6$ alkenyl, optionally substituted —$C_2$-$C_6$ alkynyl, optionally substituted —($CR^a_2$)$_n$aryl, optionally substituted —($CR^a_2$)$_n$cycloalkyl, optionally substituted —($CR^a_2$)$_n$heterocycloalkyl, —($CR^a_2$)$_k$S(=O)$R^e$, —($CR^a_2$)$_k$S(=O)$_2R^e$, —($CR^a_2$)$_k$S(=O)$_2$NR$^f$R$^g$, —($CR^a_2$)$_k$C(O)NR$^f$R$^g$, —($CR^a_2$)$_k$C(O)$OR^h$, or —($CR^a_2$)$_k$C(O)$R^e$, or when Y and Y' are both —O—, $R^{11}$ attached to —O— is independently selected from the group consisting of —H, alkyl, optionally substituted aryl, optionally substituted heterocycloalkyl, optionally substituted $CH_2$heterocycloakyl wherein the cyclic moiety contains a carbonate or thiocarbonate, optionally substituted -alkylaryl, —C($R^z$)$_2$OC(O)$NR^z_2$, —$NR^z$—C(O)—$R^y$, —C($R^z$)$_2$—OC(O)$R^y$, —C($R^z$)$_2$—O—C(O)$OR^y$, —C($R^z$)$_2$OC(O)$SR^y$, -alkyl-S—C(O)$R^y$, -alkyl-S—S-alkylhydroxy, and -alkyl-S—S—S-alkylhydroxy;

when Y is —$NR^v$— and Y" is hydrogen, —$C_1$-$C_6$-alkyl, —$CF_3$, optionally substituted —$C_2$-$C_6$ alkenyl, optionally substituted —$C_2$-$C_6$ alkynyl, optionally substituted —($CR^a_2$)$_n$aryl, optionally substituted —($CR^a_2$)$_n$cycloalkyl, optionally substituted —($CR^a_2$)$_n$heterocycloalkyl, —($CR^a_2$)$_k$S(=O)$R^e$, —($CR^a_2$)$_k$S(=O)$_2R^e$, —($CR^a_2$)$_k$S(=O)$_2$NR$^f$R$^g$, —($CR^a_2$)$_k$C(O)NR$^f$R$^g$, —($CR^a_2$)$_k$C(O)$OR^h$, -or ($CR^a_2$)$_k$C(O)$R^e$, or when Y and Y' are both —$NR^v$—, then $R^{11}$ attached to —$NR^v$— is independently selected from the group consisting of —H, —[C($R^z$)$_2$]$_q$—COOR$^y$, —C($R^x$)$_2$COOR$^y$, —[C($R^z$)$_2$]$_q$—C(O)SR$^y$, and -cycloalkylene-COOR$^y$;

when Y is —O— and Y' is NR$^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)$NR^z_2$, —$NR^z$—C(O)—$R^y$, —C($R^z$)$_2$—OC(O)$R^y$, —C($R^z$)$_2$—O—C(O)$OR^y$, —C($R^z$)$_2$OC(O)$SR^y$, -alkyl-S—C(O)$R^y$, -alkyl-S—S-alkylhydroxy, and -alkyl-S—S—S-alkylhydroxy, and $R^{11}$ attached to —$NR^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

or when Y and Y' are independently selected from —O— and —NR$^v$—, then R$^{11}$ and R$^{11}$ together form a cyclic group comprising -alkyl-S—S-alkyl-, or together R$^{11}$ and R$^{11}$ are the group:

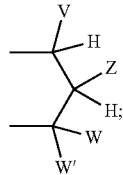

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, that is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z$$_2$)OH, —CH(C≡CR$^z$)OH, —R$^z$, —NR$^z$$_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl;

with the provisos that:

a) V, Z, W, W' are not all —H; and b) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another embodiment of the compound of Formula II, III, IV, V, VI, VII, or IX:

X is P(O)YR$^{11}$Y'R$^{11}$ or P(O)YR$^{11}$Y";

Y" is selected from the group consisting of hydrogen, —C$_1$-C$_6$-alkyl, —CF$_3$, optionally substituted —C$_2$-C$_6$ alkenyl, optionally substituted —C$_2$-C$_6$ alkynyl, optionally substituted —(CR$^a$$_2$)$_n$aryl, optionally substituted —(CR$^a$$_2$)$_n$cycloalkyl, optionally substituted —(CR$^a$$_2$)$_n$heterocycloalkyl, —(CR$^a$$_2$)$_k$S(=O)R$^e$, —(CR$^a$$_2$)$_k$S(=O)$_2$R$^e$, —(CR$^a$$_2$)$_k$S(=O)$_2$NR$^f$R$^g$, —(CR$^a$$_2$)$_k$C(O)NR$^f$R$^g$, —(CR$^a$$_2$)$_k$C(O)OR$^h$, and —(CR$^a$$_2$)$_k$C(O)R$^e$;

Y and Y' are each independently selected from the group consisting of —O—, and —NR$^v$—;

when Y is —O— and Y" is hydrogen, —C$_1$-C$_6$-alkyl, —CF$_3$, optionally substituted —(CR$^a$$_2$)$_n$aryl, —(CR$^a$$_2$)$_k$S(=O)$_2$NR$^f$R$^g$, —(CR$^a$$_2$)$_k$C(O)NR$^f$R$^g$, or —(CR$^a$$_2$)$_k$C(O)OR$^h$, or when Y and Y' are both —O—, R$^{11}$ attached to —O— is independently selected from the group consisting of —H, alkyl, —C(R$^z$)$_2$—OC(O)R$^y$, —C(R$^z$)$_2$—O—C(O)OR$^y$, and -alkyl-S—C(O)R$^y$;

when Y is —NR$^v$— and Y" is hydrogen, —C$_1$-C$_6$-alkyl, —CF$_3$, optionally substituted —(CR$^a$$_2$)$_n$aryl, —(CR$^a$$_2$)$_k$S(=O)$_2$NR$^f$R$^g$, —(CR$^a$$_2$)$_k$C(O)NR$^f$R$^g$, or —(CR$^a$$_2$)$_k$C(O)OR$^h$, or when Y and Y' are both —NR$^v$—, then R$^{11}$ attached to —NR$^v$— is independently selected from the group consisting of —H, —C(R$^z$)$_2$—COOR$^y$, and —C(R$^x$)$_2$COOR$^y$;

when Y is —O— and Y' is NR$^v$, then R$^{11}$ attached to —O— is independently selected from the group consisting of —H, alkyl, optionally substituted aryl, —C(R$^z$)$_2$—OC(O)R$^y$, —C(R$^z$)$_2$—O—C(O)OR$^y$, and -alkyl-S—C(O)R$^y$; and R$^{11}$ attached to —NR$^v$— is independently selected from the group consisting of —H, —C(R$^z$)$_2$—COOR$^y$, and —C(R$^x$)$_2$COOR$^y$;

or when Y and Y' are independently selected from —O— and —NR$^v$—, then together R$^{11}$ and R$^{11}$ are the group:

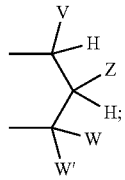

wherein:

V, W, and W' are independently selected from the group consisting of hydrogen, optionally aryl, substituted aryl, heteroaryl, and substituted heteroaryl;

Z is hydrogen

Each R$^z$ is selected from the group consisting of R$^y$ and —H;

Each $R^y$ is selected from the group consisting of alkyl and aryl;

Each $R^x$ is independently selected from the group consisting of —H and alkyl;

Each $R^v$ is selected from the group consisting of —H and lower alkyl;

with the provisos that:

a) V, Z, W, W' are not all —H; and b) when Z is —$R^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another embodiment of the compound of Formula II, III, IV, V, VI, VII, or VIII:

X is $P(O)YR^{11}Y'R^{11}$ or $P(O)YR^{11}Y''$;

Y" is selected from the group consisting of hydrogen, —$C_1$-$C_6$-alkyl, —$CF_3$, optionally substituted —$C_2$-$C_6$ alkenyl, optionally substituted —$C_2$-$C_6$ alkynyl, optionally substituted —$(CR^a{}_2)_n$aryl, optionally substituted —$(CR^a{}_2)_n$cycloalkyl, optionally substituted —$(CR^a{}_2)_n$heterocycloalkyl, —$(CR^a{}_2)_kS(=O)R^e$, —$(CR^a{}_2)_kS(=O)_2R^e$, —$(CR^a{}_2)_kS(=O)_2NR^fR^g$, —$(CR^a{}_2)_kC(O)NR^fR^g$, —$(CR^a{}_2)_kC(O)OR^h$, and —$(CR^a{}_2)_kC(O)R^e$;

Y and Y' are each independently selected from the group consisting of —O—, and —$NR^v$—;

when Y is —O— and Y" is hydrogen, —$C_1$-C-alkyl, —$CF_3$, optionally substituted —$(CH_2)_p$aryl, —$(CH_2)_pS(=O)_2NH_2$, —$(CH_2)_pC(O)NH_2$, —$(CR^a{}_2)_kC(O)OH$, or —$(CR^a{}_2)_kC(O)OCH_3$, or when Y and Y' are both —O—, $R^{11}$ attached to —O— is independently selected from the group consisting of —H, alkyl, —$CH_2$—$OC(O)R^y$, —$CH(CH_3)$—$OC(O)R^y$, —$CH_2$—O—$C(O)OR^y$, —$CH(CH_3)$—O—$C(O)OR^y$, and —$(CH_2)_2$—S—$C(O)R^y$;

when Y is —$NR^v$— and Y" is hydrogen, —$C_1$-C-alkyl, —$CF_3$, optionally substituted —$(CH_2)_p$aryl, —$(CH_2)_pS(=O)_2NH_2$, —$(CH_2)_pC(O)NH_2$, —$(CR^a{}_2)_kC(O)OH$, or —$(CR^a{}_2)_kC(O)OCH_3$, or when Y and Y' are both —$NR^v$—, then $R^{11}$ attached to —$NR^v$— is independently selected from the group consisting of —H and —$C(R^x)_2COOR^y$;

when Y is —O— and Y' is $NR^v$, then $R^{11}$ attached to —O— is independently selected from the group consisting of —H, alkyl, and optionally substituted aryl, and $R^{11}$ attached to —$NR^v$— is independently selected from the group consisting of —H and —$C(R^x)_2COOR^y$;

or when Y and Y' are independently selected from —O— and —$NR^v$—, then together $R^{11}$ and $R^{11}$ are the group:

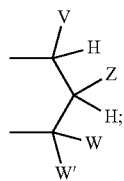

wherein:

V is aryl;

W, W' and Z are hydrogen;

Each $R^y$ is selected from the group consisting of t-butyl, iso-propyl, ethyl, and methyl;

Each $R^x$ is independently selected from the group consisting of —H and —$CH_3$;

Each $R^v$ is —H;

and pharmaceutically acceptable salts and prodrugs thereof and pharmaceutically acceptable salts of said prodrugs.

In one aspect, the compound of Formula I-IX is selected from the group consisting of:

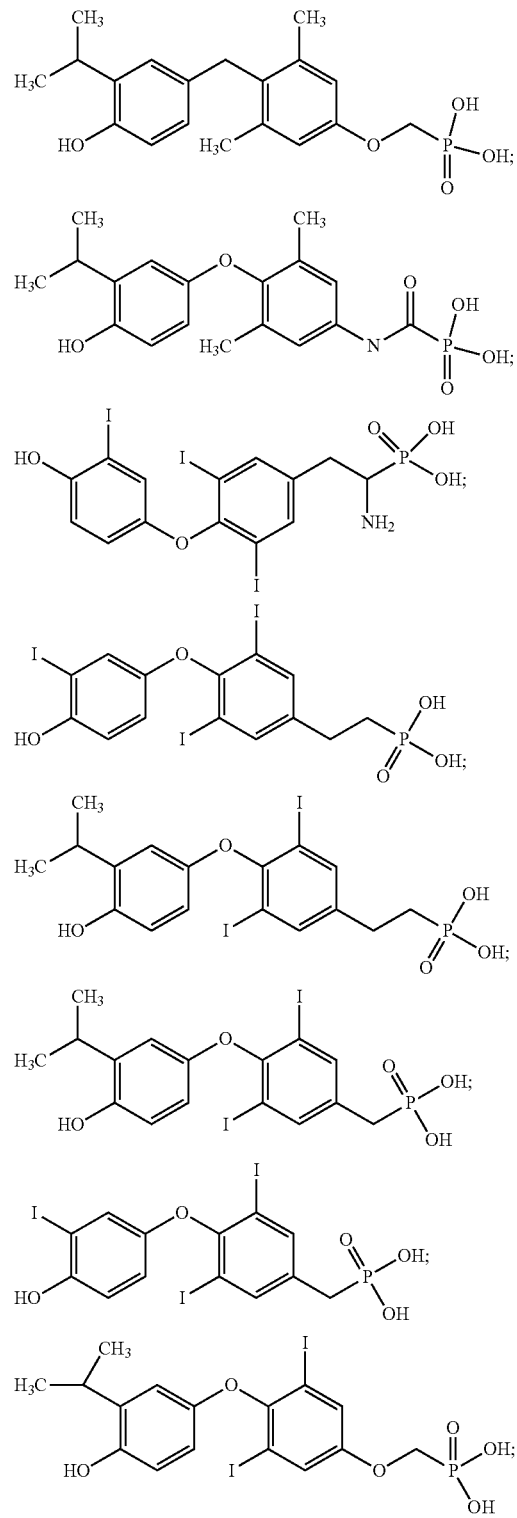

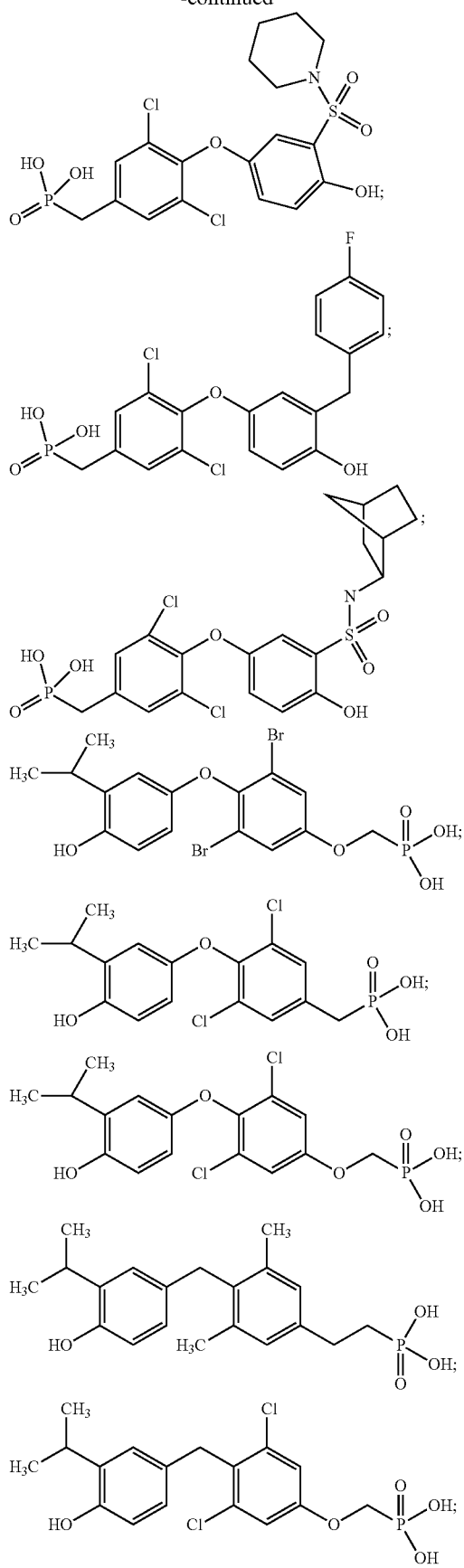
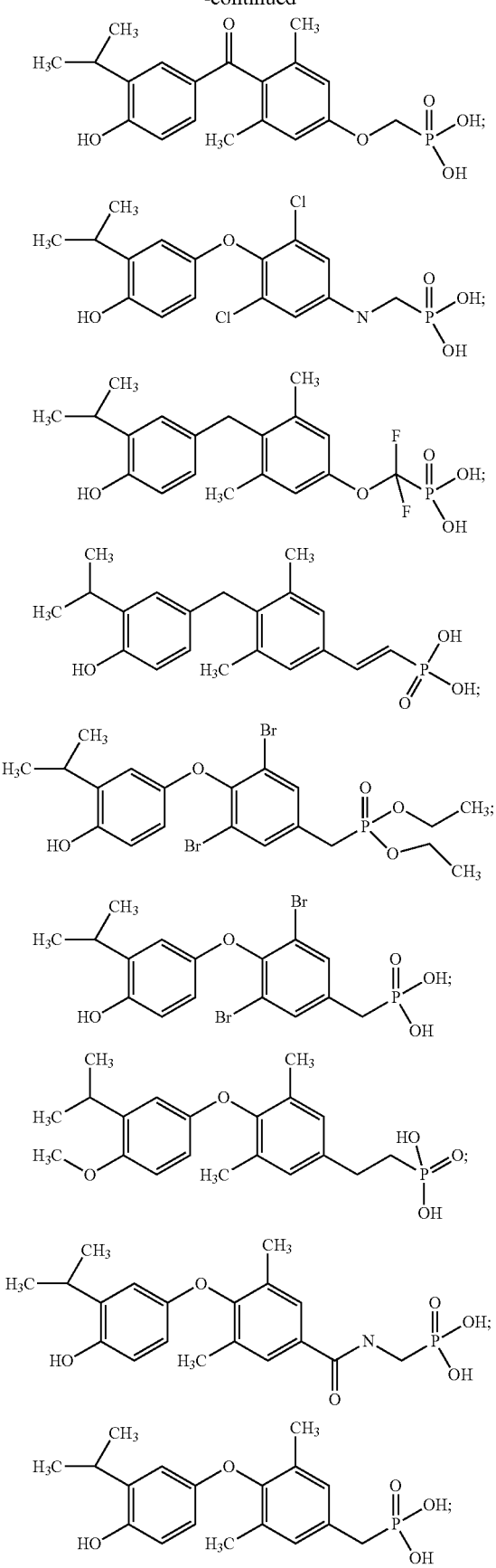

-continued
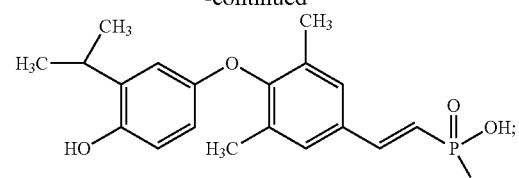
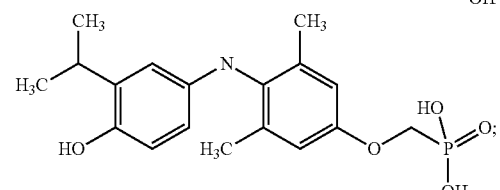
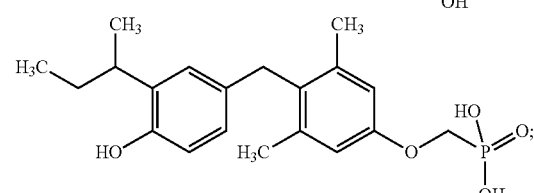
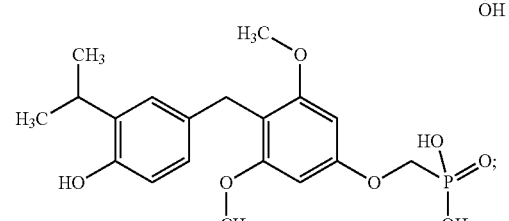
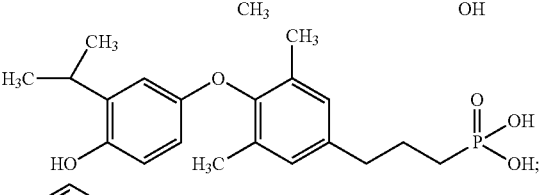
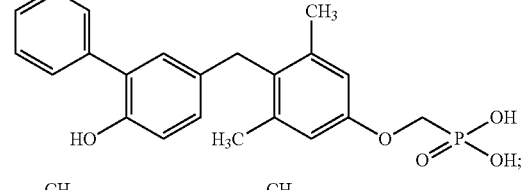
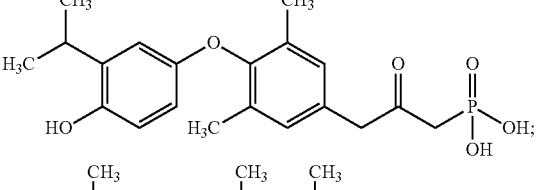
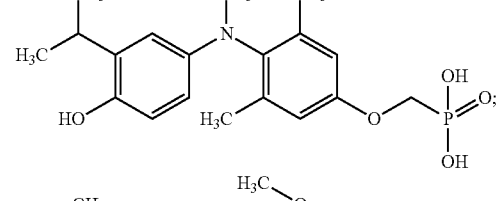
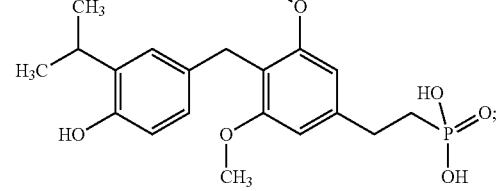
-continued
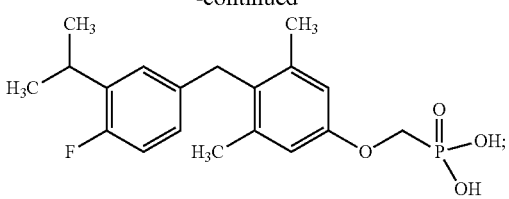
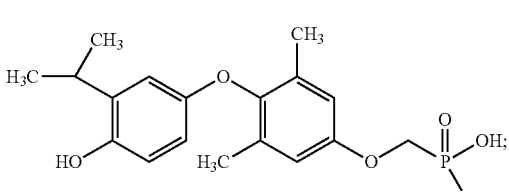
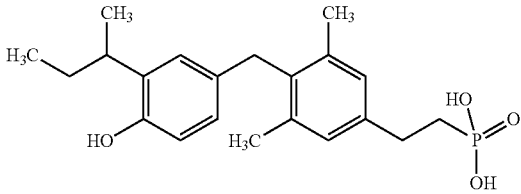
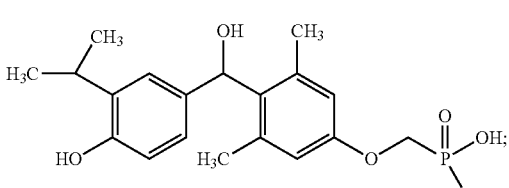
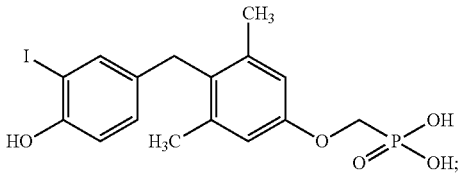
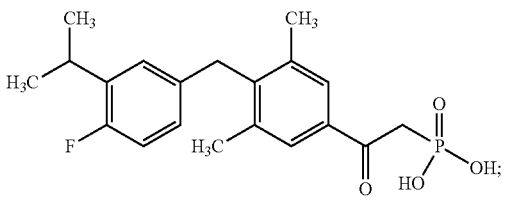
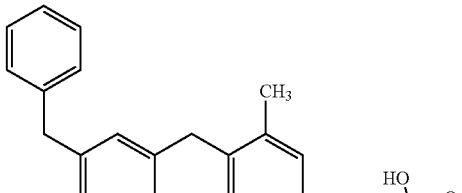
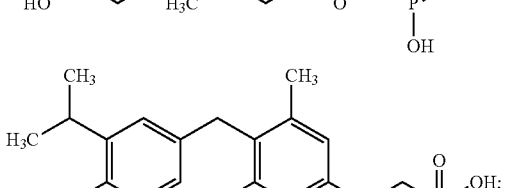

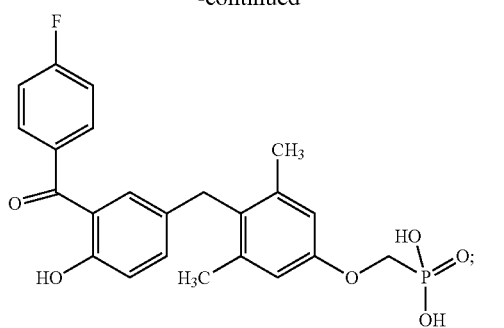
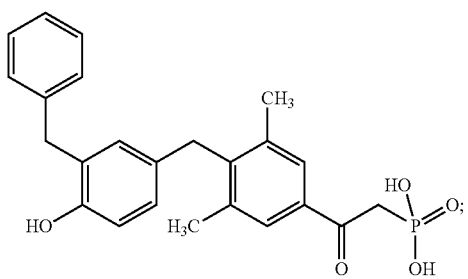
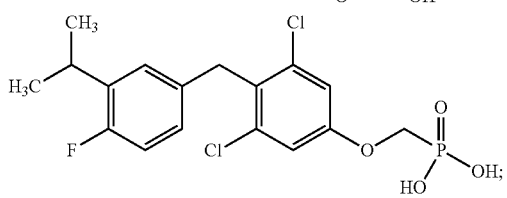
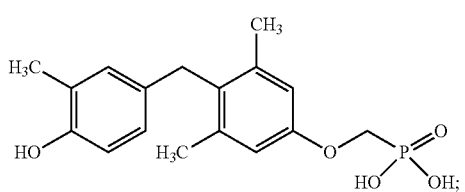
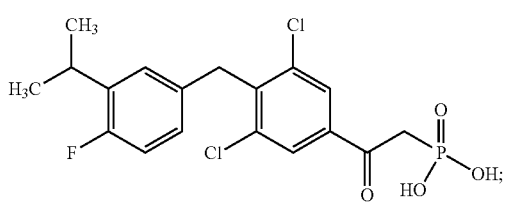
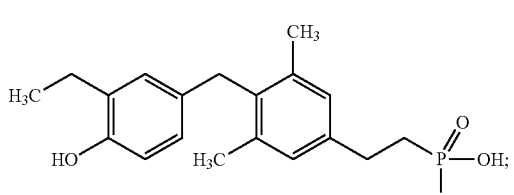
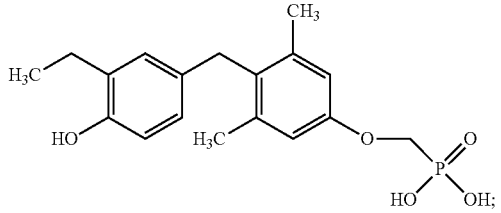
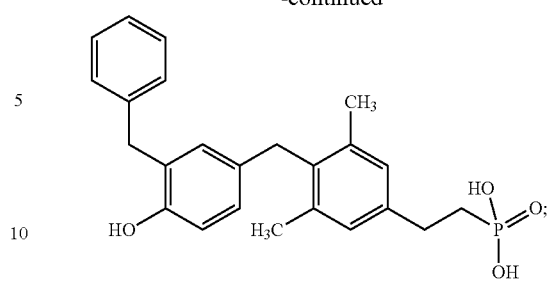
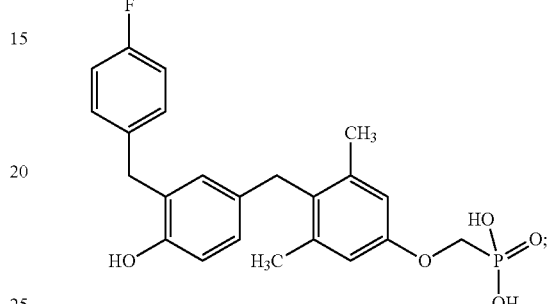
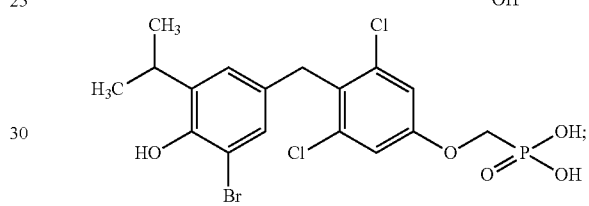
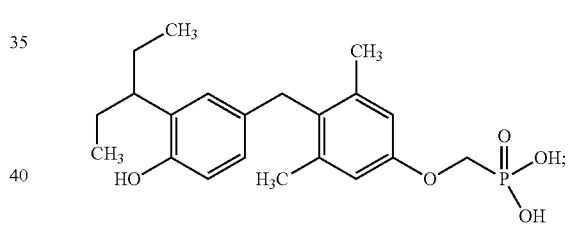
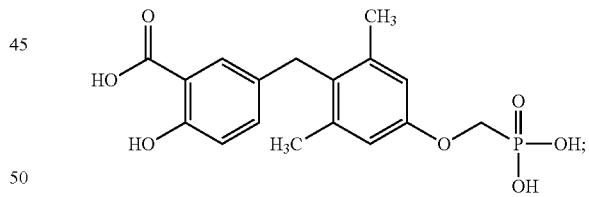
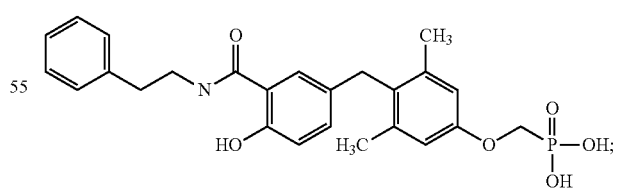
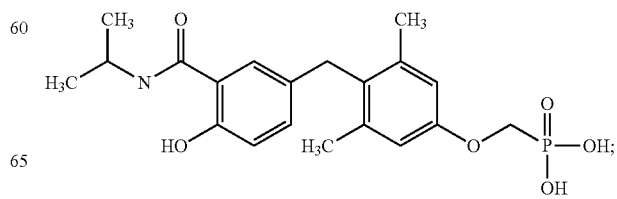

-continued
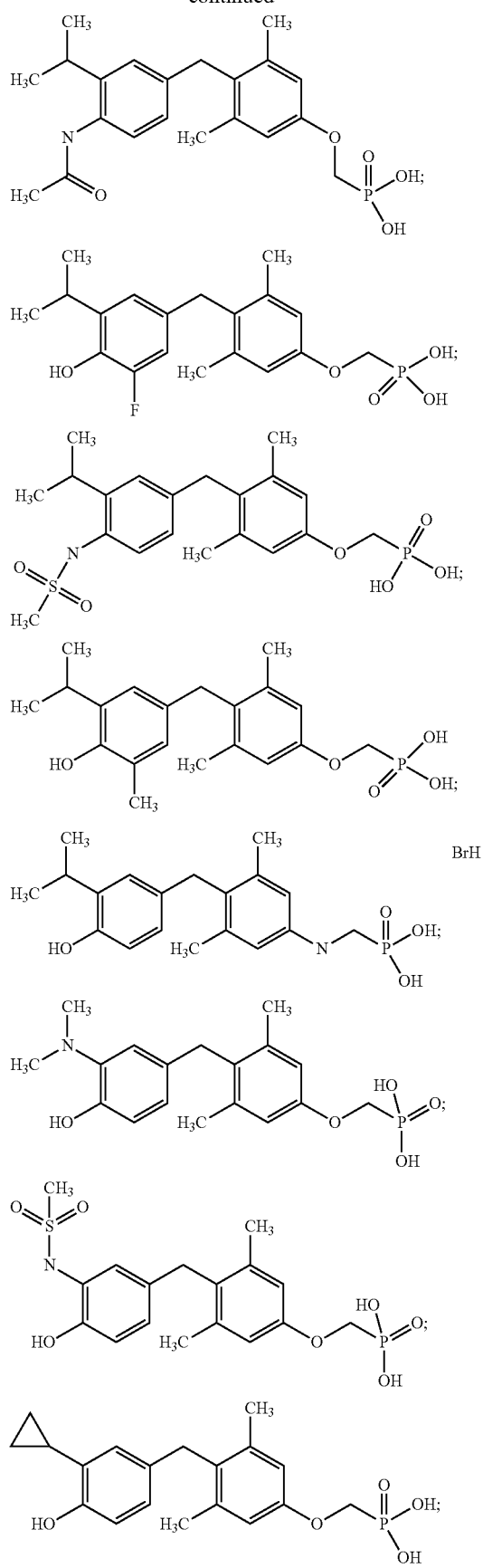
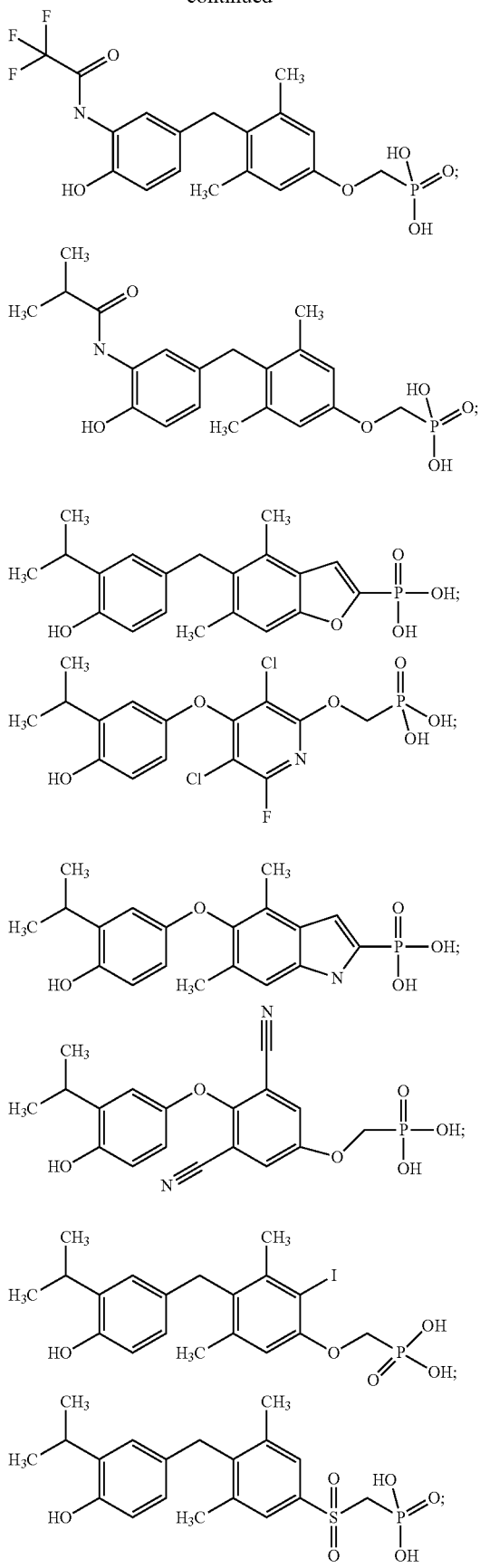

-continued
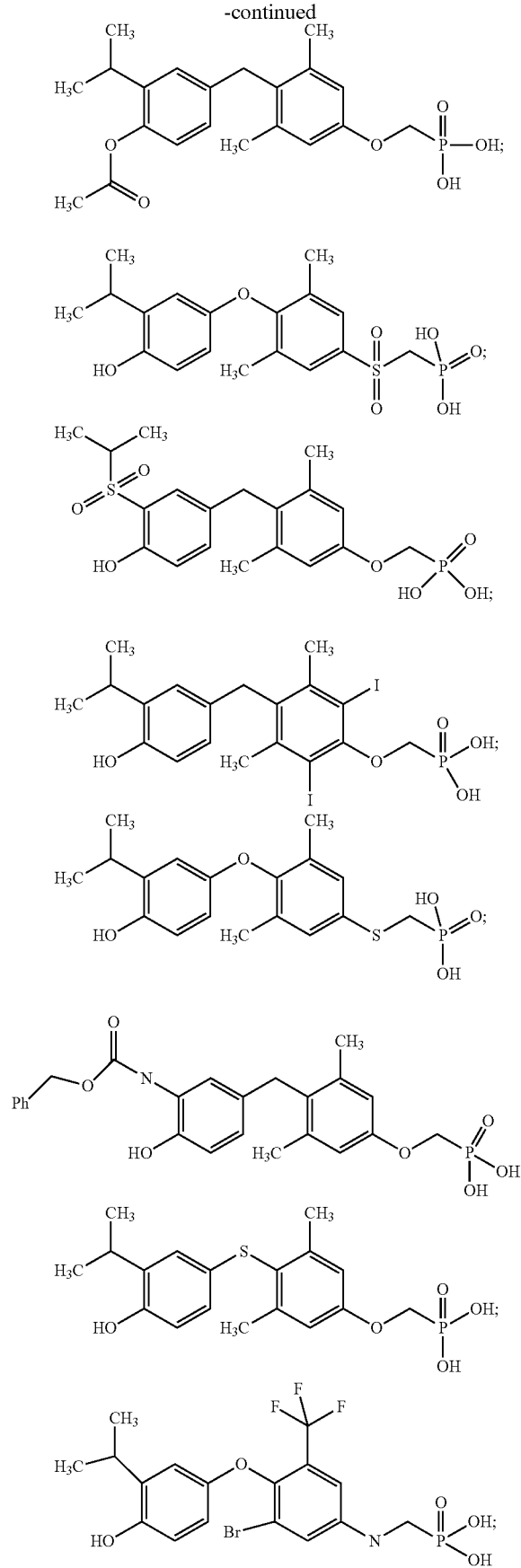
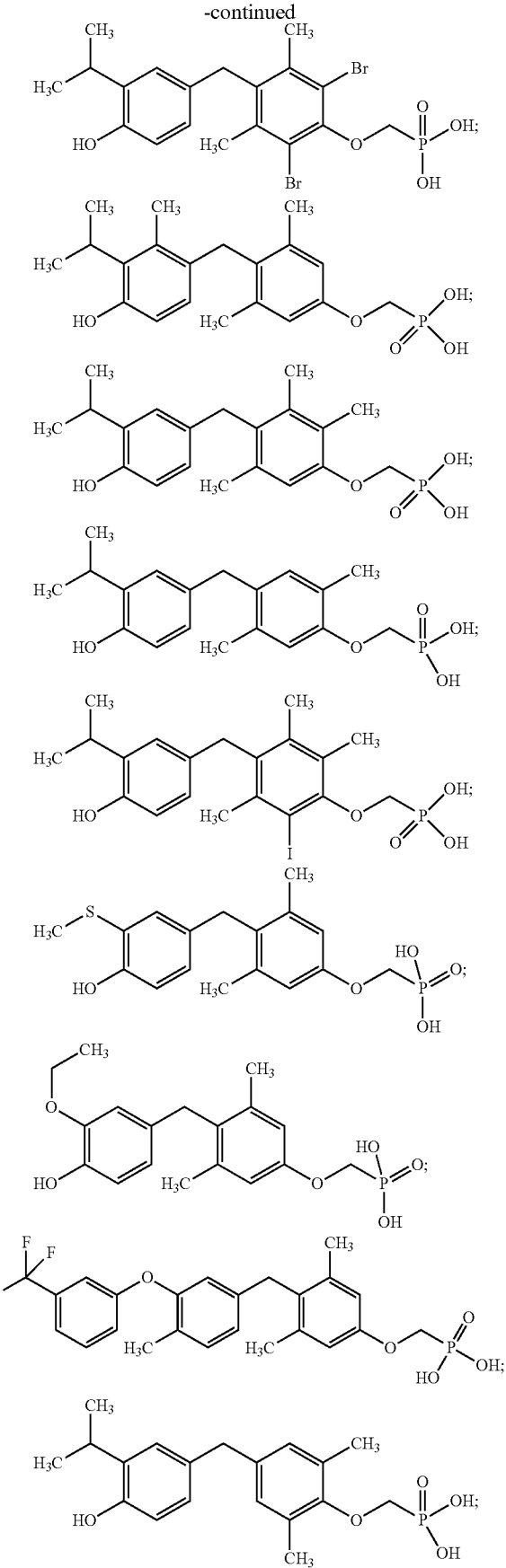

-continued

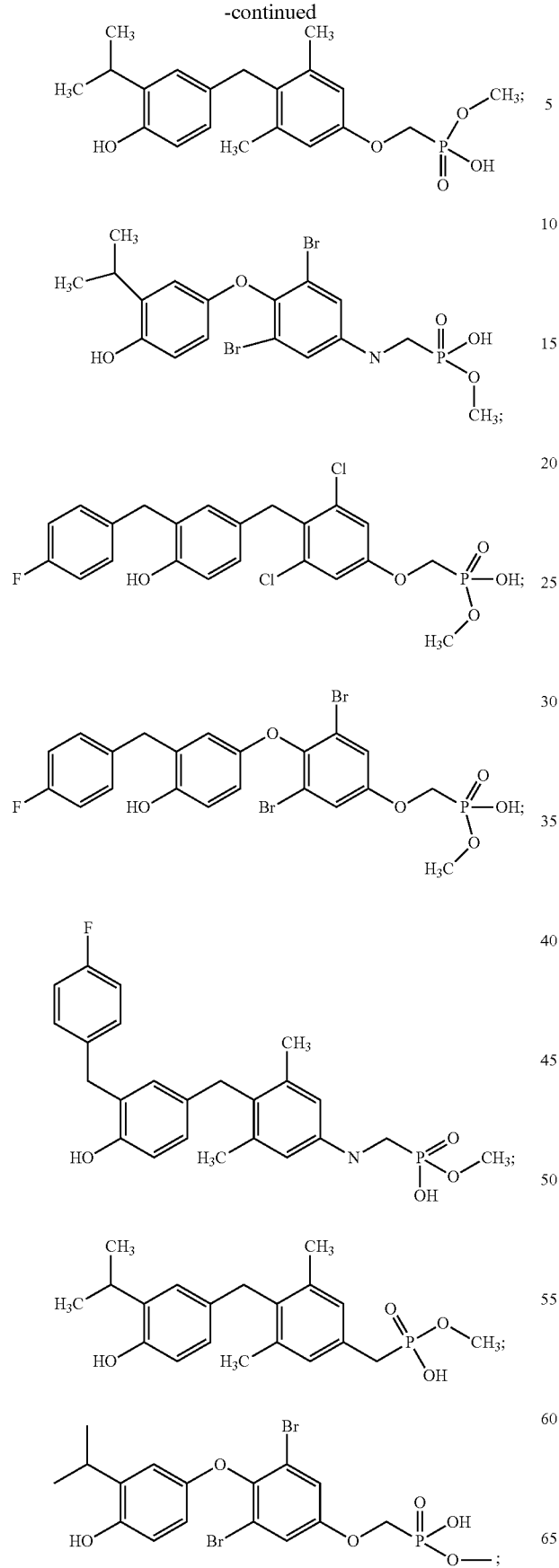

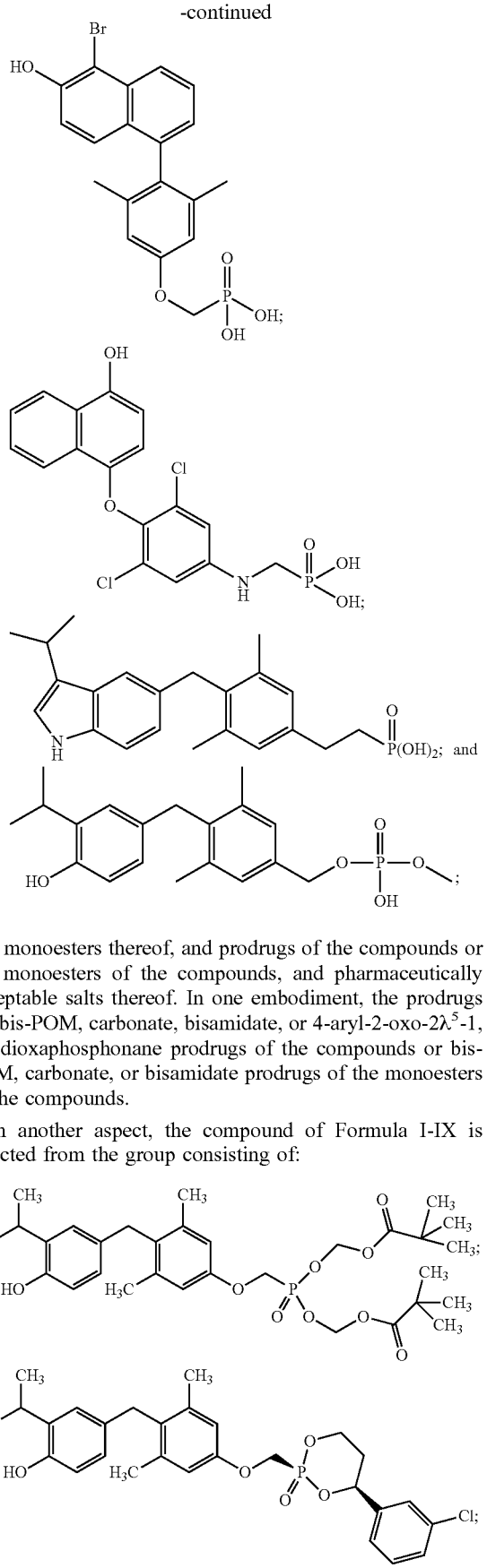

and monoesters thereof, and prodrugs of the compounds or the monoesters of the compounds, and pharmaceutically acceptable salts thereof. In one embodiment, the prodrugs are bis-POM, carbonate, bisamidate, or 4-aryl-2-oxo-$2\lambda^5$-1,3,2-dioxaphosphonane prodrugs of the compounds or bis-POM, carbonate, or bisamidate prodrugs of the monoesters of the compounds.

In another aspect, the compound of Formula I-IX is selected from the group consisting of:

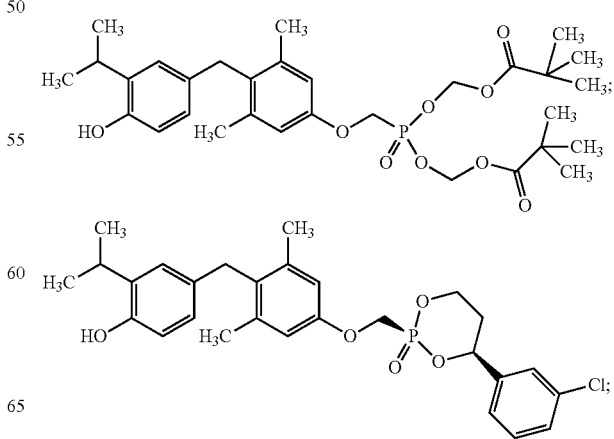

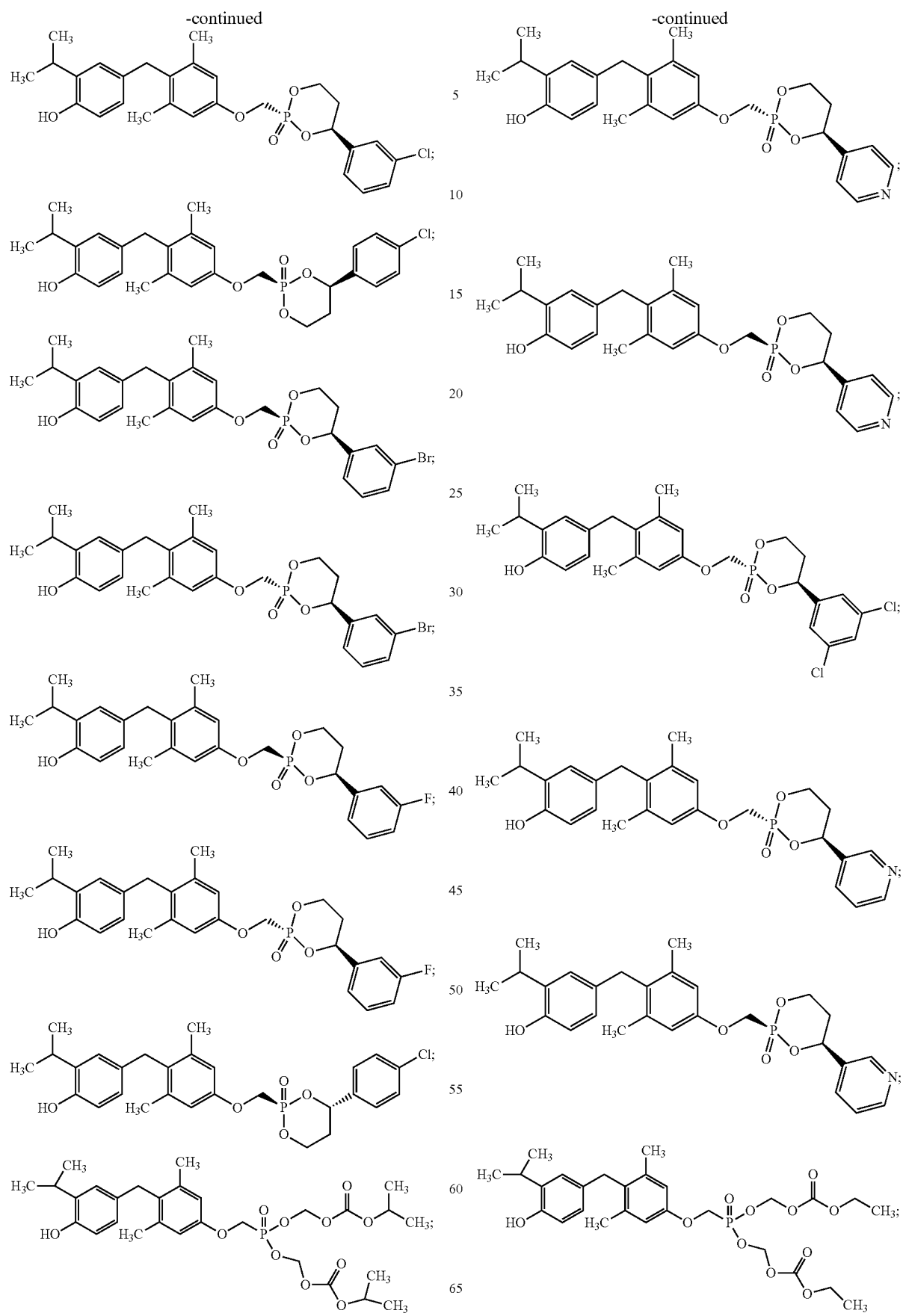

91
-continued
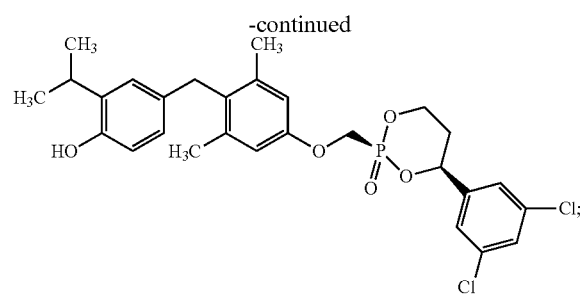
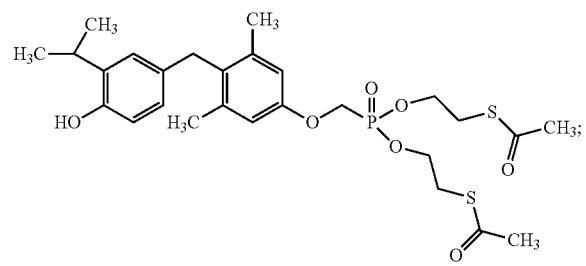
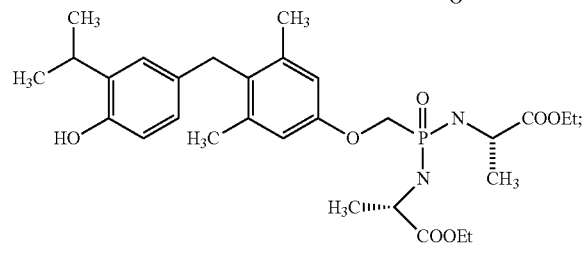
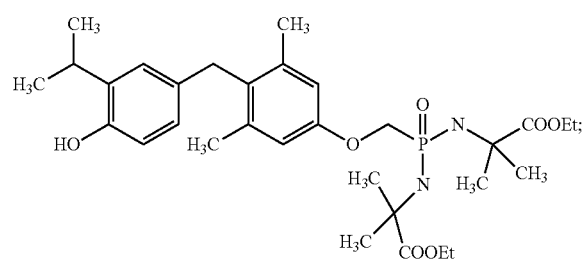
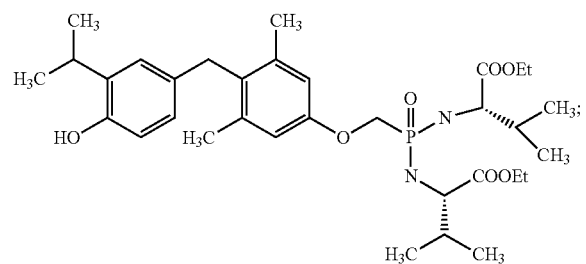
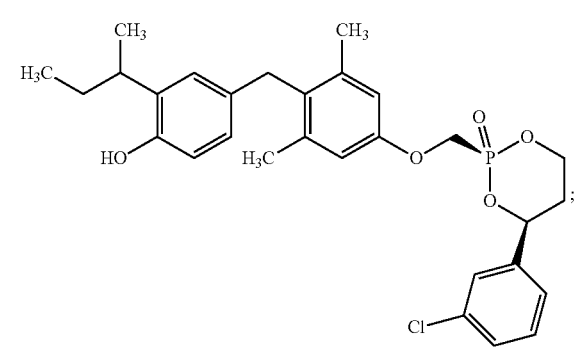
92
-continued
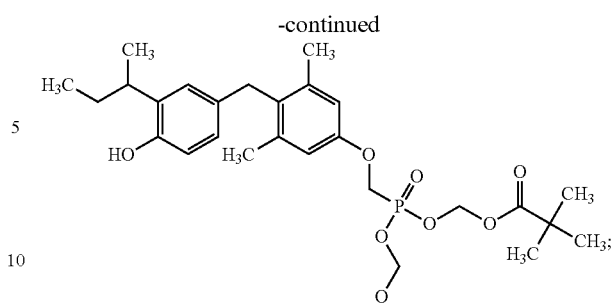
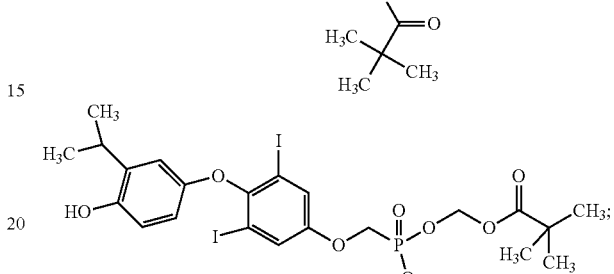
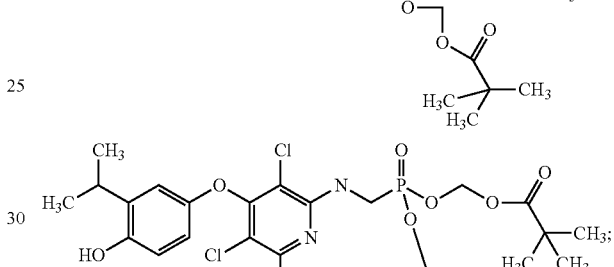
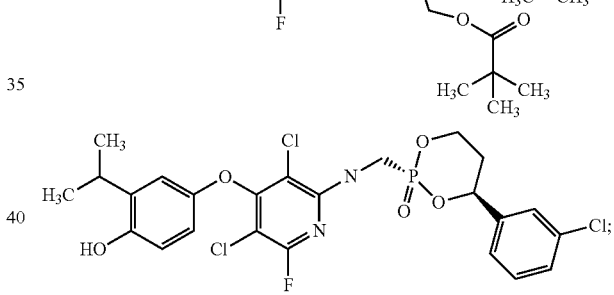
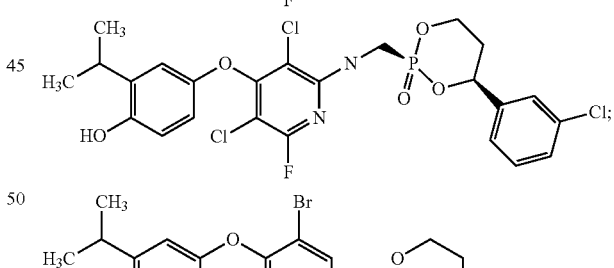
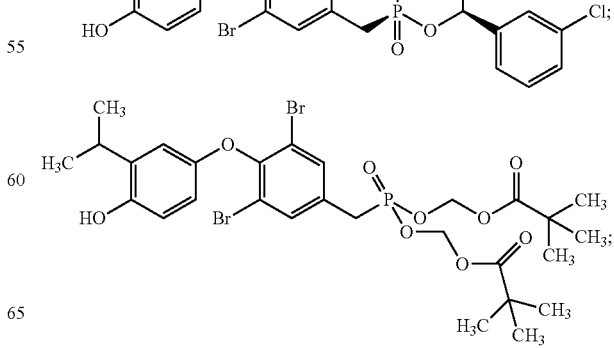

93
-continued
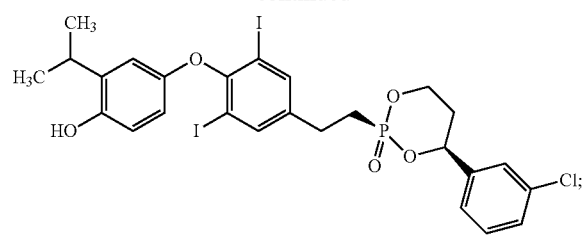
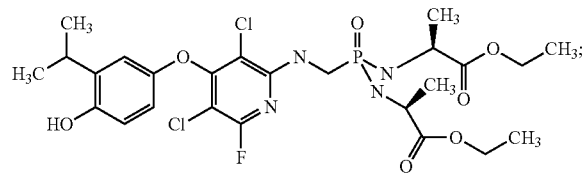
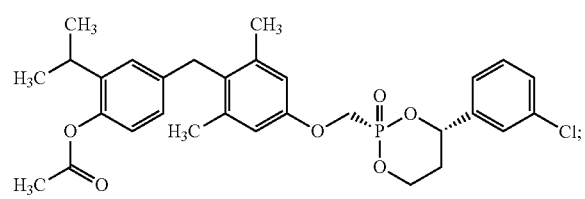
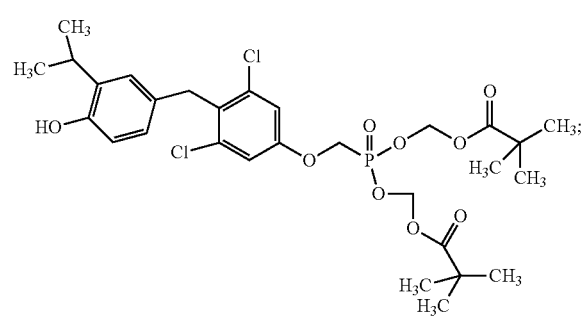
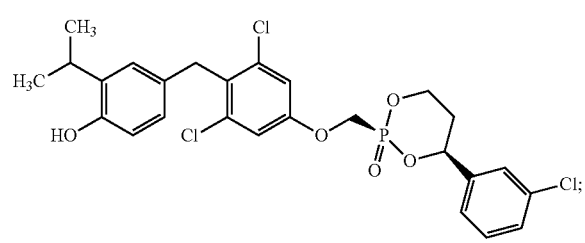
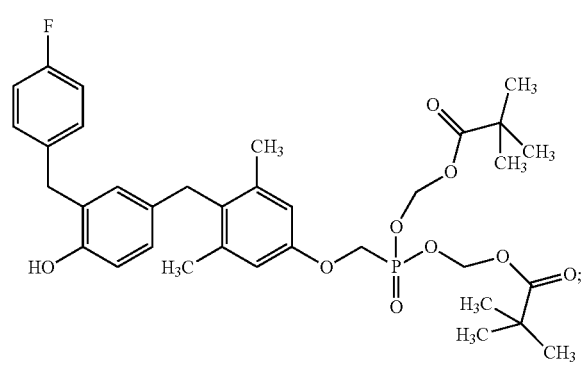
94
-continued
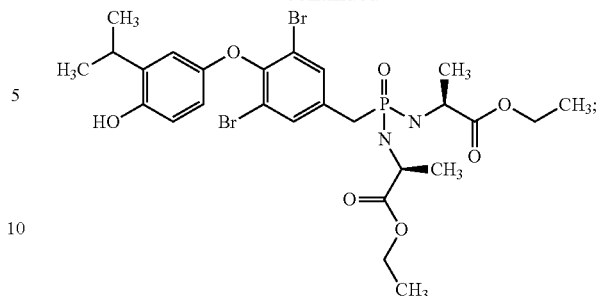
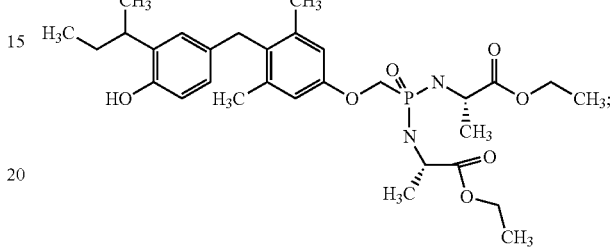
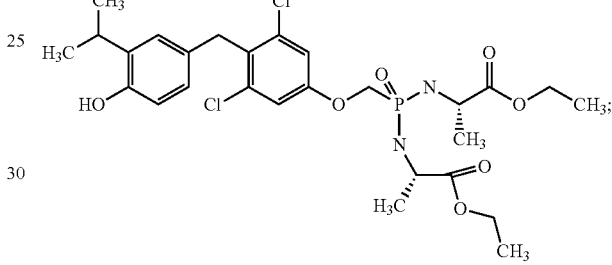
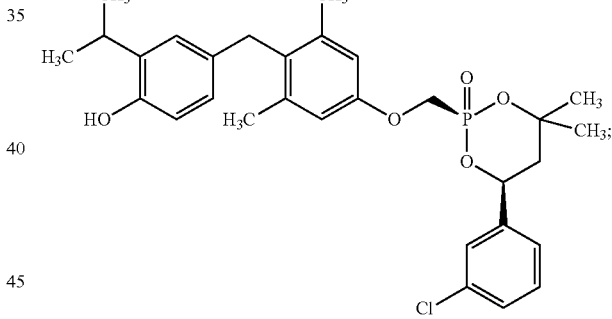
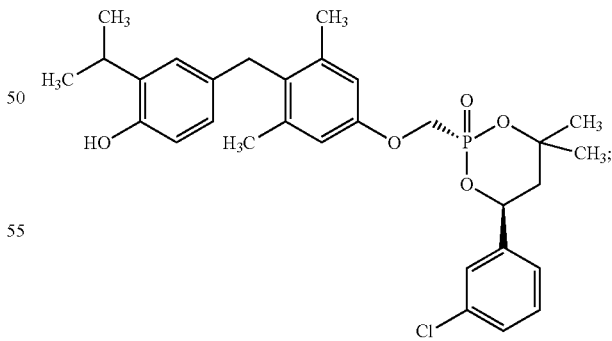
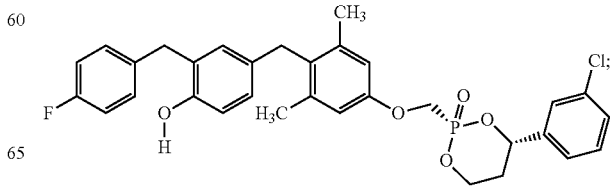

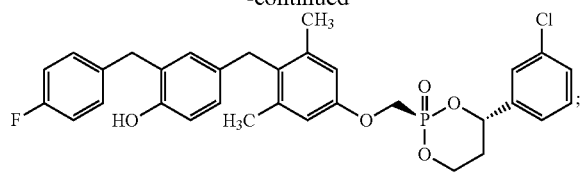
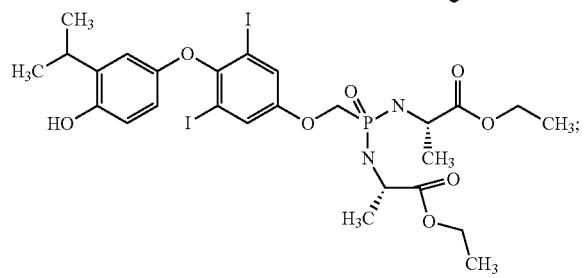
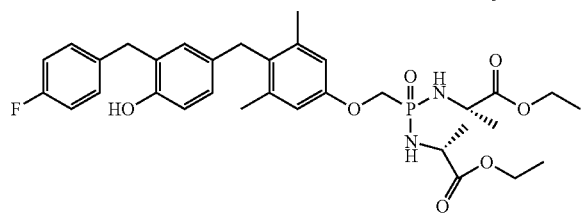
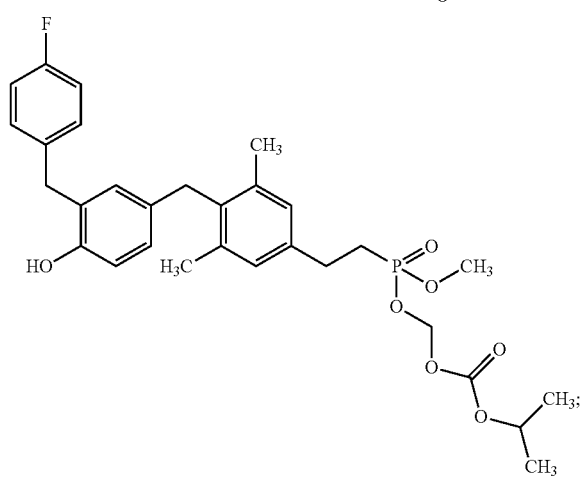
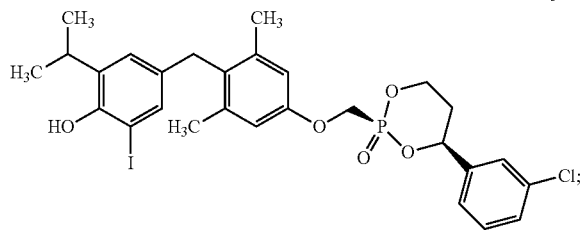
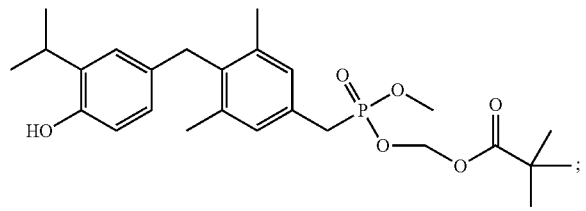
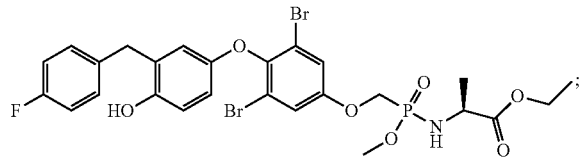
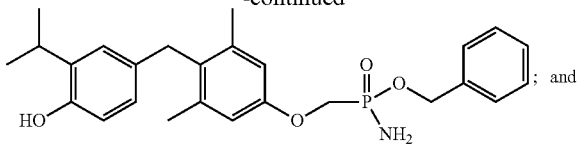
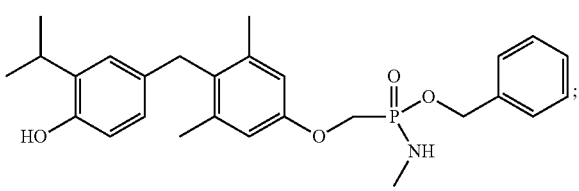
and pharmaceutically acceptable salts thereof.
In a further aspect, the compound of Formula I-IX is selected from the group consisting of:
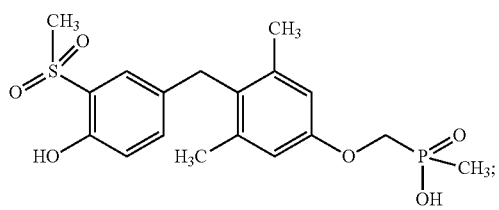
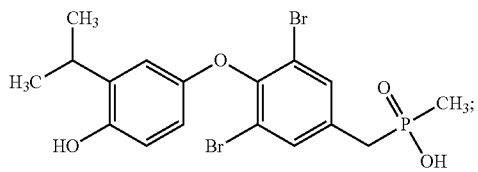
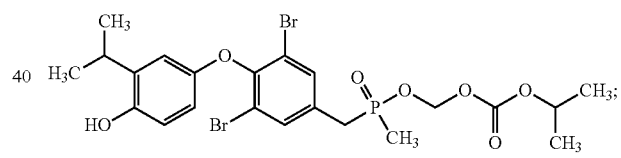
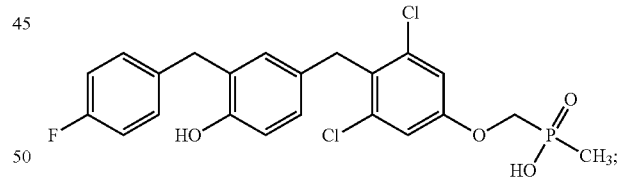
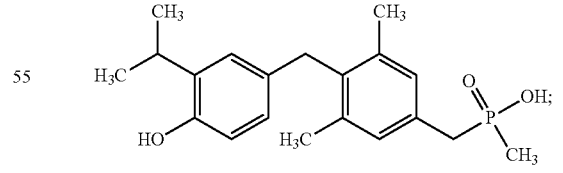
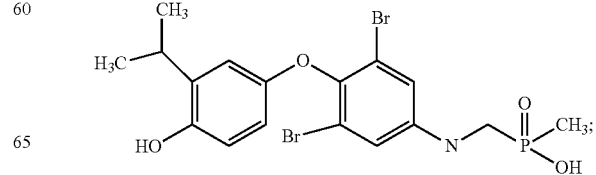

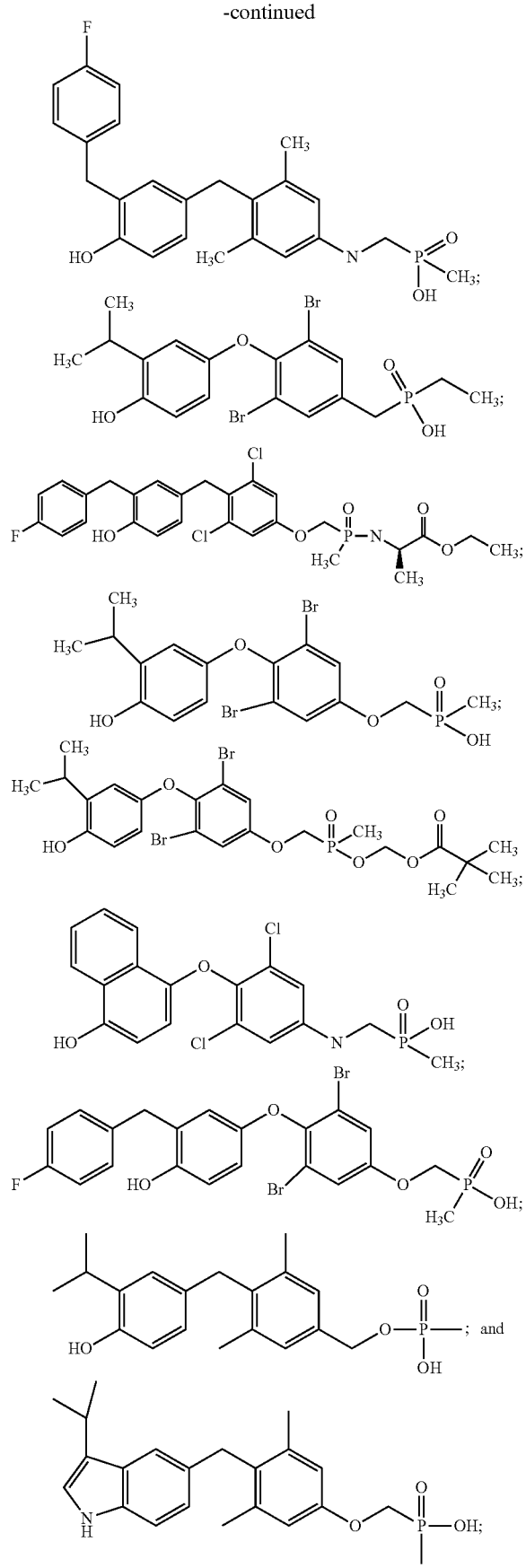

and pharmaceutically acceptable salts and prodrugs thereof. In one embodiment, the prodrugs of the above listed compounds are POM ester, carbonate, or amidate prodrugs.

Moreover, the compounds of the present invention can be administered in combination with other pharmaceutical agents that are used to lower the fat content of liver or pharmaceutical agents that are used to treat or prevent disorders that are related to or result in an increase in the fat content of liver.

The compounds of the present invention can be administered in combination with other pharmaceutical agents that are used to lower serum cholesterol such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a cholesteryl ester transfer protein (CETP) inhibitor (e.g., torcetrapib), a bile acid sequesterant (e.g., cholestyramine (Questran®), colesevelam and colestipol (Colestid®)), or a bile acid reabsorption inhibitor (see, for example, U.S. Pat. Nos. 6,245,744, 6,221,897, 6,277,831, EP 0683 773, EP 0683 774), a cholesterol absorption inhibitor as described (e.g., ezetimibe, tiqueside, pamaqueside or see, e.g., in WO 0250027), a PPARalpha agonist, a mixed PPAR alpha/gamma agonist such as, for example, AZ 242 (Tesaglitazar, (S)-3-(4-[2-(4-methanesulfony-loxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876, a MTP inhibitor such as, for example, implitapide, a fibrate, an ACAT inhibitors (e.g., avasimibe), an angiotensin II receptor antagonist, a squalene synthetase inhibitor, a squalene epoxidase inhibitor, a squalene cyclase inhibitor, combined squalene epoxidase/squalene cyclase inhibitor, a lipoprotein lipase inhibitor, an ATP citrate lyase inhibitor, lipoprotein(a) antagonist, an antioxidant or niacin (e.g., slow release niacin). The compounds of the present invention may also be administered in combination with a naturally occurring compound that act to lower plasma cholesterol levels. Such naturally occurring compounds are commonly called nutraceuticals and include, for example, garlic extract and niacin.

In one aspect, the HMG-CoA reductase inhibitor is from a class of therapeutics commonly called statins. Examples of HMG-CoA reductase inhibitors that may be used include but are not limited to lovastatin (MEVACOR; see U.S. Pat. Nos. 4,231,938; 4,294,926; 4,319,039), simvastatin (ZOCOR; see U.S. Pat. Nos. 4,444,784; 4,450,171; 4,820,850; 4,916,239), pravastatin (PRAVACHOL; see U.S. Pat. Nos. 4,346,227; 4,537,859; 4,410,629; 5,030,447 and 5,180,589), lactones of pravastatin (see U.S. Pat. No. 4,448,979), fluvastatin (LESCOL; see U.S. Pat. Nos. 5,354,772; 4,911,165; 4,739,073; 4,929,437; 5,189,164; 5,118,853; 5,290,946; 5,356,896), lactones of fluvastatin, atorvastatin (LIPITOR; see U.S. Pat. Nos. 5,273,995; 4,681,893; 5,489,691; 5,342,952), lactones of atorvastatin, cerivastatin (also known as rivastatin and BAYCHOL; see U.S. Pat. No. 5,177,080, and European Application No. EP-491226A), lactones of cerivastatin, rosuvastatin (CRESTOR; see U.S. Pat. No. 5,260,440 and RE37314, and European Patent No. EP521471), lactones of rosuvastatin, itavastatin, nisvastatin, visastatin, atavastatin, bervastatin, compactin, dihydrocompactin, dalvastatin, fluindostatin, pitivastatin, mevastatin (see U.S. Pat. No. 3,983,140), and velostatin (also referred to as synvinolin). Other examples of HMG-CoA reductase inhibitors are described in U.S. Pat. Nos. 5,217,992; 5,196,440; 5,189,180; 5,166,364;

5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237; 4,647,576; European Application Nos. 0142146A2 and 0221025A1; and PCT Application Nos. WO 86/03488 and WO 86/07054. Also included are pharmaceutically acceptable forms of the above. All of the above references are incorporated herein by reference.

Non-limiting examples of suitable bile acid sequestrants include cholestyramine (a styrene-divinylbenzene copolymer containing quaternary ammonium cationic groups capable of binding bile acids, such as QUESTRAN or QUESTRAN LIGHT cholestyramine which are available from Bristol-Myers Squibb), colestipol (a copolymer of diethylenetriamine and 1-chloro-2,3-epoxypropane, such as COLESTID tablets which are available from Pharmacia), colesevelam hydrochloride (such as WelChol Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ionene, N-(cycloalkyl)alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

In the above description, a fibrate base compound is a medicament for inhibiting synthesis and secretion of triglycerides in the liver and activating lipoprotein lipase, thereby lowering the triglyceride level in the blood. Examples include bezafibrate, beclobrate, binifibrate, ciprofibrate, clinofibrate, clofibrate, clofibric acid, ethofibrate, fenofibrate, gemfibrozil, nicofibrate, pirifibrate, ronifibrate, simfibrate and theofibrate. Such an ACAT inhibitor includes, for example: a compound having the general formula (I) disclosed in WO 92/09561 [e.g., FR-129169, of which the chemical name is N-(1,2-diphenylethyl)-2-(2-octyloxyphenyl)acetamide]; a compound having the general formula (I) including a pharmacologically acceptable salt/co-crystal, ester or prodrug thereof disclosed in the Japanese Patent Publication (Kohyo) Hei 8-510256 (WO 94/26702, U.S. Pat. No. 5,491,172) {e.g., CI-1011, of which the chemical name is 2,6-diisopropylphenyl-N-[(2,4,6-triisopropylphenyl) acetyl]sulfamate, and in the present invention CI-1011 including a pharmacologically acceptable salt/co-crystal, ester or prodrug thereof}; a compound having the general formula (I) including a pharmacologically acceptable salt/ co-crystal, ester or prodrug thereof disclosed in EP 421441 (U.S. Pat. No. 5,120,738) {e.g., F-1394, of which the chemical name is (1S,2S)-2-[3-(2,2-dimethylpropyl)-3-nonylureido]cyclohexan-1-yl 3-[(4R)—N-(2,2,5,5-tetramethyl-1,3-dioxane-4-carbonyl)amino]propionate, and in the present invention F-1394 including a pharmacologically acceptable salt/co-crystal, ester or prodrug thereof}; a compound including a pharmacologically acceptable salt/co-crystal, ester or prodrug thereof disclosed in the Japanese Patent Publication (Kohyo) 2000-500771 (WO 97/19918, U.S. Pat. No. 5,990,173) [e.g., F-12511, of which the chemical name is (S)-2',3',5'-trimethyl-4'-hydroxy-α-dodecylthio-α-phenylacetanilide, and in the present invention F-12511 including a pharmacologically acceptable salt/co-crystal, ester or prodrug thereof]; a compound having the general formula (I) including a pharmacologically acceptable salt/co-crystal, ester or prodrug thereof disclosed in the Japanese Patent Publication (Kokai) Hei 10-195037 (EP 790240, U.S. Pat. No. 5,849,732) [e.g., T-2591, of which the chemical name is 1-(3-t-butyl-2-hydroxy-5-methoxyphenyl)-3-(2-cyclohexylethyl)-3-(4-dimethylaminophenyl) urea, and in the present invention T-2591 including a pharmacologically acceptable salt/co-crystal, ester or prodrug thereof]; a compound having the general formula (I) including a pharmacologically acceptable salt/co-crystal, ester or prodrug thereof disclosed in WO 96/26948 {e.g., FCE-28654, of which the chemical name is 1-(2,6-diisopropylphenyl)-3-[(4R,5R)-4,5-di-methyl-2-(4-phosphonophenyl)-1,3-dioxolan-2-ylmethyl]urea, including a pharmacologically acceptable salt/co-crystal, ester or prodrug thereof}; a compound having the general formula (I) or a pharmacologically acceptable salt thereof disclosed in the specification of WO 98/54153 (EP 987254) {e.g., K-10085, of which the chemical name is N-[2,4-bis(methylthio)-6-methyl-3-pyridyl]-2-[4-[2-(oxazolo[4,5-b]pyridine-2-yl-thio)ethyl]piperazin-1-yl]acetamide, including a pharmacologically acceptable salt/co-crystal, ester or prodrug thereof}; a compound having the general formula (I) disclosed in WO 92/09572 (EP 559898, U.S. Pat. No. 5,475, 130) [e.g., HL-004, of which the chemical name is N-(2,6-diisopropylphenyl)-2-tetradecylthioacetamide]; a compound having the general formula (I) including a pharmacologically acceptable salt/co-crystal, ester or prodrug thereof disclosed in the Japanese Patent Publication (Kokai) Hei 7-82232 (EP 718281) {e.g., NTE-122, of which the chemical name is trans-1,4-bis[1-cyclohexyl-3-(4-dimethylaminophenyl)ureidomethyl]cyclohexane, and in the present invention NTE-122 includes pharmacologically acceptable salts of NTE-122}; a compound including a pharmacologically acceptable salt/co-crystal, ester or prodrug thereof disclosed in the Japanese Patent Publication (Kohyo) Hei 10-510512 (WO 96/10559) {e.g., FR-186054, of which the chemical name is 1-benzyl-1-[3-(pyrazol-3-yl)benzyl]-3-[2,4-bis (methylthio)-6-methylpyridi-n-3-yl]urea, and in the present invention FR-186054 including a pharmacologically acceptable salt/co-crystal, ester or prodrug thereof}; a compound having the general formula (I) including a pharmacologically acceptable salt/co-crystal, ester or prodrug thereof disclosed in WO 96/09287 (EP 0782986, U.S. Pat. No. 5,990,150) [e.g., N-(1-pentyl-4,6-dimethylindolin-7-yl)-2,2-dimethylpropaneamide, and in the present invention including a pharmacologically acceptable salt/co-crystal, ester or prodrug thereof]; and a compound having the general formula (I) including a pharmacologically acceptable salt/co-crystal, ester or prodrug thereof disclosed in WO 97/12860 (EP 0866059, U.S. Pat. No. 6,063,806) [e.g., N-(1-octyl-5-carboxymethyl-4,6-dimethylindolin-7-yl)-2,2-dimethylpropaneamide, including a pharmacologically acceptable salt/ co-crystal, ester or prodrug thereof]. The ACAT inhibitor preferably is a compound selected from the group consisting of FR-129169, CI-1011, F-1394, F-12511, T-2591, FCE-28654, K-10085, HL-004, NTE-122, FR-186054, N-(1-octyl-5-carboxymethyl-4,6-dimethylindolin-7-yl)-2,2-dimethylpropaneamide (hereinafter referred to as compound A), and N-(1-pentyl-4,6-dimethylindolin-7-yl)-2,2-dimethylpropaneamide (hereinafter referred as compound B), including a pharmacologically acceptable salt/co-crystal, ester or prodrug thereof. The ACAT inhibitor more preferably is a compound selected from the group consisting of CI-1011, F-12511, N-(1-octyl-5-carboxymethyl-4,6-dimethylindolin-7-yl)-2,2-dimethylpropaneamide (compound A), and N-(1-pentyl-4,6-dimethylindolin-7-yl)-2,2-dimethylpropaneamide (compound B), including a pharmacologically acceptable salt/co-crystal, ester or prodrug thereof; most preferred is N-(1-octyl-5-carboxymethyl-4,6-dimethylindolin-7-yl)-2,2-dimethylpropaneamide (compound A).

An angiotensin II receptor antagonist includes, for example, a biphenyl tetrazole compound or biphenylcarboxylic acid derivative such as: a compound having the general formula (I) including a pharmacologically acceptable salt/co-crystal, ester or prodrug thereof disclosed in the Japanese Patent Publication (Kokai) Sho 63-23868 (U.S. Pat. No. 5,138,069) {e.g., losartan, of which the chemical name is 2-butyl-4-chloro-1-[2'-(1H-tetrazol-5-yl)biphenyl-4-ylmethyl]-1H-imidazol-5-methanol, and in the present invention losartan including a pharmacologically acceptable salt/co-crystal, ester or prodrug thereof}; a compound having the general formula (I) including a pharmacologically acceptable salt/co-crystal, ester or prodrug thereof disclosed in the Japanese Patent Publication (Kohyo) Hei 4-506222 (WO 91/14679) {e.g., irbesartan, of which the chemical name is 2-N-butyl-4-spirocyclopentane-1-[2'-(1H-tetrazol-5-yl)biphenyl-4-ylmethyl]-2-imidazoline-5-one, and in the present invention irbesartan including a pharmacologically acceptable salt/co-crystal, ester or prodrug thereof}; a compound having the general formula (I), an ester thereof, including a pharmacologically acceptable salt/co-crystal, ester or prodrug thereof disclosed in the Japanese Patent Publication (Kokai) Hei 4235149 (EP 433983) {e.g., valsartan, of which the chemical name is (S)—N-valeryl-N-[2'-(1H-tetrazol-5-yl)biphenyl-4-ylmethyl]valine, and in the present invention valsartan including a pharmacologically acceptable salt/co-crystal, ester or prodrug thereof}; a carboxylic acid derivative having the general formula (I), including a pharmacologically acceptable salt/co-crystal, ester or prodrug thereof disclosed in the Japanese Patent Publication (Kokai) Hei 4-364171 (U.S. Pat. No. 5,196,444) {e.g., candesartan, of which the chemical name is 1-(cyclohexyloxycarbonyloxy) ethyl 2-ethoxy-1-[2'-(1H-tetrazol-5-yl)biphenyl-4-ylmethyl]-1H-benzimidazole-7-carboxylate, and in the present invention candesartan including a pharmacologically acceptable salt/co-crystal, ester or prodrug thereof (TCV-116 or the like), including a pharmacologically acceptable salt/co-crystal, ester or prodrug thereof}; a carboxylic acid derivative having the general formula (I), including a pharmacologically acceptable salt/co-crystal, ester or prodrug thereof disclosed in the Japanese Patent Publication (Kokai) Hei 5-78328 (U.S. Pat. No. 5,616,599) {e.g., olmesartan, of which the chemical name is (5-methyl-2-oxo-1,3-dioxolen-4-yl)methyl 4-(1-hydroxy-1-methylethyl)-2-propyl-1-[2'-(1H-tetrazol-5-yl)biphenyl-4-ylmethyl]imidazole-5-carboxylate, and in the present invention olmesartan includes carboxylic acid derivatives thereof, pharmacologically acceptable esters of the carboxylic acid derivatives (CS-866 or the like), including a pharmacologically acceptable salt/co-crystal, ester or prodrug thereof}; and a compound having the general formula (I), including a pharmacologically acceptable salt/co-crystal, ester or prodrug thereof disclosed in the Japanese Patent Publication (Kokai) Hei 4-346978 (U.S. Pat. No. 5,591,762, EP 502,314) {e.g., telmisartan, of which the chemical name is 4'-[[2-n-propyl-4-methyl-6-(1-methylbenzimidazol-2-yl)-benzimidazol-1-yl]methyl]biphenyl-2-carboxylate, including a pharmacologically acceptable salt/co-crystal, ester or prodrug thereof}. The angiotensin II receptor antagonist preferably is losartan, irbesartan, valsartan, candesartan, olmesartan, or telmisartan; more preferred is losartan or olmesartan; and most preferred is olmesartan.

In addition to being useful in treating or preventing certain diseases and disorders, combination therapy with compounds of this invention maybe useful in reducing the dosage of the second drug or agent (e.g., atorvastatin).

In addition, the compounds of the present invention can be used in combination with an apolipoprotein B secretion inhibitor and/or microsomal triglyceride transfer protein (MTP) inhibitor. Some apolipoprotein B secretion inhibitors and/or MTP inhibitors are disclosed in U.S. Pat. No. 5,919,795.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Meth. Enzymology* 71:455-509 (1981); and the references cited therein). A variety of these compounds are described and referenced below. U.S. Pat. No. 4,231,938 discloses certain compounds isolated after cultivation of a microorganism belonging to the genus Aspergillus, such as lovastatin. Also U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of currently or previously marketed products containing HMG-CoA reductase inhibitors include cerivastatin Na, rosuvastatin Ca, fluvastatin, atorvastatin, lovastatin, pravastatin Na and simvastatin.

Any HMG-CoA synthase inhibitor may be used as an additional compound in the combination therapy aspect of this invention. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Meth. Enzymology* 35:155-160 (1975); and *Meth. Enzymology*, 110:19-26 (1985); and the references cited therein). A variety of these compounds are described and referenced below. U.S. Pat. No. 5,120,729 discloses certain beta-lactam derivatives. U.S. Pat. No. 5,064,856 discloses certain spirolactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to those skilled in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities.

Such regulation is readily determined by those skilled in the art according to standard assays (*Meth. Enzymology* 110: 9-19 (1985)). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.* 32:357-416 (1993)).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot* 49(8):815-816 (1996), and *Bioorg. Med. Chem. Lett.* 6:1951-1954 (1996), respectively.

Any ACAT inhibitor can serve as an additional compound in the combination therapy aspect of this invention. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al described in *J. Lipid Res.*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Meth. Enzymology* 15:393-454 (1969); and *Meth. Enzymology* 110:359-373 (1985); and references cited therein). A summary of squalene synthetase inhibitors has been complied in *Curr. Op. Ther. Patents*, 861-4, (1993). EP 0 567 026 A1 discloses certain 4,1-benzoxazepine derivatives as squalene synthetase inhibitors and their use in the treatment of hypercholesterolemia and as fungicides. EP 0 645 378 A1 discloses certain seven- or eight-membered heterocycles as squalene synthetase inhibitors and their use in the treatment and prevention hypercholesterolemia and fungal infections. EP 0 645 377 A1 discloses certain benzoxazepine derivatives as squalene synthetase inhibitors useful for the treatment of hypercholesterolemia or coronary sclerosis. EP 0 611 749 A1 discloses certain substituted antic acid derivatives useful for the treatment of arteriosclerosis. EP 0 705 607 A2 discloses certain condensed seven- or eight-membered heterocyclic compounds useful as antihypertriglyceridemic agents. WO 96/09827 discloses certain combinations of cholesterol absorption inhibitors and cholesterol biosynthesis inhibitors including benzoxazepine derivatives and benzothiazepine derivatives. EP 0 701 725 A1 discloses a process for preparing certain optically-active compounds, including benzoxazepine derivatives, having plasma cholesterol and triglyceride lowering activities.

Other compounds that are currently or previously marketed for hyperlipidemia, including hypercholesterolemia, and which are intended to help prevent or treat atherosclerosis, include bile acid sequestrants, such as colestipol HCl and cholestyramine; and fibric acid derivatives, such as clofibrate, fenofibrate, and gemfibrozil. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. In one aspect lipase inhibitors comprise gastric or pancreatic lipase inhibitors. In a further aspect glucosidase inhibitors comprise amylase inhibitors. Examples of glucosidase inhibitors are those inhibitors selected from the group consisting of acarbose, adiposine, voglibose, miglitol, emiglitate, camiglibose, tendamistate, trestatin, pradimicin-Q and salbostatin. Examples of amylase inhibitors include tendamistat and the various cyclic peptides related thereto disclosed in U.S. Pat. No. 4,451,455, AI-3688 and the various cyclic polypeptides related thereto disclosed in U.S. Pat. No. 4,623,714, and trestatin, consisting of a mixture of trestatin A, trestatin B and trestatin C and the various trehalose-containing aminosugars related thereto disclosed in U.S. Pat. No. 4,273,765.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, Abrams et al., *Gastroenterology* 92:125 (1987).

A variety of lipase inhibitors are known to one of ordinary skill in the art. However, in the practice of the methods, pharmaceutical compositions, and kits of the instant invention, generally lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, SS, 7Z,1OZ)-5-[(S)-2-formamido-4-methyl-valeryloxy]-2-hexyl-3-hydroxy-7,1(t-hexadecanoic acid lactone, and tetrahydrolipostatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4-trifiuorometbylphenylurea, and the various urea derivatives related thereto, are disclosed in U.S. Pat. No. 4,405,644.

The pancreatic lipase inhibitor valilactone, and a process for the preparation thereof by the microbial cultivation of Aetinomycetes strain MG147—CF2, are disclosed in Kitahara, et al., *J. Antibiotics* 40(11):1647-50 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa et al., *J. Antibiotics* 33:1594-1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562:205-29 (1949).

The ability of RHC 80267 to inhibit the activity of myocardial lipoprotein lipase is disclosed in Carroll et al., *Lipids* 27:305-7 (1992) and Chuang et al., *J. Mol. Cell Cardiol.* 22:1009-16 (1990).

In another aspect of the present invention, the compounds of Formula I can be used in combination with an additional anti-obesity agent. The additional anti-obesity agent in one aspect is selected from the group consisting of a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

In an additional aspect the anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl} acetic acid, {4{2-(2-[6-aminopyridin-3-yl]-2(R)-hydroxyethylamino)ethoxy]phenyl}benzoic acid, {4-[2-(2{6-aminopyridin-3-yl]-2(R)-hydroxyethylamino)ethoxy]phenyl} propionic acid, and {4-[2-(2-[6-aminopyridin-3-yl]-2(R)-hydroxyethylamino)ethoxy]phenoxy} acetic acid.

In one aspect, the thyromimetic compounds present may be administered in combination with pharmaceutical agents useful for the prevention or treatment of diabetes, including impaired glucose tolerance, insulin resistance, insulin dependent diabetes mellitus (Type I) and non-insulin dependent diabetes mellitus (NIDDM or Type II). Also included in the prevention or treatment of diabetes are the diabetic complications, such as neuropathy, nephropathy, retinopathy or cataracts.

In one aspect the type of diabetes to be treated is non-insulin dependent diabetes mellitus, also known as Type II diabetes or NIDDM.

Representative agents that can be used to treat diabetes include insulin and insulin analogs (e.g., LysPro insulin); GLP-1 (7-37) (insulinotropin) and GLP-1 (7-36) —NH$_2$. Agents that enhance insulin secretion, e.g., eblorpropamide, glibenclamide, tolbutamide, tolazamide, acetohexamide, glypizide, glimepiride, repaglinide, nateglinide, meglitinide; biguanides: metformin, phenformin, buformin; A2-antagonists and imidazolines: midaglizole, isaglidole, deriglidole, idazoxan, efaroxan, fluparoxan; other insulin secretagogues linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73,945; ~3-agonists: BRL 35135, BRL 37344, RO 16-8714, ICI D7114, CL 316,243; phosphodiesterase inhibitors: -386,398; lipid-lowering agents benfluorex; antiobesity agents: fenfiuramine; vanadate and vanadium complexes (e.g., bis(cysteinamide N-octyl) oxovanadium) and peroxovanadium complexes; amylin antagonists; glucagon antagonists; gluconeogenesis inhibitors; somatostatin analogs; antilipolytic agents: nicotinic acid, acipimox, WAG 994. Also contemplated to be used in combination with a compound of the present invention are pramlintide (Symlin™), AC 2993 and nateglinide. Any agent or combination of agents can be administered as described above.

In addition, the compounds of the present invention can be used in combination with one or more aldose reductase inhibitors, DPPIV inhibitor, glycogen phosphorylase inhibitors, sorbitol dehydrogenase inhibitors, NHE-1 inhibitors and/or glucocorticoid receptor antagonists.

Any compound having activity as a fructose-1,6-bisphosphatase (FBPase) inhibitor can serve as the second compound in the combination therapy aspect of the instant invention (e.g., 2-amino-5-isobutyl-4-{2-[5-(N,N'-bis((S)-1-ethoxycarbonyl)ethyl)phosphonamido]furanyl}thiazoles).

FBPase is a key regulatory enzyme in gluconeogenesis, the metabolic pathway by which the liver synthesizes glucose from 3-carbon precursors. The term FBPase inhibitor refers to compounds that inhibit FBPase enzyme activity and thereby block the conversion of fructose-1,6-bisphosphate, the substrate of the enzyme, to fructose 6-phosphate. FBPase inhibition can be determined directly at the enzyme level by those skilled in the art according to standard methodology (e.g., Gidh-Jain et al., *J. Biol. Chem.* 269(44):27732-8 (1994)). Alternatively, FBPase inhibition can be assessed according to standard methodology by measuring the inhibition of glucose production by isolated hepatocytes or in a perfused liver, or by measuring blood glucose lowering in normal or diabetic animals (e.g., Vincent et al., *Diabetologia* 39(10):1148-55 (1996); Vincent et al., *Diabetes* 40(10):1259-66 (1991)). In some cases, in vivo metabolic activation of a compound may be required to generate the FBPase inhibitor. This class of compounds may be inactive in the enzyme inhibition screen, may or may not be active in hepatocytes, but is active in vivo as evidenced by glucose lowering in the normal, fasted rat and/or in animal models of diabetes.

A variety of FBPase inhibitors are described and referenced below; however, other FBPase inhibitors will be known to those skilled in the art. Gruber et al. U.S. Pat. No. 5,658,889 described the use of inhibitors of the AMP site of FBPase to treat diabetes; WO 98/39344 and U.S. Pat. No. 6,284,748 describe purine inhibitors; WO 98/39343 and U.S. Pat. No. 6,110,903 describe benzothiazole inhibitors to treat diabetes; WO 98/39342 and U.S. Pat. No. 6,054,587 describe indole inhibitors to treat diabetes; and WO 00/14095 and U.S. Pat. No. 6,489,476 describe heteroaromatic phosphonate inhibitors to treat diabetes. Other FBPase inhibitors are described in Wright et al., *J. Med. Chem.* 45(18):3865-77 (2002) and WO 99/47549.

The thyromimetic compounds can also be used in combination with sulfonylureas such as amaryl, alyburide, glucotrol, chlorpropamide, diabinese, tolazamide, tolinase, acetohexamide, glipizide, tolbutamide, orinase, glimepiride, DiaBeta, micronase, glibenclamide, and gliclazide.

The thyromimetic compounds can also be used in combination with antihypertensive agents. Any anti-hypertensive agent can be used as the second agent in such combinations. Examples of presently marketed products containing antihypertensive agents include calcium channel blockers, such as Cardizem, Adalat, Calan, Cardene, Coven, Dilacor, DynaCirc, Procardia XL, Sular, Tiazac, Vascor, Verelan, Isoptin, Nimotop, Norvasc, and Plendil; angiotensin converting enzyme (ACE) inhibitors, such as Accupril, Altace, Captopril, Lotensin, Mavik, Monopril, Prinivil, Univasc, Vasotec and Zestril.

Examples of compounds that may be used in combination with the compounds of the present invention to prevent or treat osteoporosis include: anti-resorptive agents including progestins, polyphosphonates, bisphosphonate(s), estrogen agonists/antagonists, estrogen, estrogen/progestin combinations, Premarin, estrone, estriol or 17α- or 17β-ethynyl estradiol); progestins including algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol; and bone resorption inhibiting polyphosphonates including polyphosphonates such as of the type disclosed in U.S. Pat. No. 3,683,080, the disclosure of which is incorporated herein by reference. Examples of polyphosphonates include geminal diphosphonates (also referred to as bis-phosphonates), tiludronate disodium, ibandronic acid, alendronate, resindronate zoledronic acid, 6-amino-1-hydroxy-hexylidene-bisphosphonic acid and 1-hydroxy-3(methylpentylamino)-propylidene-bisphosphonic acid. Salts, co-crystals and esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, and hexane-6-amino-1-hydroxy-1,1-diphosphonic acid.

Estrogen agonist/antagonist include 3-(4-(1,2-diphenyl-but-1-enyl)-phenyl)-acrylic acid, tamoxifen: (ethanamine, 2-(–4-(1,2-diphenyl-1-butenyl)phenoxy)-N,N-dimethyl, (Z)-2-,2-hydroxy-1,2,3-propanetricarboxylate(1:1)) and related compounds which are disclosed in U.S. Pat. No. 4,536,516, the disclosure of which is incorporated herein by reference, 4-hydroxy tamoxifen, which is disclosed in U.S. Pat. No. 4,623,660, the disclosure of which is incorporated herein by reference, raloxifene: (methanone, (6-hydroxy-2-(4-hydroxyphenyl)benzo[b]thien-3-yl)(4-(2-(1-piperidinyl) ethoxy)phenyl)-hydrochloride) which is disclosed in U.S. Pat. No. 4,418,068, the disclosure of which is incorporated herein by reference, toremifene: (ethanamine, 2-(4-(4-chloro-1,2-diphenyl-1-butenyl)phenoxy)-N,N-dimethyl, (Z)-,2-hydroxy-1,2,3-propanetricarboxylate (1:1) which is disclosed in U.S. Pat. No. 4,996,225, the disclosure of which is incorporated herein by reference, centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference, levormeloxifene, idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference, 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference, 6-(4-hydroxy-phenyl)-5-(4-(2-piperidin-1-yl-ethoxy)-benzyl)-naphthalen-2-ol, which is disclosed in U.S. Pat. No. 5,484,795, the disclosure of which is incorporated herein by reference, (4-(2-(2-aza-bicyclo [2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc, TSE-424 (Wyeth-Ayerst Laboratories) and arazoxifene, cis-6-(4-fluoro-phenyl)-5-(4-(2-piperidin-1-yl-ethoxy)-phenyl)-5,6,-

7,8-tetrahydro-naphthalene-2-ol; (−)-cis-6-phenyl-5-(4-(2-pyrrolidin-1-yl-ethoxy)-phenyl)-5,6,7,8-tetrahydro-naphthalene-2-ol (also known as lasofoxifene); cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; 1-(4'-pyrrolidinolethoxyphenyl)-2-phenyl-6-hydroxy-1,2,3,4-tetrahydroisoquinoline, 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs. Further anti-osteoporosis agents includes a selective androgen receptor modulator (SARM) Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino[5,6-g]quinoline derivatives and piperidino[3,2-g]quinolinone derivatives. Other examples include cypterone, also known as (1b,2b)-6-chloro-1,2-dihydro-17-hydroxy-3'-H-cyclopropa[1,2]pregna-1,4,6-triene-3,20-dione is disclosed in U.S. Pat. No. 3,234,093. Chlormadinone, also known as 17-(acetyloxy)-6-chloropregna-4,6-diene-3,20-dione, in its acetate form, acts as an anti-androgen and is disclosed in U.S. Pat. No. 3,485,852. Nilutamide, also known as 5,5-dimethyl-3-[4-nitro-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of bicalutamide are discussed by Tucker et al., *J. Med. Chem.* 31:885-887 (1988). Hydroxyflutamide, a known androgen receptor antagonist in most tissues, has been suggested to function as a SARM for effects on IL-6 production by osteoblasts as disclosed in Hofbauer et al., *J. Bone Miner. Res.* 14:1330-1337 (1999). Additional SARMs have been disclosed in U.S. Pat. No. 6,017,924; WO 01/16108, WO 01/16133, WO 01/16139, WO 02/00617, WO 02/16310, U.S. Patent Application Publication No. US 2002/0099096, U.S. Patent Application Publication No. US 2003/0022868, WO 03/011302 and WO 03/011824. All of the above references are hereby incorporated by reference herein.

Formulations

Unit dose amounts and dose scheduling for the pharmaceutical compositions of the present invention can be determined using methods well known in the art. In one aspect, the compounds of the invention are administered orally in a total daily dose of about 0.375 µg/kg/day to about 3.75 mg/kg/day. In another aspect the total daily dose is from about 3.75 µg/kg/day to about 0.375 mg/kg/day. In another aspect the total daily dose is from about 3.75 µg/kg/day to about 37.5 µg/kg/day. In another aspect the total daily dose is from about 3.75 µg/kg/day to about 60 µg/kg/day. In a further aspect the dose range is from 30 µg/kg/day to 3.0 mg/kg/day. In one aspect, the compounds of the invention are administered orally in a unit dose of about 0.375 µg/kg to about 3.75 mg/kg. In another aspect the unit dose is from about 3.75 µg/kg to about 0.375 mg/kg. In another aspect the unit dose is from about 3.75 µg/kg to about 37.5 µg/kg. In another aspect the unit dose is from about 3.75 µg/kg to about 60 µg/kg. In one aspect, the compounds of the invention are administered orally in a unit dose of about 0.188 µg/kg to about 1.88 mg/kg. In another aspect the unit dose is from about 1.88 µg/kg to about 0.188 mg/kg. In another aspect the unit dose is from about 1.88 µg/kg to about 18.8 µg/kg. In another aspect the unit dose is from about 1.88 µg/kg to about 30 µg/kg. In one aspect, the compounds of the invention are administered orally in a unit dose of about 0.125 µg/kg to about 1.25 mg/kg. In another aspect the unit dose is from about 1.25 µg/kg to about 0.125 mg/kg. In another aspect the unit dose is from about 1.25 µg/kg to about 12.5 µg/kg. In another aspect the unit dose is from about 1.25 µg/kg to about 20 µg/kg. In one embodiment the unit dose is administered once a day. In another embodiment the unit dose is administered twice a day. In another embodiment the unit dose is administered three times a day. In another embodiment the unit dose is administered four times a day.

Dose refers to the equivalent of the free acid. The use of controlled-release preparations to control the rate of release of the active ingredient may be preferred. The daily dose may be administered in multiple divided doses over the period of a day. Doses and dosing schedules may be adjusted to the form of the drug or form of delivery used. For example, different dosages and scheduling of doses may be used when the form of the drug is in a controlled release form or intravenous delivery is used with a liquid form.

Compounds of this invention when used in combination with other compounds or agents may be administered as a daily dose or an appropriate fraction of the daily dose (e.g., bid). Administration of compounds of this invention may occur at or near the time in which the other compound or agent is administered or at a different time. When compounds of this invention are used in combination with other compounds or agents, the other compound or agent (e.g., atorvastatin) may be administered at the approved dose or a lower dose.

For the purposes of this invention, the compounds may be administered by a variety of means including orally, parenterally, by inhalation including but not limited to nasal spray, topically, implantables or rectally in formulations containing pharmaceutically acceptable carriers, adjuvants and vehicles. The term parenteral as used here includes subcutaneous, intravenous, intramuscular, and intra-arterial injections with a variety of infusion techniques. Intra-arterial and intravenous injection as used herein includes administration through catheters. Oral administration is generally preferred.

Pharmaceutical compositions containing the active ingredient may be in any form suitable for the intended method of administration. When used for oral use for example, tablets, pellets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain, one or more agents including sweetening agents, flavoring agents, coloring agents and preserving agents, in order to provide a palatable preparation. Tablets and pellets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets and pellets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders, pellets, and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

In another aspect the pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 0.2 to 2000 μmol (approximately 0.1 to 1000 mg) of active material compounded with an appropriate and convenient amount of carrier material which may vary from about 5 to about 99.9% of the total compositions. It is preferred that the pharmaceutical composition be prepared which provides easily measurable amounts for administration. For example, an aqueous solution intended for intravenous infusion should contain from about 0.05 to about 500 μmol (approximately 0.025 to 250 mg) of the active ingredient per milliliter of solution in order that infusion of a suitable volume at a rate of about 30 mL/h can occur.

As noted above, formulations suitable for oral administration may be presented as discrete units such as capsules, cachets, pellets, or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. Tablets may optionally be provided with an enteric coating, to provide release in parts of the gut other than the stomach. This is particularly advantageous with the compounds of the present invention when such compounds are susceptible to acid hydrolysis.

Pharmaceutical compositions comprising the compounds of the present invention can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to treat or control the condition in a minimum amount of time. Advantages of controlled-release formulations include; 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized forms of compositions of the invention and thus effect controlled delivery of the drug. Examples of specific anion exchangers include, but are not limited to, DUOLITE A568 and DUOLITE AP143 (Rohm & Haas, Spring House, Pa. USA).

One embodiment of the invention encompasses a unit dosage form which comprises a compound of the present invention or a pharmaceutically acceptable salt, or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS that can be used to administer compounds and compositions of the invention include, but are not limited to, the OROS Push-Pull, Delayed Push-Pull, Multi-Layer Push-Pull, and Push-Stick Systems, all of which are well known. Additional OROS systems that can be used for the controlled oral delivery of compounds and compositions of the invention include OROS-CT and L-OROS. Id.; see also, Delivery Times, vol. II, issue II (Alza Corporation).

Conventional OROS oral dosage forms are made by compressing a drug powder (e.g., a T3 mimetic composition of the present invention) into a hard tablet, coating the tablet with cellulose derivatives to form a semipermeable membrane, and then drilling an orifice in the coating (e.g., with a laser). (Kim, Controlled Release Dosage Form Design, 231-238 Technomic Publishing, Lancaster, Pa. 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS drug delivery systems cannot be used to effectively deliver drugs with low water solubility.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a compound of the present invention, including a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a compound of the present invention, including a polymorph, solvate, hydrate, dehydrate, co-crystal, anhydrous, or amorphous form thereof. See U.S. Pat. No. 6,342,249, the entirety of which is incorporated herein by reference.

Transdermal Delivery System: The controlled release formulations of the present invention may be formulated as a transdermal delivery system, such as transdermal patches. In certain embodiments of the present invention, a transdermal patch comprises a compound of the present invention contained in a reservoir or a matrix, and an adhesive which allows the transdermal device to adhere to the skin, allowing the passage of the active agent from the transdermal device through the skin of the patient. Once the compound has penetrated the skin layer, the drug is absorbed into the blood stream where it exerts desired pharmaceutical effects. The transdermal patch releases the compound of the present invention in a controlled-release manner, such that the blood levels of the a compound of the present invention is maintained at a therapeutically effective level through out the dosing period, and the blood levels of the a compound of the present invention is maintained at a concentration that is sufficient to reduce side effects associated with immediate release dosage forms but not sufficient to negate the therapeutic effectiveness of the compound.

Transdermal refers to the delivery of a compound by passage through the skin or mucosal tissue and into the blood stream. There are four main types of transdermal patches listed below.

1. Single-layer Drug-in-Adhesive: The adhesive layer of this system also contains the drug. In this type of patch the adhesive layer not only serves to adhere the various layers together, along with the entire system to the skin, but is also responsible for the releasing of the drug. The adhesive layer is surrounded by a temporary liner and a backing.
2. Multi-layer Drug-in-Adhesive: The multi-layer drug-in adhesive patch is similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing.
3. Reservoir: Unlike the Single-layer and Multi-layer Drug-in-adhesive systems the reservoir transdermal system has a separate drug layer. The drug layer is a liquid compartment containing a drug solution or suspension separated by the adhesive layer. This patch is also backed by the backing layer.
4. Matrix: The Matrix system has a drug layer of a semisolid matrix containing a drug solution or suspension. The adhesive layer in this patch surrounds the drug layer partially overlaying it.

Other modes of transdermal delivery are known in the art and are included in the present invention.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In one aspect the unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Synthesis of Compounds Useful in the Present Invention

The compounds in this invention may be prepared by the processes described in relevant published literature procedures that are used by those skilled in the art. Carboxylic acid-containing compounds and related compounds may be prepared as disclosed in U.S. Pat. Nos. 6,465,687 and 6,747,048, U.S. Published Application Nos. 2004/0097589, 2004/0116387, 2004/0220147, and 2005/0004184, WO 00/07972, WO 01/36365, and WO 2004/007430, each herein incorporated by reference. In addition, the following Schemes may be used to prepare phosphorus-containing compounds. It should be understood that the following Schemes are provided solely for the purpose of illustration and do not limit the invention which is defined by the claims. In all applicable structures contained in the Schemes described in this invention, PG refers to a protecting group and FG refers to a functional group that can be transformed into T. Protection and deprotection in the Schemes may be carried out according to the procedures generally known in the art (e.g., "Protecting Groups in Organic Synthesis," 3rd Edition, Wiley, 1999).

All stereoisomers of the compounds of the instant invention are contemplated, either in admixture or in pure or substantially pure form. The processes for preparation can utilize racemates, enantiomers or diastereomers as starting materials. When enantiomeric or diastereomeric products are prepared, they can be separated by conventional methods, for example, chromatographic or fractional crystallization.

Preparation of A Phosphonate Prodrug

Prodrugs can be introduced at different stages of the synthesis. Most often these prodrugs are made from the phosphonic acids because of their lability.

Phosphonic acids of Formula I-VII can be alkylated with electrophiles such as alkyl halides and alkyl sulfonates under nucleophilic substitution conditions to give phosphonate esters. For example, compounds of Formula I-VII wherein $YR^{11}$ is an acyloxyalkyl group can be prepared by direct alkylation of compounds of Formula I-VII with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates.

Dimethylformamide dialkyl acetals can also be used for the alkylation of phosphonic acids (*Collect. Czech Chem. Commu.* 59:1853 (1994)). Compounds of Formula I-VII wherein $YR^{11}$ is a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sci.* 76:180 (1987)).

Alternatively, these phosphonate prodrugs can be synthesized by the reactions of the corresponding dichlorophosphonates and an alcohol (*Collect Czech Chem. Commun.* 59:1853 (1994)). For example, a dichlorophosphonate is reacted with substituted phenols and arylalkyl alcohols in the presence of a base such as pyridine or TEA to give the compounds of Formula I-VII wherein $YR^{11}$ is an aryl group (*J. Med. Chem.* 39:4109 (1996); *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a dichlorophosphonate and 2-hydroxyethyldisulfide under standard conditions. Dichlorophosphonates are also useful for the preparation of various phosphonamides as prodrugs. For example, treatment of a dichlorophosphonate with ammonia gives both a monophosphonamide and a diphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate.

Such reactive dichlorophosphonates can be generated from the corresponding phosphonic acids with a chlorinating agent (e.g., thionyl chloride, *J. Med Chem.* 1857 (1994); oxalyl chloride, *Tetrahedron Lett.* 31:3261 (1990); phosphorous pentachloride, *Synthesis* 490 (1974)). Alternatively, a dichlorophosphonate can be generated from its corresponding disilyl phosphonate esters (*Synth. Commu.* 17:1071 (1987)) or dialkyl phosphonate esters (*Tetrahedron Lett.* 24:4405 (1983); *Bull. Soc. Chim.* 130:485 (1993)).

It is envisioned that compounds of Formula I-VII can be mixed phosphonate ester (e.g., phenyl and benzyl esters, or phenyl and acyloxyalkyl esters) including the chemically combined mixed esters such as phenyl and benzyl combined prodrugs reported in *Bioorg. Med. Chem. Lett.* 7:99 (1997).

Dichlorophosphonates are also useful for the preparation of various phosphonamides as prodrugs. For example, treatment of a dichlorophosphonate with an amine (e.g. an amino acid alkyl ester such as L-alanine ethyl ester) in the presence of a suitable base (e.g. triethylamine, pyridine, etc.) gives the corresponding bisphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate. Direct couplings of a phosphonic acid with an amine (e.g. an amino acid alkyl ester such as L-alanine ethyl ester) are also reported to give the corresponding bisamidates under Mukaiyama conditions (*J. Am. Chem. Soc.*, 94:8528 (1972)).

The SATE (S-acetyl thioethyl) prodrugs can be synthesized by the coupling reaction of the phosphonic acids of Formula I-VII and S-acyl-2-thioethanol in the presence of DCC, EDCI or PyBOP (*J. Med. Chem.* 39:1981 (1996)).

Cyclic phosphonate esters of substituted 1,3-propane diols can be synthesized by either reactions of the corresponding dichlorophosphonate with a substituted 1,3-propanediol or coupling reactions using suitable coupling reagents (e.g., DCC, EDCI, PyBOP; *Synthesis* 62 (1988)). The reactive dichlorophosphonate intermediates can be prepared from the corresponding acids and chlorinating agents such as thionyl chloride (*J. Med. Chem.* 1857 (1994)), oxalyl chloride (*Tetrahedron Lett.* 31:3261 (1990)) and phosphorus pentachloride (*Synthesis* 490 (1974)). Alternatively, these dichlorophosphonates can also be generated from disilyl esters (*Synth. Commun.* 17:1071 (1987)) and dialkyl esters (*Tetrahedron Lett.* 24:4405 (1983); *Bull. Soc. Chim. Fr.*, 130:485 (1993)).

Alternatively, these cyclic phosphonate esters of substituted 1,3-propane diols are prepared from phosphonic acids by coupling with diols under Mitsunobu reaction conditions (*Synthesis* 1 (1981); *J. Org. Chem.* 52:6331 (1992)), and other acid coupling reagents including, but not limited to, carbodiimides (*Collect. Czech. Chem. Commun.* 59:1853 (1994); *Bioorg. Med. Chem. Lett.* 2:145 (1992); *Tetrahedron Lett.* 29:1189 (1988)), and benzotriazolyloxytris-(dimethylamino) phosphonium salts (*Tetrahedron Lett.* 34:6743 (1993)).

Phosphonic acids also undergo cyclic prodrug formation with cyclic acetals or cyclic ortho esters of substituted propane-1,3-diols to provide prodrugs as in the case of carboxylic acid esters (*Helv. Chim. Acta.* 48:1746 (1965)). Alternatively, more reactive cyclic sulfites or sulfates are also suitable coupling precursors to react with phosphonic acid salts. These precursors can be made from the corresponding diols as described in the literature.

Alternatively, cyclic phosphonate esters of substituted 1,3-propane diols can be synthesized by trans esterification reaction with substituted 1,3-propane diol under suitable conditions. Mixed anhydrides of parent phosphonic acids generated in situ under appropriate conditions react with diols to give prodrugs as in the case of carboxylic acid esters (*Bull. Chem. Soc. Jpn.* 52:1989 (1979)). Aryl esters of phosphonates are also known to undergo transesterification with alkoxy intermediates (*Tetrahedron Lett* 38:2597 (1997); *Synthesis* 968 (1993)).

One aspect of the present invention provides methods to synthesize and isolate single isomers of prodrugs of phosphonic acids of Formula I-VII. Because phosphorus is a stereogenic atom, formation of a prodrug with a racemic substituted-1,3-propane-diol will produce a mixture of isomers. For example, formation of a prodrug with a racemic 1-(V)-substituted-1,3-propane diol gives a racemic mixture of cis-prodrugs and a racemic mixture of trans-prodrugs. In an other aspect, the use of the enantioenriched substituted-1,3-propane diol with the R-configuration gives enantioenriched R-cis- and R-trans-prodrugs. These compounds can be separated by a combination of column chromatography and/or fractional crystallization.

A. Deprotection of A Phosphonate Ester

Compounds of Formula II-VII wherein X is —$PO_3H_2$ may be prepared from phosphonate esters using the known cleavage methods. Silyl halides are generally used to cleave various phosphonate esters and give the desired phosphonic acid upon mild hydrolysis of the resulting silyl phosphonate esters. When needed, acid scavengers (for example, HMDS) can be used for the acid sensitive compounds. Such silyl halides include TMSCl (*J. Org. Chem.* 28:2975 (1963)), TMSBr (*Tetrahedron Lett.* 155 (1977)) and TMSI (*J. Chem. Soc., Chem. Commu.* 870 (1978)). Alternatively, phosphonate esters can be cleaved under strong acid conditions (*Tetrahedron Lett.* 33:4137 (1992); *Synthesis-Stuttgart* 10:955 (1993)). Those phosphonate esters can also be cleaved via dichlorophosphonates prepared by treating the phosphonate esters with halogenating agents such as $PCl_5$, $SOCl_2$ and $BF_3$ (*J. Chem. Soc.* 238 (1961)) followed by aqueous hydrolysis to give the phosphonic acids. Aryl and benzyl phosphonate esters can be cleaved under hydrogenolysis conditions (*Synthesis* 412 (1982); *J. Med. Chem.* 281208 (1985)) or metal reduction conditions (*J. Chem. Soc.* 99:5118 (1977)). Electrochemical (*J. Org. Chem.* 44:4508 (1979)) and pyrolysis (*Synth. Commu.* 10:299 (1980)) conditions have been used to cleave various phosphonate esters.

Introduction of A Phosphonate Group

The introduction of a phosphonate group can generally be accomplished according to known methods. Compounds of Formula I, II, III, V, VI, and VII wherein T is —O($CR^b_2$)($CR^a_2$)$_n$—, —S($CR^b_2$)($CR^a_2$)$_n$— or —N($R^c$)($CR^b_2$)($CR^a_2$)$_n$— may be prepared by coupling a phenol, thiophenol, or aniline with a phosphonate ester component such as I($CR^b_2$)($CR^a_2$)$_n$P(O)(OEt)$_2$, TsO($CR^b_2$)($CR^a_2$)$_n$P(O)(OEt)$_2$, or TfO($CR^b_2$)($CR^a_2$)$_n$P(O)(OEt)$_2$ in the presence of a base such as NaH, $K_2CO_3$, KO-t-Bu or TEA (*Tetrahedron Lett.* 27:1477 (1986); *J. Chem. Soc. Perkin Tran* 1 1987 (1994)) as described in Scheme 1. Following the procedures described as above, deprotection of the phosphonate ester 2 gives the desired phosphoric acid 3.

Compounds of Formula I, II, III, V, VI, and VII wherein T is —N($R^b$)C(O)($CR^a_2$)$_n$— can be prepared by coupling an aniline 1 (M=NH) with a carboxylic acid containing a phosphonate moiety (EtO)$_2$P(O)($CR^a_2$)$_{1-2}$CO$_2$H in the presence of DCC or EDC according to the known methods (for example, *J. Org. Chem.* 42:2019 (1977)) or converting an aniline 1 (M=NH) to an isocyanate with diphosgene followed by reacting with P(OEt)$_3$ (*J. Org. Chem.* 1661 (1956); *Tetrahedron Lett.* 37:5861 (1996)). Deprotection of the phosphonate ester 2 as described above leads to the phosphonic acid 3.

For compounds of Formula I, II, III, V, VI, and VII wherein T is —($CR^a_2$)$_k$—, the phosphonate group can be introduced by a number of known methods. For example, the coupling reaction of a phenyl bromide (*J. Org. Chem.* 64:120 (1999)), iodide (*Phosphorus Sulfur* 130:59 (1997)) or triflate (*J. Org. Chem.* 66:348 (2001)) with diethyl phosphonate in the presence of a Pd catalyst is widely used within the art (when k is 0). Other methods such as Michaelis-Arbuzov reaction (*Chem. Rev.* 81:415 (1981)) can also be an efficient way to introduce the phosphonate group by coupling a benzyl or arylalkyl halide with triethyl phosphonate (when m is 1-3).

For compounds of Formula I, II, III, V, VI, and VII wherein T is —($CR^a_2$)$_n$—$CR^b$=$CR^b$—, the phosphonate group can be introduced by coupling an aldehyde and tetraethyl methylenediphosphonate in the presence of a base such as NaH, NaOH or KO-t-Bu (*Tetrahedron Lett.* 29:3007 (1988)). For compounds of Formula I, II, III, V, VI, and VII wherein T is —$CR^b$=$CR^b$—($CR^a_2$)$_n$— or —($CR^a_2$)—$CR^b$=$CR^b$—($CR^a_2$)—, the phosphonate group can be introduced by Michaelis-Arbuzov reaction of the corresponding olefinic halide with triethyl phosphite.

For compounds of Formula II, III, V, VI, and VII wherein T is —($CR^a_2$)$_m$(CO)—, the phosphonate group can be introduced by reacting diethyl phosphite with an acid chloride (*J. Org. Chem.* 29:3862 (1964); *Tetrahedron* 54:12233 (1998)) or an aldehyde followed by oxidation (*Tetrahedron* 52:9963 (1996)). Also, this type of compounds can be transformed into the compounds of Formula I, II, III, V, VI, and VII wherein T is —($CR^a_2$)$_n$CH(NR$^b$R$^c$)— according to known procedures (*Tetrahedron Lea.* 37:407 (1996)).

For compounds of Formula I, II, III, V, VI, and VII wherein T is —(CO)($CR^a_2$)$_m$—, the phosphonate group can be introduced by a number of known methods such as reacting a substituted benzoyl chloride with diethylphosphonoacetic acid (*Synthetic Commu.* 30:609 (2000)) or a phosphonate copper reagent (*Tetrahedron Lett.* 31:1833 (1990)). Alternatively, coupling of triethyl phosphonate with a silyl enol ether (*Synthetic Commu.* 24:629 (1994)) or a α-bromobenzophenone (*Phosphorus Sulfur* 90:47 (1994)) can also introduce the phosphonate group.

For compounds of Formula I, II, III, V, VI, and VII wherein T is —C(O)NH($CR^b_2$)($CR^a_2$)$_p$—, the phosphonate group can be introduced by coupling reaction of a substituted benzoic acid and an aminophosphonate according to the standard amide bond formation methods (*Tetrahedron Lett.* 31:7119 (1990); *Tetrahedron Lett.* 30:6917 (1989); *J. Org. Chem.* 58:618 (1993)).

For compounds of Formula I, II, III, V, VI, and VII wherein T is —($CR^a_2$)C(O)($CR^a_2$)$_n$— or ($CR^a_2$)$_n$C(O)($CR^a_2$), the phosphonate group can be introduced by reacting a benzyl bromide with a functionalized phosphonate (*Tetrahedron Lett.* 30:4787 (1989)). Alternatively, a coupling reaction of a substituted phenylacetate and methylphosphonate also yields the desired product (*J. Am. Chem. Soc.* 121:1990 (1999)).

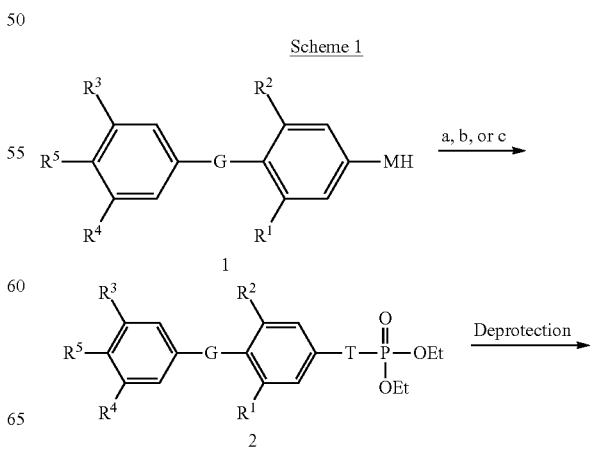

Scheme 1

-continued

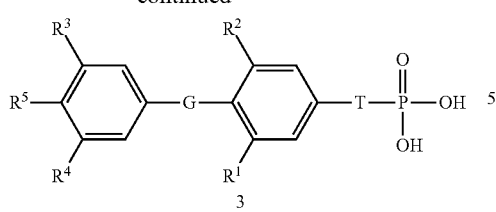

a. I(CR$^a_2$)$_n$P(O)(OEt)$_2$,
   or TsO(CR$^a_2$)$_n$P(O)(OEt)$_2$
b. P(O)(OEt)$_2$(CR$^a_2$)$_n$CO$_2$H, DCC
c. Diphosgene, P(OEt)$_3$
M = O, S, NH
T = O(CR$^a_2$)$_n$, S(CR$^a_2$)$_n$, NR$^b$(CR$^a_2$)$_n$, NR$^b$(CO)CR$^a_2$)$_n$ Construction of the Diaryl Ring Compounds of Formula I, II, III, IV, V, and VII wherein G is —O— can be prepared according to known methods. As described in Scheme 2, 2a is reacted with 2b at room temperature in the presence of Cu powder and a suitable base such as TEA, diisopropylamine or pyridine to provide the coupling product 4 (*J. Med. Chem.* 38:695 (1995)). Deprotection of the methoxy group with suitable reagents such as boron tribromide, boron trichloride or boron trifluoride in CH$_2$Cl$_2$ gives the intermediate 5. Introduction of the phosphonate group followed by deprotection of the phosphonate ester as described in Scheme 1 leads to the desired phosphonic acid 6. Those skilled in the art can use other known methods such as coupling of an arylboronic acid and a phenol in the presence of Cu(OAc)$_2$ (*Tetrahedron Lett.* 39:2937 (1998)), nucleophilic substitution of a fluorobenzene (*Synthesis-Stuttgart* 1:63 (1991)) or iodobenzene (*J. Am. Chem. Soc.* 119:10539 (1997)) with a phenol and coupling of a bromobenzene with a phenol in the presence of Pd$_2$(dba)$_3$ (*Tetrahedron Lea.* 38:8005 (1997)) to form the diaryl ether system.

-continued

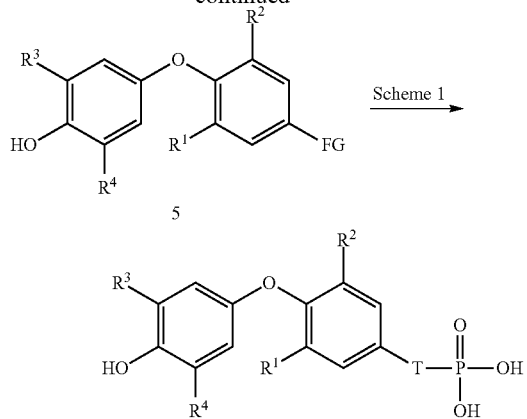

FG = functional group that can be transformed into T

For compounds of Formula I, H, HI, IV, V, and VII wherein G is —CH$_2$—, the installation of the diaryl ring can be accomplished by a number of known methods. For example, as described in Scheme 3, benzyl alcohol 7 is formed by treatment of 3a with n-BuLi at −78° C. in THF followed by reacting with 3b (*Bioorg. Med. Chem. Lett.* 10:2607 (2000)). Hydrogenolysis with Pd—C or dehydroxylation of benzyl alcohol 7 by NaBH$_4$ (*Synthetic Commu.* 17:1001 (1987)) and (i-Bu)$_3$Al (*Synthesis* 736 (1987)) followed by removal of the protecting group gives the diaryl intermediate 8. Phosphonic acid 9 is formed from 8 according to the same procedures as described in Scheme 1. Alternatively, coupling of benzyl bromide with an aryl Grignard reagent (*Tetrahedron Lett.* 22:2715 (1981)), an arylboronic acid (*Tetrahedron. Lett.* 40:7599 (1999)) or a zinc reagent (*Chem. Lett.* 11:1241 (1999)) and reduction of a diaryl ketone (*J. Org. Chem.* 51:3038 (1986)) are all widely used methods for the construction of the diaryl ring.

Scheme 2

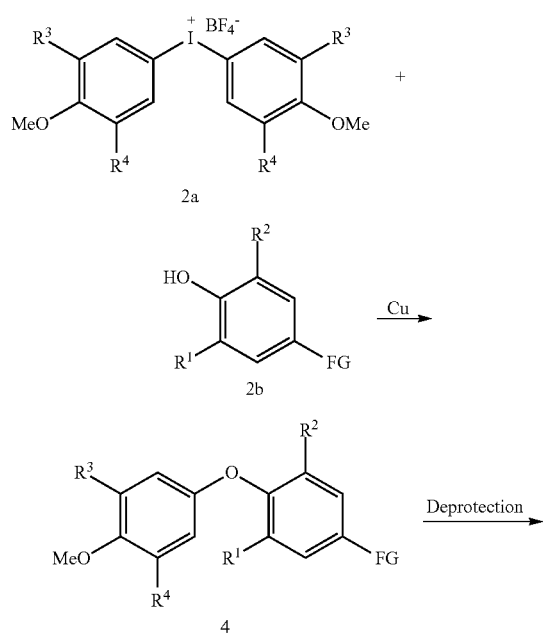

Scheme 3

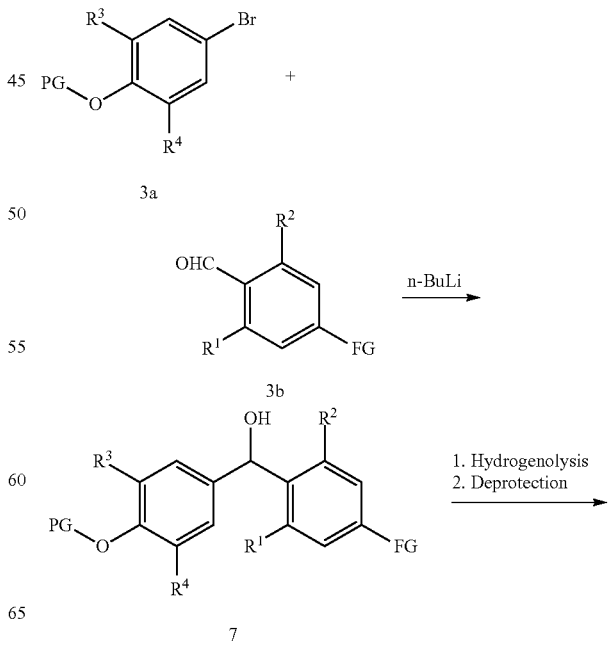

-continued

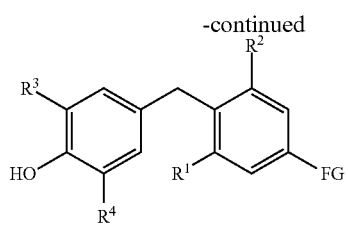

8

Scheme 1
→

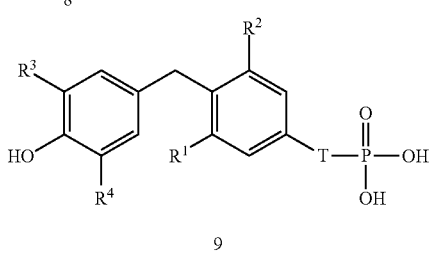

9

PG = protecting group
FG = functional group that can be transformed into T

For compounds of Formula I, II, III, IV, V, and VII wherein G is —S—, —S(═O)— or —S(═O$_2$)—, the formation of the diaryl ring can be achieved according to known methods. As illustrated in Scheme 4, 3a can be reacted with 4a in the presence of a catalyst such as Pd$_2$(dba)$_3$ or CuBr to provide the diaryl sulfide 10 (*Tetrahedron* 57:3069 (2001); *Tetrahedron Lett.* 41:1283 (2000)). Phosphonic acid 12 is formed from 10 after removal of the protecting groups followed by the same procedures as described in Scheme 1. The diaryl sulfide 10 can also be converted to the sulfoxide 13 according to known methods (*Synthetic Commu.* 16:1207 (1986); *J. Org. Chem.* 62:4253 (1997); *Tetrahedron Lett.* 31:4533 (1990)), which leads to the phosphonic acid 15 following the same procedures as described in Scheme 1. Also, the biaryl sulfide 10 can be converted to the sulfone (*Tetrahedron Lett.* 32:7353 (1991); *J. Prakt. Chem.* 160 (1942)) which leads to the phosphonic acid (G is —S(═O$_2$)—) following the same procedures as described above. In addition, nucleophilic substitution of chlorobenzene and bromobenzene with a thiol is also an efficient way to install the diaryl sulfide ring (*J. Med. Chem.* 31:254 (1988); *J. Org. Chem.* 63:6338 (1998)).

Scheme 4

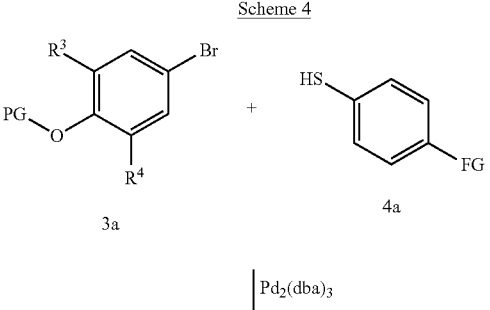

3a    4a

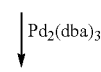

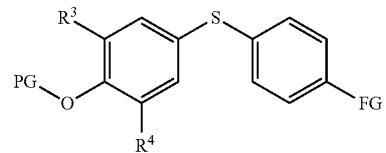

10

 Deprotection        Oxidation 

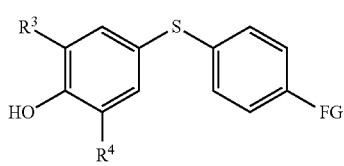

11

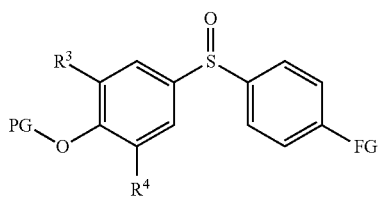

13

↓ Scheme 1        ↓ Deprotection

-continued

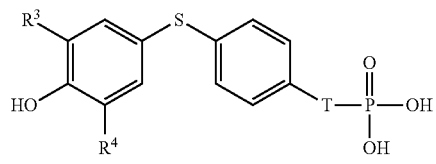

12

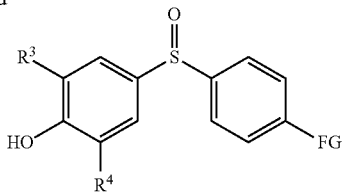

14

↓ Scheme 1

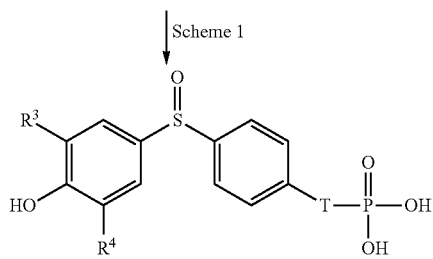

15

PG = protecting group
FG = functional group that can be transformed into T

For compounds of Formula I, II, III, IV, V, and VII wherein G is —NH— or —N($C_1$-$C_4$ alkyl)-, the diarylamine backbone can be formed by a number of known methods. Among those conditions, one widely used by those skilled in the art is the coupling reaction of an aniline with an aryl bromide (*J. Org. Chem.* 64:5575 (1999); *J. Org. Chem.* 62:6066 (1997); *Tetrahedron Lett.* 37:6993 (1996); *Org. Lett* 1:2057 (1999)) or an aryl tosylate (*J. Org. Chem.* 62:1268 (1997)) in the presence of a catalyst such as $PdCl_2$ or $Pd_2(dba)_3$. As illustrated in Scheme 5, the diarylamine intermediate 16 can be prepared by coupling of bromide 3a and aniline 5a in the presence of $Pd_2(dba)_3$. After removal of the protecting group, the diarylamine 17 is converted to the phosphonic acid 18 following the same procedures as described in Scheme 1. Alternatively, coupling of an aniline and aryl halide using other catalysts such as copper-bronze (*Org. Synth.* 2:446 (1943); *J. Org. Chem.* 20 (1955)) and $Cu(OAc)_2$ (*J. Med. Chem.* 1986, 4:470 (1986); *Synthetic Commu.* 26:3877 (1996)) to construct the diarylamine backbone is also a feasible approach.

Scheme 5

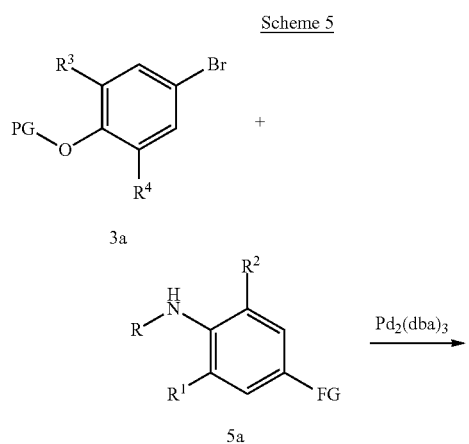

-continued

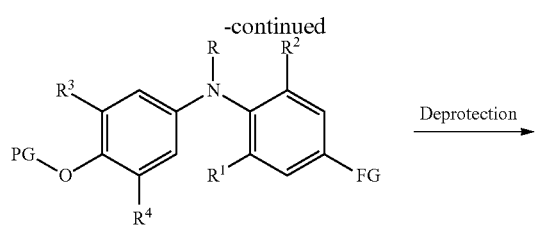

16

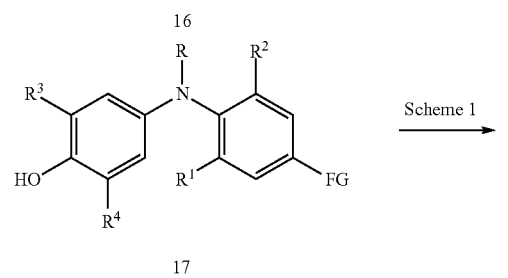

17

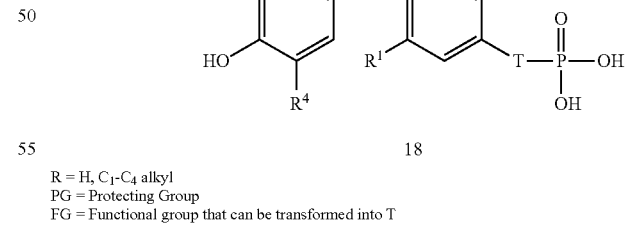

18

R = H, $C_1$-$C_4$ alkyl
PG = Protecting Group
FG = Functional group that can be transformed into T For compounds of Formula I, II, III, IV, V, and VII wherein G is —CHF— or —$CF_2$—, the diaryl backbone can be established from the benzyl alcohol 7. Accordingly, as described in Scheme 6, benzyl alcohol 7 can be converted to the benzyl fluoride 19 by reacting with DAST in $CH_2Cl_2$ according to lawn procedures (*J. Chem. Soc., Chem. Commu.* 11:511 (1981); *Tetrahedron Lett.* 36:6271 (1995); *Tetrahedron* 14:2875 (1988)). Also, the benzyl alcohol 7 can be easily oxidized to the benzophenone 22 according to known methods such as MnO$_2$ oxidation, PCC oxidation, Swern oxidation and Dess-Martin oxidation, which is subsequently converted to the benzyl difluoride 23 by treatment with DAST (*J. Fluorine* 61:117 (1993)) or other known reagents (*J. Org. Chem.* 51:3508 (1986); *Tetrahedron* 55:1881 (1999)). After removal of the protecting groups, the benzyl fluoride 20 and difluoride 24 are converted to the desired phosphonic acids following the same procedures as described in Scheme 1.

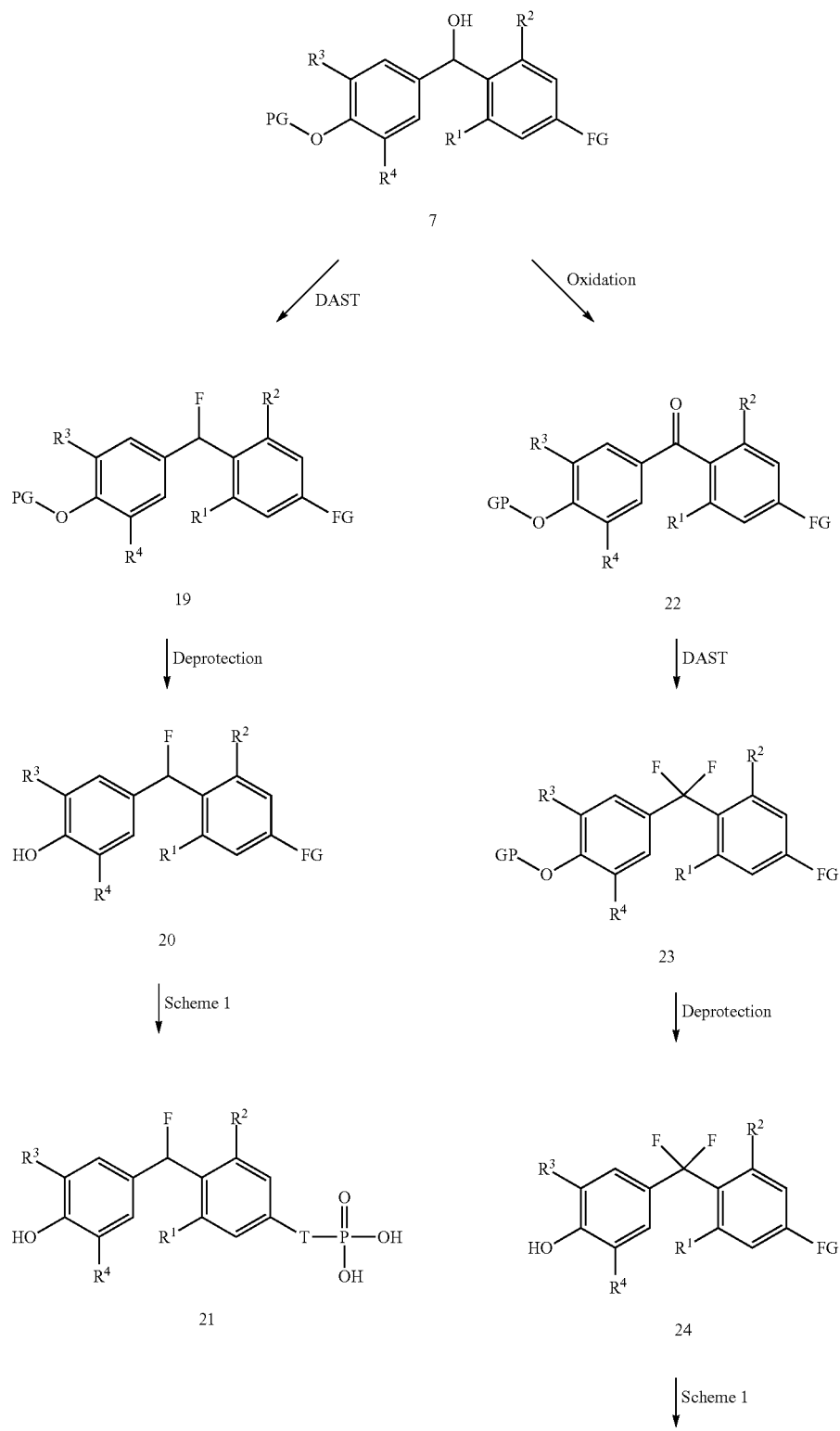

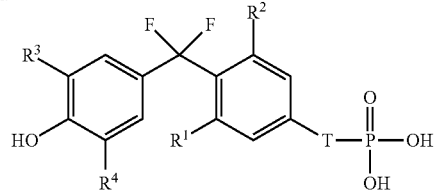

25

PG = Protecting Group
FG = Functional group that can be transformed into T

Compounds of Formula I, II, III, IV, V, and VII wherein G is —CH(OH)— or —C(O)— can be prepared from the intermediates 7 and 22. Removal of the protecting groups of 7 and 22 followed by introduction of the phosphate and deprotection as described in Scheme 1 provides the desired phosphonic acids of Formula I.

Synthesis of Compounds of Formula IV

The synthesis of compounds of Formula IV where A is —NH— and B is —CH— or —C-alkyl- can be accomplished from the corresponding amino diaryl precursor 1 using the well-known, to those skilled in the art, Fisher indole synthesis (Scheme 6a) (*Phosphorus and Sulfur* 37:41-63 (1988)). Alternatively, the aryl-indole scaffold is constructed using the procedures previously described and the phosphonic acid moiety is introduced by making the anion next to the nitrogen of the indole derivative, protected at the nitrogen, with a base such as BuLi and quenching the anion with diethyl chlorophosphate. Further protecting group and functional group manipulations of intermediates 2 provide compounds of Formula IV.

Scheme 6a

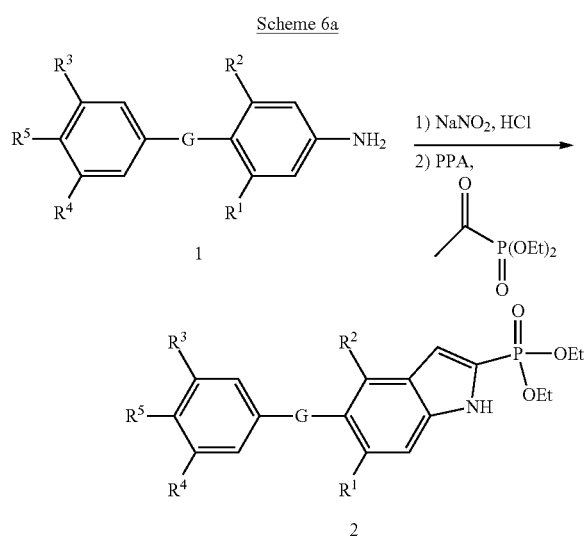

Compounds of Formula IV where A is —O— and B is —CH— are synthesized from the corresponding diaryl phenol precursor 3 and ring cyclization with the dimethylacetal of bromoacetaldehyde to give benzofuran 4 (Scheme 6b) (*J. Chem. Soc., Perkin Trans.* 1, 4:729 (1984)). The phosphonic acid moiety can then be introduced by making the anion next to the oxygen of the benzofuran with a base such as BuLi and quenching the anion with diethyl chlorophosphate to provide phosphonate 5. Further protecting group and functional group manipulations of intermediate 5 provides compounds of Formula II.

Scheme 6b

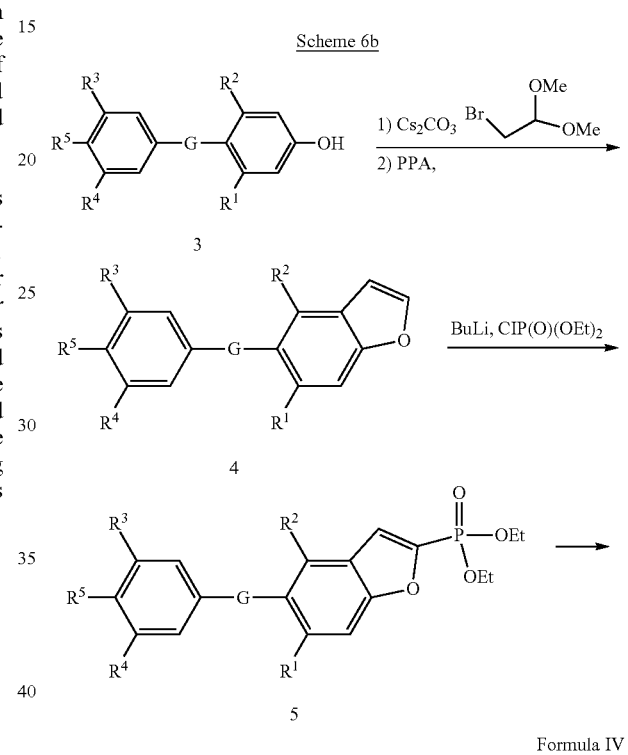

Formula IV

Compounds of Formula IV where A is —NH—, —O— or —S— and B is —N— can be made from condensation of the corresponding diaryl precursor 6 with an orthoformate such as triethyl orthoformate in presence of acid to give heterocycle 7 (*Org. Prep. Proced. Int.*, 22(5):613-618 (1990)). The phosphonic acid moiety can then be introduced by making the anion at the 2-position of the heterocycle 7 with a base such as BuLi and quenching the anion with diethyl chlorophosphate to give phosphonate 8. Further protecting group and functional group manipulations of intermediates 8 provide compounds of Formula II.

Scheme 6c

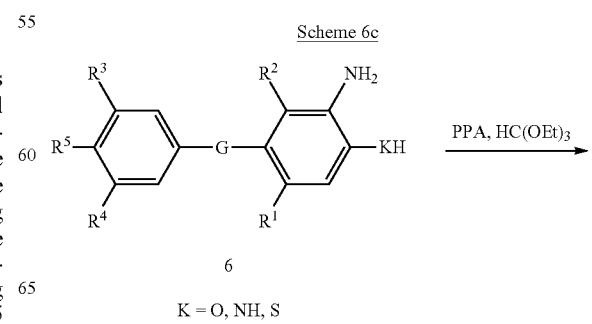

K = O, NH, S

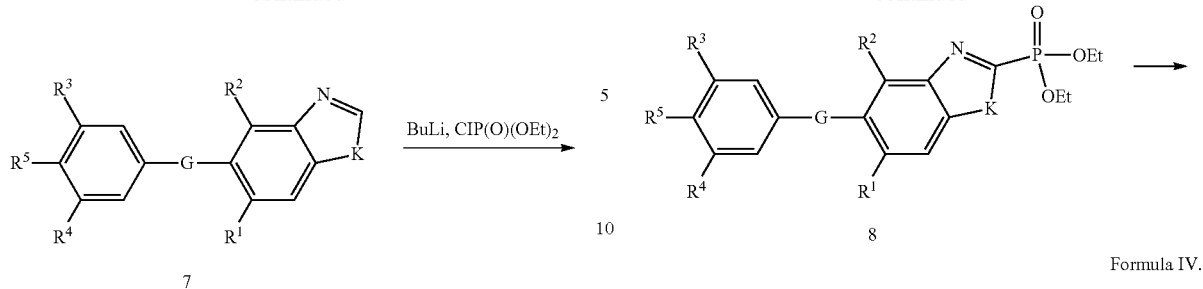

Formula IV.

Synthesis of Compounds of Formula V

Scheme 6d

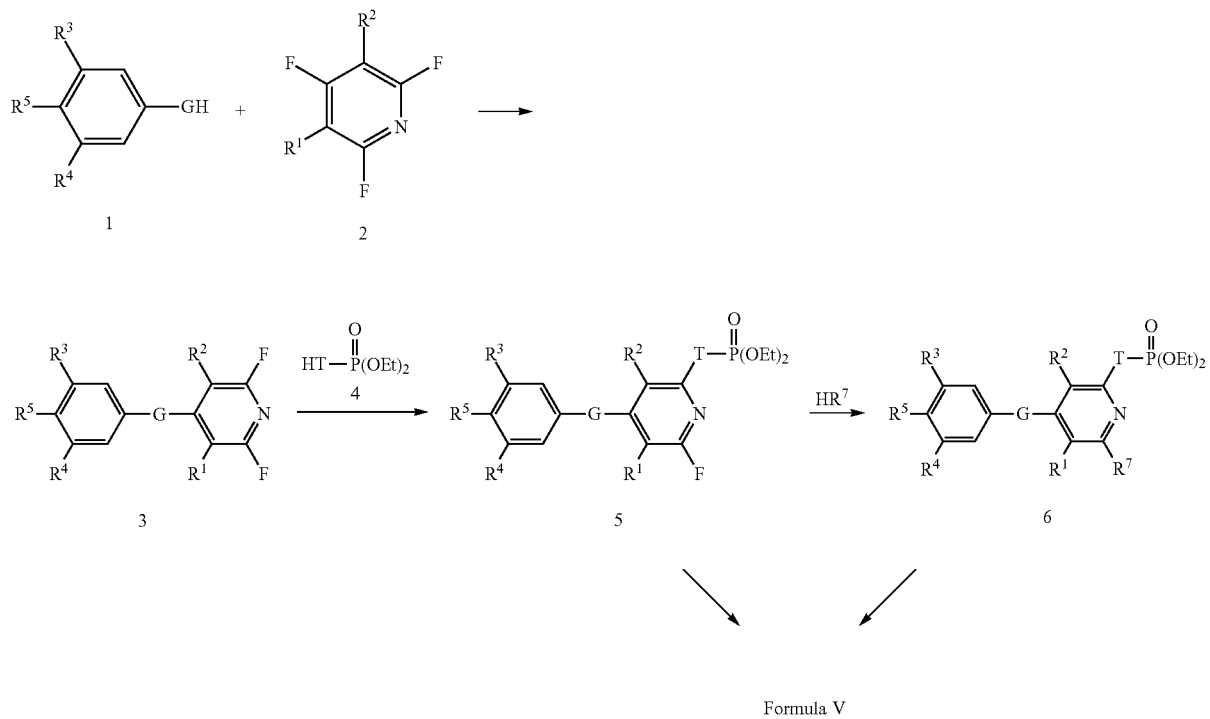

Formula V

The general synthesis of compounds of Formula V wherein G is —O—, —S— or —NH— utilizes the displacement of an appropriately substituted phenol, thiophenol or aniline 1 with a pentasubstituted pyridine such as 3,5-dichloro-2,4,6-trifluoro-pyridine 2 to provide intermediate 3 (Scheme 6d) (*Org. Prep. Proced. Int.* 32(5):502-504 (2000)). Subsequent displacement of the 2-fluoro and 6-fluoro substituents on the pyridine ring with nucleophiles 4 and $HR^7$ sequentially provide intermediates 5 and 6. Examples of suitable nucleophiles, include but are not limited to, diethyl hydroxymethyl-phosphonate and diethyl aminomethyl-phosphonate. Example of reactants $HR^7$, include but are not limited to, alkylthiol, sodium alkoxide, alkylamine or benzylamine. Compounds of Formula V where G is —S(=O)— and —S(=O)$_2$— can be derived from intermediates 5 and 6 when G is —S— via oxidation with an oxidizing agent such as mCPBA. Further protecting group and functional group manipulations of intermediates 5 and 6 will provide compounds of Formula V.

Scheme 6e

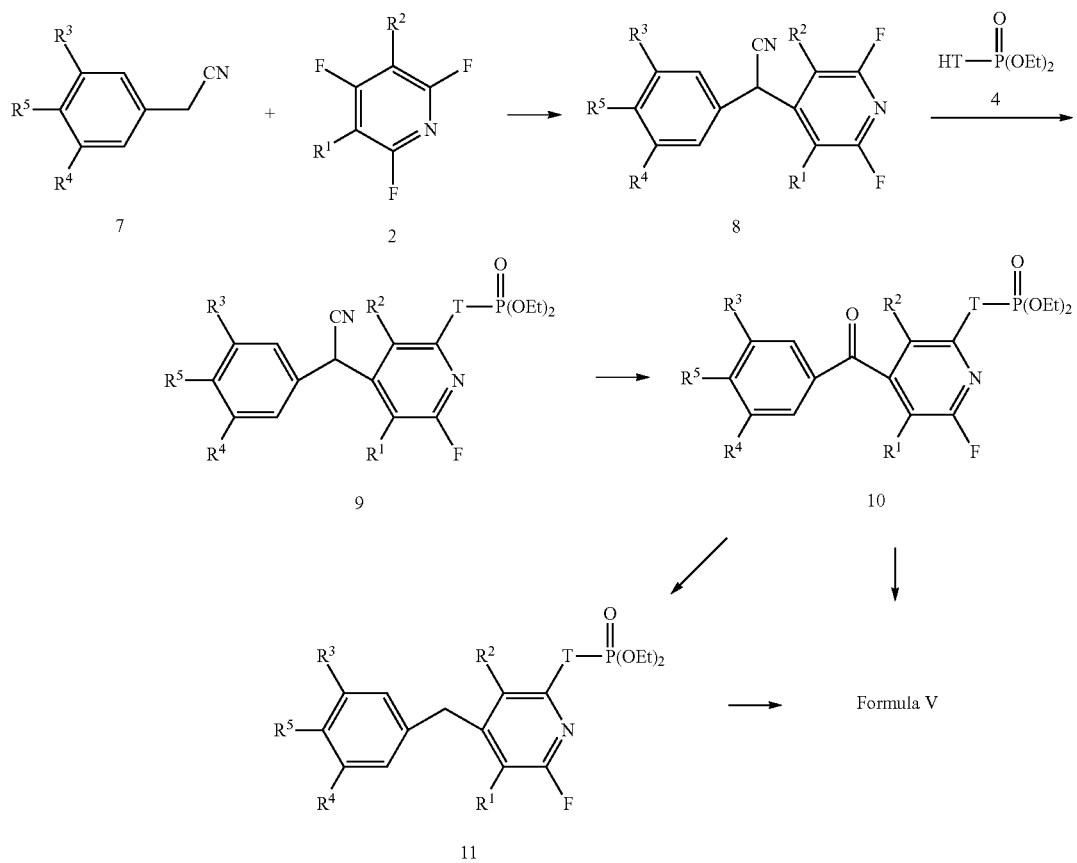

Compounds of Formula V wherein G is —CH₂— or —C(O)— are synthesized according to scheme 6e. Condensation of benzyl cyanide 7 with pentasubstituted pyridine 2 provide intermediate 8. Displacement of 2-fluoro with reagent 4 gives intermediate 9. Oxidation of benzyl cyanide 9 provides keto derivative 10 which after deprotection and functional group manipulation gives a compound of Formula V. Alternatively, reductive deoxygenation of keto intermediate followed by deprotection and functional group manipulation gives a compound of Formula V.

Synthesis of Compounds of Formula VI

Biaryl compounds of formula VI can be synthesized by coupling a boronic acid, or its pinacol ester, of a properly derivatized naphtyl moiety with a properly substituted aryl iodide, bromide or triflate using conditions commonly employed for a Suzuki reaction (Hoye et al., *J. Org. Chem.* 61:7940 (1996); Hoye et al., *Tetrahedron Lett.* 3:3097 (1996); Anton et al., *Chem. Ber.* 125:2325 (1992); Anton et al., *Chem. Ber.* 126:517 (1993); Shieh et al., *J. Org. Chem.* 57:379 (1992); Nakano et al., *Synthesis* 12:1425 (1997); Kumar, *J. Org. Chem.* 62:8535 (1997); Blettner et al., *J. Org. Chem.* 64:3885 (1999).

Synthesis of Phosphonic Acid Monoesters

Compound of the invention where the acidic group is a phosphonic acid monoester may be prepared from the diester intermediate, used for the synthesis of phosphonic acid thyromimetic, by monosaponification. Monohydrolysis of one of the ester groups on the phosphonate may be accomplished by treatment of phosphonate diesters with aqueous alkaline solution such as NaOH, KOH or LiOH at rt or while heating. Sodium azide can also be used in DMF (*Bioorg. Med. Chem. Lett.* 14(13),3559-62 (2004)) to accomplished the monosaponification. Alternatively, organic bases such as morpholine or N-methyl-piperazine can be used to hydrolyze one of the phosphonate ester groups (*Synth. Comm.* 34(2):331-344 (2004)).

Synthesis of Phosphinic Acids

The introduction of a phosphinic acid group can generally be accomplished according to known methods. An efficient way to synthesize phosphinic acid is to convert a phosphonate diester to its corresponding monochloridate-monoester using one of many chlorinating agents such as PCl₅ (*Can. J. Chem.* 76(3):313-18 (1998)), oxalyl chloride (*Tetrahedron Lett.* 44(12):1445-48 (2003)), thionyl chloride (*J. Med. Chem.* 45(4):919-29 (2002)) or phosgene (*Recl. Trav. Chim. Pays-Bas* 78:59-61 (1959)) and to introduce the carbon-based substituent on the phosphorus atom via a Grignard reagent (*J. Chem. Soc. Perkin Trans.* 1 17:2179-86 (1996)), a lithium anion (*J. Med. Chem.* 33(11):2952-56 (1990)) or an enolate (*Bioorg Med. Chem.* 5(7):1327-38 (1997)) to produce the desired phosphinate ester. The phosphinic acid is then generated by saponification with aqueous NaOH, KOH or LiOH or using one of the many methods known to deprotect phosphonic acids such as TMSBr or TMSCl/KI. Alternatively, phosphinic acids can be generated from phosphonic acid monoesters by making the monochloridate-monoester with chlorinating reagents such as thionyl chloride or oxalyl chloride, and introducing the substituent on the phosphorus as above.

Compounds of Formula I wherein T is —O(CR$^b_2$)(CR$^a_2$)$_n$—, —S(CR$^b_2$)(CR$^a_2$)$_n$— or —N(R$^c$)(CR$^b_2$)(CR$^a_2$)$_n$— may be prepared by coupling a phenol, thiophenol, or aniline with a phosphinate ester component such as I(CR$^b_2$)(CR$^a_2$)$_n$P(O)(OEt)(lower alkyl), TsO(CR$^b_2$)(CR$^a_2$)$_n$P(O)(OEt)(lower alkyl), or TfO(CR$^b_2$)(CR$^a_2$)$_n$P(O)(OEt)(lower alkyl) in the presence of a base such as NaH, K$_2$CO$_3$, Cs$_2$CO$_3$, KO-t-Bu or TEA (*J. Am. Chem. Soc.* 114(19):7604-06 (1992)). These phosphinate ester components can be synthesized by condensation of a mono phosphinate, such as ethyl methylphosphinate, with formaldehyde in presence of a base such Et$_3$N (*Tetrahedron Asymetry* 13(7):735-38 (2002)).

Compounds of Formula I wherein T is —N(R$^b$)C(O)(CR$^a_2$)$_n$— can be prepared by coupling an aniline with a carboxylic acid containing a phosphinate moiety (lower alkyl)(EtO)P(O)(CR$^a_2$)$_{1-2}$CO$_2$H in the presence of DCC or EDC according to the known methods (*Syn. Lett.* 9:1471-74 (2002)) or converting an aniline to a phenyl isocyanate with diphosgene followed by reacting with a mono-substituted phosphinate (*Zh. Obshch. Khim.* 26:3110-11 (1956)). Alternatively, condensation of the carbon anion of a phosphinate provides the β-amido-phosphinate (*J. Org. Chem.* 45(12): 2519-22 (1980)).

For compounds of Formula I wherein T is —(CR$^a_2$)$_k$—, the phosphonate group can be introduced by a number of known methods. For example, the coupling reaction of a phenyl halide (*Synthesis*, 14:2216-20 (2003)) with mono-substituted phosphinate in the presence of a Pd catalyst is widely used within the art (when k is 0). Other methods such as Michaelis-Arbuzov can also be an efficient way to introduce the phosphinate group by coupling a benzyl or arylalkyl halide with a phosphonite diester (when m is 1-3) (*Org. Lett.* 5(17):3053-56 (2003)). Alternatively, phosphinates can be synthesized by coupling of mono-substituted phosphinate esters with olefins, such as styrenes, in the presence of t-Bu$_2$O$_2$ (*Justus Liebig Ann. Chem.* 741-50 (1974)) or (PhCO)$_2$O$_2$ (*J. Gen. Chem. USSR* 30:2328-32 (1960)).

For compounds of Formula I wherein T is —(CR$^a_2$)$_n$—CR$^b$=CR$^b$—, the phosphonate group can be introduced by coupling an acetylene and a monosubstituted phosphinate in the presence of a catalyst such as Ni(PPh$_2$Me), Ni(cod)$_2$ (*J. Am. Chem. Soc.* 126(16):5080-81 (2004)) or Me$_2$Pd(PPh$_2$)$_2$ (*J. Am. Chem. Soc.* 124(15):3842-43 (2002)). For compounds of Formula I wherein T is —CR$^b$=CR$^b$—(CR$^a_2$)$_n$— or —(CR$^a_2$)—CR$^b$=CR$^b$—(CR$^a_2$)—, the phosphinate group can be introduced by Michaelis-Arbuzov reaction of the corresponding olefinic halide with a phosphonite diester.

For compounds of Formula I wherein T is —(CR$^a_2$)$_m$(CO)—, the phosphinate group can be introduced by reacting a phosphonite diester with an acyl chloride in the presence of sodium (*J. Gen. Chem. USSR* 34:4007-9 (1964)) or an aldehyde in the presence of lithium phenoxide followed by an oxidation (*Tetrahedron Lett.* 45(36:6713-16 (2004)). Alternatively, treatment of an acyl chloride with a phosphonate diester provides access to α-keto-phosphinate (*J. Chem. Soc. Perkin Trans.* 1, 659-66 (1990)).

For compounds of Formula I wherein T is —(CO)(CR$^a_2$)$_m$—, the phosphinate group can be introduced by a number of known methods such as reacting a substituted benzoate ester with the anion of a phosphinate made with a base such as BuLi or LDA (*Bull. Soc. Chim. Fr.* 3494-3502 (1972)). Alternatively, coupling the anion of a phosphinate with a substituted benzaldehyde followed by an oxidation provides access to the β-keto-phosphinate (*J. Med. Chem.* 38(17):3297-3312 (1995)).

For compounds of Formula I wherein T is —C(O)NH(CR$^b_2$)(CR$^a_2$)$_p$—, the phosphonate group can be introduced by a coupling reaction of an aminophosphinate (*Synthesis* 1074-76 (1995)) with substituted benzoyl chloride (*J. Organomet. Chem.* 178:157-69 (1979)) or a substituted benzoic acid according to the standard amide bond formation methods (*Bioorg. Med. Chem. Lett.* 6(14):1629-34 (1996)).

For compounds of Formula I wherein T is —(CR$^a_2$)C(O)(CR$^a_2$)$_n$—, the phosphinate group can be introduced by reacting a substituted phenylacetate with a functionalized anion of a phosphinate made with a base such as BuLi or LDA (*Bull. Soc. Chim. Fr.* 3494-3502 (1972)).

Synthesis of Cyclic Phosphinic Acids and Cyclic Phosphoric Acids

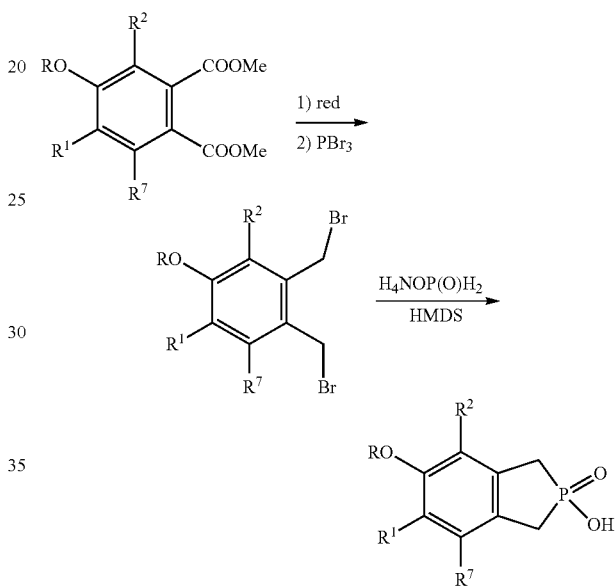

Cyclic phosphinic acids can be synthesized starting from a 1,2-dicarboxylate-benzene precursor (*J. Am. Chem. Soc.* 101:7001-08 (1979)) which is reduced to the di-benzylic alcohol and brominated with PBr$_3$ to give the di-benzylic bromide precursor (*Synth. Commun.* 14(6):507-514 (1984)). Double Arbuzov condensation of the di-benzylic bromide with bis(trimethylsilyloxy)phosphine, made from the reaction of ammonium hypophosphite and hexamethyldisilazane, provides the cyclic phosphinate ester (*J. Org. Chem.* 60:6076-81 (1995)) which can be converted to the phosphinic acid by saponification with NaOH or TMSBr. Alternatively, the di-benzyl bromide precursor can be obtained by bromination of a substituted 1,2-dimethyl benzene with bromine or N-bromosuccinimide (*J. Chem. Soc.* 3358-61 (1959)) or direct bromomethylation by reacting formaldehyde and HBr in presence of acetic acid (*J. Phys. Chem.* 108(4):5145-55 (2004)).

Cyclic phosphonates can be synthesized by condensing a di-benzylic alcohol with trimethylphosphite (*Bull. Acad. Sci., USSR Div. Chem. Sci.* 37:1810-14 (1988)) to get the cyclic phosphite which is then converted to the cyclic phosphonate by a photo-Arbuzov rearrangement (*J. Organomet. Chem.* 646:239-46 (2002)). Alternatively, the cyclic phosphite can be obtained by condensing a di-benzylic alcohol with HMPT (*J. Org. Chem.* 57(10):2812-18 (1992)) or diethylphosphoramidous dichloride to get a cyclic phosphoramidous diester which is then converted to the cyclic phosphite by reaction with an alcohol, such as methanol or phenol, in the presence of an activating agent such as tetrazole or methylthio-tetrazole (*J. Org. Chem.* 61:7996-97 (1996)). The phosphonic acid is then obtained by selective monosaponification.

Synthesis of Prodrugs of Phosphinic Acids and Phosphonate Monoesters

Prodrugs can be introduced at different'stages of the synthesis. Most often these prodrugs are made from the phosphonic acid monoesters and phosphinic acids because of their lability.

Phosphinic acids and phosphonic acid monoesters can be alkylated with electrophiles such as alkyl halides and alkyl sulfonates under nucleophilic substitution conditions to give phosphonate esters. For example, compounds of Formula I wherein YR$^{11}$ is an acyloxyalkyl group can be prepared by direct alkylation of compounds of Formula I with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates.

Dimethylformamide dialkyl acetals can also be used for the alkylation of phosphinic acids and phosphonic acid monoesters (*Collect. Czech Chem. Commu.* 59:1853 (1994)). Compounds of Formula I wherein YR$^{11}$ is a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sd.* 76:180 (1987)).

Alternatively, these phosphinate and monoester phosphonate prodrugs can be synthesized by the reactions of the corresponding chlorophospho(i)nate and an alcohol (*Collect Czech Chem. Commun.* 59:1853 (1994)). For example, a chlorophospho(i)nate is reacted with substituted phenols and arylalkyl alcohols in the presence of a base such as pyridine or TEA to give the compounds of Formula I wherein YR$^{11}$ is an aryl group (*J. Med. Chem.* 39:4109 (1996); *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a chlorophospho(i)nate and 2-hydroxyethyldisulfide under standard conditions. Chlorophospho(i)nates are also useful for the preparation of various phospho(i)namides as prodrugs. For example, treatment of a chlorophospho(i)nate with ammonia gives the phospho(i)namide.

Such reactive dichlorophosphonates can be generated from the corresponding phosphinic acids and phosphonic acid monoesters with a chlorinating agent (e.g., thionyl chloride, *J. Med. Chem.* 1857 (1994); oxalyl chloride, *Tetrahedron Lett.* 31:3261 (1990); phosphorous pentachloride, *Synthesis* 490 (1974)). Alternatively, a dichlorophosphonate can be generated from its corresponding silyl phosphinate ester or phosphonic acid monoester (*Synth. Commu.* 17:1071 (1987)) or alkyl phosphinate esters (*Tetrahedron Lett.* 24:4405 (1983); *Bull. Soc. Chico.* 130:485 (1993)).

Chlorophospho(i)nates are also useful for the preparation of various phosphonamides as prodrugs. For example, treatment of a chlorophospho(i)nate with an amine (e.g. an amino acid alkyl ester such, as L-alanine ethyl ester) in the presence of a suitable base (e.g. triethylamine, pyridine, etc.) gives the corresponding phosphor(i)namide. Direct couplings of phosphinic acids or phosphonic acid monoesters with an amine (e.g. an amino acid alkyl ester such as L-alanine ethyl ester) are also reported to give the corresponding amidate under Mukaiyama conditions (*J. Am. Chem. Soc.* 94:8528 (1972)).

The SATE (S-acetyl thioethyl) prodrugs can be synthesized by the coupling reaction of the phosphinic acids or phosphonic acid monoesters of Formula I and S-acyl-2-thioethanol in the presence of DCC, EDCI or PyBOP (*J. Med. Chem.* 39:1981 (1996)).

Preparation of Key Precursors

A. Preparation of Compounds with Substituents on the Ring

Starting material and key intermediates required for the synthesis of the compounds in this invention are either commercially available or prepared using an existing method in the literature or a modification of a known method. Syntheses of some of those compounds are described herein.

Precursor 2a is prepared by reacting an anisole with iodine trifluoroacetate according to the reference procedures (*J. Med. Chem.* 38:695 (1995)). Anisoles with different R$^3$ and R$^4$ groups are either commercially available or can be prepared according to the literature procedures (e.g., *J. Med. Chem.* 32:320 (1989)).

Starting material 2b is either commercially available or prepared according to known procedures. For example, compounds of 2b wherein FG is NH$_2$-derived group can be prepared by reacting 3a with benzophenone into in the presence of a Pd catalyst such as Pd$_2$(dba)$_3$ or Pd(OAc)$_2$ (*Tetrahedron Lett.* 38:6367 (1997); *J. Am. Chem. Soc.* 120:827 (1998)). Compounds of 2b wherein FG is S-derived group can be prepared by reacting a feasible 4-aminoanisole with NaNO$_2$ and potassium ethyl xanthate (*J. Am. Chem. Soc.* 68 (1946); *Heterocycles* 26:973 (1987)).

The useful precursor 3a can either be commercially available reagents or prepared according to the existing methods. As described in Scheme 7, a simple protection of commercially available 4-bromophenol 7b with different R$^3$ and R$^4$ groups according to the procedures known in the art leads to 3a. Compound 3a can also be prepared by bromination of protected phenol 7d (*J. Org. Chem.* 53:5545 (1988); *J. Org. Chem.* 59:4473 (1994); *Synthesis-Stuttgart* 10:868 (1986)). Introduction of various R$^3$ and R$^4$ groups to 4-bromophenol 7a can be carried out to give 7b which leads to 7a after protection (*Tetrahedron Lett.* 36:8453 (1995); *J. Heterocyclic Chem.* 28:1395 (1991); *J. Fluorine Chem.* 40:23 (1988); *Synthesis-Stuttgart* 11:1878 (1999); *Synthetic Commu.* 16:681 (1986)). 7b can also be prepared by the bromination of phenol 7c (*J. Comb. Chem.* 2:434 (2000); *Chem. Soc. Jpn.* 61:2681 (1988); *Synthesis-Stuttgart* 5:467 (1992); *Org. Synth.* 72:95 (1993)).

Scheme 7

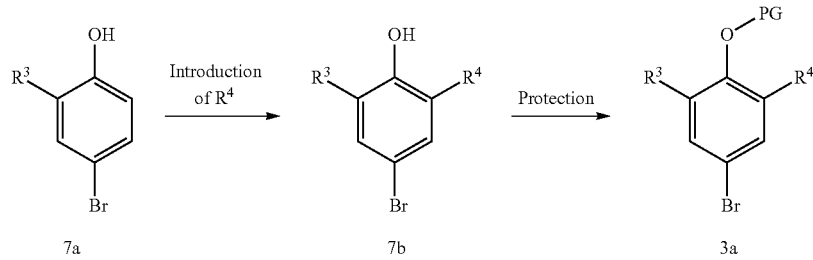

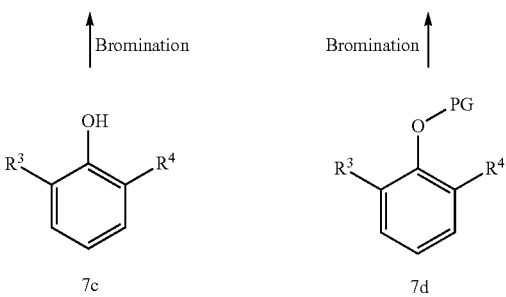

A number of methods are available for the preparation of the benzaldehyde 3b. As illustrated in Scheme 8, bromobenzene 8a can be converted to benzaldehyde 3b by reacting with DMF (*Aust. J. Chem.* 51:177 (1998); *Bioorg. Med Chem. Lett.* 10:2607 (2000)) or carbon monoxide in the presence of a palladium catalyst (*Bull. Chem. Soc. Jpn* 67:2329 (1994)). 3b may be formed by oxidation of benzyl alcohol 8c using common methods such as $MnO_2$ oxidation, PCC oxidation, Swern oxidation and Dess-Martin oxidation. Reduction of benzonitrile 8b and benzoyl chloride 8d also produces benzaldehyde 3b. (*Org. Synth.* 3:551 (1995); *J. Org. Chem.* 46:602 (1981)).

Scheme 8

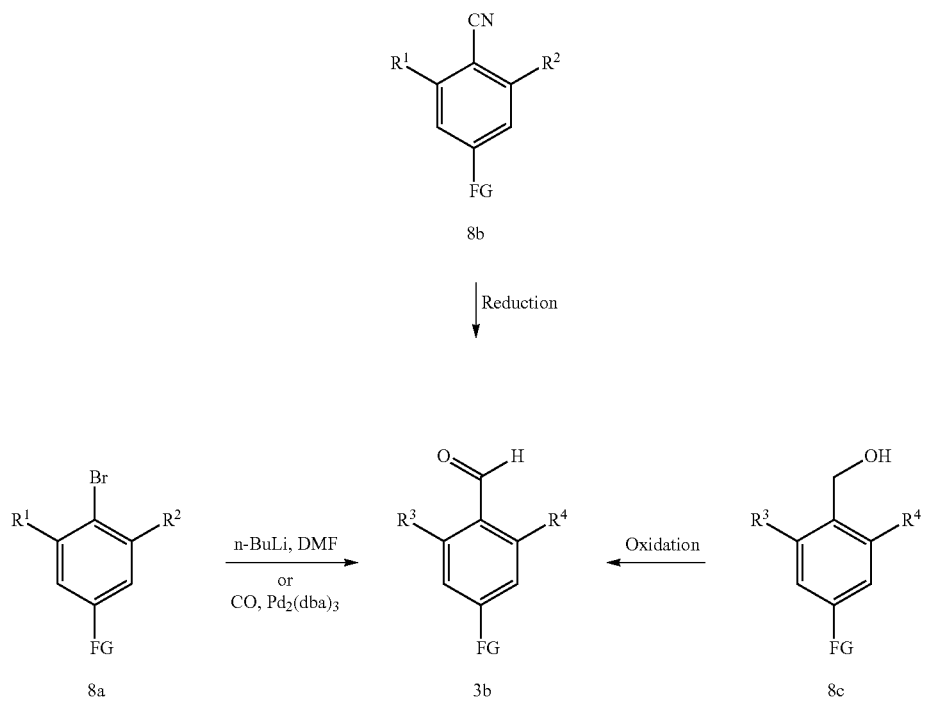

-continued

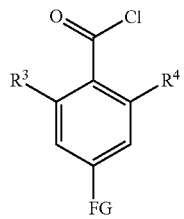

8d

For some of the compounds of Formula II-V, the $R^3$ and $R^4$ groups can be introduced after the biaryl ring backbone is installed. As illustrated in Scheme 9, the intermediate 4 ($R^3$, $R^4$=H) is converted to the benzylaldehyde 26 upon treatment with $SnCl_4$ and methoxymethyl dichloride. Various alkyl groups ($C_1$-$C_{12}$) are introduced by reacting the benzylaldehyde 26 with a Wittig reagent followed by the reduction of the resulting alkene with $Et_3SiH$ to afford the intermediate 27 (*J. Med. Chem.* 31:37 (1988)). Also, benzylaldehyde 31 can be oxidized by $NaOCl_2$ to give the benzoic acid 29 (*Bioorg. Med. Chem. Lett.* 13:379 (2003)) which can be reacted with an alcohol or amine under standard conditions to give the ester or amide 30. Intermediates 27 and 30 can be converted to the corresponding phosphonic acids 28 and 33 following the same procedures as described in Scheme 2. In addition, deprotection of intermediate 4 provides the phenol 32 which can be converted to a variety of sulfonamides 33 upon treatment with $ClSO_3H$ and an amine. Phosphonic acids ($R^3$=$S(=O)_2NR^fR^g$) can be formed following the same procedures as described in Scheme 1.

Scheme 9

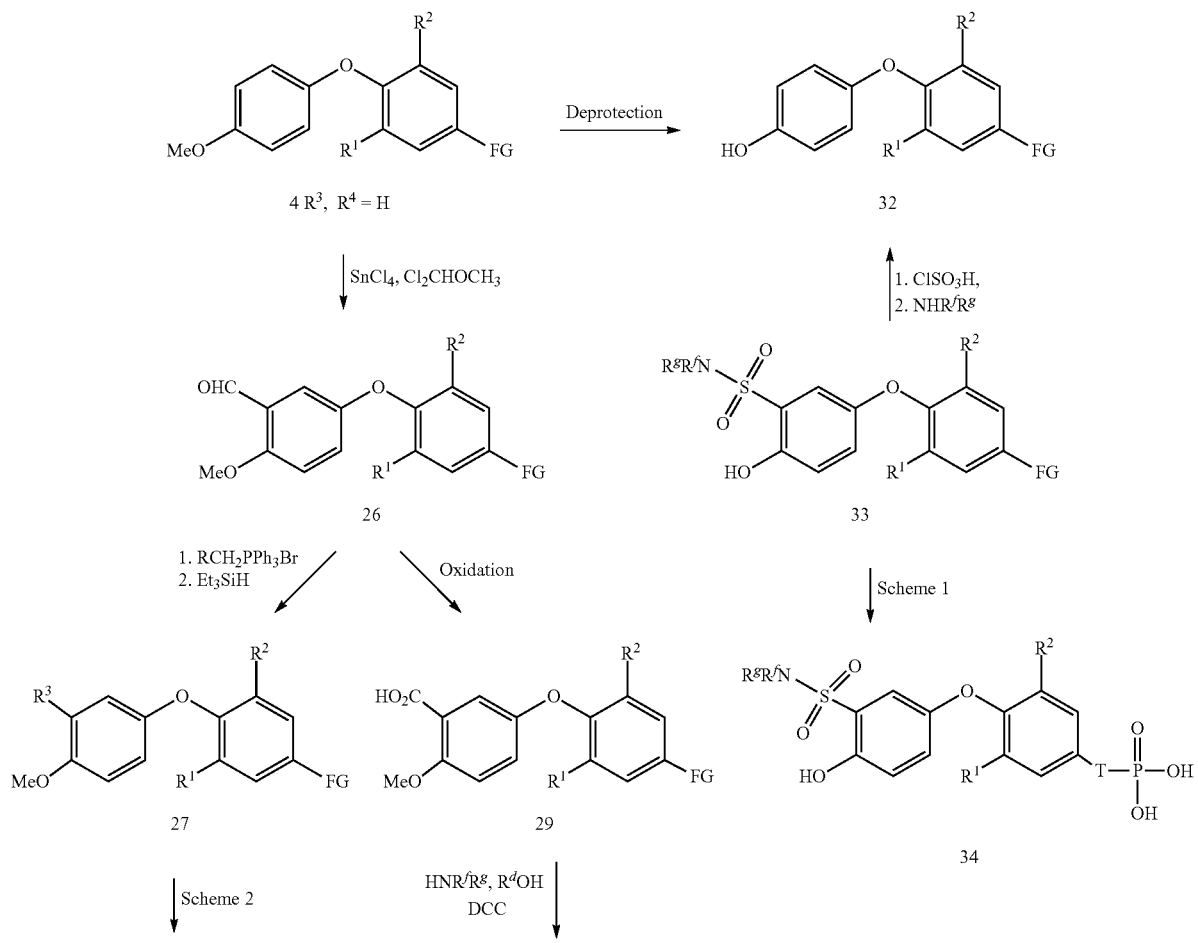

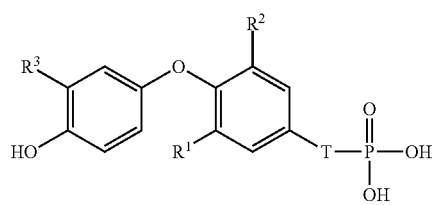

28

R³ = C₁-C₁₂ alkyl

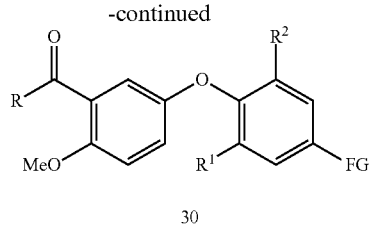

30

↓ Scheme 2

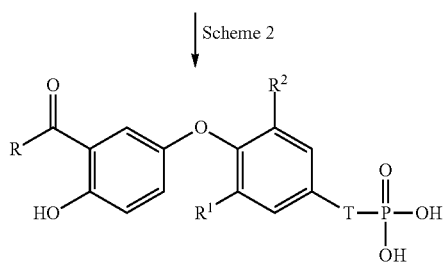

31

R = NR$^f$R$^g$, OR$^d$

B. Preparation of 1,3-Diols

Various methods can be used to prepare 1,3-propanediols such as 1-substituted, 2-substituted, 1,2- or 1,3-annulated 1,3-propanediols.

1. 1-Substituted 1,3-propanediols 1,3-Propanediols useful in, the synthesis of compounds in the present invention can be prepared using various synthetic methods. As described in Scheme 10, additions of an aryl Grignard to a 1-hydroxy-propan-3-al give 1-aryl-substituted 1,3-propanediols (path a). This method is suitable for the conversion of various aryl halides to 1-arylsubstituted-1,3-propanediols (*J. Org. Chem.* 53:911 (1988)). Conversions of aryl halides to 1-substituted 1,3-propanediols can also be achieved using Heck reactions (e.g., couplings with a 1,3-diox-4-ene) followed by reductions and subsequent hydrolysis reactions (*Tetrahedron Lett.* 33:6845 (1992)). Various aromatic aldehydes can also be converted to 1-substituted-1,3-propanediols using alkenyl Grignard addition reactions followed by hydroboration-oxidation reactions (path b).

Scheme 10

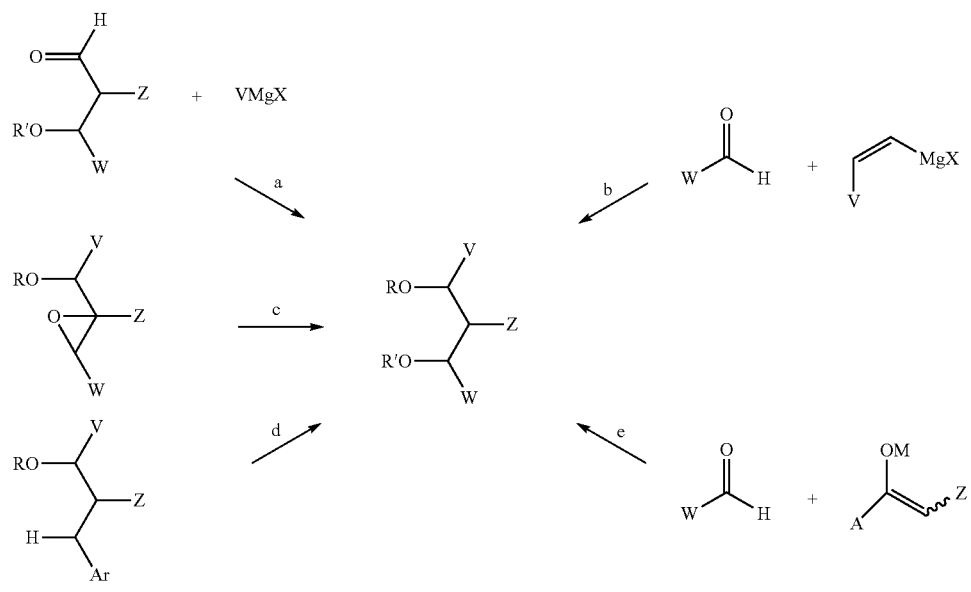

X = I, Br, Cl
A = OR, NR(R')
M = Metal

Aldol reactions between an enolate (e.g., lithium, boron, tin enolates) of a carboxylic acid derivative (e.g., tert-butyl acetate) and an aldehyde (e.g., the Evans's aldol reactions) are especially useful for the asymmetric synthesis of enantioenriched 1,3-propanediols. For example, reaction of a metal enolate of t-butyl acetate with an aromatic aldehyde followed by reduction of the ester (path e) gives a 1,3-propanediol (*J. Org. Chem.* 55:4744 (1990)). Alternatively, epoxidation of cinnamyl alcohols using known methods (e.g., Sharpless epoxidations and other asymmetric epoxidation reactions) followed by reduction reactions (e.g., using Red-Al) give various 1,3-propanediols (path c). Enantioenriched 1,3-propanediols can be obtained via asymmetric reduction reactions (e.g., enantioselective borane reductions) of 3-hydroxy-ketones (*Tetrahedron Lett.* 38:761 (1997)). Alternatively, resolution of racemic 1,3-propanediols using various methods (e.g., enzymatic or chemical methods) can also give enantioenriched 1,3-propanediol. Propan-3-ols with a 1-heteroaryl substituent (e.g., a pyridyl, a quinolinyl or an isoquinolinyl) can be oxygenated to give 1-substituted 1,3-propanediols using N-oxide formation reactions followed by a rearrangement reaction in acetic anhydride conditions (path d) (*Tetrahedron* 37:1871 (1981)).

2. 2-Substituted 1,3-propanediols

A variety of 2-substituted 1,3-propanediols useful for the synthesis of compounds of Formula I-VII can be prepared from various other 1,3-propanediols (e.g., 2-(hydroxymethyl)-1,3-propanediols) using conventional chemistry (*Comprehensive Organic Transformations*, VCH, New York, 1989). For example, as described in Scheme 11, reductions of a trialkoxycarbonylmethane under known conditions give a triol via complete reduction (path a) or a bis(hydroxymethyl)acetic acid via selective hydrolysis of one of the ester groups followed by reduction of the remaining two other ester groups. Nitrotriols are also known to give triols via reductive elimination (path b) (*Synthesis* 8:742 (1987)). Furthermore, a 2-(hydroxymethyl)-1,3-propanediol can be converted to a mono acylated derivative (e.g., acetyl, methoxycarbonyl) using an acyl chloride or an alkyl chloroformate (e.g., acetyl chloride or methyl chloroformate) (path d) using known chemistry (*Protective Groups In Organic Synthesis*; Wiley, N.Y., 1990). Other functional group manipulations can also be used to prepare 1,3-propanediols such as oxidation of one the hydroxymethyl groups in a 2-(hydroxymethyl)-1,3-propanediol to an aldehyde followed by addition reactions with an aryl Grignard (path c). Aldehydes can also be converted to alkyl amines via reductive amination reactions (path e).

Scheme 11

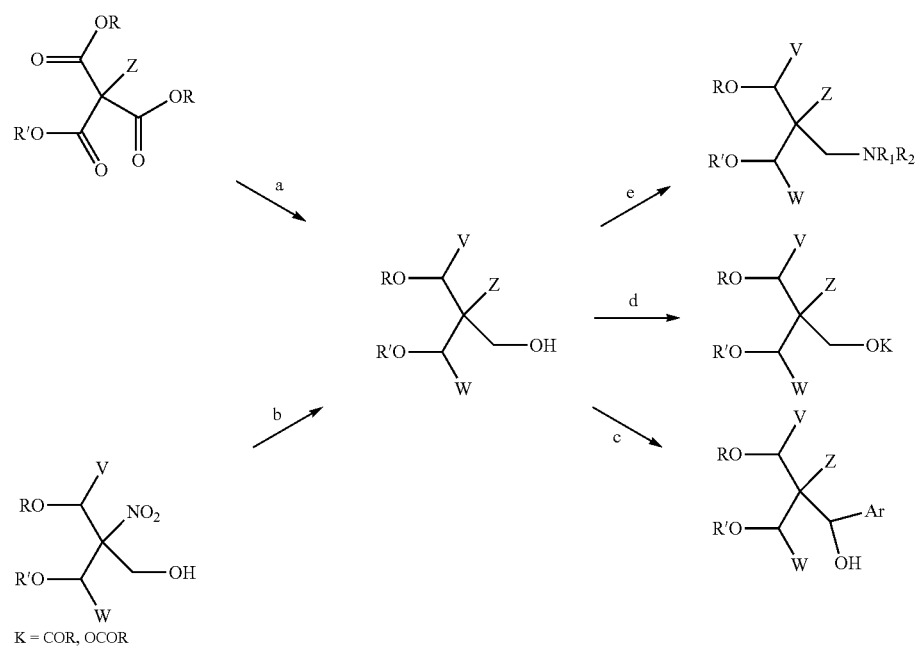

3. Annulated 1,3-propane Diols

Compounds of Formula I-VII wherein V and Z or V and W are connected by four carbons to form a ring can be prepared from a 1,3-cyclohexanediol. For example, cis,cis-1,3,5-cyclohexanetriol can be modified to give various other 1,3,5-cyclohexanetriols which are useful for the preparations of compounds of Formula I wherein $R^{11}$ and $R^{11}$ together are

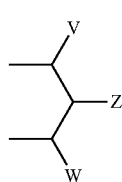

wherein together V and W are connected via 3 atoms to form a cyclic group containing 6 carbon atoms substituted with a hydroxy group. It is envisioned that these modifications can be performed either before or after formation of a cyclic phosphonate 1,3-propanediol ester. Various 1,3-cyclohexanediols can also be prepared using Diels-Alder reactions (e.g., using a pyrone as the diene: *Tetrahedron Lett.* 32:5295 (1991)). 2-Hydroxymethylcyclohexanols and 2-hydroxymethylcyclopentanols are useful for the preparations of compounds of Formula I wherein $R^{11}$ and $R^{11}$ together are

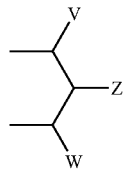

wherein together V and Z are connected via 2 or 3 atoms to form a cyclic group containing 5 or 6 carbon atoms. 1,3-Cyclohexanediol derivatives are also prepared via other cycloaddition reaction methodologies. For example, cycloadducts from the cycloaddition reactions of a nitrite oxide and an olefin can be converted to a 2-ketoethanol derivative which can be further converted to a 1,3-propanediol (including 1,3-cyclohexanediol, 2-hydroxymethylcyclohexanol and 2-hydroxymethylcyclopentanol) using known chemistry (*J. Am. Chem. Soc.* 107:6023 (1985)). Alternatively, precursors to 1,3-cyclohexanediol can be made from quinic acid (*Tetrahedron Lett.* 32:547 (1991)).

EXPERIMENTAL

Example 1

Examples of the method of the invention includes the following. It will be understood that these examples are exemplary and that the method of the invention is not limited solely to these examples.

For the purposes of clarity and brevity compounds are referred to by compound numbers (from the Table below) in the biological examples below.

| Structure | Compound Number |
|---|---|
| 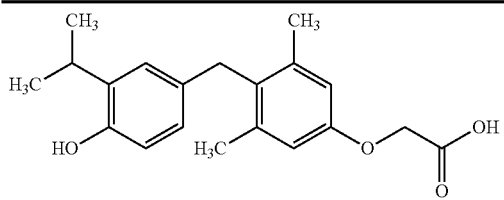 | 17 |
| 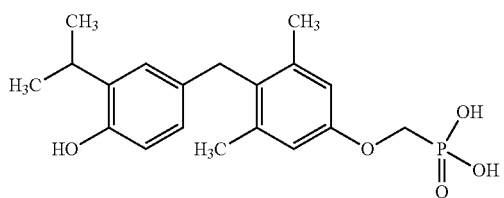 [SMILES: Cc1cc(OCP(=O)(O)O)cc(C)c1Cc1ccc(O)c(C(C)C)c1] | 7 |
| 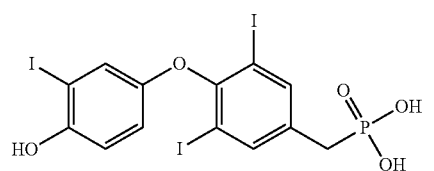 [SMILES: O=P(O)(O)Cc1cc(I)c(Oc2ccc(O)c(I)c2)c(I)c1] | 6 |

-continued

| Structure | Compound Number |
|---|---|
| (structure with phosphonate propanediol ester and chlorophenyl) | cis-13-1 |
| (TRIAC structure) | TRIAC |
| (dichloro analog structure) | 18 |

Example A

Chronic Exposure to Thyroid Receptor Agonists in Normal Rats

The purpose of these studies was to compare the difference in efficacy to clear liver triglyceride content between T3 and various T3 mimetics that are carboxylic acids and T3 mimetics that are phosphonic acids. In one example, T3 and Compounds 7 and 17, which differ only in that for Compound 7, the X moiety of Formula II is —P(O)OH$_2$ and for Compound 17, X is —C(O)OH, were compared. In the same example TRIAC and Compound 6, which differ only in that for Compound 6, X is —P(O)OH$_2$ and for TRIAC, X is —C(O)OH, were compared. Efficacy was measured by analyzing total liver triglycerides.

Methods: Normal rats (Sprague-Dawley) were maintained on a standard diet. Compounds 7, 17, 6, TRIAC or T3 were administered by continuous infusion using an osmotic pump (Alzet; subcutaneous implant) at a dose of 1 mg/kg/day. The compounds were dissolved in 0.1N NaOH solution and the pH adjusted to 7.4-8.0. The compounds were brought up to an appropriate volume using PBS and BSA to maintain solubility within the pump. The compounds were chemically stable in the excipient at 37° C. for 7 days. Body weights were measured and the change from the starting body weight was calculated. The 4.5% reported for the vehicle animals represent a 4.5% increase in body weight over the course of the experiment.

Sections of liver were removed and frozen. Liver triglycerides were analyzed following lipid extraction by the Bligh Dyer method (Bligh and Dyer, *Can. J. Med. Sci.* 37(8):911-7 (1959), incorporated herein by reference). Total triglycerides were analyzed in the liver extracts by an enzymatic assay (Thermo Electron Corporation). Total lipid was normalized to initial liver weight and triglyceride content was normalized to liver weight mGPDH activity was analyzed in isolated mitochondria using 2-(4-iodophenyl)-3-(4-nitrophenyl)-5-phenyl tetrazolium chloride as the terminal electron acceptor (Gardner R S, Analytical Biochemistry 59:272 (1974)). Commercially available GPDH was used in each assay as a standard (Sigma, St. Louis, Mo.).

Results: T3 did not significantly decrease liver triglyceride content. However, all synthetic thyroid receptor ligands tested unexpectedly and significantly decrease hepatic triglyceride content. T3, compound 17 and TRIAC all produced a loss of body weight over the course of the experiment, in agreement with previously reported results.

TABLE 2

| Compound | Triglycerides (mg/g liver) | Body Weight (% change from start) | Liver mGPDH activity (% vehicle) |
|---|---|---|---|
| vehicle | 5.3 ± 1.5 | 4.5 ± 2.4 | 100 ± 4 |
| T3 | 3.6 ± 0.6 | −8.2 ± 1.5 | 406 ± 54 |
| 17 | 1.8 ± 0.3 | −5.4 ± 1.0 | 426 ± 45 |
| 7 | 1.3 ± 0.4 | 9.1 ± 1.5 | 399 ± 40 |
| TRIAC | 1.5 ± 0.4 | −1.7 ± 0.6 | 384 ± 28 |
| 6 | 1.3 ± 0.2 | 8.7 ± 0.8 | 291 ± 37 |

Conclusion: synthetic thyroid receptor ligands, but not T3, decrease hepatic triglyceride content, while all thyroid receptor ligands increase mitochondrial activity.

Example B

Chronic Exposure to Thyroid Receptor Agonists in ob/ob Mice

The purpose of these studies was to compare the difference in efficacy to clear liver triglyceride content between Compound cis-13-1 and T3 in ob/ob mice.

Methods: ob/ob mice were maintained on a standard diet. Compound cis-13-1 was administered at doses of 3, 10 and 30 mg/kg/d orally in a CMC suspension. T3, 100 nmole/kg/d, was administered as an aqueous solution subcutaneously. Liver triglycerides were analyzed as described in example A. Epididymal fat pads were removed and weighed. Clinical chemistry analysis was performed by LabCorp (San Diego, Calif.).

Results: T3 did not significantly decrease liver triglyceride content (FIG. 1). However, Compound cis-13-1 decreased hepatic triglyceride content at 10 and 30 mg/kg/d (FIG. 1). Compound cis-13-1 did not decrease epididymal fat pad (EFP) weight. T3 significantly decreased EFP weight, consistent with a well described effect of T3 on lipolysis. Treatment of ob/ob mice for 9 weeks with cis-13-1 caused a >50% decrease in ALT levels from 634 IU/L in the vehicle treated group, indicating an improvement in liver function.

TABLE 3

| Treatment | Liver Trigs (mg/g) | EFP weight (g) |
|---|---|---|
| Vehicle | 109 ± 6 | 4.5 ± 0.2 |
| T3 | 86 ± 5 | 2.0 ± 0.1* |
| cis-13-1 | | |
| 3 | 87 ± 6 | 4.4 ± 0.1 |
| 10 | 66 ± 10* | 4.7 ± 0.1 |
| 30 | 59 ± 6* | 4.4 ± 0.1 |

Conclusion: Synthetic thyroid receptor ligands, but not T3, decrease hepatic triglyceride content following long-term administration.

Example C

Chronic Exposure to Thyroid Receptor Agonists in ZDF Rats

The purpose of these studies was to compare the difference in efficacy to clear liver steatosis between Compounds cis-13-1 and 18 in Zucker diabetic fatty (ZDF) rats.

Methods: ZDF rats were maintained on a standard diet (5008). Compounds cis-13-1 or 18 were administered orally at the indicated doses using a CMC suspension. Liver steatosis was analyzed visually following H&E staining of paraffin embedded liver sections. TSH was measured using a rodent specific kit (Amersham Biosciences). At the end of the experiment, the left ventricle was cannulated with a high fidelity catheter-tip transducer (Millar) via the right carotid artery. Left ventricle pressure, its first derivative (LV dP/dt), lead I ECG, and heart rate triggered off the ECG waveform, were recorded.

Results: Compounds cis-13-1 and 18 visually decreased hepatic steatosis compared to control in ZDF rats (FIGS. 2A-2D). No significant decreases in TSH were observed following 4 weeks of treatment with cis-13-1. When heart rates and other cardiovascular parameters were measured, there were no significant changes from vehicle in any parameter in animals treated with cis-13-1.

Conclusion: Synthetic thyroid receptor ligands decrease hepatic steatosis following long-term administration in ZDF rats. Further, the decrease in steatosis occurred with a suitable safety profile regarding TSH and cardiovascular changes.

Example D

Chronic Exposure to Thyroid Receptor Agonists in DIO Mice

The purpose of these studies was to compare the ability of Compound cis-13-1 to clear liver steatosis in diet induced obesity (DIO) mice.

Methods: C57l316 mice were maintained on a 60% Kcal from fat diet. Compound cis-13-1 was administered at doses of 30 mg/kg/d orally in a CMC suspension for 10 weeks. Liver steatosis was analyzed visually following H&E staining of paraffin embedded liver sections. TSH was measured using a rodent specific kit (Amersham Biosciences). Heart rates were measured using a Lead I ECG with the heart rate calculated from the ECG waveform.

Figure 3A:
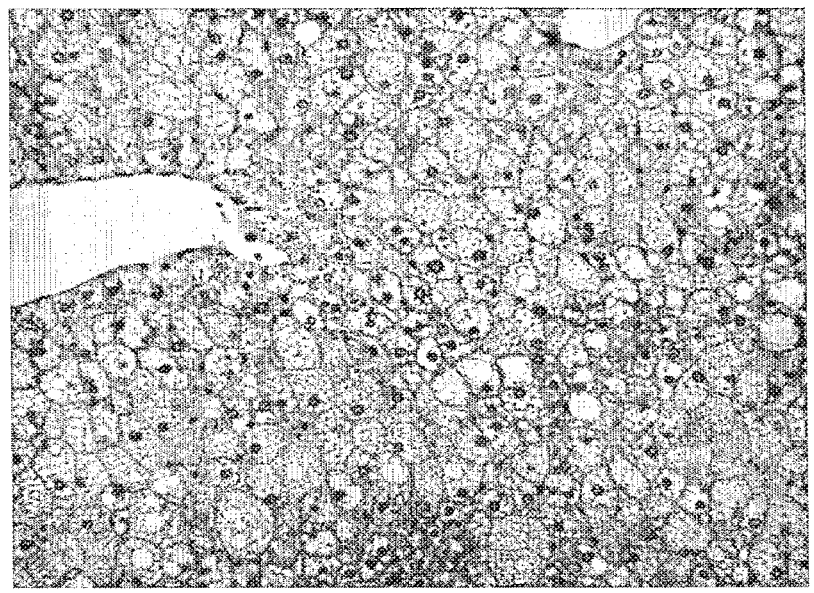
FIG. 3A shows an H & E stained section of liver from a DIO mouse treated with vehicle.
Figure 3B:
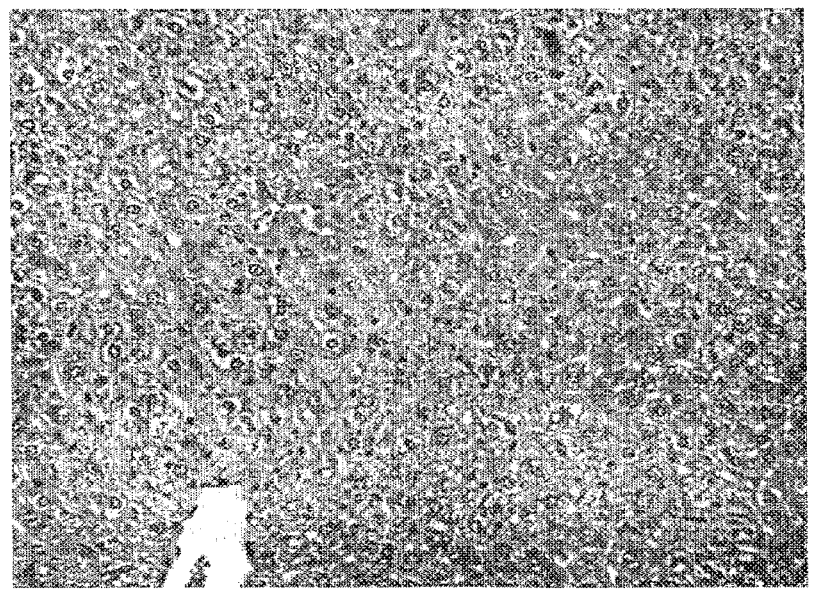
FIG. 3B shows an H & E stained section of liver from a DIO mouse treated with Compound cis-13-1 (30 mg/kg/d).

Results: Compound cis-13-1 decreased hepatic steatosis in DIO mice following 10 weeks of treatment (FIGS. 3A and 3B). There were no abnormalities in the ultrastructure of mitochondria from DIO mice treated with cis-13-1. No significant decreases in TSH were observed following 10 weeks of treatment with cis-13-1. When heart rates were measured, there was no significant change in heart rate with cis-13-1.

Conclusion: Compound cis-13-1 decreases hepatic steatosis following long-term administration. Further, the decrease in steatosis occurred with a suitable safety profile regarding TSH and cardiovascular changes.

Example E

Chronic Exposure to Thyroid Receptor Agonists in Normal Mice

The purpose of these studies was to compare the ability of Compound cis-13-1 to change liver gene expression.

Methods: C57Bl6 mice were maintained on a normal rodent diet. Compound cis-13-1 was administered at doses of 30 mg/kg/d orally in a CMC suspension for 1 week. Changes in levels of mRNA for liver and heart genes are analyzed using reverse transcriptase followed by real-time PCR analysis. The analysis is performed using an iCycler instrument (Biorad) and appropriate primers by means of standard methodology (e.g., Schwab D A et al. *Life Sciences* 66:1683-94(2000)). The amounts of mRNA are normalized to an internal control, typically, cyclophilin.

Results: Compound cis-13-1 increased CPT-1 expression 3.5-fold in normal mice, to a level similar to that observed with T3.

Conclusion: Compound cis-13-1 can increase mitochondrial liver gene expression.

OVERALL CONCLUSIONS

Compounds cis-13-1, 7, 6, TRIAC, 17 and 18 decreased either hepatic triglyceride content or visually decreased hepatic steatosis in several animal models.

In either rats or mice treated with T3, no significant changes in hepatic triglyceride content were observed. In multiple models, T3 produced the expected changes. In normal rats, T3 (a) decreased body weight; and (b) increased mGPDH activity. In ob/ob mice, epididymal fat pad weight was decreased, consistent with an increase in lipolysis. Therefore, in the experimental models, T3 retained expected physiologic effects without producing a change in hepatic steatosis.

Synthetic thyroid hormone ligands, but not naturally occurring triiodothyronine, can be useful for clearance of hepatic steatosis.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

We claim:

1. A method of treating or ameliorating a fatty liver disease in an animal, comprising administering to said animal a therapeutically effective amount of a thyromimetic compound of Formula III:

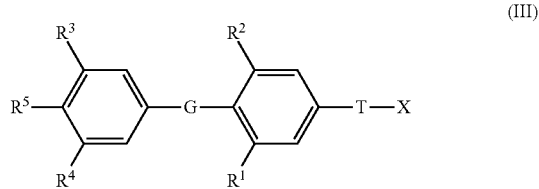

(III)

or a pharmaceutically acceptable salt thereof, wherein:
G is —CH$_2$—;
T is selected from the group consisting of —(CH$_2$)$_k$— and —O(CH$_2$)$_k$—;
k is an integer from 0-4;
R$^1$ and R$^2$ are each independently selected from the group consisting of hydrogen, halogen, and optionally substituted —C$_1$-C$_4$ alkyl;
R$^3$ and R$^4$ are each independently selected from the group consisting of hydrogen, halogen, and optionally substituted —C$_1$-C$_4$ alkyl;
R$^5$ is selected from the group consisting of —OH and —F;
X is selected from carboxylic acid or esters thereof, phosphonic acid, phosphonic acid monoester and —P(O)YR$^{11}$Y'R$^{11}$;
Y and Y' are each independently selected from the group consisting of —O— and —NR$^v$—;
when Y and Y' are both —O—, then each R$^{11}$ is independently selected from the group consisting of —C(R$^z$)$_2$—OC(O)R$^y$, —C(R$^z$)$_2$—O—C(O)OR$^y$, and -alkyl-S—C(O)R$^y$;
when Y and Y' are both —NR$^v$—, then each R$^{11}$ is —C(R$^x$)$_2$COOR$^y$;
or when Y and Y' are independently selected from —O— and —NR$^v$—, then together R$^{11}$ and R$^{11}$ are the group:

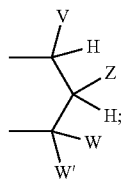

V, W, and W' are independently selected from the group consisting of hydrogen, optionally substituted alkyl, aryl, substituted aryl, heteroaryl, and substituted heteroaryl;
R$^v$ is hydrogen;
R$^z$ is hydrogen;
R$^y$ is alkyl; and
R$^x$ is hydrogen or lower alkyl;
wherein said compound binds to a thyroid receptor.

2. The method of claim 1, wherein said fatty liver disease is selected from the group consisting of steatosis, non-alcoholic fatty liver disease, and non-alcoholic steatohepatitis.

3. The method of claim 1, wherein said compound binds to a thyroid receptor with a Ki of ≤1 μM.

4. The method of claim 3, wherein said thyroid receptor is TRα1.

5. The method of claim 3, wherein said thyroid receptor is TRβ1.

6. The method of claim 3, wherein said compound binds to a thyroid receptor with a Ki of ≤100 nM.

7. The method of claim 6, wherein said thyroid receptor is TRα1.

8. The method of claim 6, wherein said thyroid receptor is TRβ1.

9. The method of claim 1, wherein said compound activates said thyroid receptor.

10. The method of claim 9, wherein said thyroid receptor is TRα1.

11. The method of claim 9, wherein said thyroid receptor is TRβ1.

12. The method of claim 9, wherein said compound increases mRNA expression of a gene selected from the group consisting of LDL receptor, ACC, FAS, spot-14, CPT-1, CYP7A, apo AI, and mGPDH.

13. The method of claim 1, wherein said thyromimetic compound is administered in the form of a pharmaceutical composition.

14. The method of claim 13, wherein said pharmaceutical composition is in the form of a controlled release composition, transdermal patch, tablet, hard capsule, or soft capsule.

15. The method of claim 1, wherein said thyromimetic compound is administered orally in a unit dose of about 0.375 μg/kg to 3.375 mg/kg.

16. The method of claim 1, wherein said thyromimetic compound is administered orally in a total daily dose of about 0.375 mg/kg/day to about 3.75 mg/kg/day, equivalent of the free acid.

17. The method of claim 1, wherein;
T is —CH$_2$ or —OCH$_2$;
R$^1$ and R$^2$ are each independently selected from the group consisting of hydrogen, halogen, and —C$_1$-C$_4$ alkyl;
R$^3$ and R$^4$ are each independently selected from the group consisting of hydrogen, halogen, and —C$_1$-C$_4$ alkyl;
R$^5$ is —OH; and
X is carboxylic acid or phosphonic acid.

18. A method of treating or ameliorating a fatty liver disease in an animal, comprising administering to said animal a therapeutically effective amount of a thyromimetic compound selected from the group consisting of:

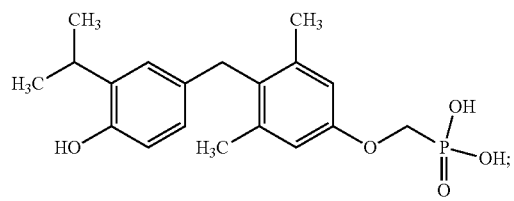 [SMILES: Cc1cc(OCP(=O)(O)O)cc(C)c1Cc1ccc(O)c(C(C)C)c1]

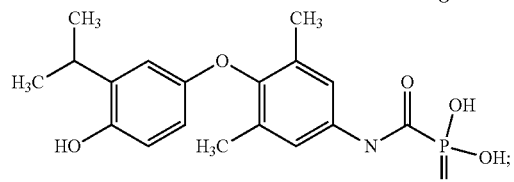

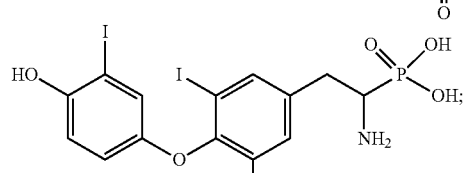

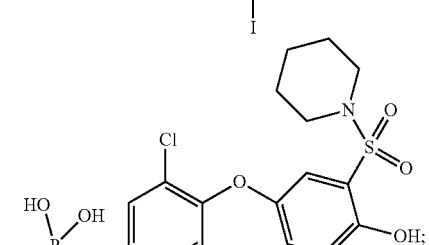

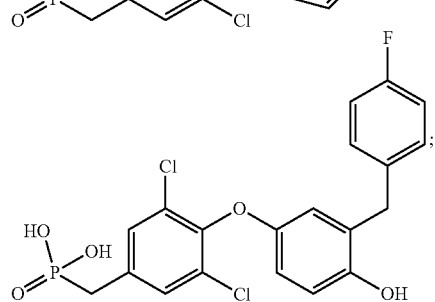

-continued

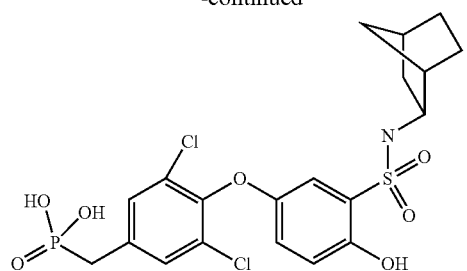

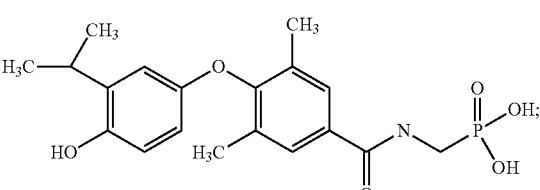

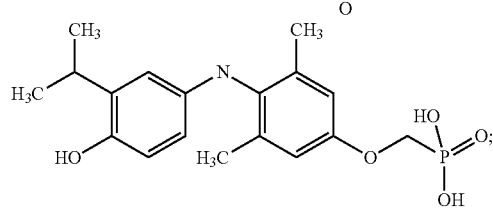

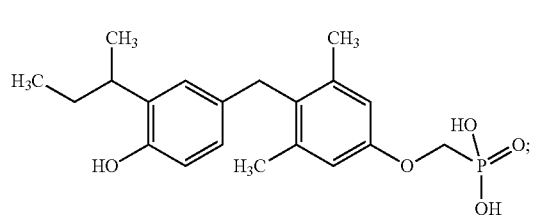

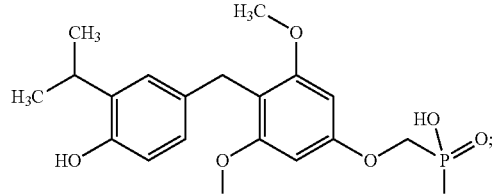

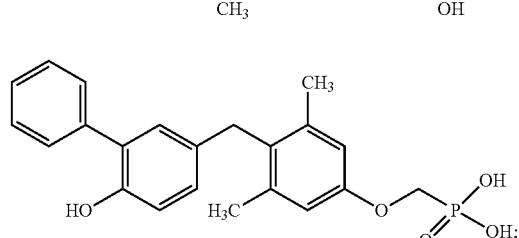

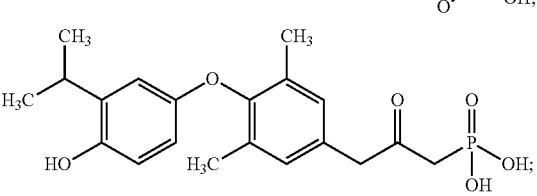

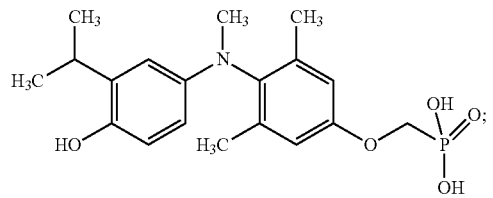

-continued
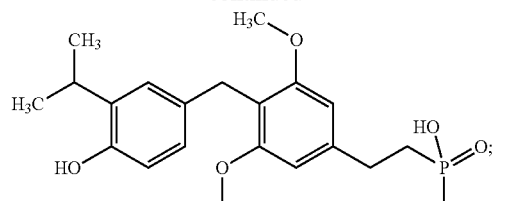
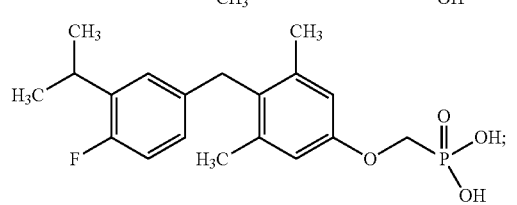
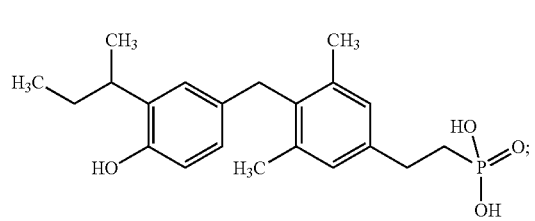
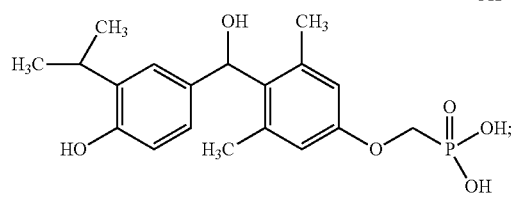
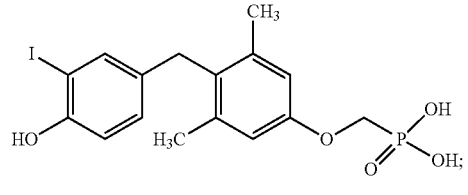
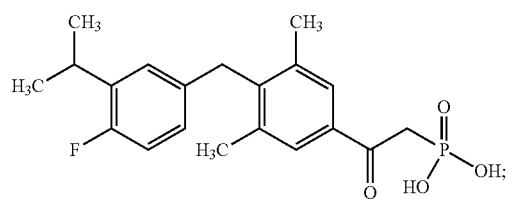
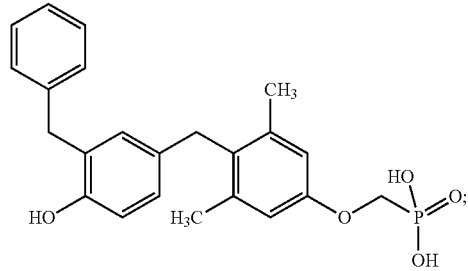 [SMILES: Cc1cc(OCP(=O)(O)O)cc(C)c1Cc1ccc(O)c(Cc2ccccc2)c1]
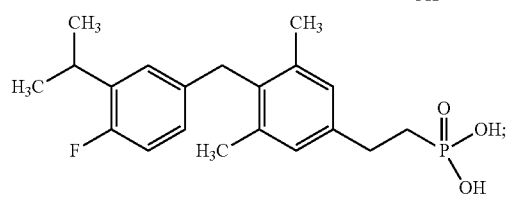
-continued
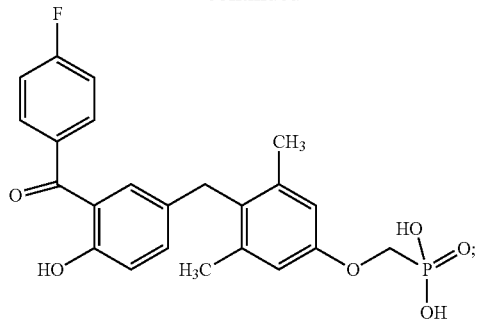
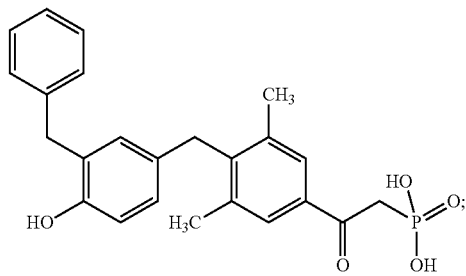
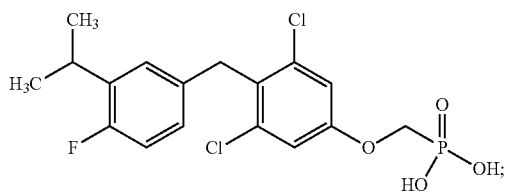
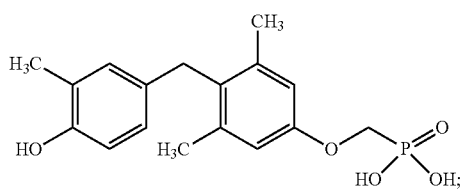
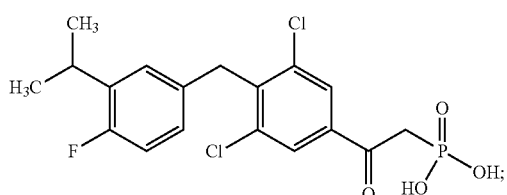
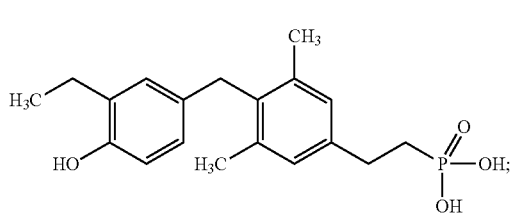
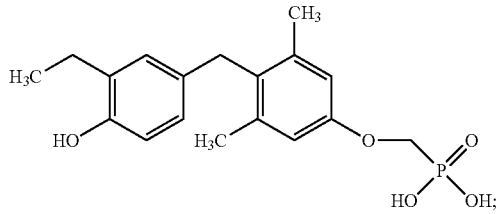

157
-continued
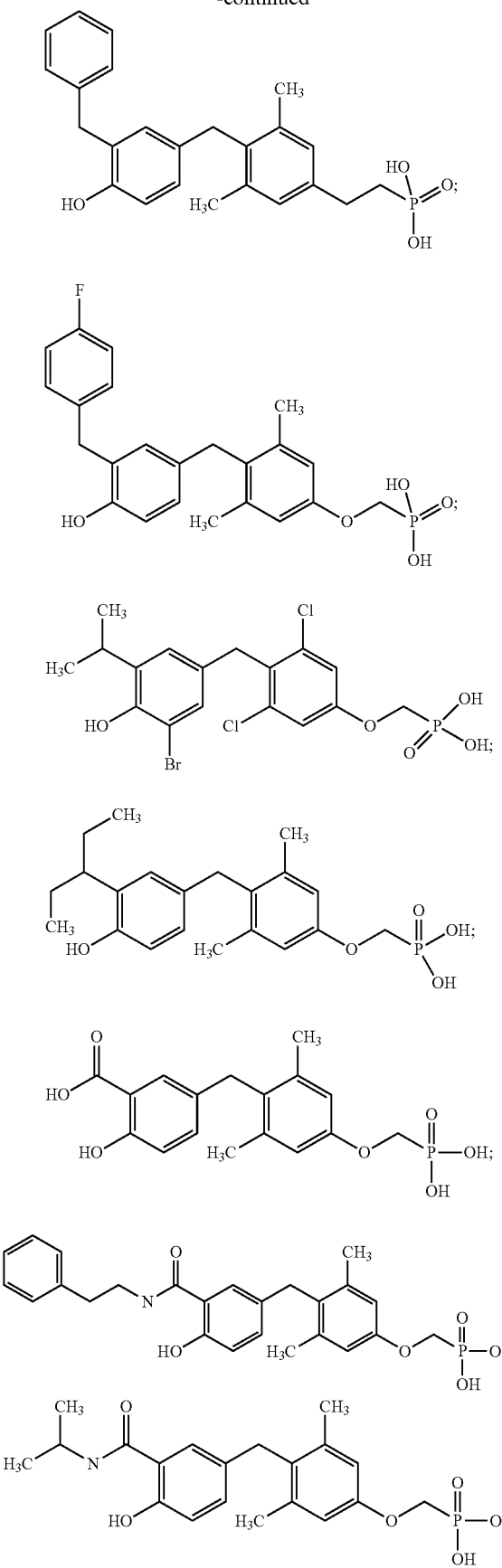
158
-continued
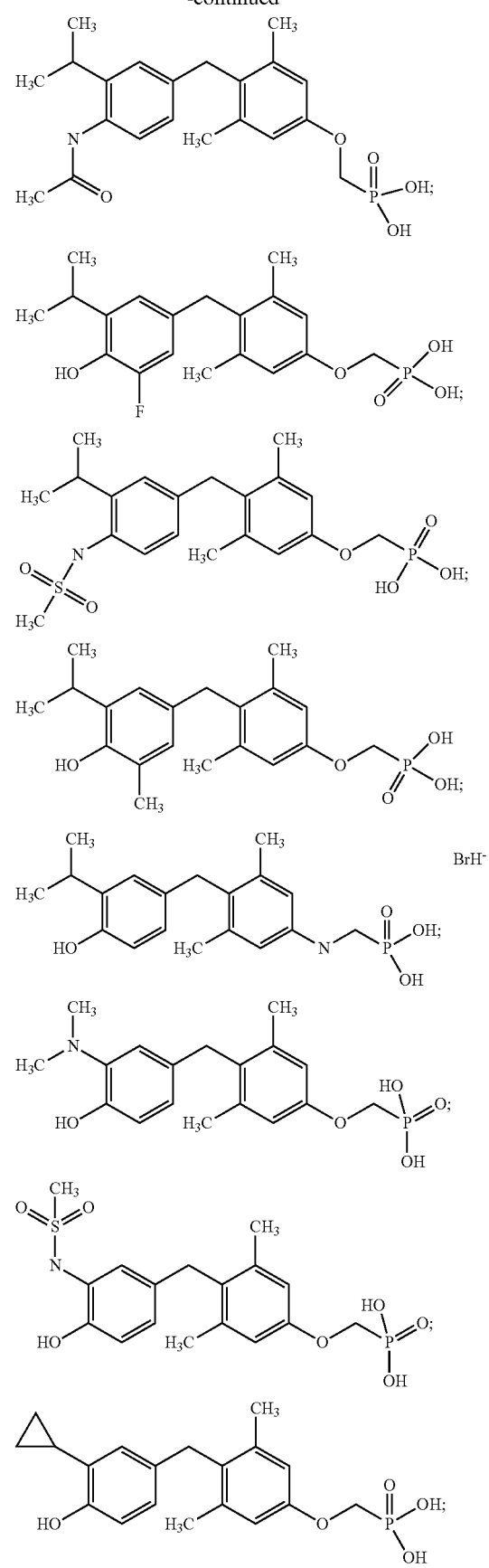

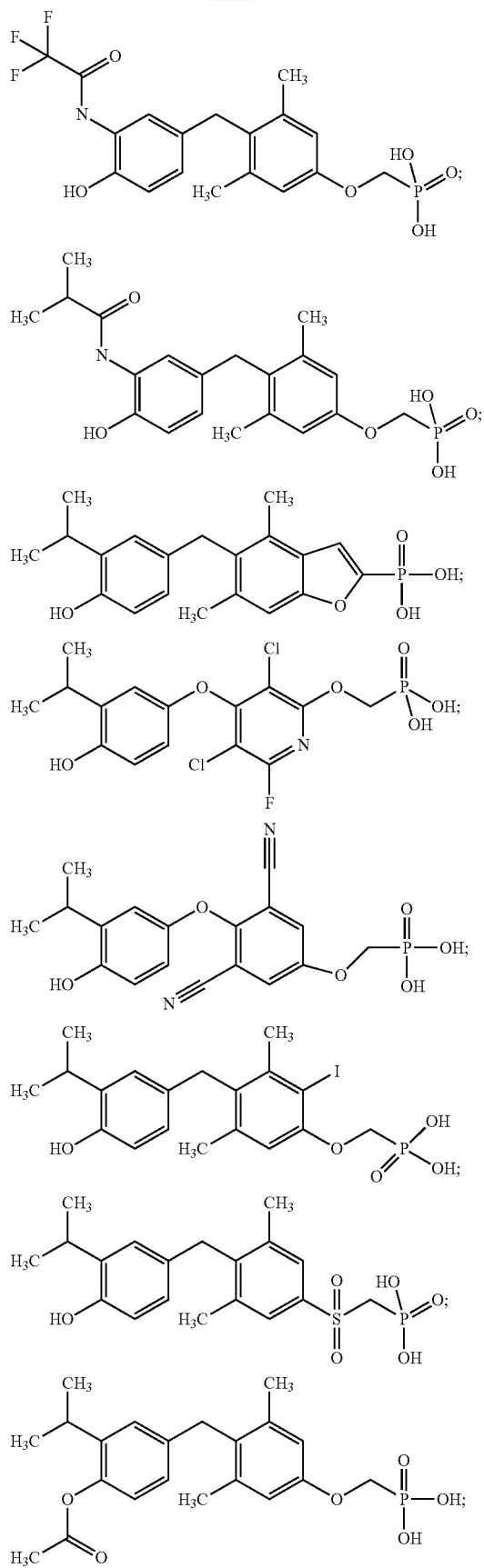
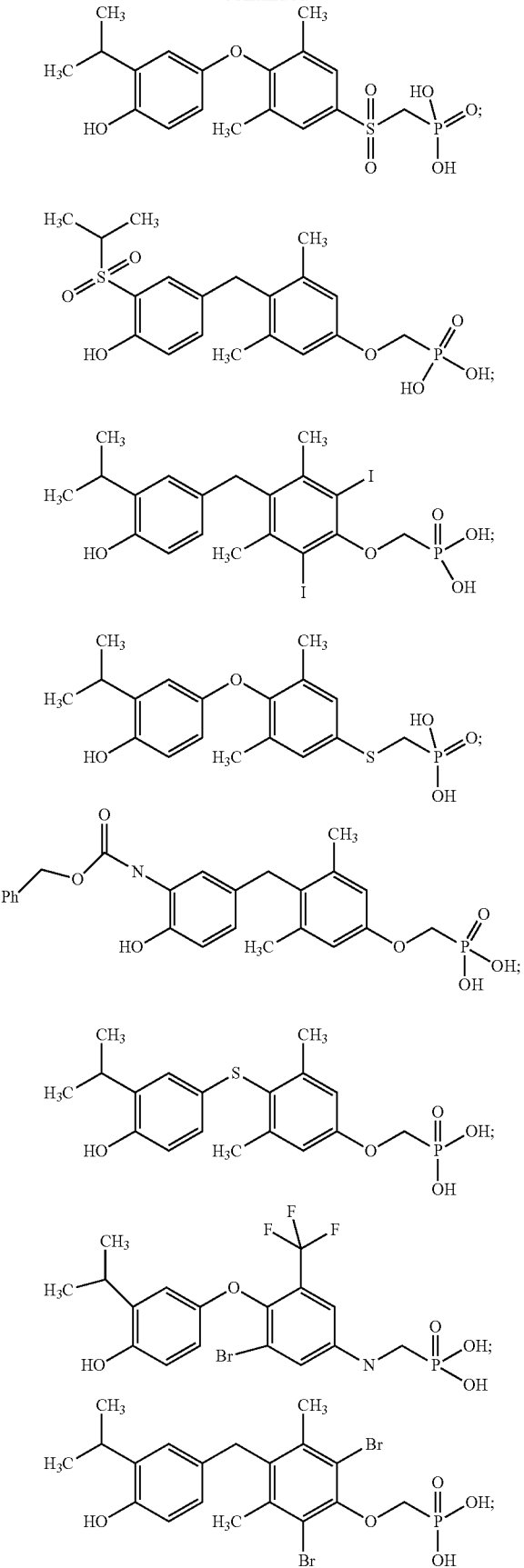

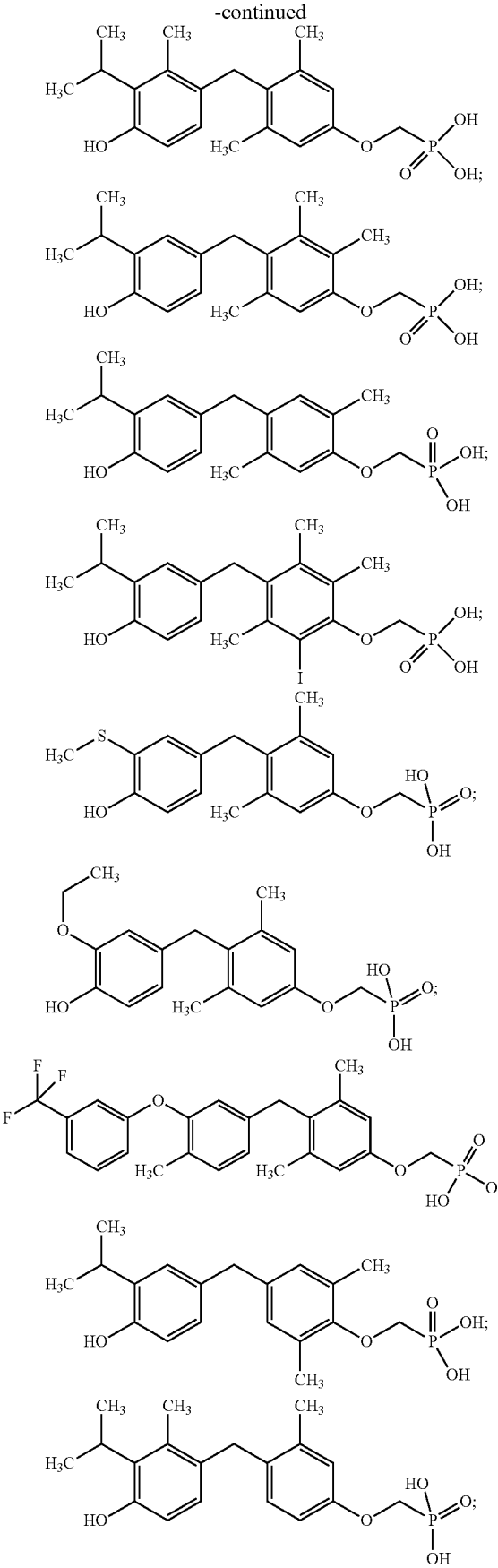
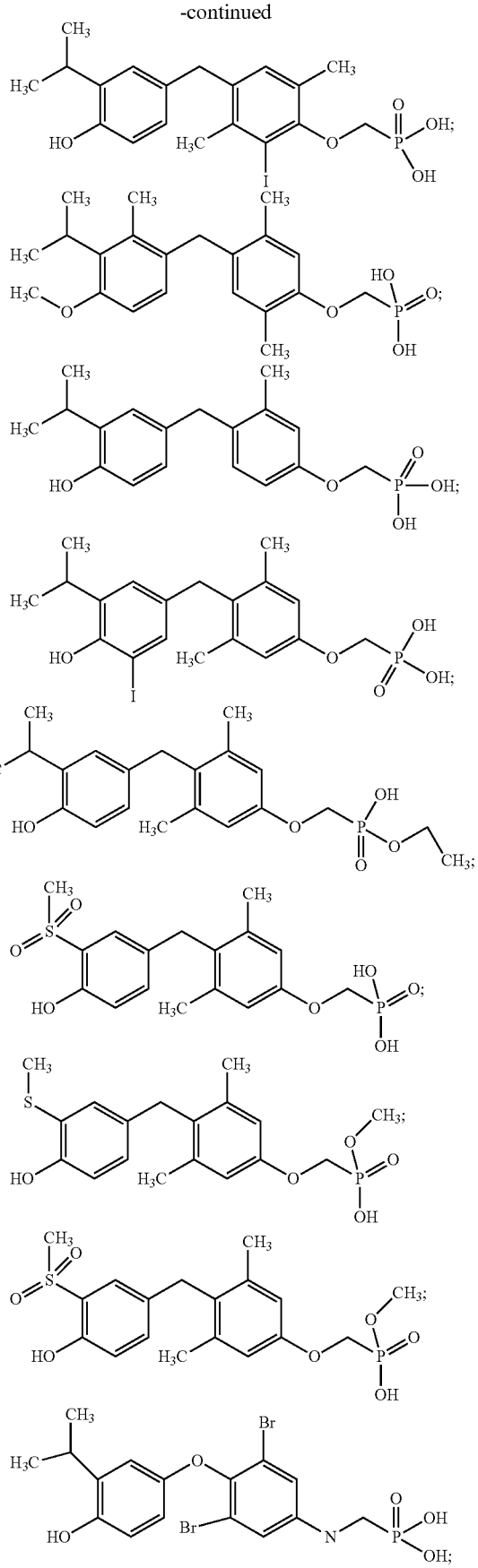

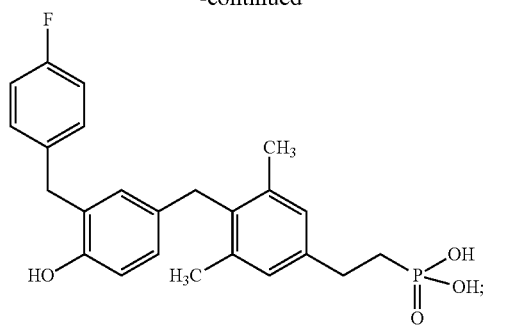
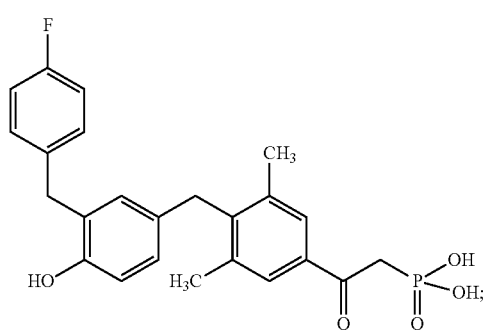
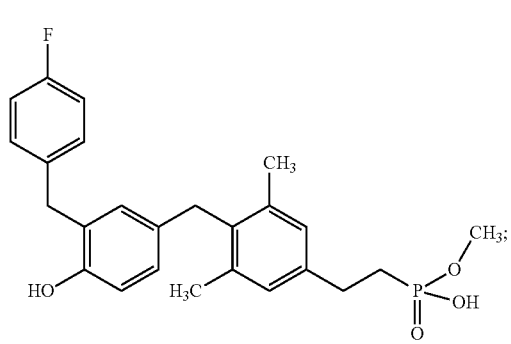
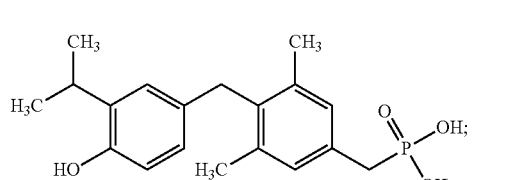
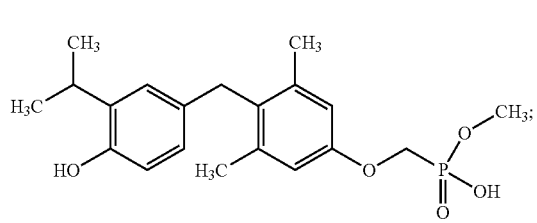
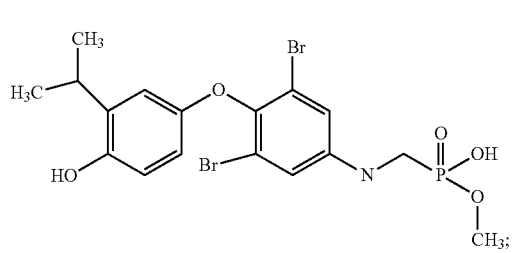
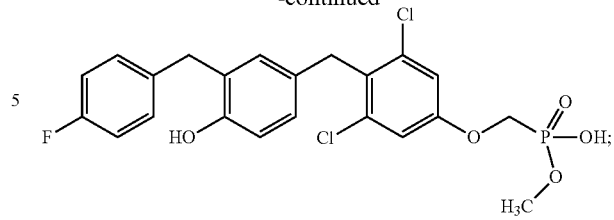
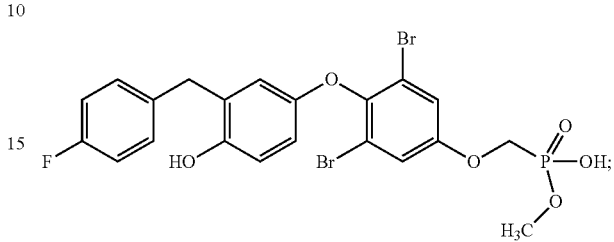
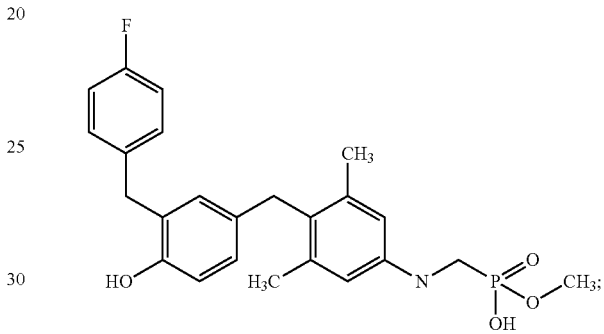
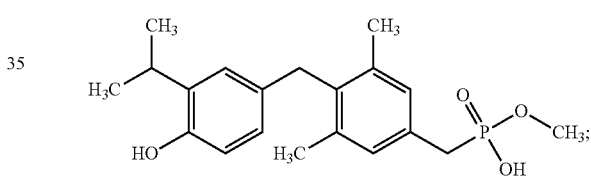
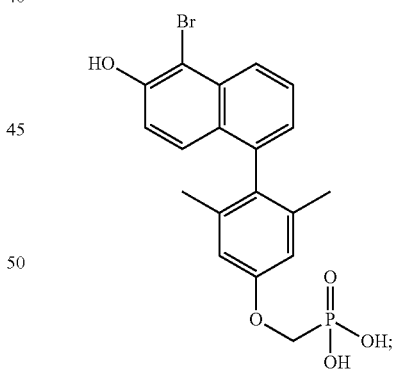
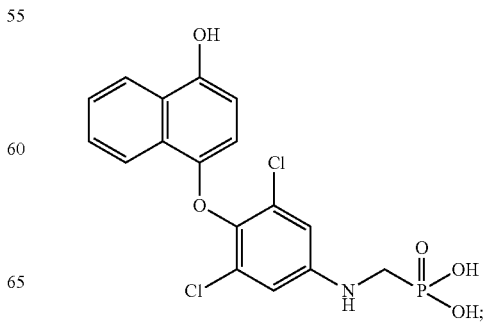

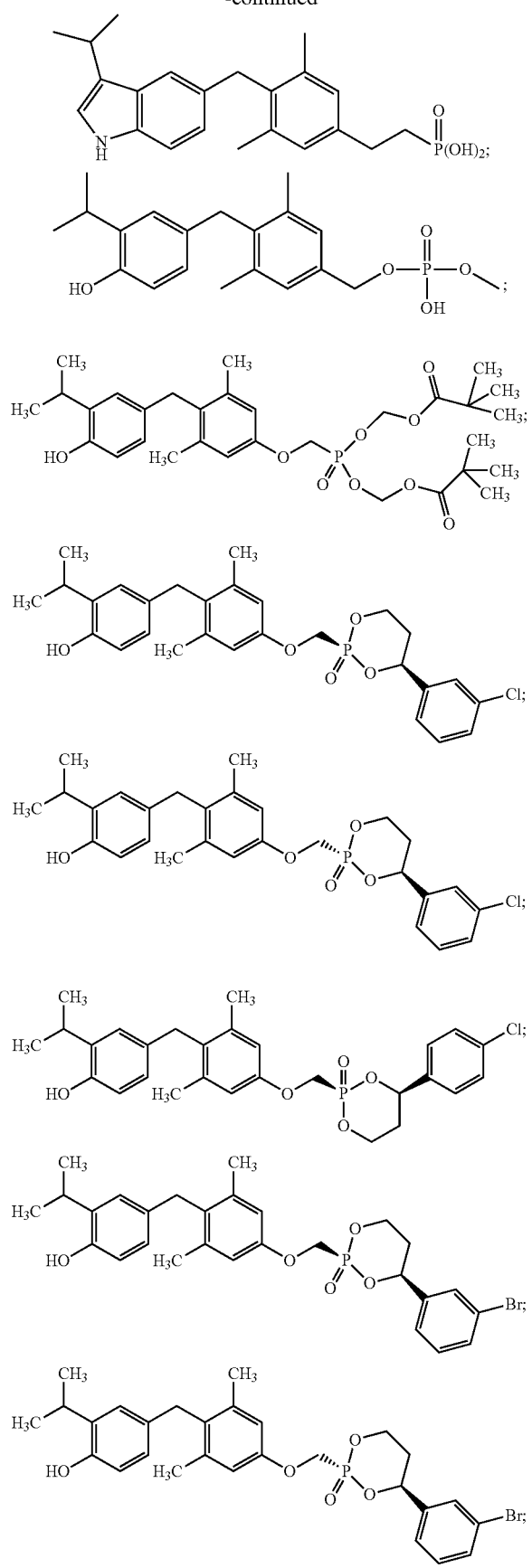
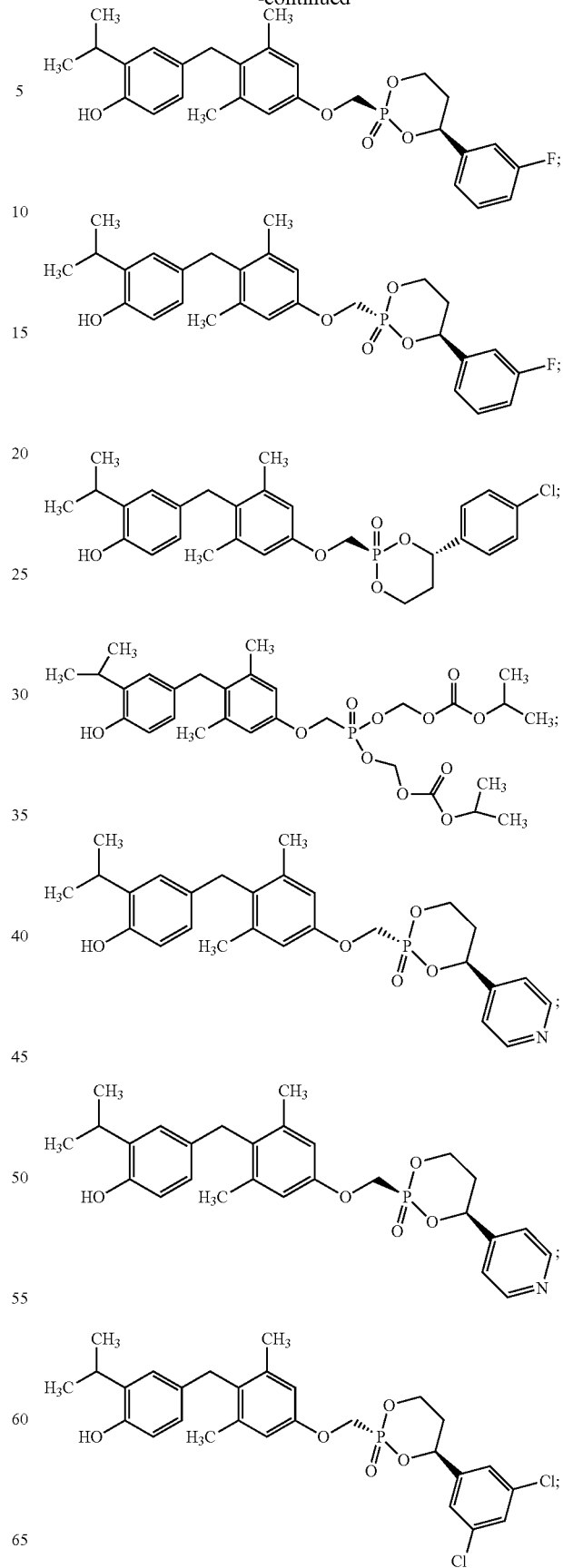

167
-continued
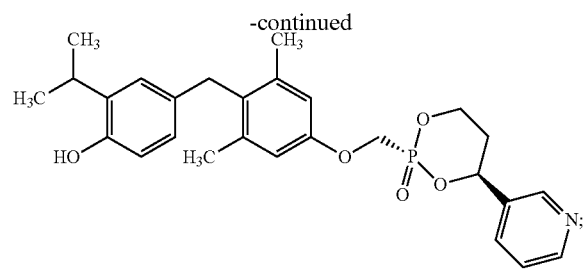
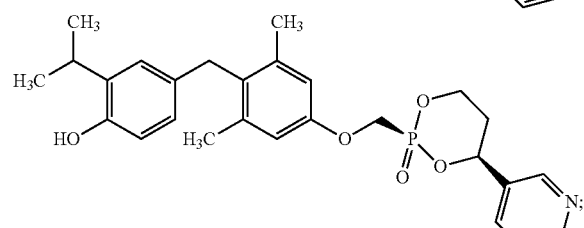
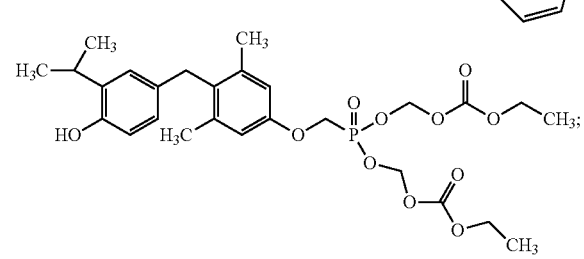
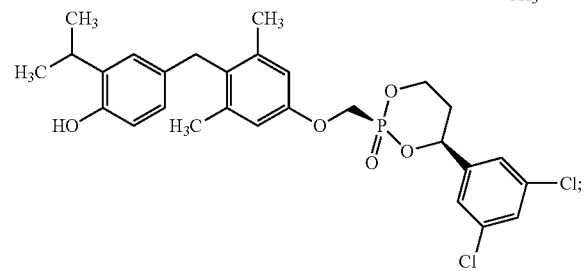
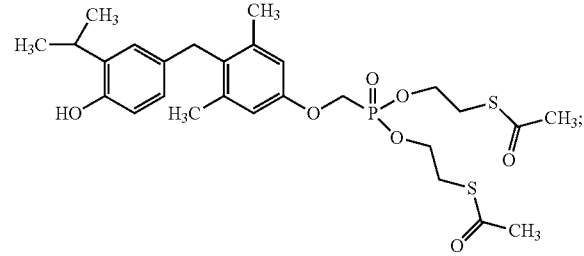
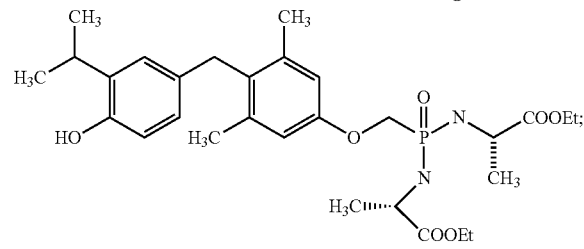
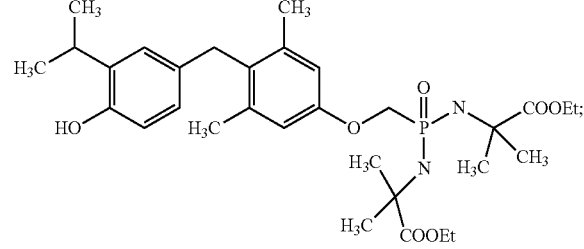
168
-continued
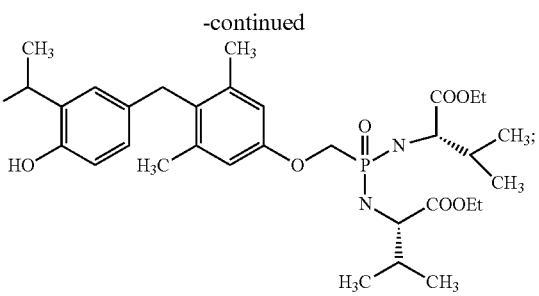
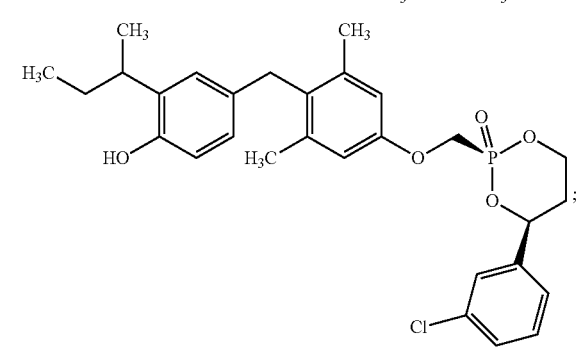
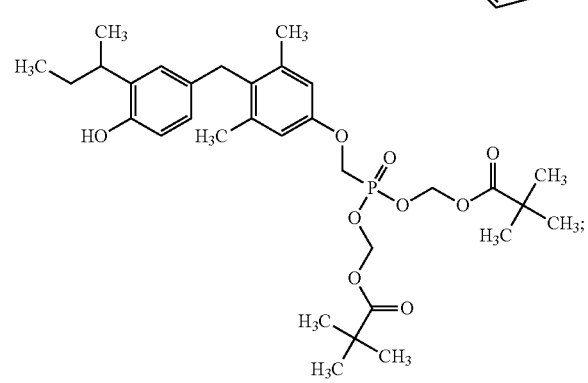
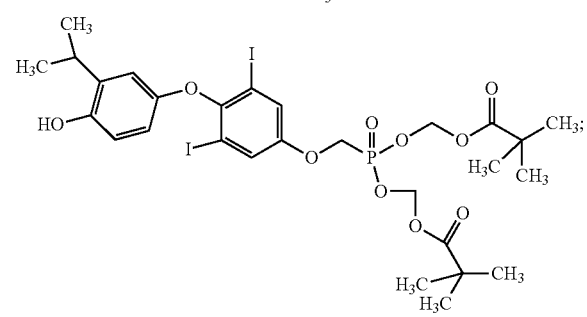
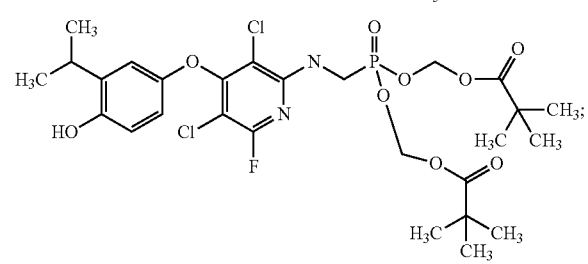
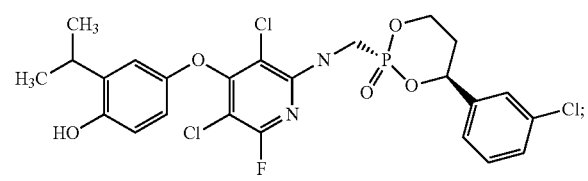

169
-continued
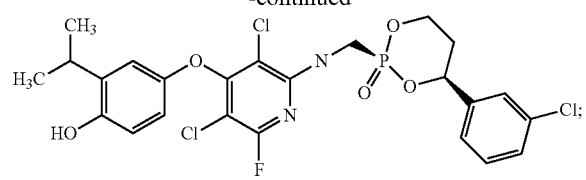
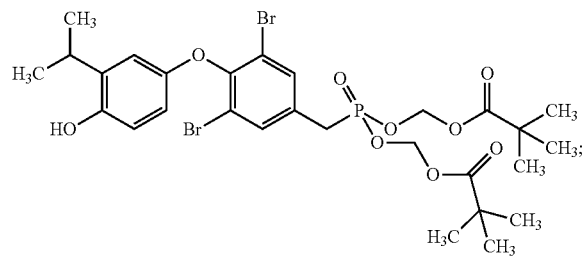
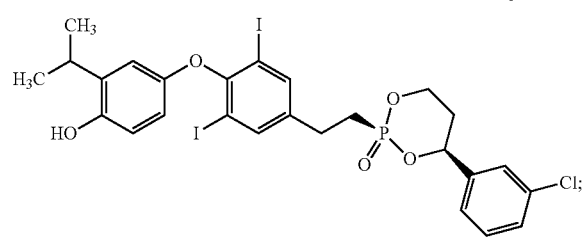
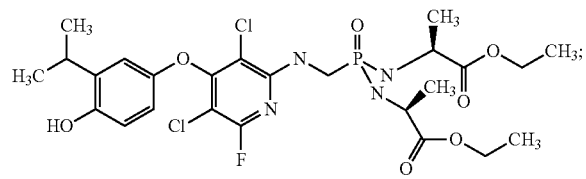
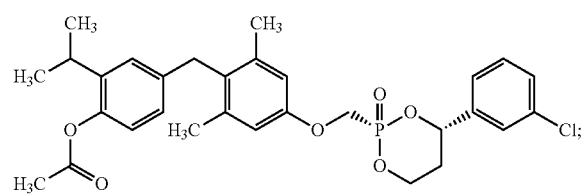
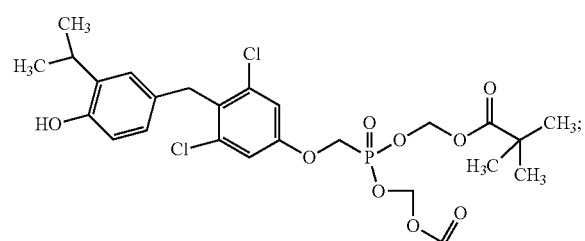
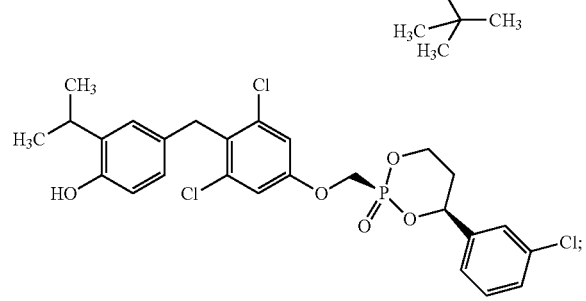
170
-continued
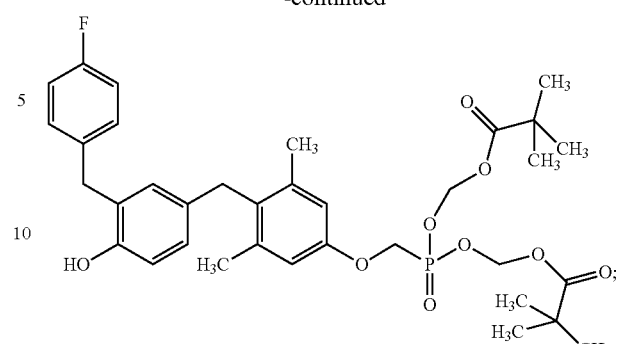
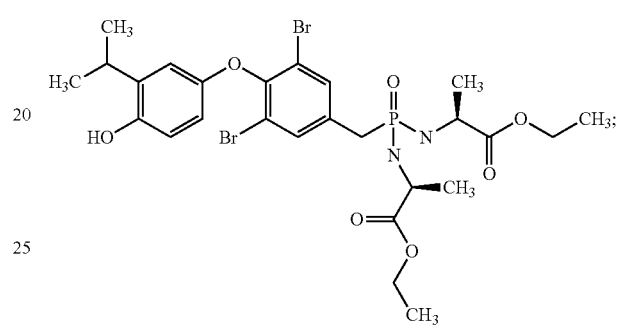
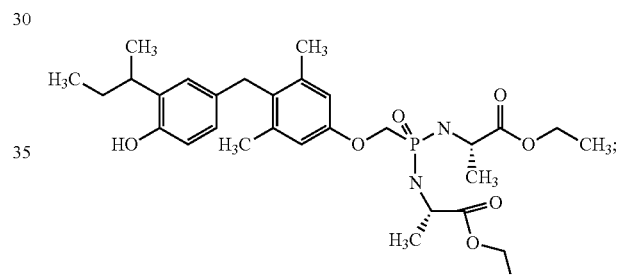
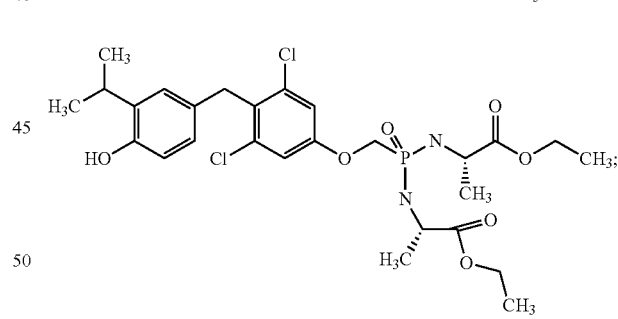
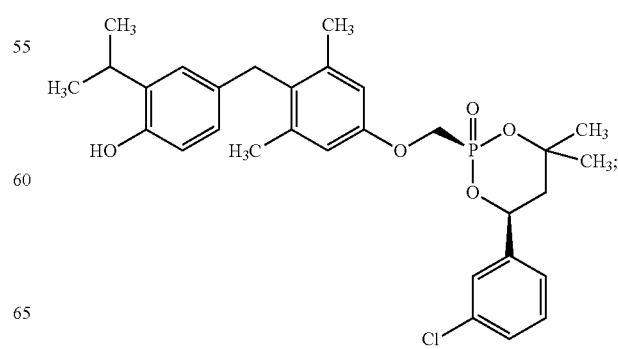

-continued
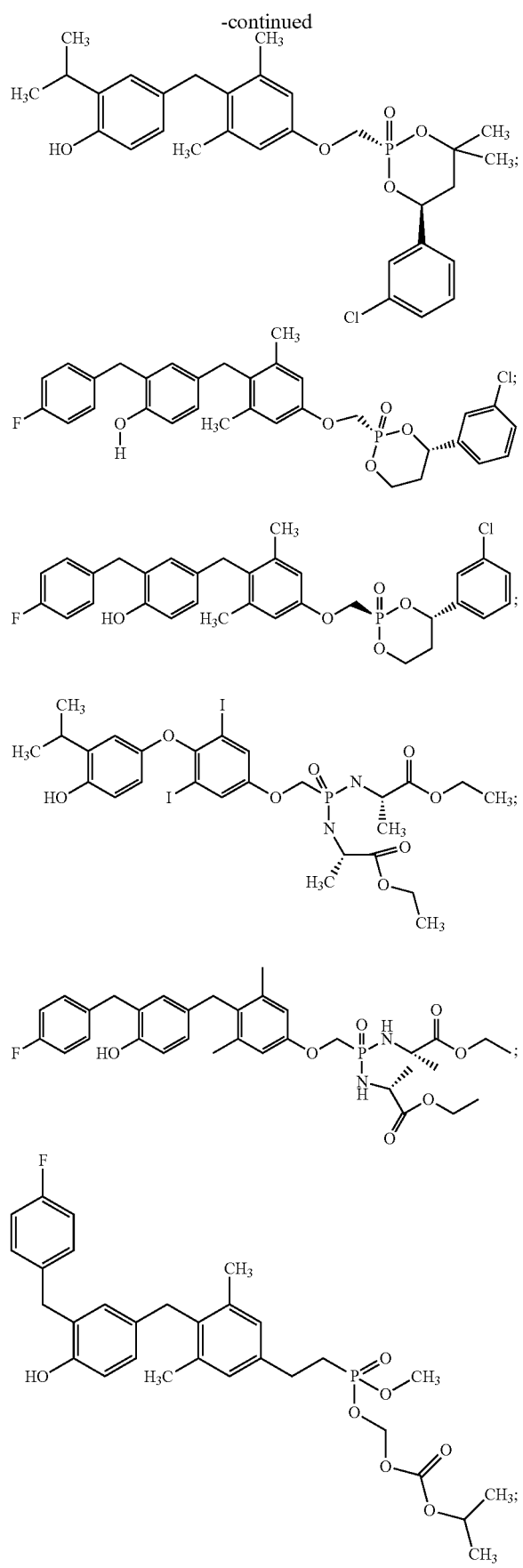
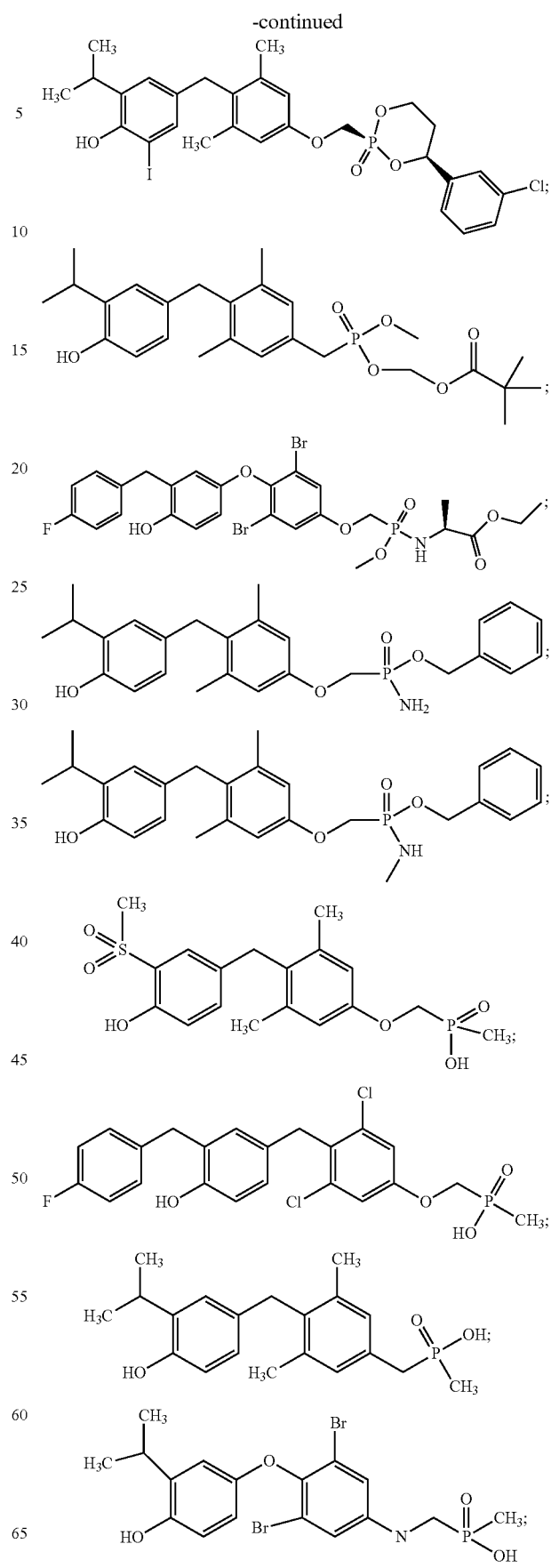

-continued

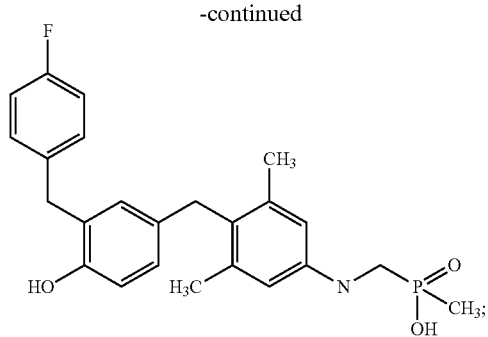

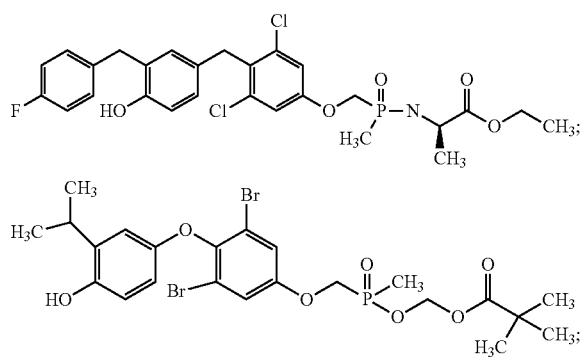

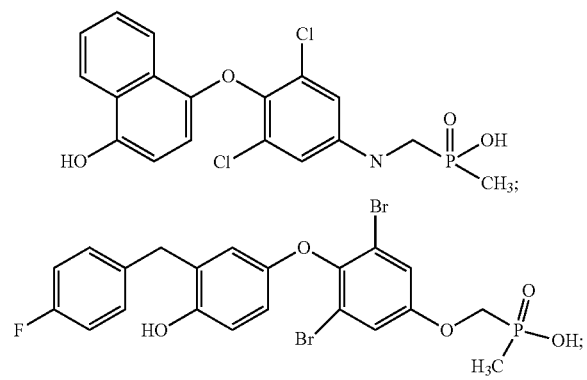

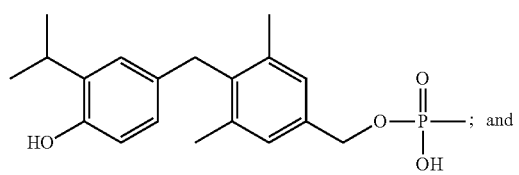

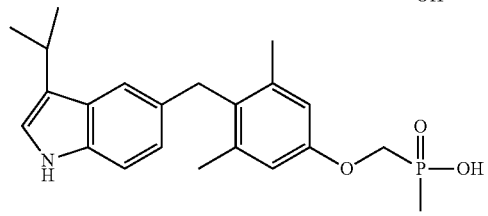

and pharmaceutically acceptable salts thereof;
wherein said compound binds to a thyroid receptor.

19. A method of treating or ameliorating a fatty liver disease in an animal, comprising administering to said animal a therapeutically effective amount of a thyromimetic compound, wherein said thyromimetic compound is a compound of Formula III:

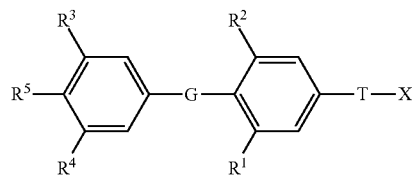

(III)

or a pharmaceutically acceptable salt thereof, wherein:

G is selected from the group consisting of —O— and —CH$_2$—;

T is —O(CH$_2$)$_k$—;

k is an integer from 0-4;

R$^1$ and R$^2$ are each independently selected from the group consisting of hydrogen, halogen, and optionally substituted —C$_1$-C$_4$ alkyl;

R$^3$ is selected from the group consisting of hydrogen, halogen, and —OH;

R$^4$ is selected from the group consisting of hydrogen, halogen, and —OH;

R$^5$ is selected from the group consisting of —OH and —F;

X is selected from carboxylic acid or esters thereof, phosphonic acid, phosphonic acid monoester and P(O)YR$^{11}$Y'R$^{11}$;

Y and Y' are each independently selected from the group consisting of —O— and —NR$^v$—;

when Y and Y' are both —O—, then each R$^{11}$ is independently selected from the group consisting of —C(R$^z$)$_2$—OC(O)R$^y$, —C(R$^z$)$_2$—O—C(O)OR$^y$, and -alkyl-S—C(O)R$^y$, when Y and Y' are both —NR$^v$—, then each R$^{11}$ is —C(R$^x$)$_2$COOR$^y$, or when Y and Y' are independently selected from —O— and —NR$^v$—, then together R$^{11}$ and R$^{11}$ are the group:

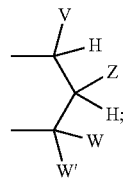

V, W, and W' are independently selected from the group consisting of hydrogen, optionally substituted alkyl, aryl, substituted aryl, heteroaryl, and substituted heteroaryl;

R$^v$ is hydrogen;

R$^z$ is hydrogen;

R$^y$ is alkyl; and

R$^x$ is hydrogen or lower alkyl;

wherein said compound binds to a thyroid receptor.

20. The method of claim 1, wherein:

Y and Y' are both —O—;

R$^{11}$ is —C(R$^z$)$_2$—OC(O)R$^y$, or together R$^{11}$ and R$^{11}$ are the group:

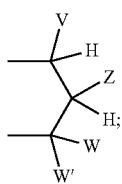

and

V, W, and W' are independently selected from the group consisting of hydrogen and substituted aryl.

21. The method of claim 20, wherein:
T is —OCH$_2$—;
R$^1$ and R$^2$ are each methyl;
R$^3$ is optionally substituted —C$_1$-C$_4$ alkyl;
R$^4$ is hydrogen; and
R$^{11}$ is —C(R$^z$)$_2$—OC(O)R$^y$.

22. The method of claim 21, wherein R$^3$ is -methyl-phenyl and R$^y$ is t-butyl.

23. The method of claim 1, wherein the compound is:

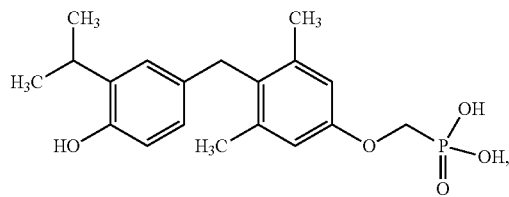

or a pharmaceutically acceptable salt thereof.

24. The method of claim 1, wherein the compound is:

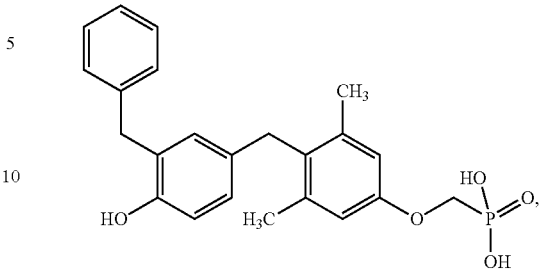

or a pharmaceutically acceptable salt thereof.

25. The method of claim 1, wherein the compound is:

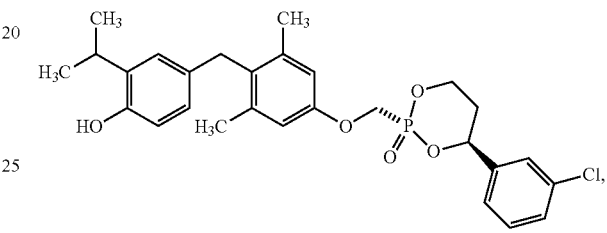

or a pharmaceutically acceptable salt thereof.

* * * * *